(12) United States Patent
Zhou

(10) Patent No.: US 10,449,553 B2
(45) Date of Patent: Oct. 22, 2019

(54) MAGNETIC BIOLOGICAL ENTITY SEPARATION DEVICE AND METHOD OF USE

(71) Applicant: Yuchen Zhou, San Jose, CA (US)

(72) Inventor: Yuchen Zhou, San Jose, CA (US)

( * ) Notice: Subject to any disclaimer, the term of this patent is extended or adjusted under 35 U.S.C. 154(b) by 42 days.

(21) Appl. No.: 15/911,116

(22) Filed: Mar. 3, 2018

(65) Prior Publication Data

US 2019/0270092 A1   Sep. 5, 2019

Related U.S. Application Data

(63) Continuation of application No. 15/911,115, filed on Mar. 3, 2018.

(51) Int. Cl.
| | |
|---|---|
| *G01N 33/543* | (2006.01) |
| *B03C 1/30* | (2006.01) |
| *B01L 3/00* | (2006.01) |
| *B03C 1/28* | (2006.01) |
| *B01F 11/02* | (2006.01) |
| *G01N 35/00* | (2006.01) |

(52) U.S. Cl.
CPC ............ *B03C 1/30* (2013.01); *B01F 11/0266* (2013.01); *B01L 3/502761* (2013.01); *B03C 1/288* (2013.01); *G01N 33/54326* (2013.01); *G01N 33/54333* (2013.01); *G01N 35/0098* (2013.01); *B01L 2200/0647* (2013.01); *B01L 2200/0668* (2013.01); *B01L 2400/0439* (2013.01); *B03C 2201/18* (2013.01); *B03C 2201/26* (2013.01); *G01N 2035/00554* (2013.01)

(58) Field of Classification Search
USPC ................. 210/695; 422/128, 255, 527, 63; 436/526
See application file for complete search history.

(56) References Cited

U.S. PATENT DOCUMENTS

| | | | |
|---|---|---|---|
| 4,759,775 | A | 7/1988 | Peterson et al. |
| 5,902,489 | A | 5/1999 | Yusada et al. |
| 5,972,721 | A * | 10/1999 | Bruno ....................... B03C 1/01 209/213 |
| 6,216,538 | B1 | 4/2001 | Yasuda et al. |
| 6,254,830 | B1 | 7/2001 | Pivarnik et al. |
| 6,929,750 | B2 | 8/2005 | Laurell et al. |
| 7,474,184 | B1 | 1/2009 | Humphries et al. |
| 8,273,302 | B2 | 9/2012 | Takahashi et al. |
| 8,573,060 | B2 | 11/2013 | Huang et al. |
| 9,476,855 | B2 | 10/2016 | Ward et al. |
| 2004/0069708 | A1 | 4/2004 | Laurell et al. |
| 2005/0106064 | A1 | 5/2005 | Laurell et al. |
| 2006/0094051 | A1 * | 5/2006 | Lee ................... B01L 3/502761 435/6.11 |
| 2006/0240572 | A1 | 10/2006 | Carron et al. |
| 2007/0182517 | A1 | 8/2007 | Humphries et al. |
| 2008/0160630 | A1 * | 7/2008 | Liu ..................... B01L 3/50273 436/164 |

(Continued)

*Primary Examiner* — Erik B Crawford

(57) ABSTRACT

The current invention relates to the method and apparatus to magnetically separate biological entities with magnetic labels from a fluid sample. The claimed methods separate biological entities with magnetic labels by using a magnetic device. The claimed methods further include processes to dissociate biological entities magnetic conglomerate after magnetic separation.

2 Claims, 93 Drawing Sheets

(56) References Cited

U.S. PATENT DOCUMENTS

| | | |
|---|---|---|
| 2010/0317093 A1* | 12/2010 | Turewicz ............ B01L 3/50273 |
| | | 435/287.2 |
| 2011/0033922 A1 | 2/2011 | Landers et al. |
| 2012/0100546 A1* | 4/2012 | Lowery, Jr. .......... C12Q 1/6895 |
| | | 435/6.12 |
| 2013/0330739 A1 | 12/2013 | Yu |
| 2014/0120570 A1 | 5/2014 | Yu et al. |
| 2014/0231315 A1 | 8/2014 | Laurell et al. |
| 2015/0010939 A1 | 1/2015 | Warner et al. |
| 2015/0177111 A1 | 6/2015 | Warmer et al. |
| 2015/0253226 A1 | 9/2015 | Augustsson et al. |
| 2015/0308971 A1 | 10/2015 | Bisgaard et al. |

\* cited by examiner

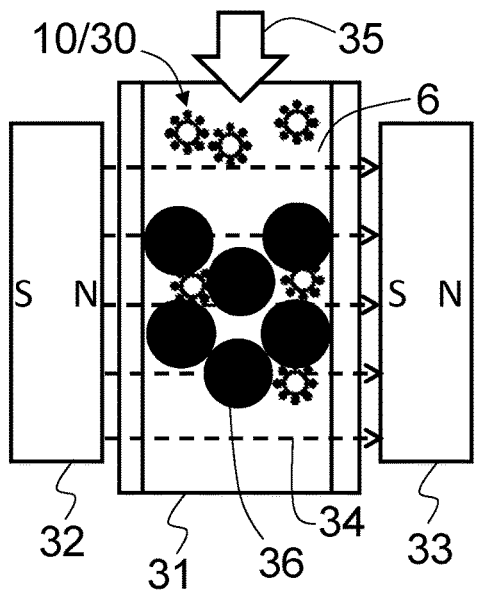
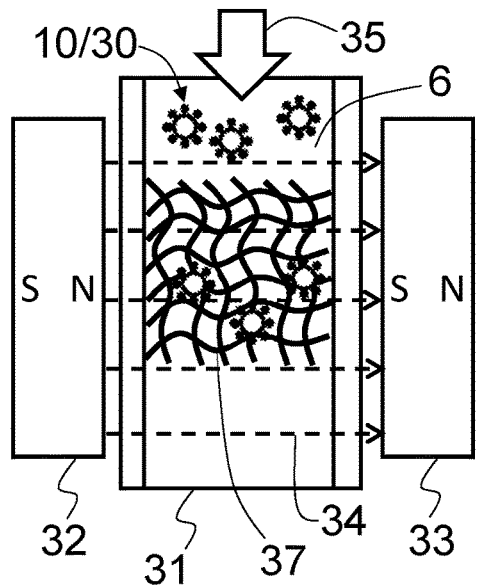
FIG. 3A (Prior Art)          FIG. 3B (Prior Art)
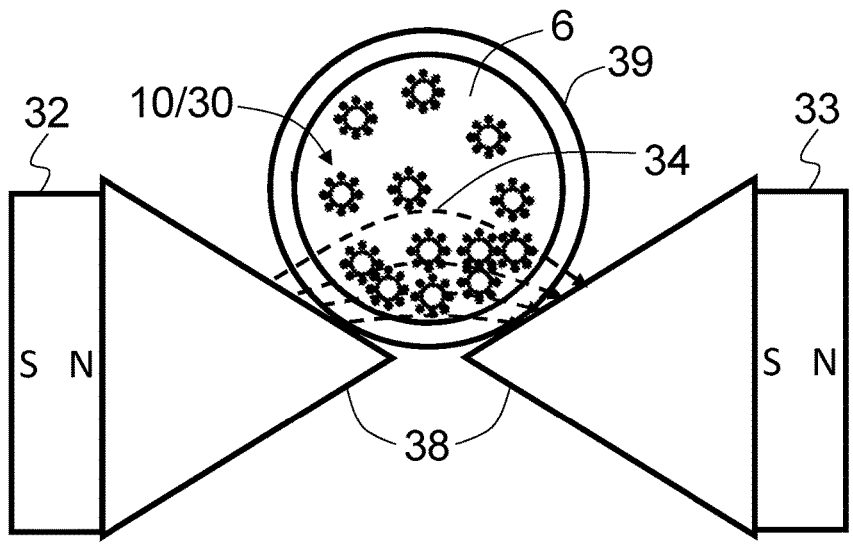
FIG. 3C (Prior Art)

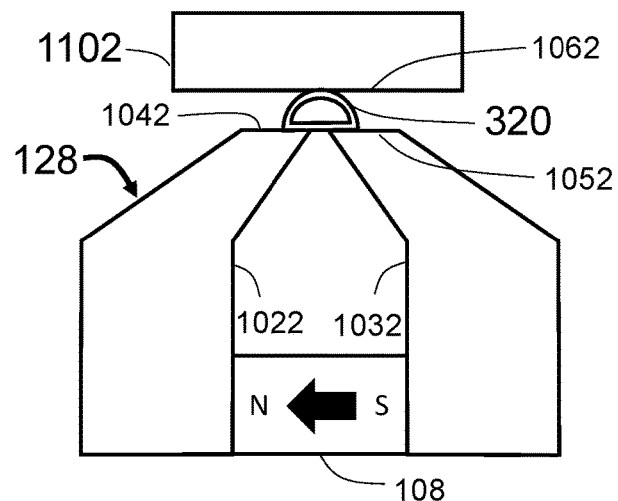
FIG. 20A
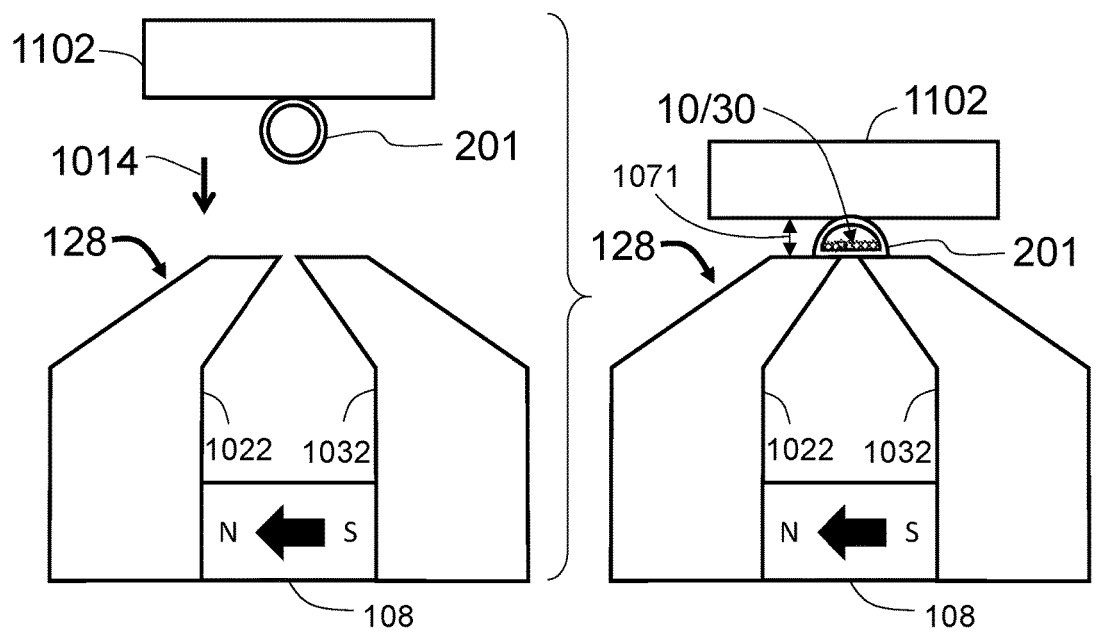
FIG. 20B  FIG. 20C

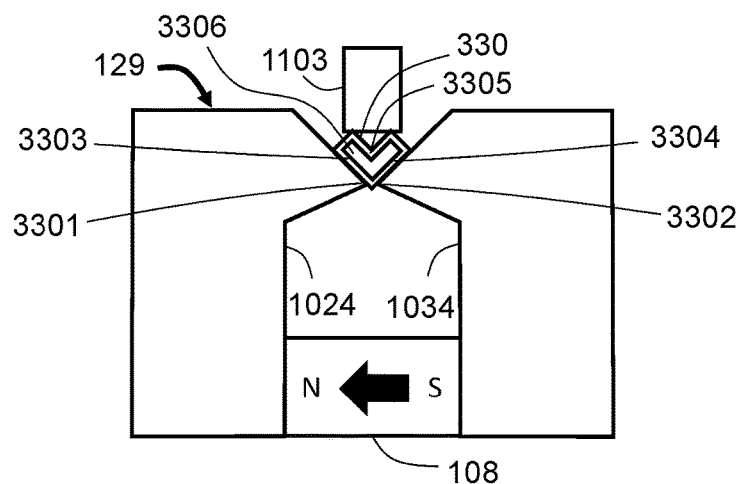
FIG. 21A
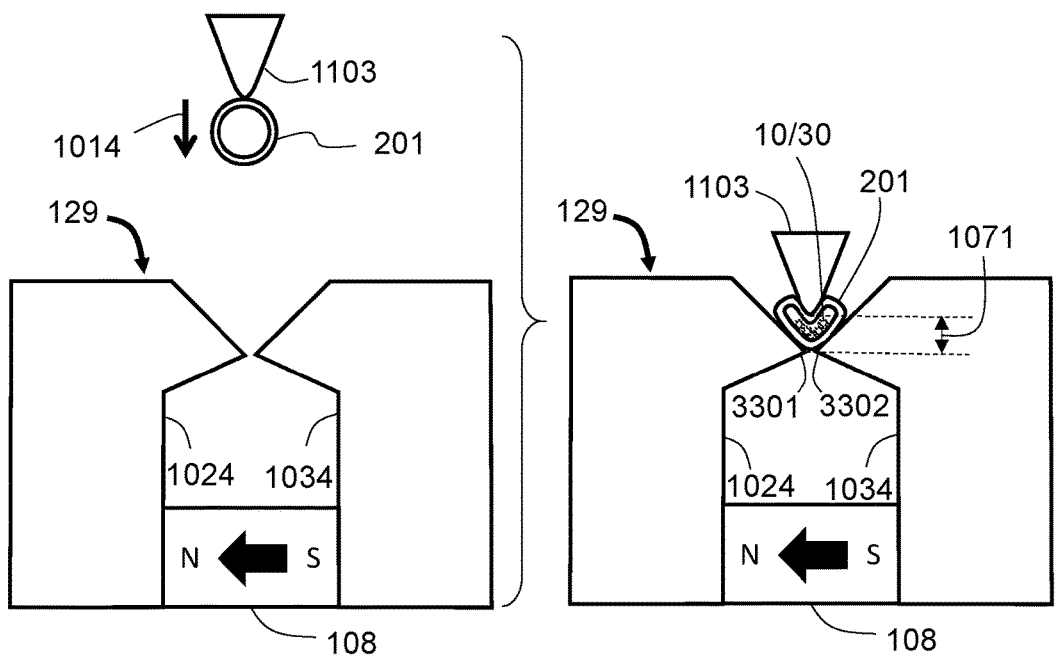
FIG. 21B  FIG. 21C

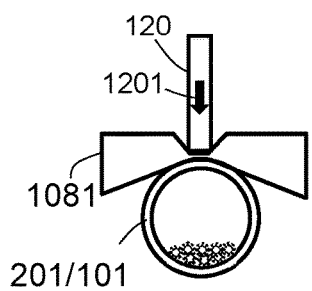
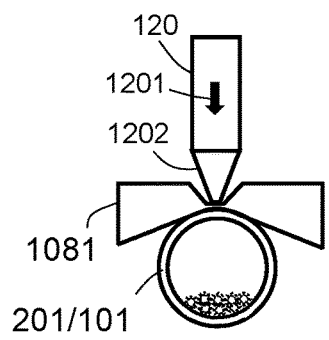
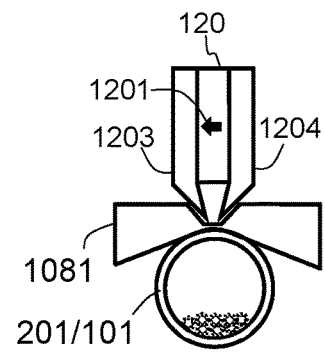
FIG. 25A          FIG. 25B          FIG. 25C
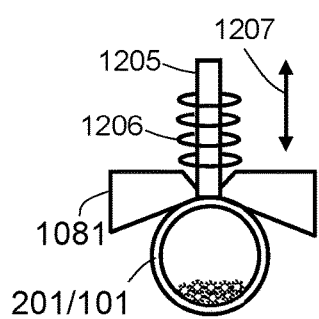
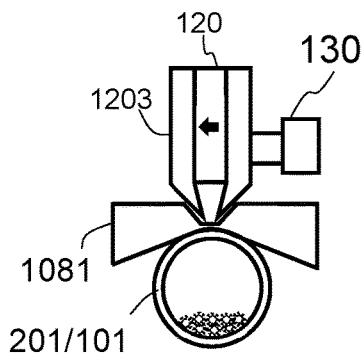
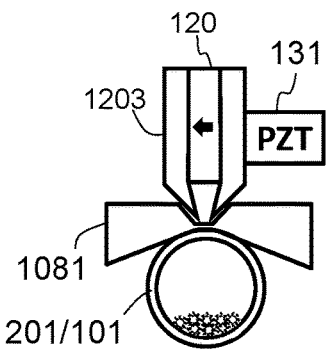
FIG. 25D          FIG. 25E          FIG. 25F

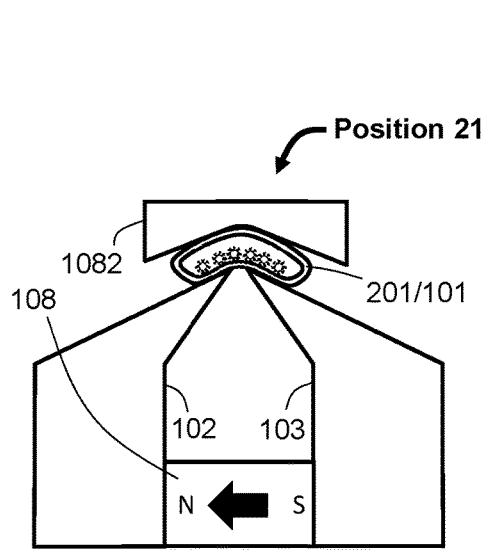
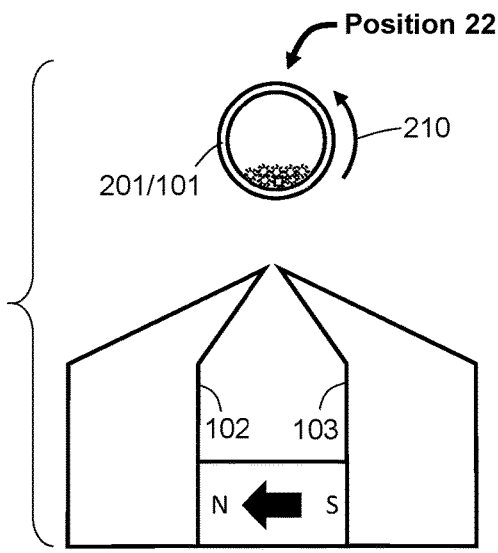
FIG. 26A  FIG. 26B
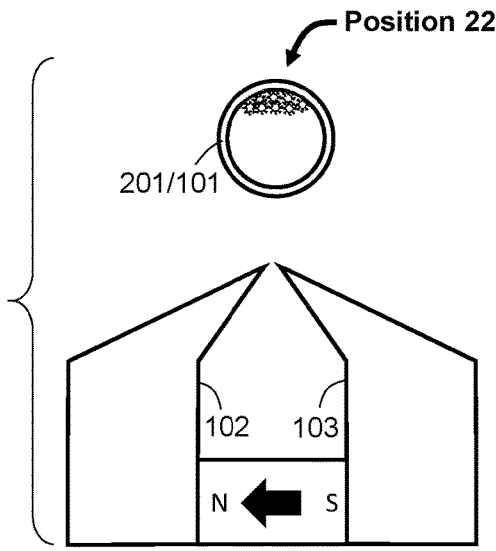
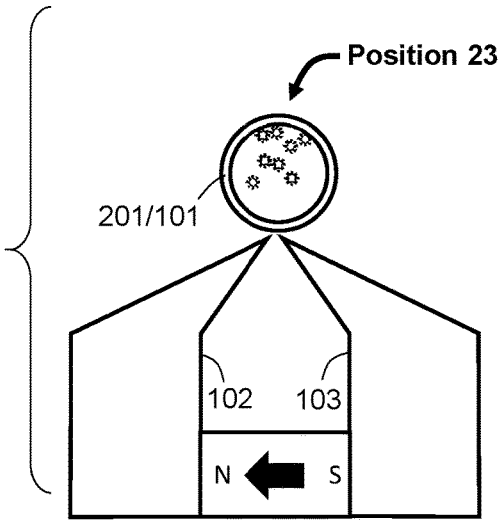
FIG. 26C  FIG. 26D 5806
Add into target sample magnetic labels hybridized with antibodies or ligands, which specifically bind to surface antigens or receptors on target cells or entities,

58061
Add into target sample magnetic labels and fluorescent labels which are hybridized with antibodies or ligands, and specifically bind to same or different surface antigens or receptors on target cells or entities

*FIG. 76A*

5807
Incubate target sample to form magnetic labels binding to target cells or entities

58071
Incubate target sample to form magnetic labels and fluorescent labels binding to target cells or entities

*FIG. 76B*

MAGNETIC BIOLOGICAL ENTITY SEPARATION DEVICE AND METHOD OF USE

BACKGROUND

The current invention generally relates to methods and apparatus to separate biological entities, including cells, bacteria and molecules from human blood, body tissue, body fluid and other human related biological samples. The disclosed methods and apparatus may also be utilized to separate biological entities from animal and plant samples. More particularly, the current invention relates to the methods and apparatus for achieving separation of biological entities with using one or more of a micro-fluidic separation device/chip ("UFL"), and one or more of a magnetic separation device ("MAG"), individually or in combination. For description purpose, "cells" will be used predominantly hereafter as a typical representation of biological entities in general. However, it is understood that the methods and apparatus as disclosed in this invention may be readily applied to other biological entities without limitation.

Separation of biological entities from a fluid base solution, for example separating a specific type of white blood cells from human blood, typically involves a first step of identifying the target biological entities with specificity, and followed by a second step of physical extraction of the identified target biological entities from the fluid base solution. In human blood, different types of biological cells may have various types of surface antigens or surface receptors, which are also referred to as surface markers in this invention. Certain surface markers on a given type of cells may be unique to said type of cells and may be used to identify said type of cells from blood sample with specificity.

FIG. 1A through FIG. 1C show examples of identifying or labeling target cells 1, with using superparamagnetic labels 2 ("SPL") as in FIG. 1A, using optical fluorescent labels 3 ("OFL") as in FIG. 1B, and using both the SPL 2 and OFL 3 together as in FIG. 1C.

In FIG. 1A, cell 1 has surface markers 11. SPLs 2 are conjugated with surface antibodies or ligands, also referred to as "probe" 21, which specifically bind to the surface markers 11 of cell 1. Large quantity of SPL 2 having probes 21 are put into the solution where cell 1 resides. After incubation processes 9, a plurality of SPLs 2 are bound to cell 1 surface with probes 21 selectively bound to surface markers 11 with specificity. Thus, cells 1 is magnetically identified or labeled by SPLs 2, i.e. magnetically labeled cell 10. A magnetic field with sufficient field gradient may be applied to cell 10 to produce a physical force on the SPLs 2 attached to the cells 10 surface. With sufficient strength, the physical force working through the SPLs 2 on cell 10 may be used to separate and physically remove cell 10 from its liquid solution.

In FIG. 1B, cell 1 has surface markers 12. OFLs 3 are conjugated with probes 22, which specifically bind to the surface markers 12 of cell 1. Large quantity of OFLs 3 having probes 23 are put into the solution where cell 1 resides. After incubation processes 9, a plurality of OFLs 3 are bound to cell 1 surface with probes 22 selectively bound to surface markers 12 with specificity. Thus, cells 1 is optically identified or labeled by OFLs 3, i.e. optically labeled cell 20. By using an optical based cell separation system, cell 1 may be separated from its liquid solution based on the optical signal that OFL 3 produces under an excitation light. One type of such optical based cell separation system is a flow cytometer, wherein said liquid solution is streamed through a conduit within said flow cytometer as a continuous flow. At least one excitation light source produces a light spot upon said liquid flow through said conduit at a first optical wavelength. In presence of OFL 3 in the light spot, OFL3 is excited by first wavelength and radiates optical light at a second wavelength. When cell 1 with bound OFLs 3 passes said light spot within said flow, OFLs 3 bound to cell 1 radiate optical signal in second wavelength, whereas strength of said optical signal as well as duration while cell 1 passes the light spot may be used to identify presence of cell 1 by the flow cytometer, which then diverts cell 1 into a second liquid flow path or mechanically remove cell 1 from the liquid flow, thus separating cell 1 from fluid base. In practice, OFL 3 bound to cell 1 may be in various types of fluorescent dyes or quantum dots, producing exited optical light at multiple wavelengths. A plurality of excitation light sources may also be used in same flow cytometer system to produce excitation light spots at different locations of the liquid flow with different excitation light wavelength. Combination of various wavelength produced by OFL 3 on same cell 1 may be used to increase specificity of separation of cell 1, especially when a combination of various types of surface markers 12 is needed to specifically identify a sub-category target cell 1 population from a major category of same type of cells, for example CD4-T cells from other white blood cells.

In FIG. 1C, cell 1 has both surface markers 11 and 12. SPLs 2 conjugated with probes 21 and OFLs 3 conjugated with probes 22 are both bound to cell 1 surface after incubation processes 9 to form magnetically and optically labeled cell 30. Cell 30 allows for separation of cell 30 with a combination of magnetic separation and an optical based cell separation system, where a the magnetic separation through SPLs 2 may provide a fast first stage separation of cell category including cell 30, while the optical separation through OFLs 3 may provide a second stage separation of cell 30 after magnetic separation with more specificity. Alternatively, cell 30 may be separated via OFLs 3 in a first stage and via SPLs 2 in a second stage. In either case, SPLs 2 and OFLs 3 together may help increase speed, efficiency and specificity in separation of cell 1 compared with FIG. 1A and FIG. 1B.

FIG. 2A shows an example of conventional magnetic separation through SPL 2. In a container 5, liquid solution 6 contains cells 10 of FIG. 1A or cells 30 of FIG. 1C that are bound with plurality of SPLs 2 on cell surface. Magnet 4, preferably a permanent magnet, is positioned in proximity to wall of container 5. Magnet 4 has a magnetization represented by arrow 41 indicating a north pole ("N") and a south pole ("S") on top and bottom surfaces of the magnet 4. Magnetic field produced by the magnetization 41 in the solution 6 is higher at the container 5 wall directly opposing the N surface of the magnet 4, and lower at locations within solution 6 further away from the magnet 4, thus creating a magnetic field gradient pointing towards the magnet 4 within the solution 6. SPLs 2 bound to cell 10/30 are superparamagnetic, which are effectively non-magnetic in absence of magnetic field, but will gain magnetic moment in presence of the magnetic field produced by the magnet 4. With the magnetic moment of SPLs 2 and the magnetic field gradient from magnet 4, cells 10/30 will be pulled by the force produced by the magnetic field from magnet 4 towards magnet 4. After sufficient time 7, cells 10/30 may be depleted from solution 6 and form conglomerate at inside surface of the container 5 wall opposing magnet 4. In conventional practice, solution 6 may be removed from container 5, while maintaining magnet 4 position relative to container 5 thus cells 10/30 are retained as conglomerate against container 5 inside surface. Afterwards, magnet 4 may be removed from container 5. With absence of magnetic field, conglomerate of cells 10/30, together with any non-bound free SPLs in the conglomerate, shall self-demagnetize over extensive time to be non-magnetic and cells 10/30 may be removed from container 5 as individual cells 10/30.

Conventional method as shown in FIG. 2A has limitations in actual applications. For the SPL 2 to be superparamagnetic, the size of the fundamental superparamagnetic particles ("SPN") contained in SPL 2, for example iron oxide particles, shall be in the range of 10 nm (nanometer) to 30 nm, where a smaller particle size makes the particles more effectively superparamagnetic but harder to gain magnetic moment in presence of magnetic field, while a larger particle size makes the particles more difficult to become non-magnetic when magnetic field is removed. SPL 2 is typically composed of SPNs dispersed in a non-magnetic matrix. For example, certain SPL 2 is a solid sphere formed by SPNs evenly mixed within a polymer base, typically in the size of larger than 1 um (um). In another case, SPL 2 is solid bead formed by SPNs mixed within an oxide or nitride base, for example iron oxide nanoparticles mixed in silicon oxide base, which can be in the size of a few hundred nanometers or tens of nanometers. For the cells 10/30 of FIG. 2A to be suitable for additional cellular processes, including cell culture and cell analysis, SPL 2 size is desirable to be smaller than the cell itself, which is usually a few ums. Thus, SPL 2 with sub-um size (<1 um) is desired. SPL 2 size less than 500 nm is more preferred. SPL 2 size less than 200 nm is most preferred. However, when SPL 2 average size is smaller, variation of SPL 2 size becomes larger statistically. FIG. 2B shows example schematics of single SPL 2 magnetic moment in the presence of an applied magnetic field. Solid curve 22 indicates SPL 2 having a population nominal size, or average size, where SPL 2 magnetic moment increases with higher magnetic field. With magnetic field strength increasing from 0 to Hs, nominal size SPL magnetic moment increases with field strength in a linear trend at beginning, until reaching a saturation region where magnetic moment plateaus to Ms, which is determined by the saturation moment of the SPNs material within the SPL 2. For SPL 2 with a smaller size than nominal size, curve 23 indicates that at the same magnetic field strength, smaller size SPL 2 gains a lower moment, and thus experiencing a lower magnetic force, and requires a higher field to reach saturation magnetic moment Ms. For a larger size SPL 2 than nominal size, curve 24 indicates larger size SPL 2 is easier to saturate to Ms with a lower field and gains a higher moment at same magnetic field strength.

Now referring back to FIG. 2A, for SPL 2 with sub-um size that is suitable for cell separation and cellular processes, conventional method of FIG. 2A has limitation of not being able to produce high magnetic field strength and strong magnetic field gradient in solution 6 at locations further away from the container 5 wall opposing magnet 4 N surface. Therefore, smaller size SPL 2 of curve 23 of FIG. 2B at farther end of the container 5 from magnet 4 may be difficult to magnetize by magnet 4 field and experiences smaller force to move the cell 10/30 towards magnet 4. To reach complete depletion of cells 10/30 in solution 6 within container 5, it may require significant amount of time. Meanwhile, volume of container 5 is limited also due to magnetic field strength from magnet 4 may not be sufficient to magnetize the smaller SPL 2 of curve 23 of FIG. 2B at large container 5 sizes. Besides overall process being slow, another drawback in conventional method of FIG. 2A is that the operation as described in FIG. 2A typically involves air exposure of cells 10/30 conglomerate during the steps of solution removal and later removal of cells 10/30 from container 5. Such air exposure poses challenge in achieving sterile separation of cells 10/30 for clinical purpose, as well as risk of cell 10/30 damage or death that negatively affects further cellular processes of cell 10/30.

FIG. 3A shows another example of magnetic separation of cells 10/30 with SPL 2 in prior art. In FIG. 3A, solution 6 containing cells 10/30 is passed through a column 31 that is filled with ferromagnetic or ferromagnetic spheres 36. By applying a magnetic field across the column with magnets 32 and 33, where dashed lines 34 indicates applied magnetic field direction, spheres 36 may be magnetized by the field and producing localized magnetic field in gaps between neighboring spheres 36. Such local field and field gradient between spheres 36 gaps may be strong, due to the small dimensions of the gaps, to effectively magnetize SPL 2 of all sizes when SPL 2 in solution 6 passes through the gaps between the spheres 35 during a downward flow of solution 6 as indicated by arrow 35, where SPL 2 may be attracted to various spheres 36 surface and separated from the solution 6. Prior art of FIG. 3A may effectively avoid the air exposure issue of FIG. 2A, and may possess at a higher separation speed of cells 10/30 than FIG. 2A during the flow 35. However, an intrinsic issue of FIG. 3A method is that with the spheres 36 being ferromagnetic or ferromagnetic and is much larger in size than cells 10/30, magnetic domains in spheres 36 will exist even after removal of magnets 32 and 33 from the column 31. Such magnetic domains, and domain walls between the domains, will inevitably produce local magnetic field around the surface of the spheres 36, which will keep the SPLs 2 on cells 10/30 magnetized and strongly attracting the cells 10/30 when magnets 32 and 33 are removed. Therefore, the cells 10/30 are inherently more difficult to be removed from the column 31 in FIG. 3A than FIG. 2A. Cells 10/30 loss due to not completely removed from column 31 after separation is inherently high. In certain prior art method, a pressurized high speed buffer flow may be used to force wash the cells 10/30 from the spheres in column 36. However, such forced flow will inevitably causes mechanical damage to the cells and will still leave significant percentage of cells 10/30 in column 31 due to the strong domain wall field of spheres 36. Besides cells 10/30 loss, another intrinsic issue of FIG. 3A method is introducing spheres 36 as foreign materials in the flow of solution 6, which is not desirable for sterile process needed for clinical applications.

FIG. 3B then shows another prior similar to method of FIG. 3A, except mesh 37 made of ferromagnetic or ferromagnetic wires are introduced in the column 31 instead of spheres or blocks 36. When magnetic field 34 is applied by the magnets 32 and 33, wires of mesh 37 are magnetized and adjacent wires of mesh 37 produce local magnetic field around the wires. Clearances between wires of the mesh allow fluid 6 to flow in direction 35 within the column. When cells 10/30 is in proximity to wires of mesh 37, cells 10/30 may be attracted to the wire surface due to the local magnetic field and field gradient produced by the wires of the mesh 37. Compared to FIG. 3A prior art, FIG. 3B may adjust size of wires and size of clearance of mesh 37 to tradeoff between cells 10/30 separation speed and cell loss in column. However, in practice, due to the gap between spheres 36 is much smaller than clearance size in mesh 37, cells 10/30 separation speed in FIG. 3B is slower than FIG. 3A, while FIG. 3B still possesses the same cells loss issue of FIG. 3A, where domains in the wires of mesh 37 maintains SPL 2 magnetic moment after magnets 32 and 33 are removed and cells 10/30 are attracted to the wires by the domain and domain wall. Cells 10/30 loss due to the magnetic domains in wires of mesh 37 also exists in FIG. 3B. Additionally, FIG. 3B is same as FIG. 3A in introducing mesh 37 as foreign materials in the flow of solution 6, which is not desirable for sterile process.

FIG. 3C shows another prior art, where magnets 32 and 33 are each attached with a soft magnetic flux guide 38 with an apex. The flux guides 38 produce localized magnetic field between the apexes of the guides 38 with high field strength and high gradient close to the apexes. FIG. 3C shows the cross-sectional view of the conduit 39, which is intrinsically a circular tubing, whereas solution 6 containing cells 10/30 flows along the tubing 39 length in the direction perpendicular to the cross-section view. Tubing 39 is positioned on one side of the gap of the apexes. Magnetic field lines 34 exhibit a higher density closer to the gap indicates both higher magnetic field strength and higher magnetic field gradient towards the gap. Magnetic field 34 produces effective force on cells 10/30 in solution 6 and pulls the cells 10/30 from solution 6 towards the tubing 39 inside wall that is closest to the apexes of the guides 38. Prior art of FIG. 3C when compared to prior art of FIG. 3A and FIG. 3B has the advantages of: (1) not introducing foreign material in the flow path; (2) when magnets 32 and 33 are removed from tubing together with guides 38, there is no ferromagnetic or ferromagnetic sphere 36 or mesh 37 in the tubing, thus avoiding the domain structures related loss of cells 10/30.

However, prior art of FIG. 3C also has intrinsic deficiencies. First deficiency is the flow speed of solution 6, or flow rate, in the tubing 39 is limited by the prior art design of FIG. 3C. The separation speed of cells 10/30 of prior art as in FIG. 3C is not sufficient for many applications. Circular tubing conduit 39 as shown in FIG. 3C experiences high field and high field gradient at lower end of tubing 39, where cells 10/30 closer to the lower end of tubing 39 may experience a high force that pulls them to move towards the tubing 39 lower wall inner surface much faster. However, for the cells 10/30 closer to the top end of the tubing 39, due to the narrow wedge gap and position of the tubing 39 being on one side of the gap, magnetic field and gradient is significantly lower than the lower end. Thus cells 10/30 closer to the top end of the tubing 39 experiences a much smaller force and moves to lower end of tubing 39 at a much slower speed. For a limited length of the tubing 39 in the perpendicular to cross-sectional view direction, all cells 10/30 within the fluid 6 flowing through the tubing 39 need to be separated from solution 6 to form a conglomerate on the inside surface of the tubing close to the apexes before solution 6 exits the tubing 39. Due to slower speed of cells 10/30 moving from top of the tubing 39, flow rate of solution 6 needs to be slow such that it can allow enough time for all the cells 10/30 near top of tubing 39 to be attracted into the conglomerate. If solution 6 flows through the tubing 39 at higher speed, it will cause incomplete separation of cells 10/30 from solution. Such limitation on flow rate due to the circular design of tubing 39, where tubing top end being further away from high field and high gradient apexes cannot be cured by a smaller size tubing 39. A smaller cross-sectional size circular tubing 39 will bring the top end of the tubing 39 closer to the wedge gap. However, due to the smaller cross-section size, volume of solution 6 flowing through the tubing 39 in a unit time frame, i.e. flow rate of solution 6, will reduce when flow speed of solution 6 maintains. To maintain same flow rate as in a larger tubing 39, solution 6 flow speed needs to increase, which then gives less time for cells 10/30 at top end of smaller size tubing 39 to move to the conglomerate site, and offsets the effect of small size tubing 39.

A second deficiency of FIG. 3C prior art is the inability to dissociate individual cell 10/30 from conglomerate of cells 10/30 and non-bound free SPL 2, as the conglomerate will not self-demagnetize with ease after magnets 32 and 33, together will guides 38, are removed from tubing 39 in actual applications. Demagnetization of SPL 2 relies on the SPNs within SPL 2 being effectively nanoparticles. However, as the conglomerate forms an effective larger body of superparamagnetic material, the SPNs within SPL 2 experiences magneto-static field from a large number of closely packed SPNs from neighboring SPL 2 in the conglomerate, which reduces the super-paramagnetic nature of the SPNs. In one case, the SPL 2 of cells 10/30 within conglomerate requires extensive time to self-demagnetize, which is not practical for many applications. In another case, the conglomerate won't self-demagnetize due to the SPN being more ferromagnetic in conglomerate form, which is undesirable. High pressure flushing as utilized in FIG. 3A is not effective in FIG. 3C, as majority of the circular tubing 39 inner area is occupied by empty space, while conglomerate is compacted on the lower end of tubing 39, such flush will mainly flow through the top section of the tubing 39 without producing enough friction force on the conglomerate of cells 10/30 to remove the cells 10/30 from the tubing 39 lower wall. As prior art does not provide an effective method to dissociate conglomerate and remove cells 10/30 from tubing 39, such deficiency of FIG. 3C prior art is limiting its application.

Prior arts are limited either in causing cell loss and introducing foreign materials in the flow path, or limited in the flow rate of solution 6 and the ability to extract separated cells from conglomerate with an effective dissociation method.

It is desired to have a method and an apparatus that can achieve high flow rate magnetic separation of cells 10/30 without introducing foreign material in the flow path of the biological solution, and being able to dissociate cells 10/30 from conglomerate in a practically short time without damaging the cells.

SUMMARY OF THE INVENTION

This invention describes novel methods and novel magnetic separation devices ("MAG") that are able to: (1) separate biological entities bound with SPL from biological solution with high flow rate, without exposure of biological entities to air, and without introducing foreign material in the flow path of the biological solution carrying the biological entities; (2) dissociate the biological entities from the magnetically separated conglomerate.

This invention further describes novel methods and novel micro-fluidic separation devices ("UFL") that separate biological entities from biological solutions based on the size of the biological entities.

This invention further describes novel methods and novel apparatus using MAG and UFL individually and in combination to separate biological entities from biological solutions for various separation applications.

This invention further describes methods of pre-symptom early tumor detection and methods of using MAG and UFL during the process of tumor detection.

The methods, components and apparatus as disclosed by this invention may be utilized to separate biological entities, including cells, bacteria and molecules, from human blood, human body tissue, human bones, human body fluid, human hairs, other human related biological samples, as well as biological entities from animal and plant samples alike without limitation.

BRIEF DESCRIPTION OF THE DRAWINGS

FIG. 3A is a cross-sectional view of a prior art magnetic cell separator.

FIG. 3B is a cross-sectional view of a prior art magnetic cell separator.

FIG. 3C is a cross-sectional view of a prior art magnetic cell separator.

FIG. 20A illustrates cross-sectional view of the eighth embodiment of MAG with a rotated "D" shape rigid channel in separation position.

FIG. 20B illustrates cross-sectional view of the eighth embodiment of MAG with a flexible channel.

FIG. 20C illustrates cross-sectional view of the eighth embodiment of MAG having a flexible channel in separation position with cells being separated.

FIG. 21A illustrates cross-sectional view of the ninth embodiment of MAG having a "V" shape rigid channel in separation position.

FIG. 21B illustrates cross-sectional view of the ninth embodiment of MAG with a flexible channel.

FIG. 21C illustrates cross-sectional view of the ninth embodiment of MAG having a flexible channel in separation position with cells being separated.

FIG. 25A illustrates a flexible channel holder at demagnetization position, where DMAG magnet is a permanent magnet.

FIG. 25B illustrates a flexible channel holder at demagnetization position, where DMAG magnet is a permanent magnet attached with a soft magnetic pole.

FIG. 25C illustrates a flexible channel holder at demagnetization position, where DMAG magnet is a permanent magnet attached with a pair of soft magnetic poles.

FIG. 25D illustrates a flexible channel holder at demagnetization position, where DMAG magnet is an electromagnet.

FIG. 25E illustrates flexible channel holder at demagnetization position, where mechanical vibration is applied to DMAG magnet by a motor.

FIG. 25F illustrates flexible channel holder at demagnetization position, where ultrasound vibration is applied to DMAG magnet by a PZT.

FIG. 26A illustrates the third embodiment of MAG having a flexible channel in separation position with cells being separated.

FIG. 26B illustrates the flexible channel of FIG. 26A departs from MAG and rotates.

FIG. 26C illustrates the conglomerate of separated cells in the flexible channel of FIG. 26B being rotated to top end of the flexible channel.

FIG. 26D illustrates the flexible channel of FIG. 26C moves to demagnetization position.

FIG. 59B illustrates fluidic lines of FIG. 59A being connected to, or attached with, various fluidic devices to realize sample processing through a single MAG.

FIG. 60A illustrates example of closed and disposable fluidic lines for sample processing through a single UFL.

FIG. 60B illustrates fluidic lines of FIG. 60A being connected to, or attached with, various fluidic devices to realize sample processing through a single UFL.

FIG. 61A illustrates replacing peristaltic pumps of FIG. 56B with using pressurized chambers on input sample bags to drive fluid through fluidic lines.

FIG. 61B illustrates replacing peristaltic pumps of FIG. 56B with using vacuum chambers on output sample bags to drive fluid through fluidic lines.

FIG. 62A illustrates replacing peristaltic pumps of FIG. 57B with using pressurized chambers on input sample bags to drive fluid through fluidic lines.

FIG. 62B illustrates replacing peristaltic pumps of FIG. 57B with using vacuum chambers on output sample bags to drive fluid through fluidic lines.

FIG. 63A illustrates replacing peristaltic pumps of FIG. 58B with using pressurized chambers on input sample bags to drive fluid through fluidic lines.

FIG. 63B illustrates replacing peristaltic pumps of FIG. 58B with using vacuum chambers on output sample bags to drive fluid through fluidic lines.

FIG. 64A illustrates replacing peristaltic pumps of FIG. 59B with using pressurized chambers on input sample bags to drive fluid through fluidic lines.

FIG. 64B illustrates replacing peristaltic pumps of FIG. 59B with using vacuum chambers on output sample bags to drive fluid through fluidic lines.

FIG. 65A illustrates replacing peristaltic pumps of FIG. 60B with using pressurized chambers on input sample bags to drive fluid through fluidic lines.

Figure 60A:
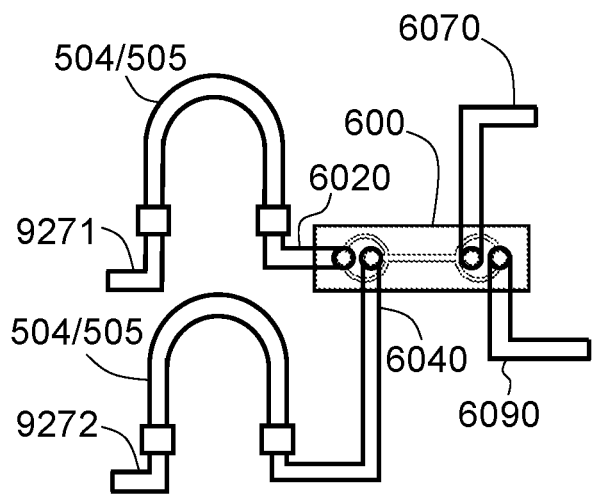
Figure 60B:
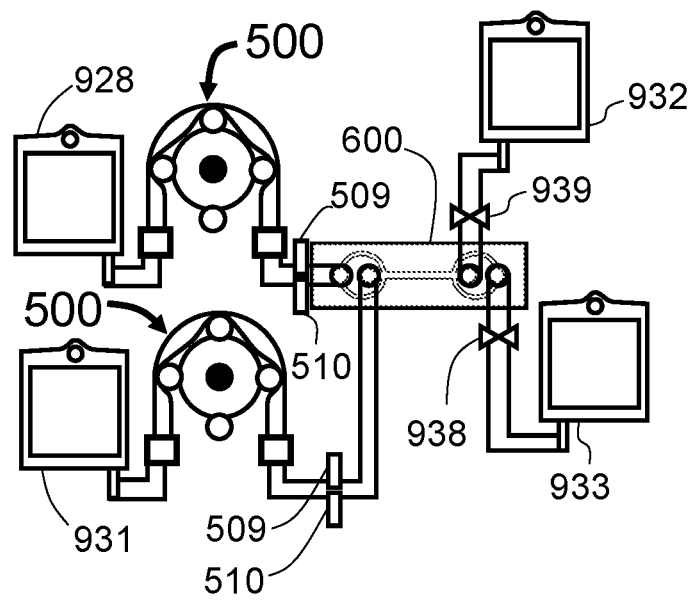
Figure 65A:
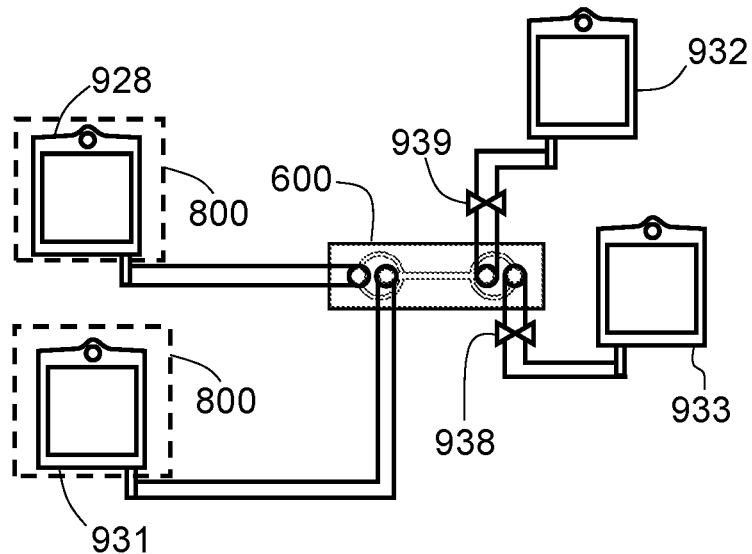
Figure 65B:
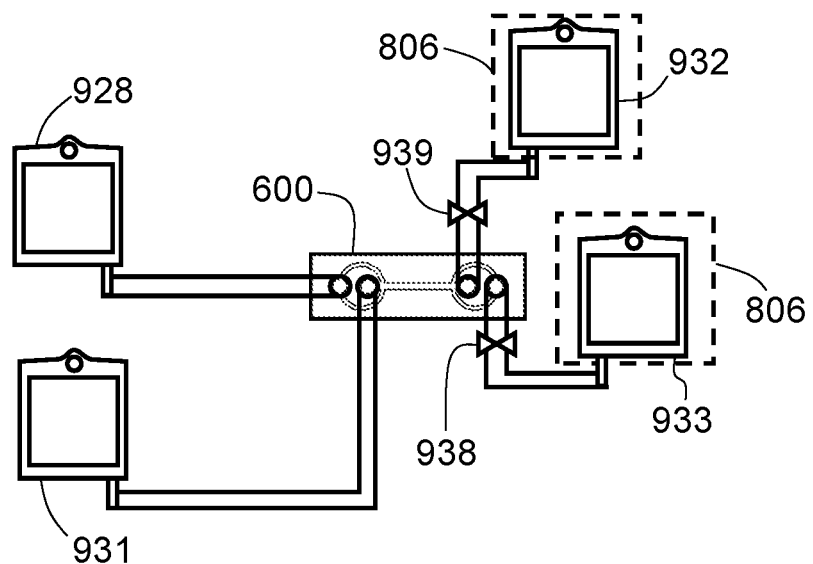

FIG. 65B illustrates replacing peristaltic pumps of FIG. 60B with using vacuum chambers on output sample bags to drive fluid through fluidic lines.

Figure 66:
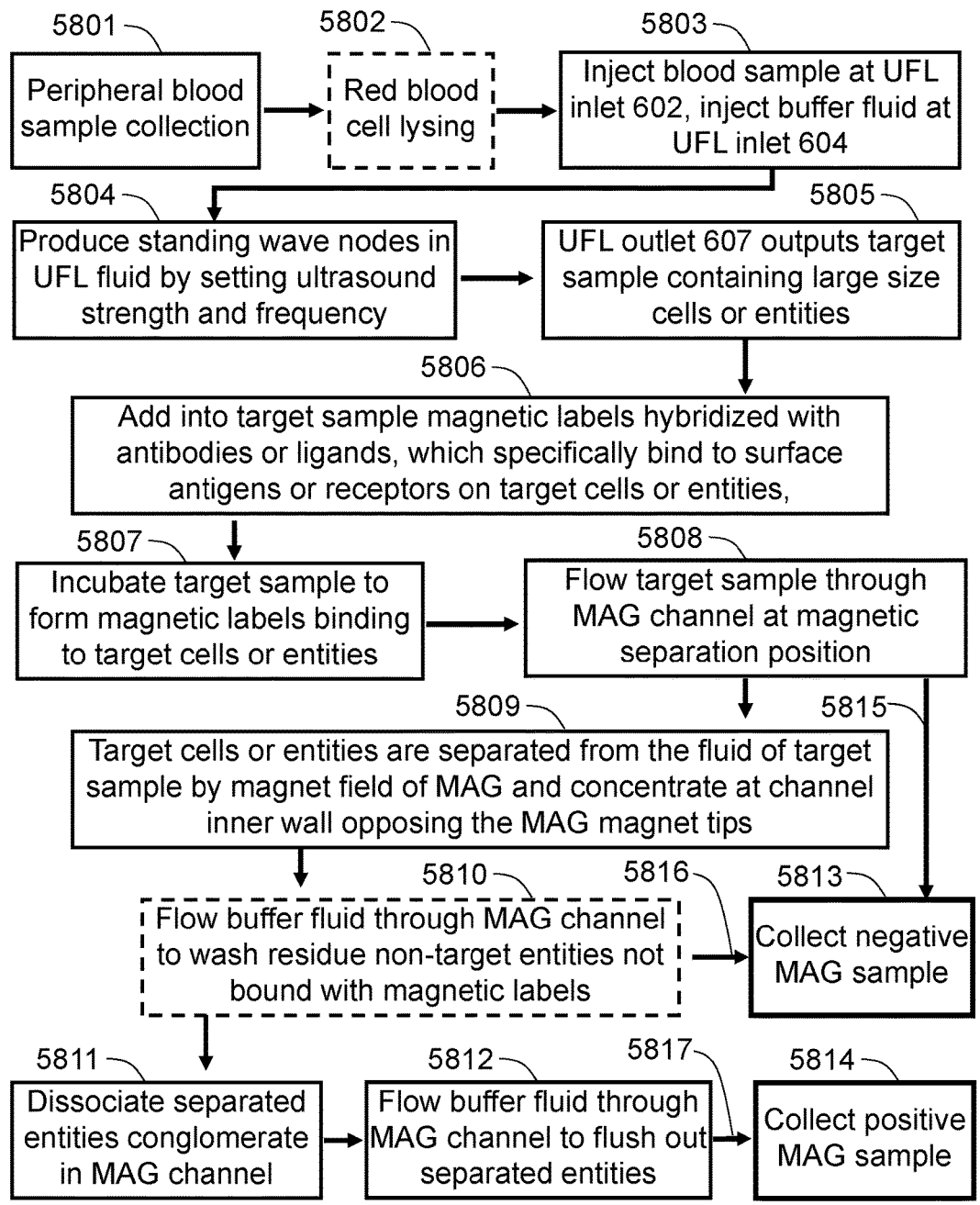

FIG. 66 illustrates a first process flow to separate biological entities from peripheral blood using UFL and MAG.

Figure 67:
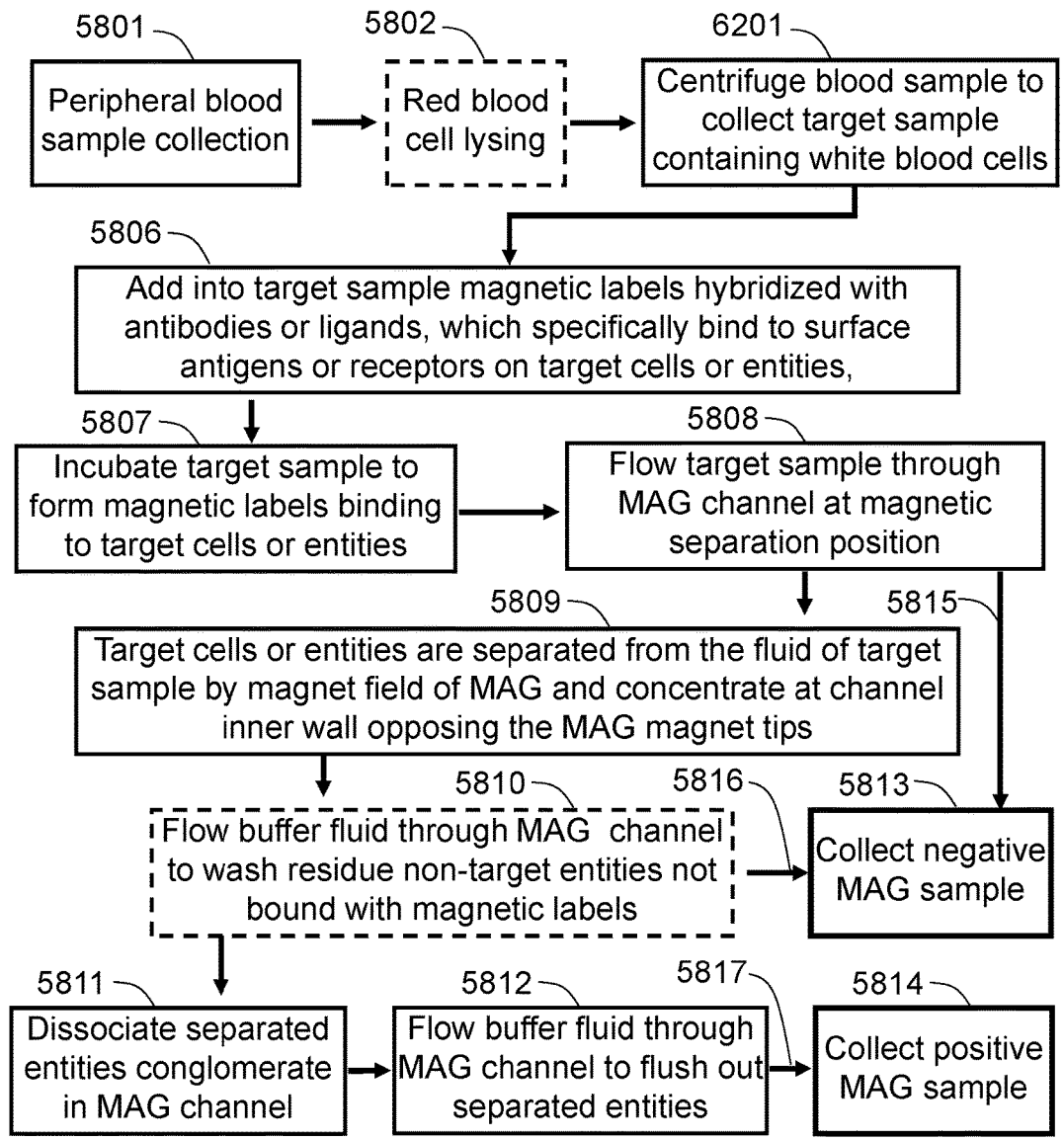

FIG. 67 illustrates a second process flow to separate biological entities from peripheral blood using MAG.

Figure 68:
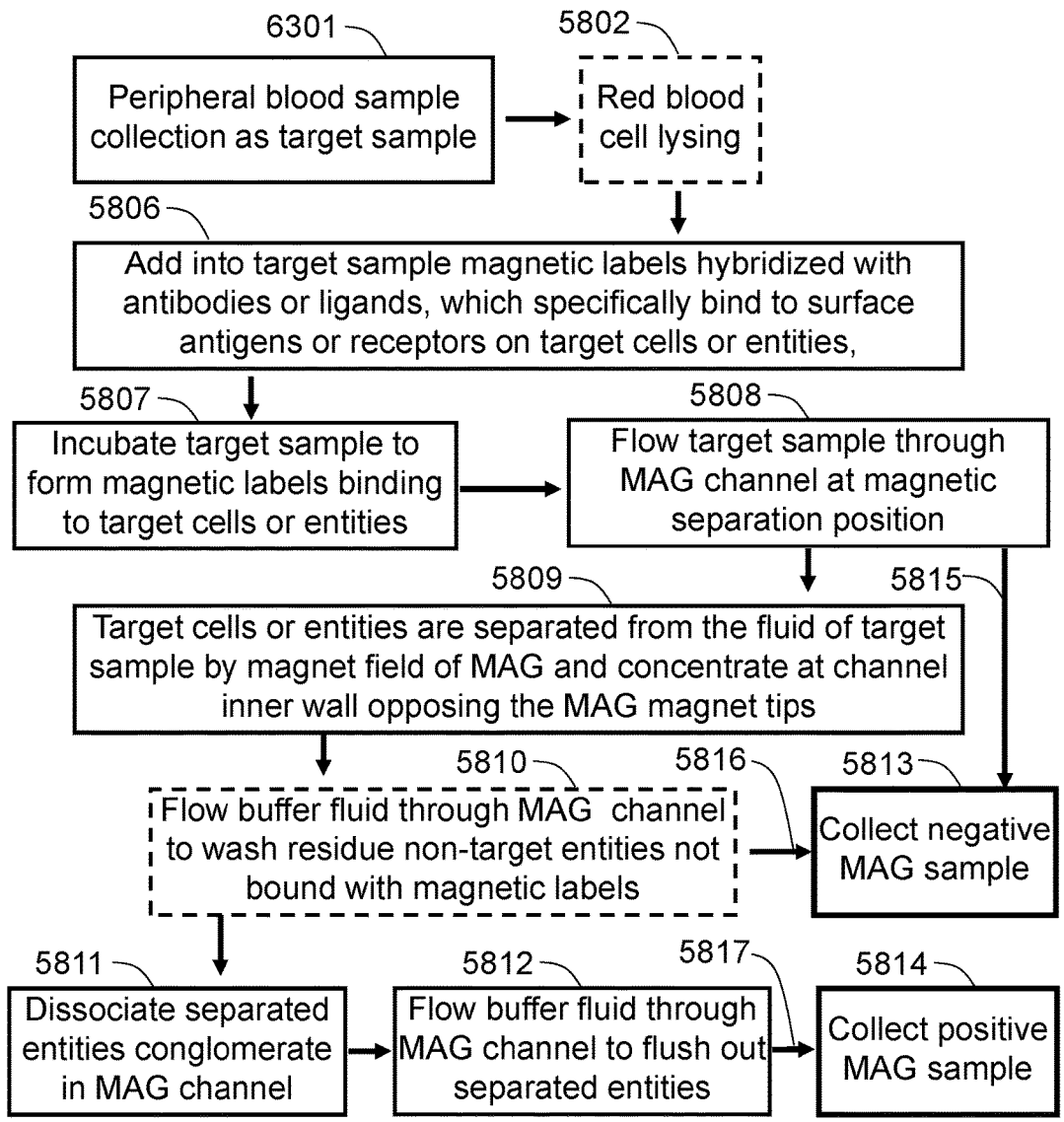

FIG. 68 illustrates a third process flow to separate biological entities from peripheral blood using MAG.

Figure 69:
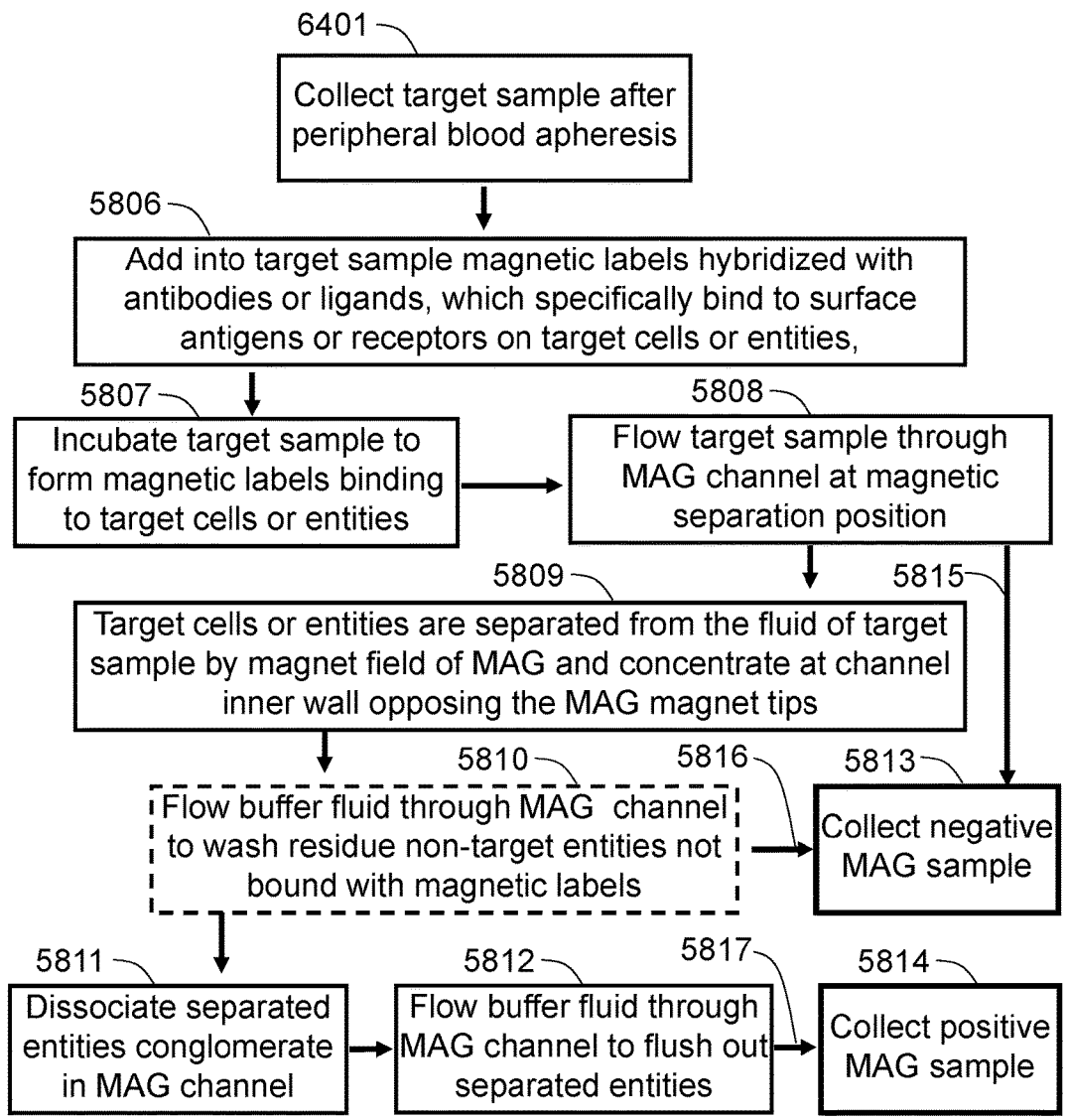

FIG. 69 illustrates a fourth process flow to separate biological entities from peripheral blood using MAG.

Figure 70:
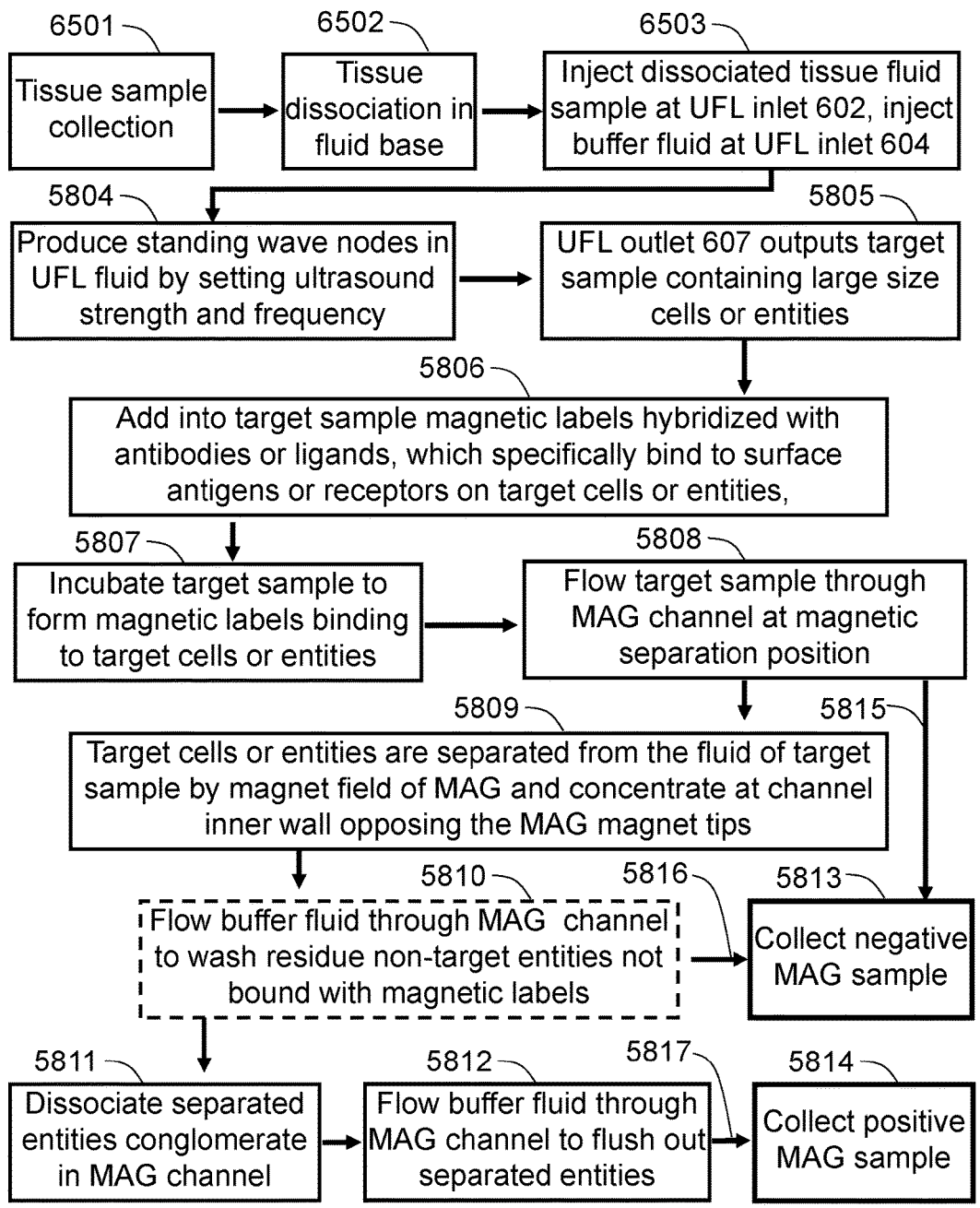

FIG. 70 illustrates a fifth process flow to separate biological entities from tissue sample using UFL and MAG.

Figure 71:
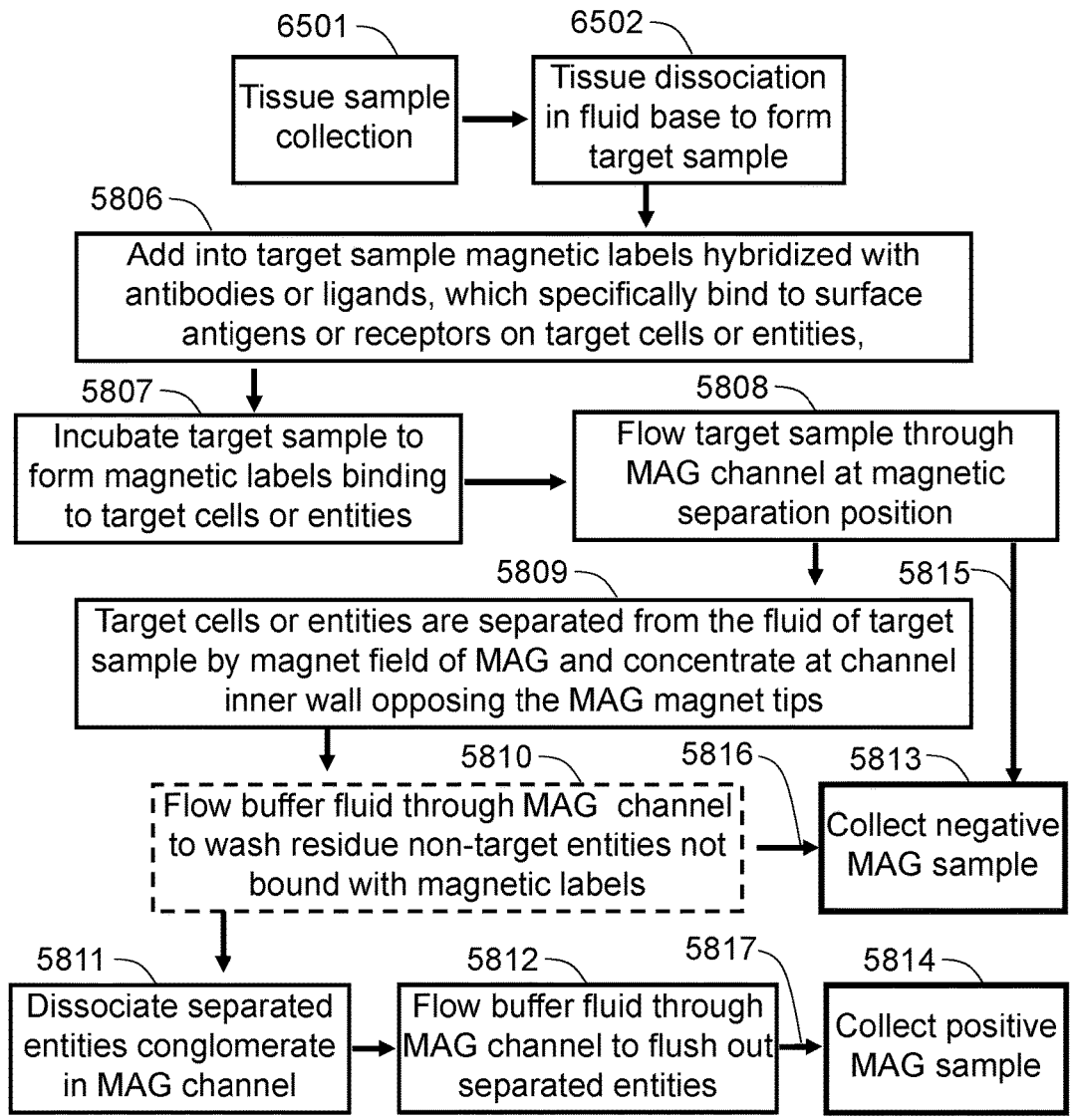

FIG. 71 illustrates a sixth process flow to separate biological entities from tissue sample using MAG.

Figure 72:
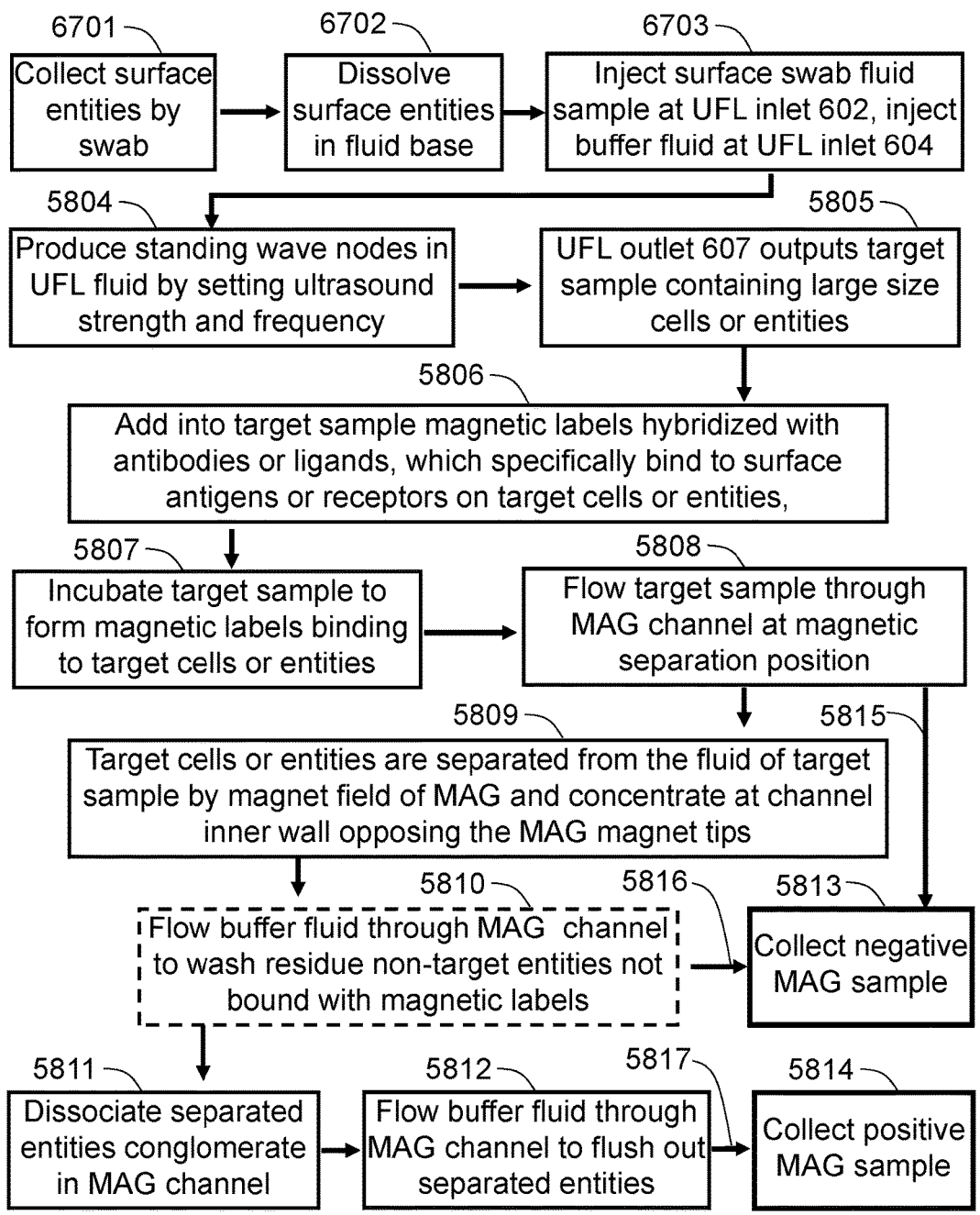

FIG. 72 illustrates a seventh process flow to separate biological entities from surface swab sample using UFL and MAG.

Figure 73:
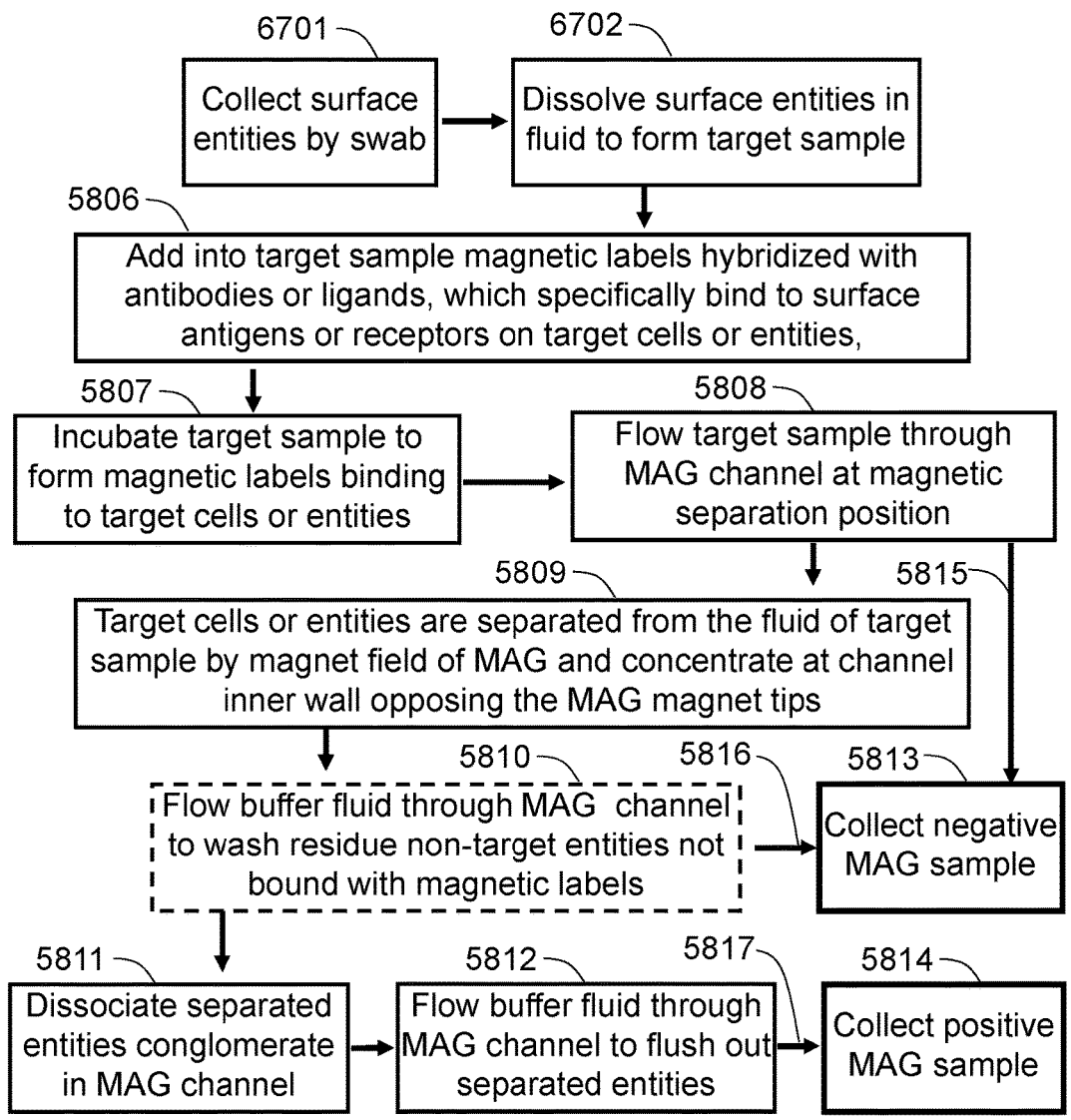

FIG. 73 illustrates an eighth process flow to separate biological entities from surface swab sample using MAG.

Figure 74:
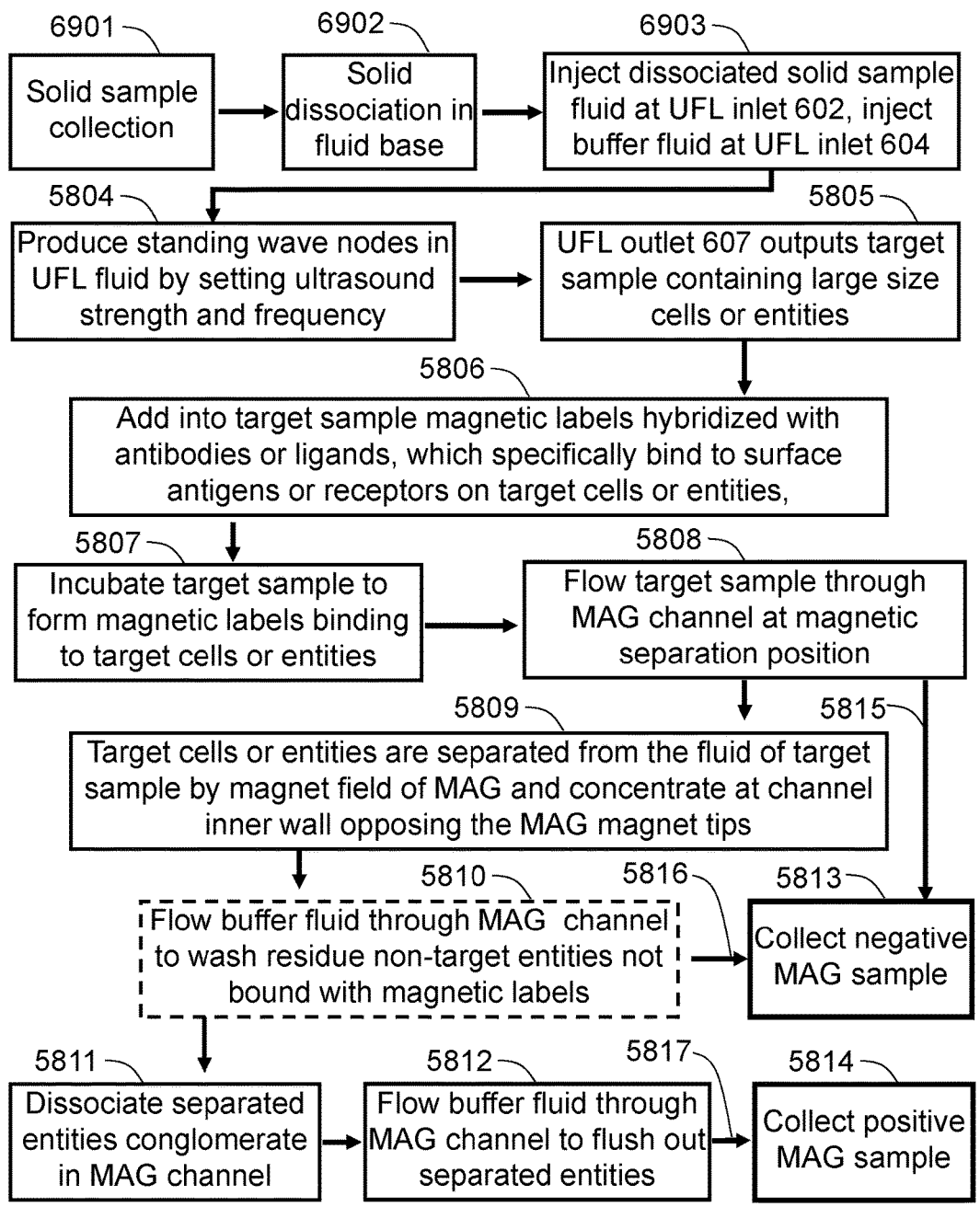

FIG. 74 illustrates a ninth process flow to separate biological entities from solid sample using UFL and MAG.

Figure 75:
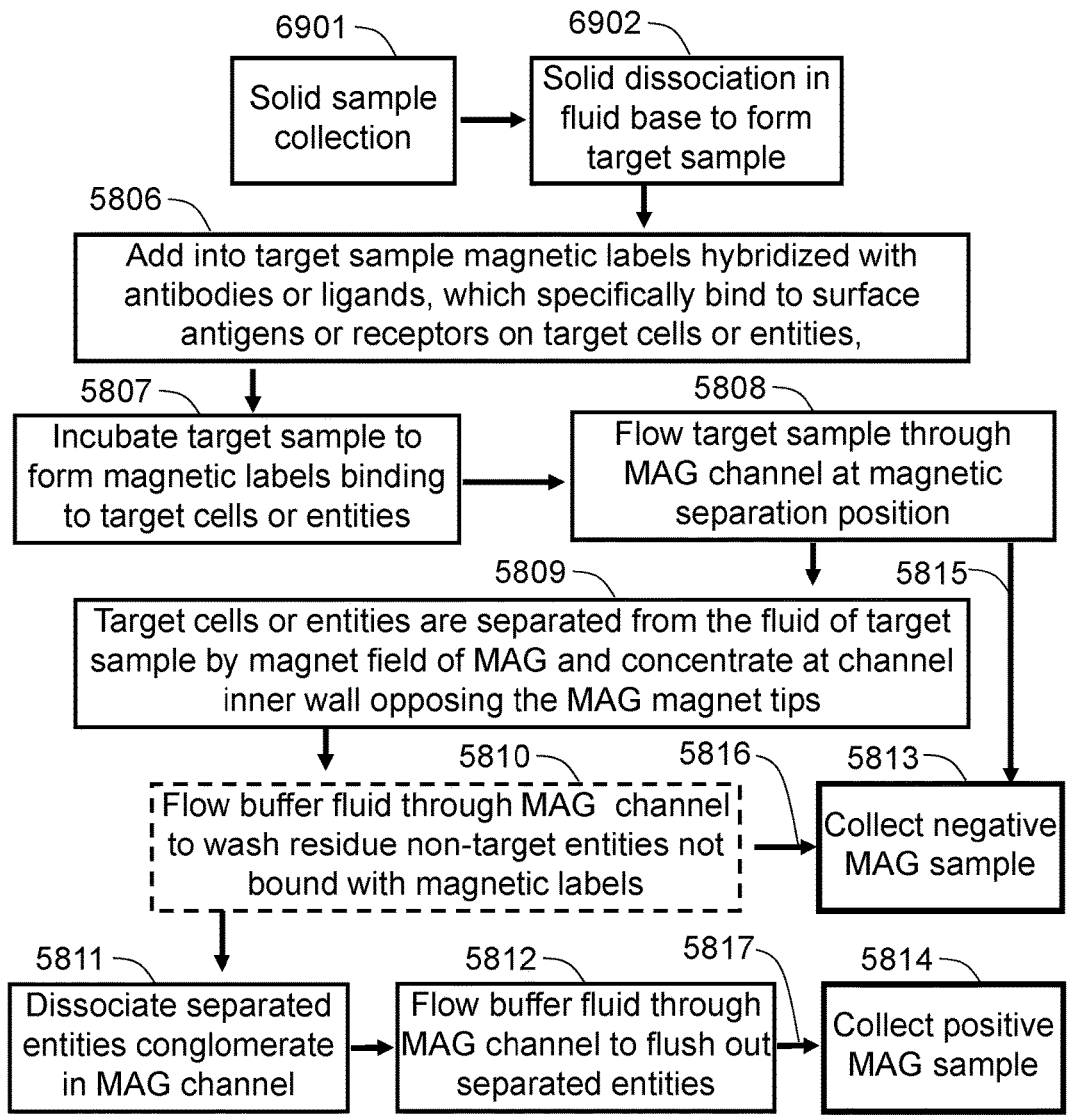

FIG. 75 illustrates a tenth process flow to separate biological entities from solid sample using MAG.

FIG. 76A illustrates addition of both magnetic and fluorescent labels into fluid samples for specific binding to target cells or entities.

FIG. 76B illustrates incubation of both magnetic and fluorescent labels at same time to form specific binding to target cells or entities.

Figure 77A:
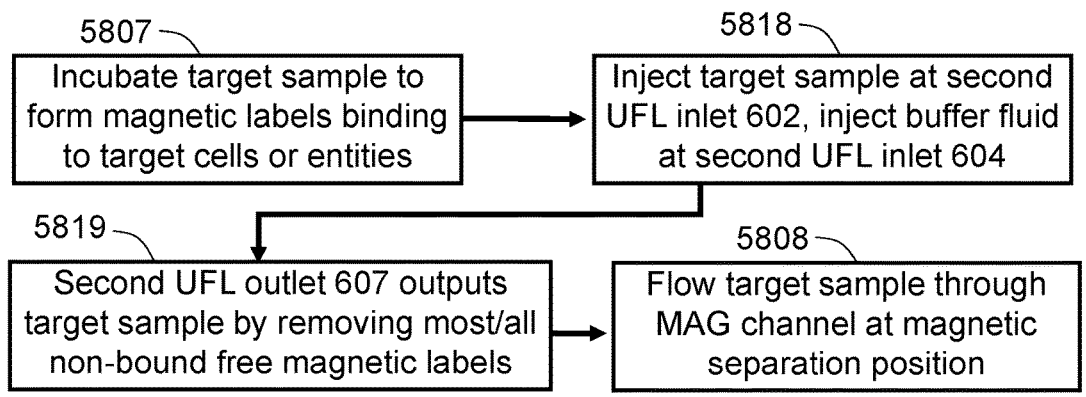

FIG. 77A illustrates process of removing non-bound free magnetic labels from sample fluid by UFL before magnetic separation by MAG.

Figure 77B:
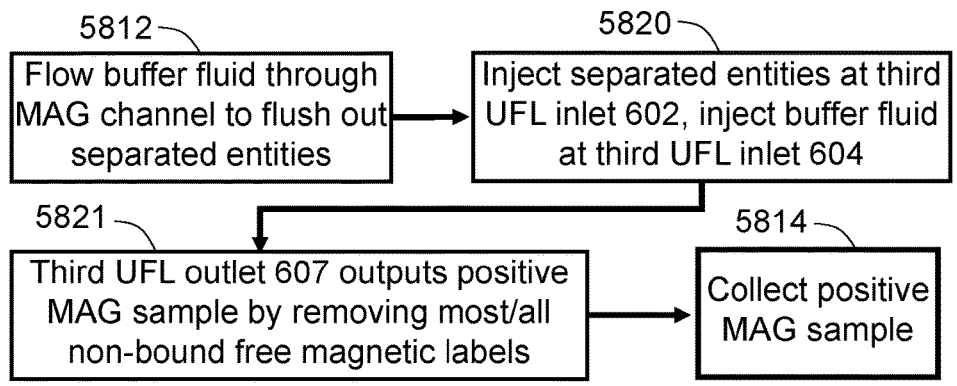

FIG. 77B illustrates process of removing non-bound free magnetic labels from sample fluid by UFL after magnetic separation by MAG.

Figure 78A:
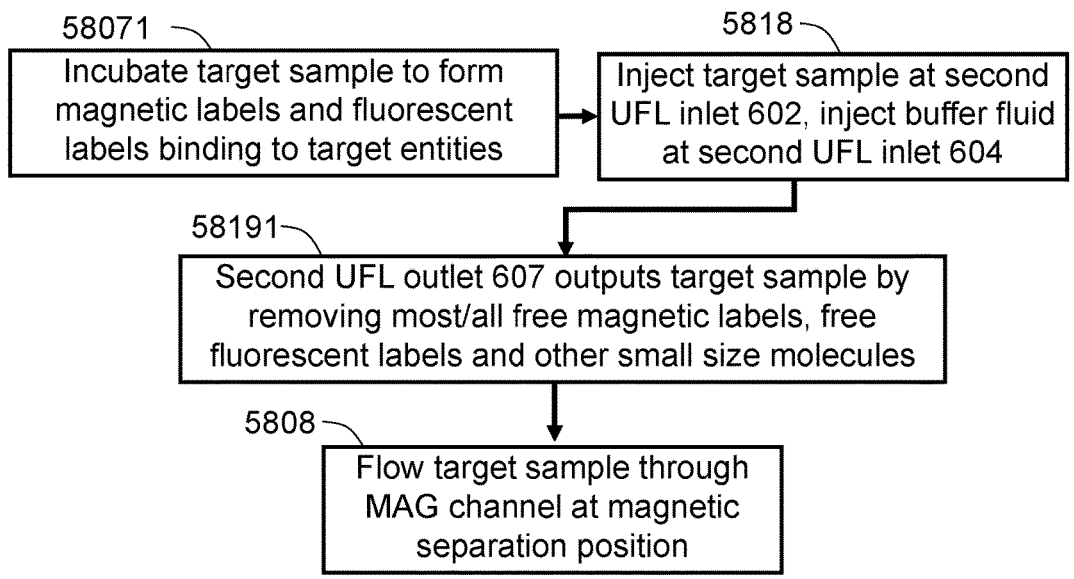

FIG. 78A illustrates process of removing non-bound free magnetic labels and free fluorescent labels from sample fluid by UFL before magnetic separation by MAG.

Figure 78B:
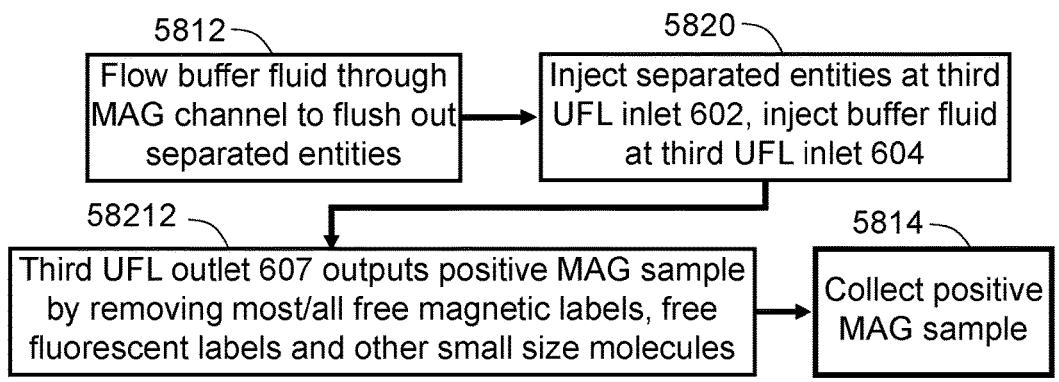

FIG. 78B illustrates process of removing non-bound free magnetic labels and free fluorescent labels from sample fluid by UFL after magnetic separation by MAG.

Figure 79:
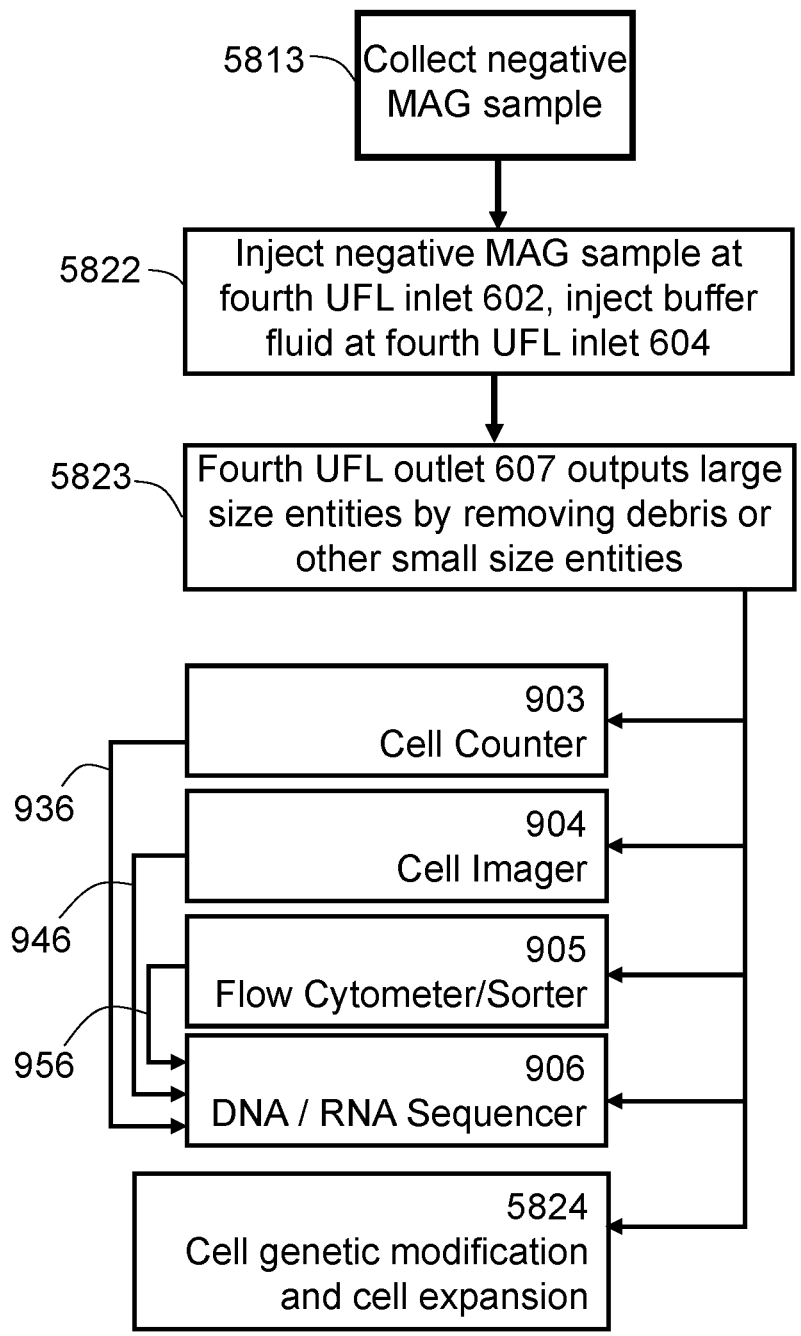

FIG. 79 illustrates continued process of negative MAG sample through UFL and various cell processing devices and procedures.

Figure 80:
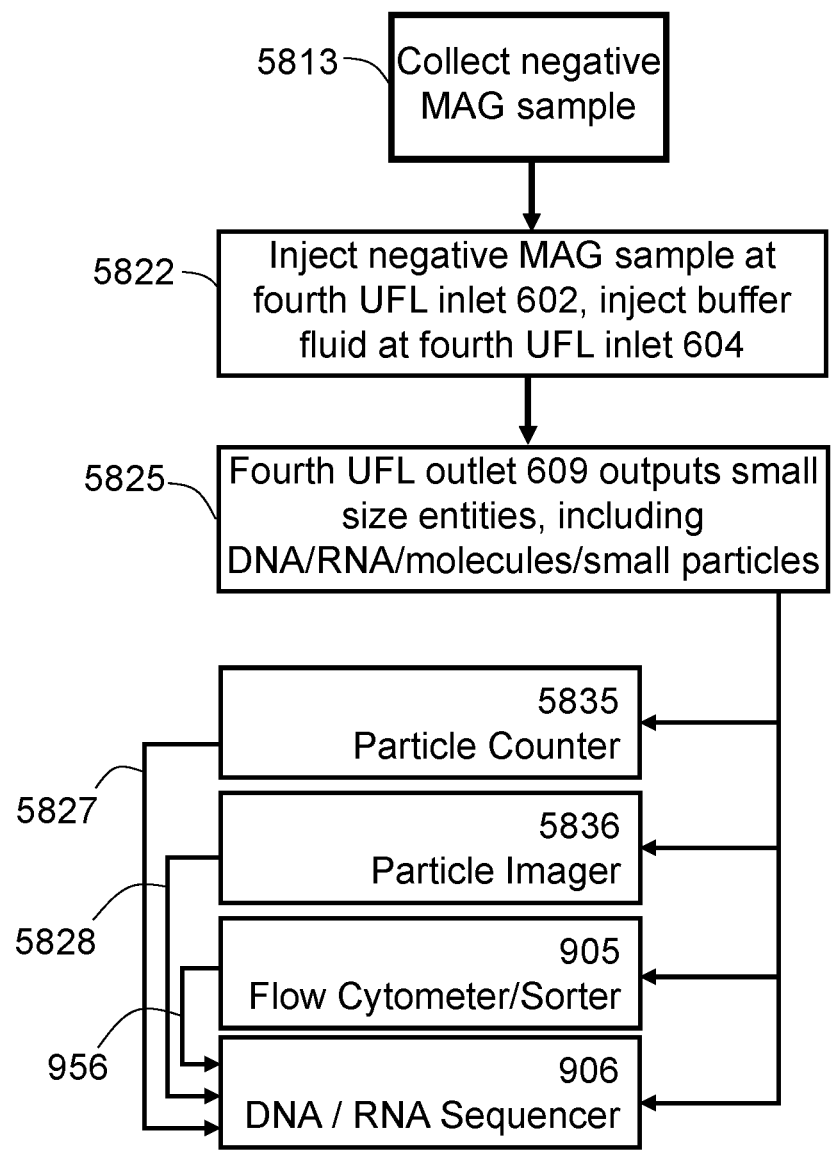

FIG. 80 illustrates continued process of negative MAG sample through UFL and various particle or molecule processing devices.

Figure 81:
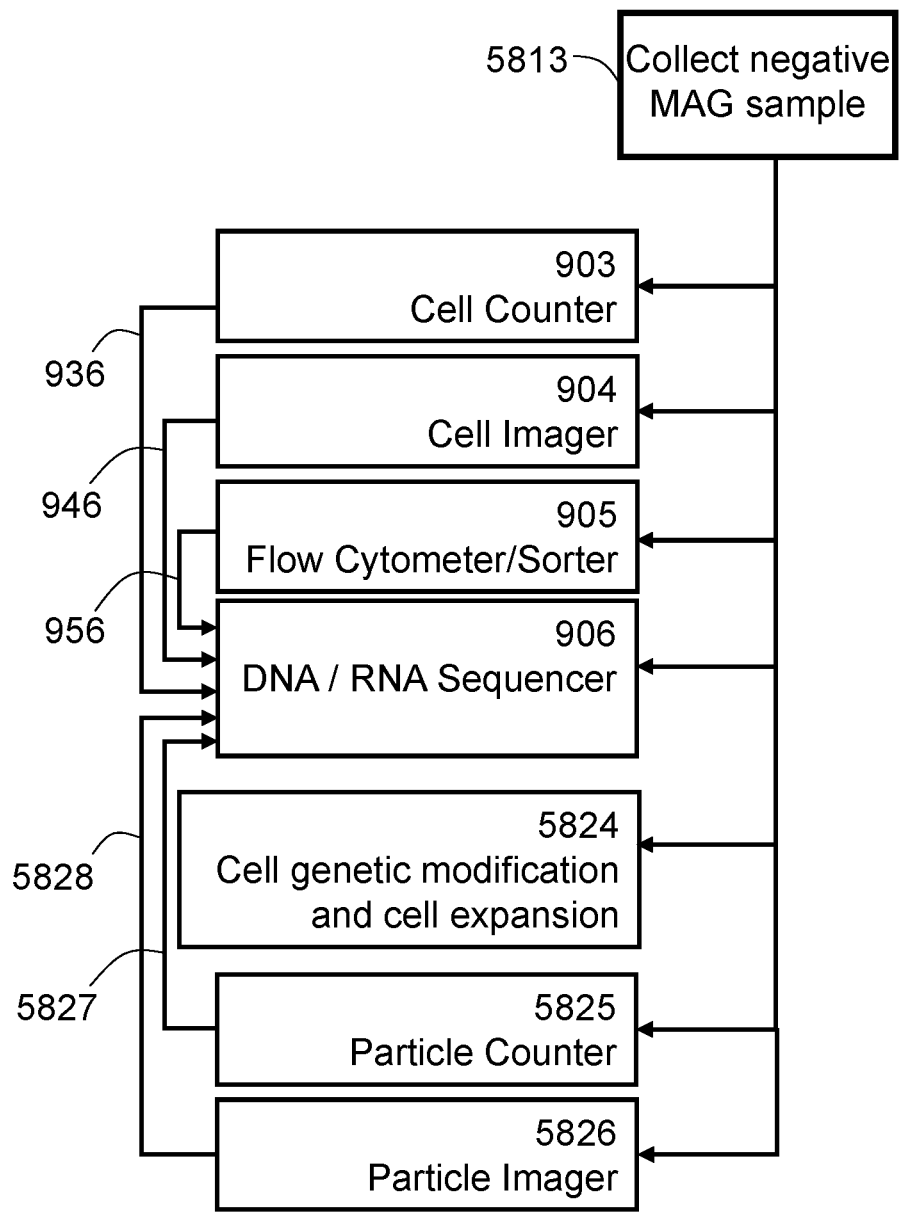

FIG. 81 illustrates entities analysis of negative MAG sample after MAG separation into various analyzing devices.

Figure 82:
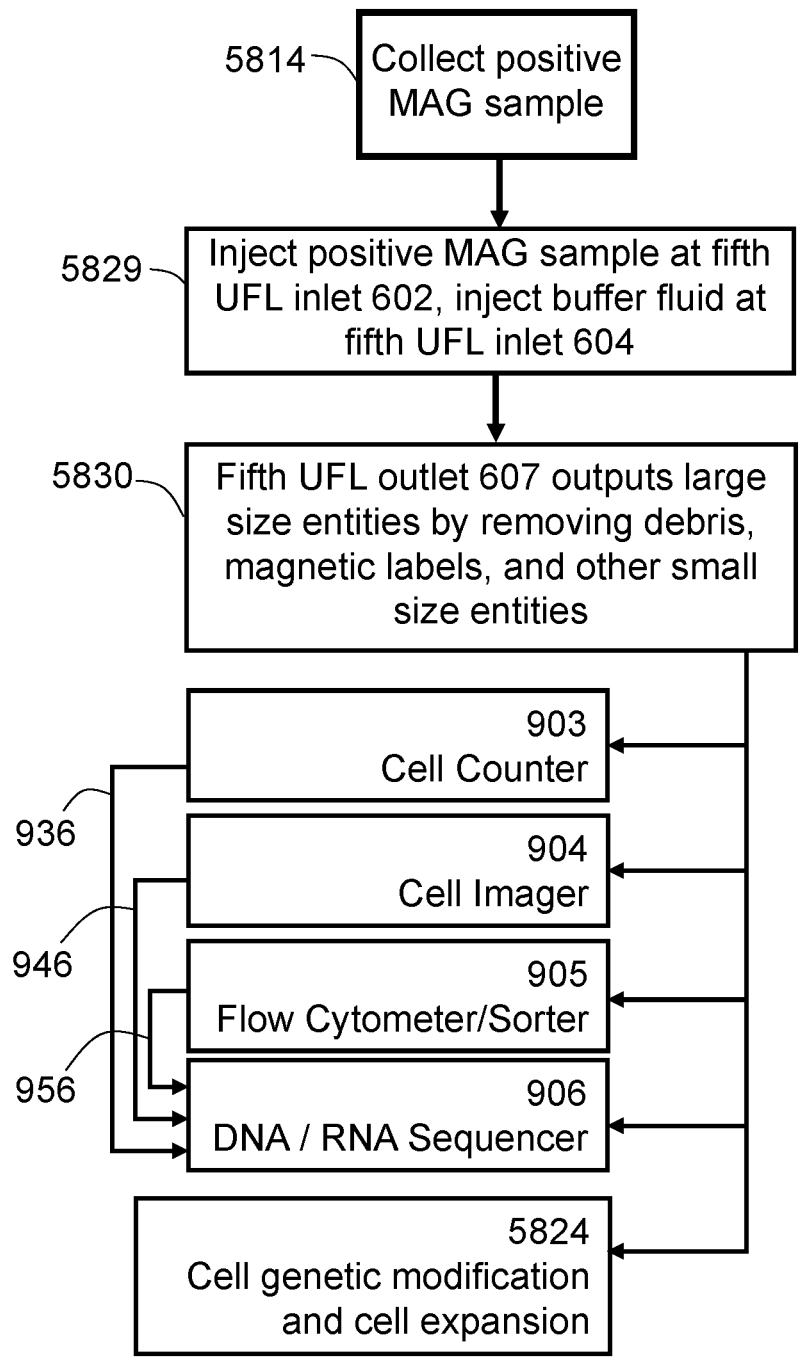

FIG. 82 illustrates continued process of positive MAG sample through UFL and various cell processing devices and procedures.

Figure 83:
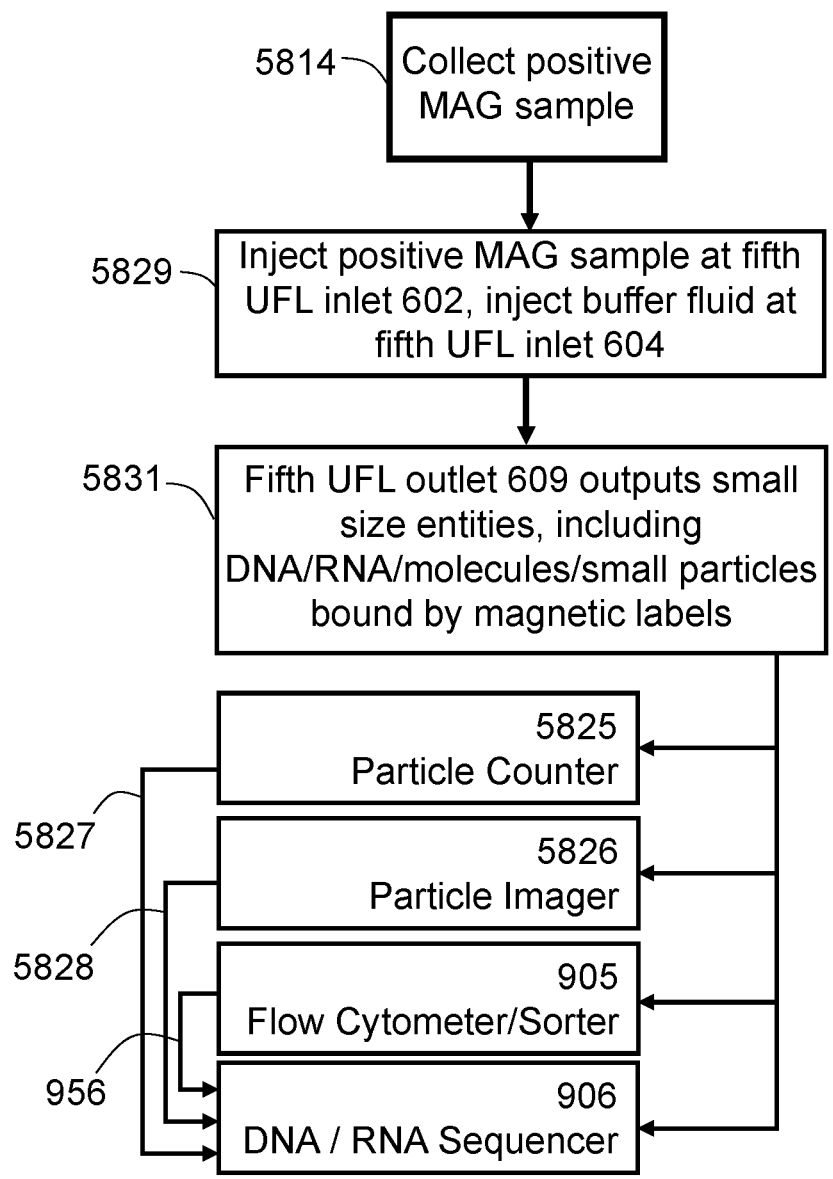

FIG. 83 illustrates continued process of positive MAG sample through UFL and various particle or molecule processing devices.

Figure 84:
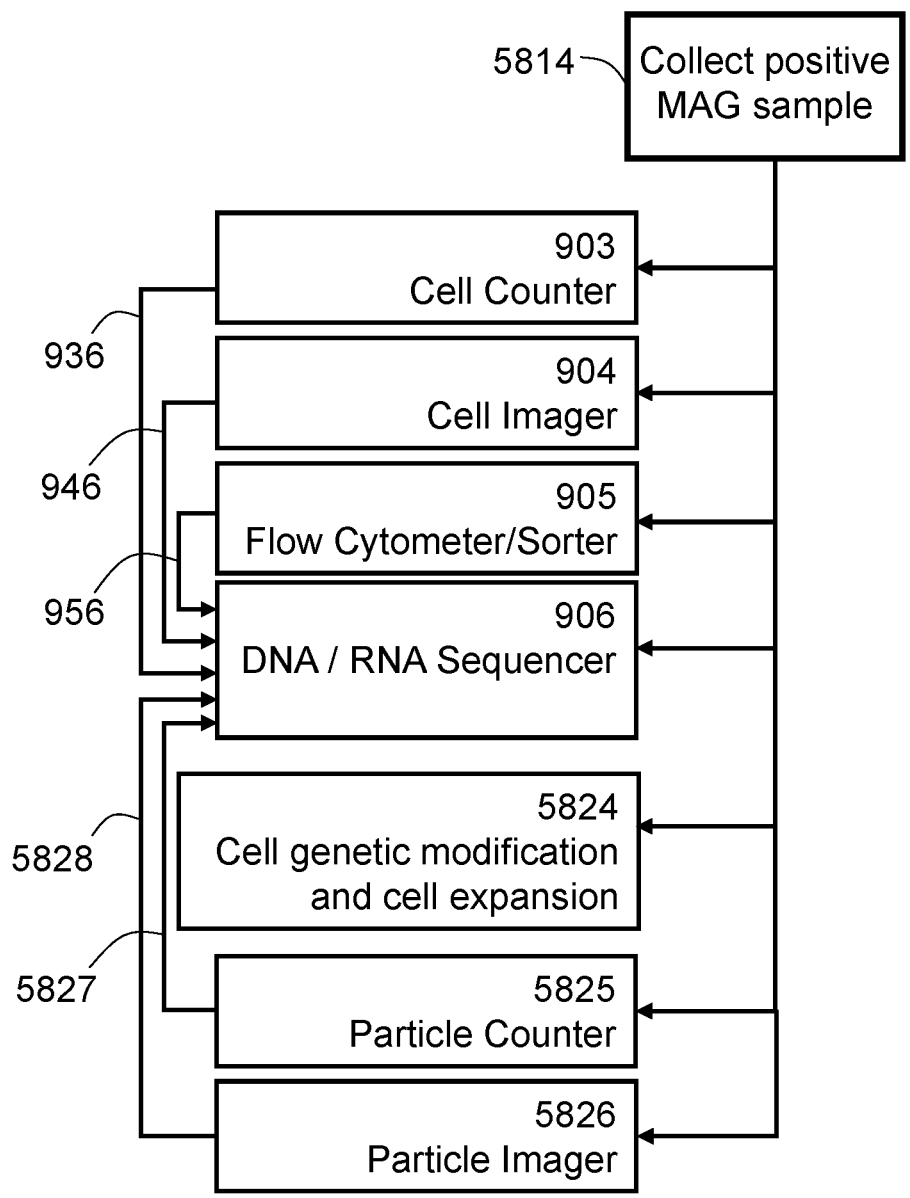

FIG. 84 illustrates entities analysis of positive MAG sample after MAG separation into various analyzing devices.

Figure 85A:
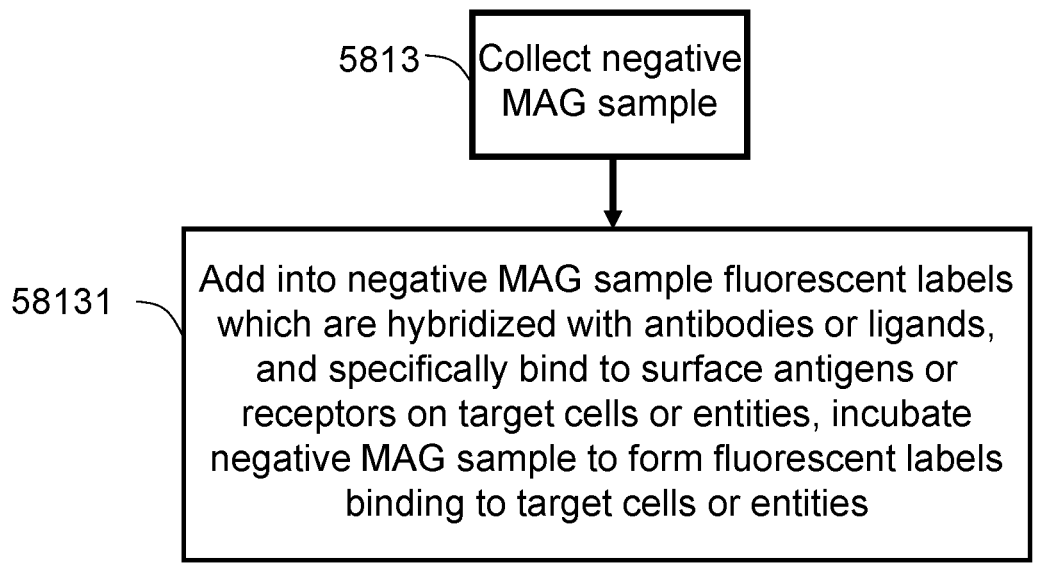

FIG. 85A illustrates adding fluorescent labels to specifically bind to target entities within negative MAG sample immediately after negative MAG sample collection.

Figure 85B:
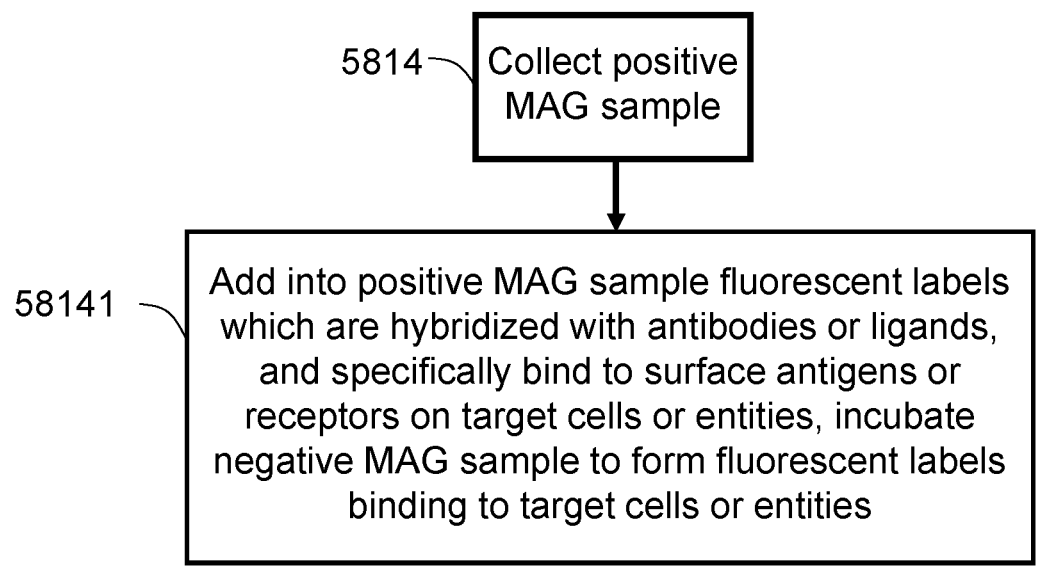

FIG. 85B illustrates adding fluorescent labels to specifically bind to target entities within positive MAG sample immediately after positive MAG sample collection.

Figure 86A:
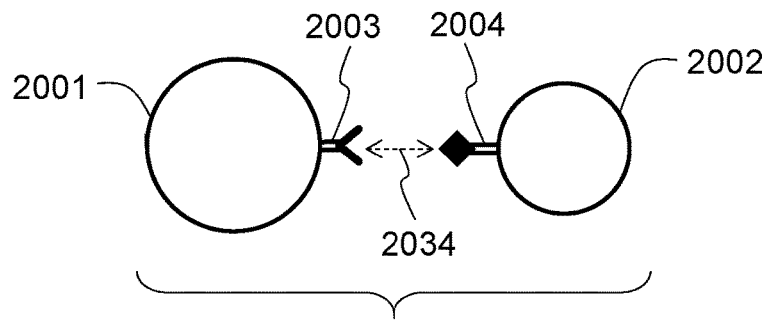
Figure 86B:
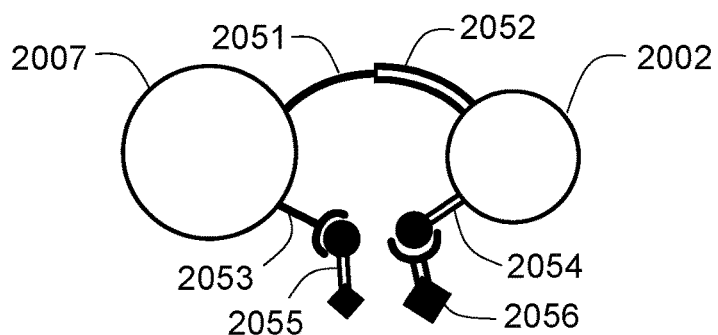
Figure 86C:
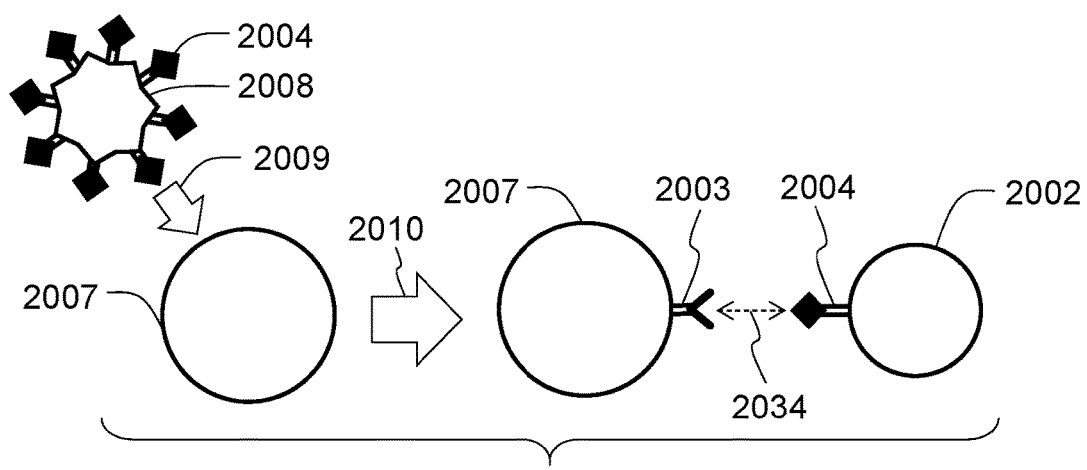
Figure 87:
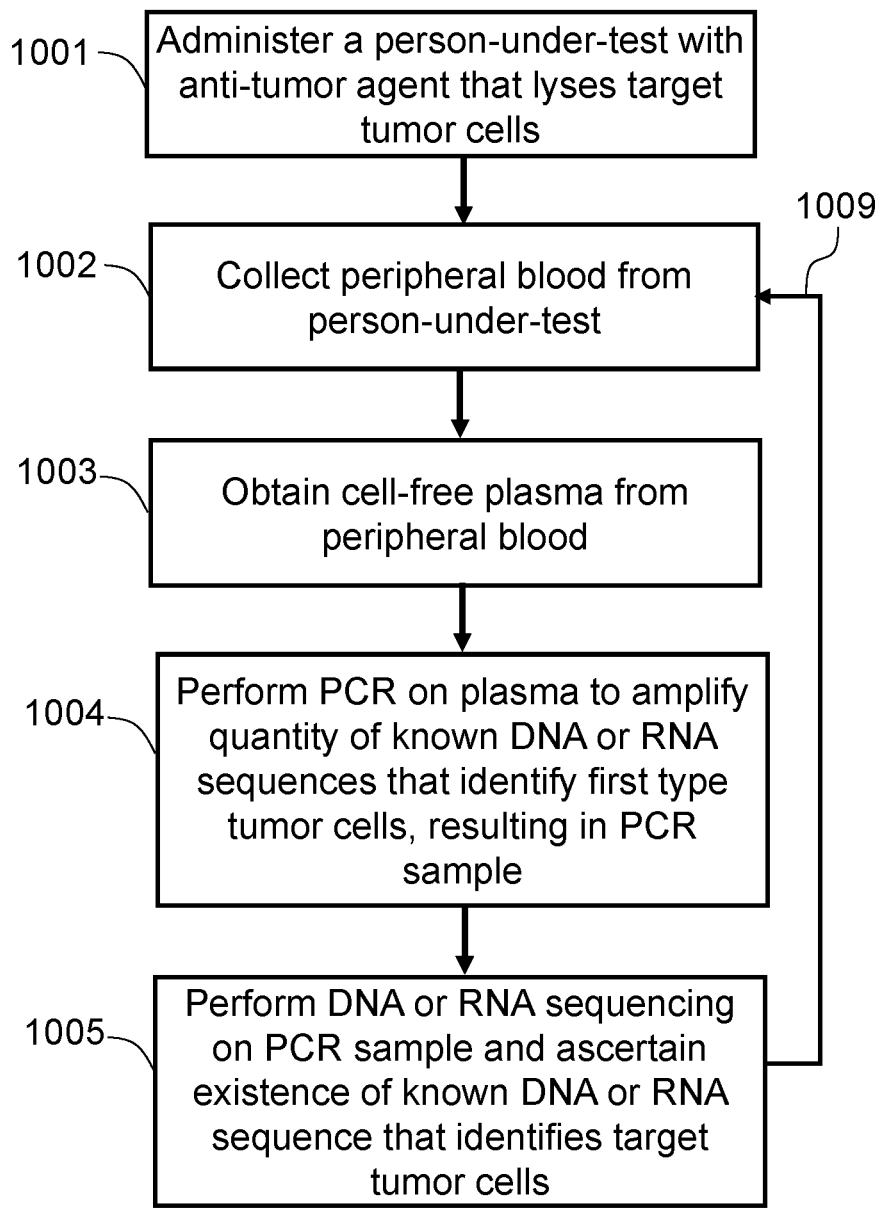
Figure 88:
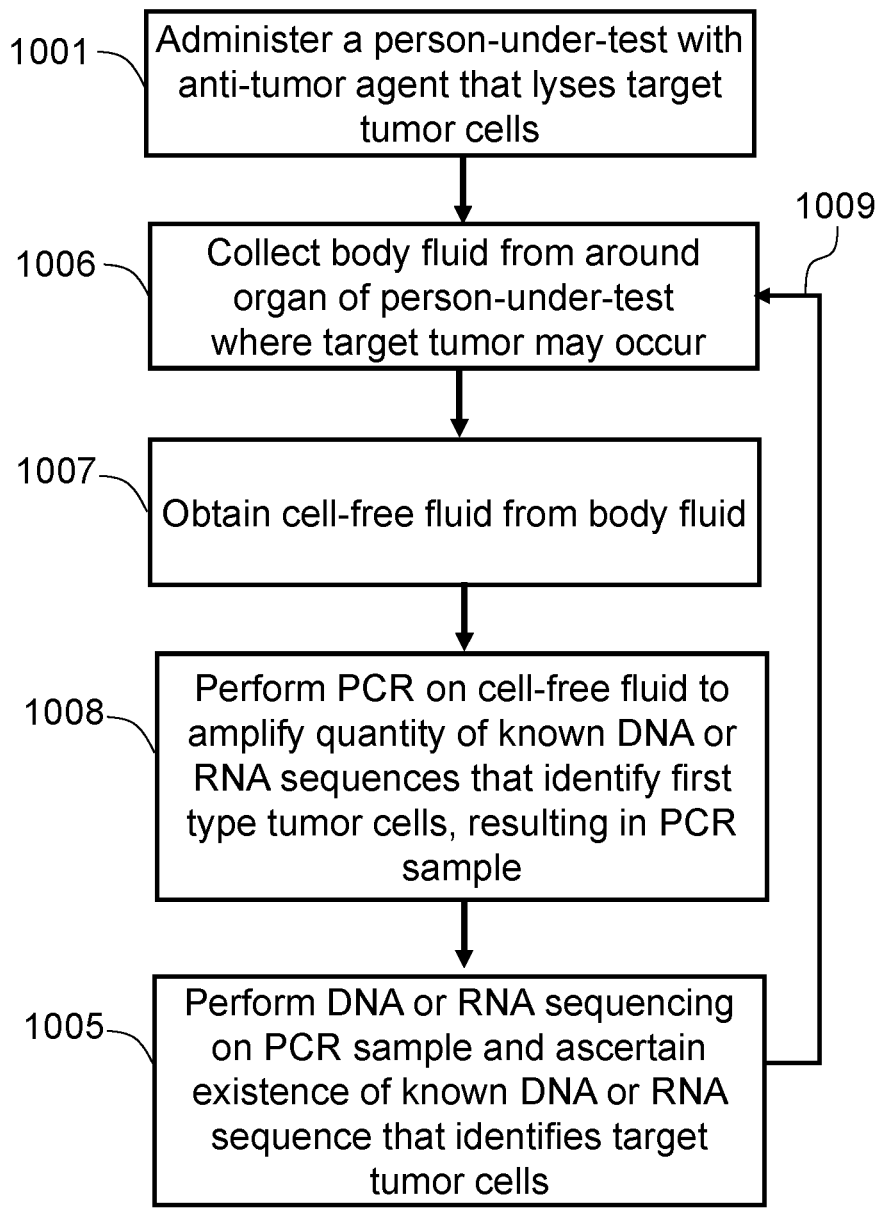
Figure 89:
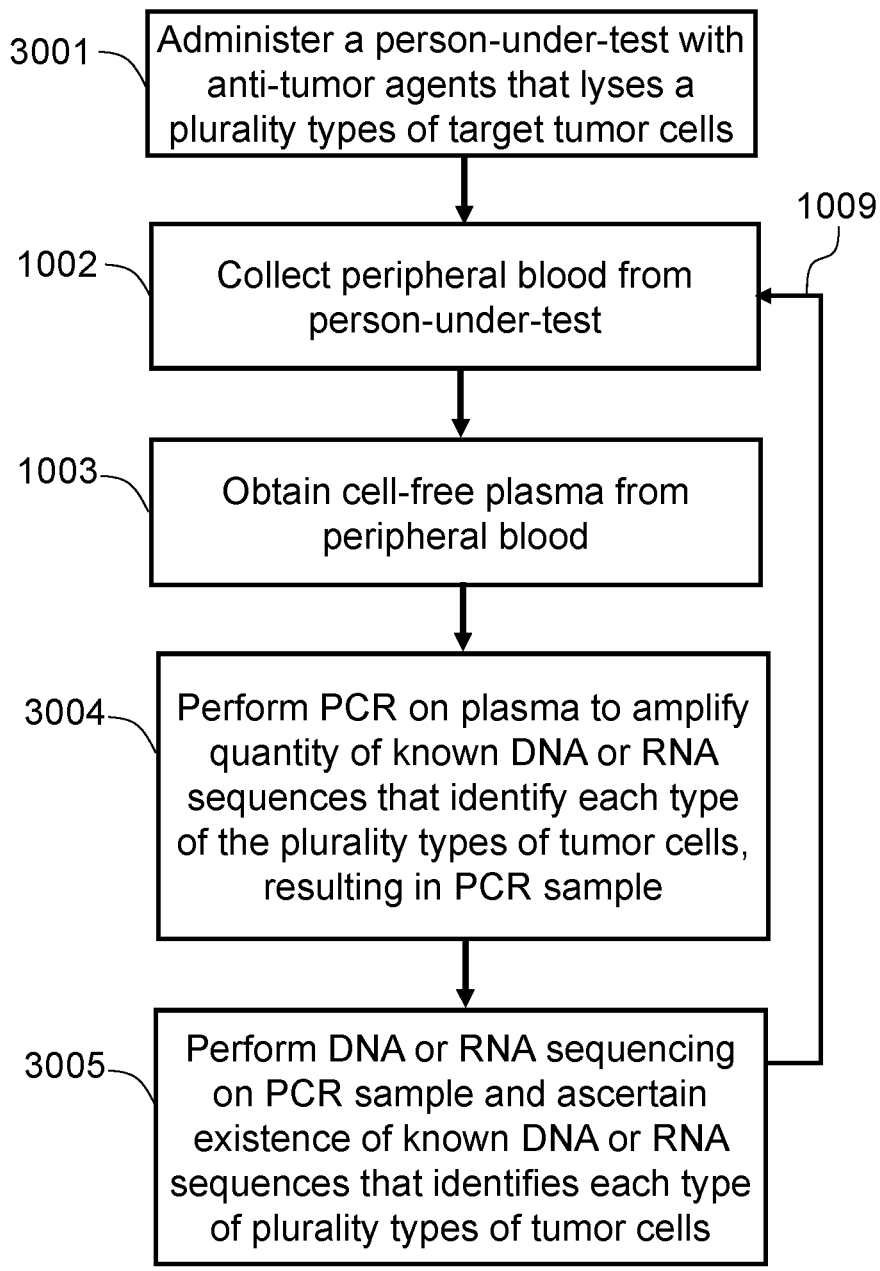
Figure 90:
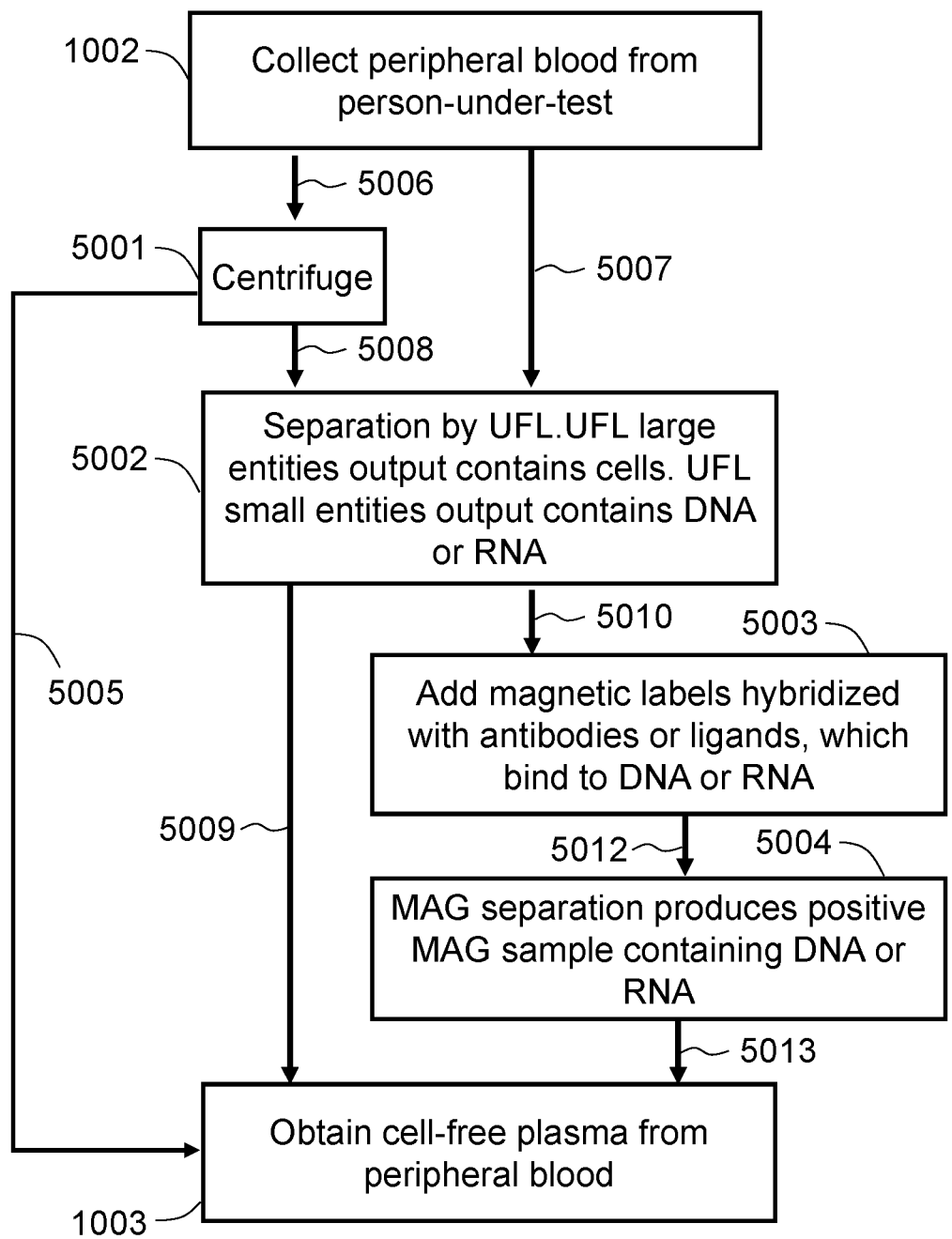
Figure 91:
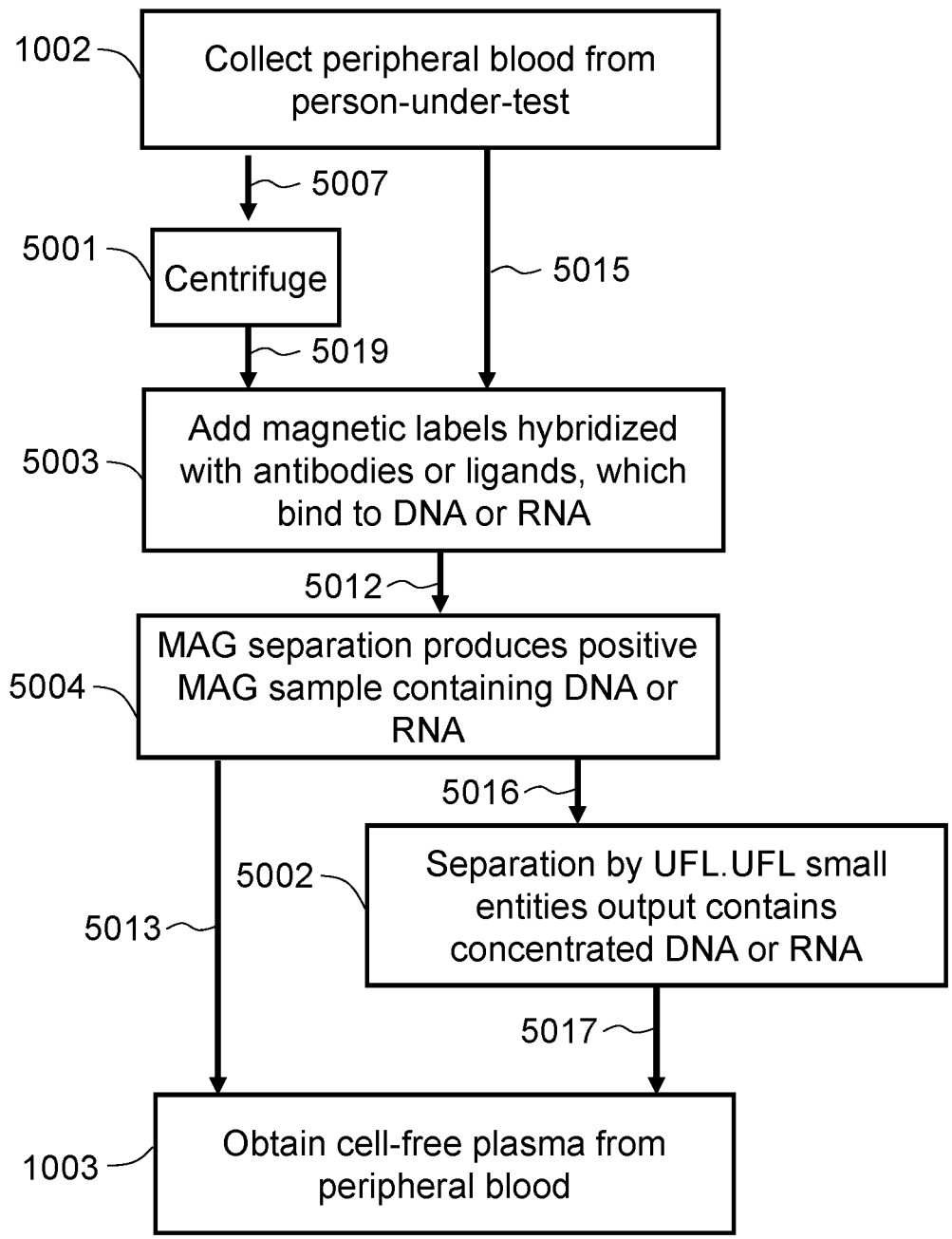
Figure 92:
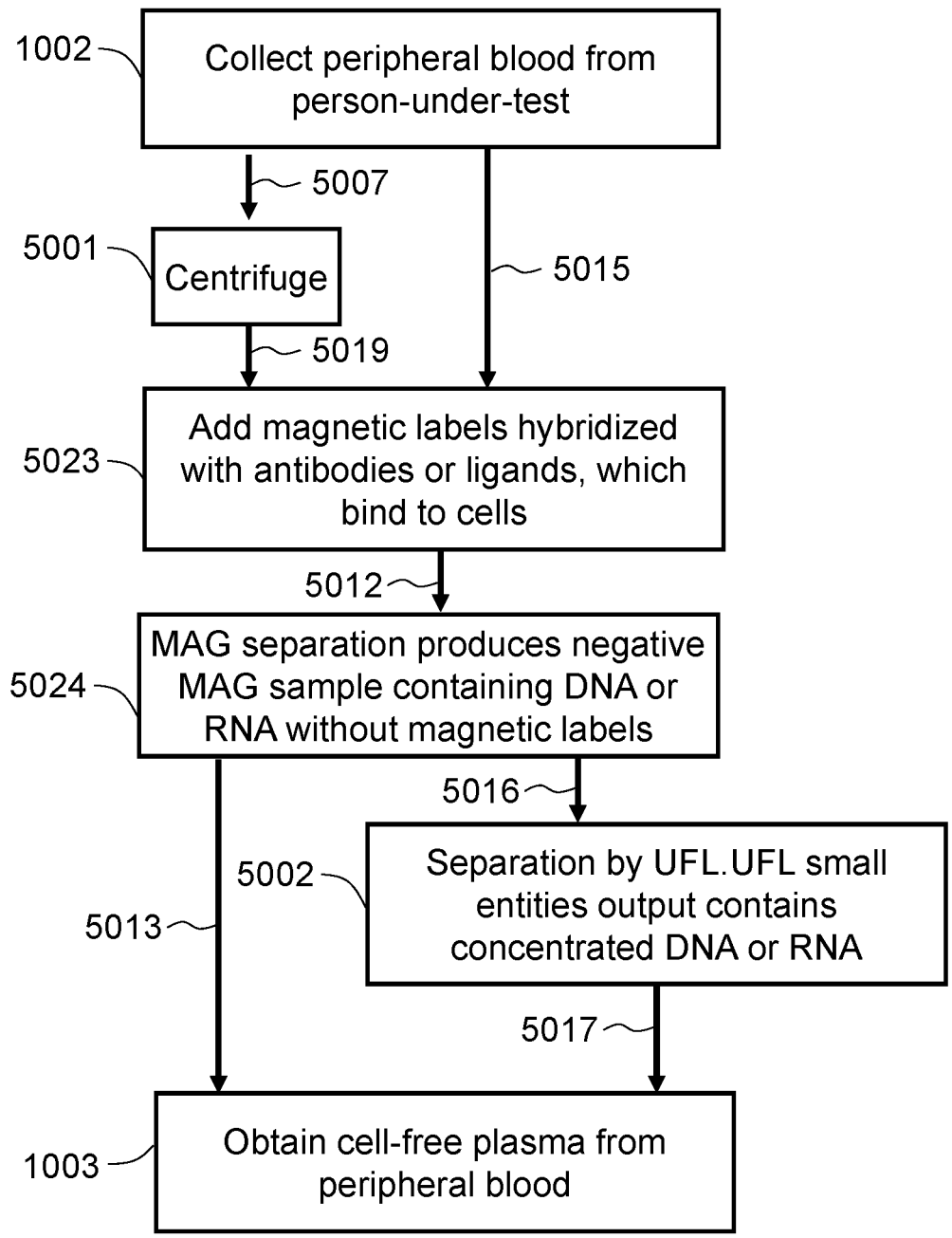
Figure 93:
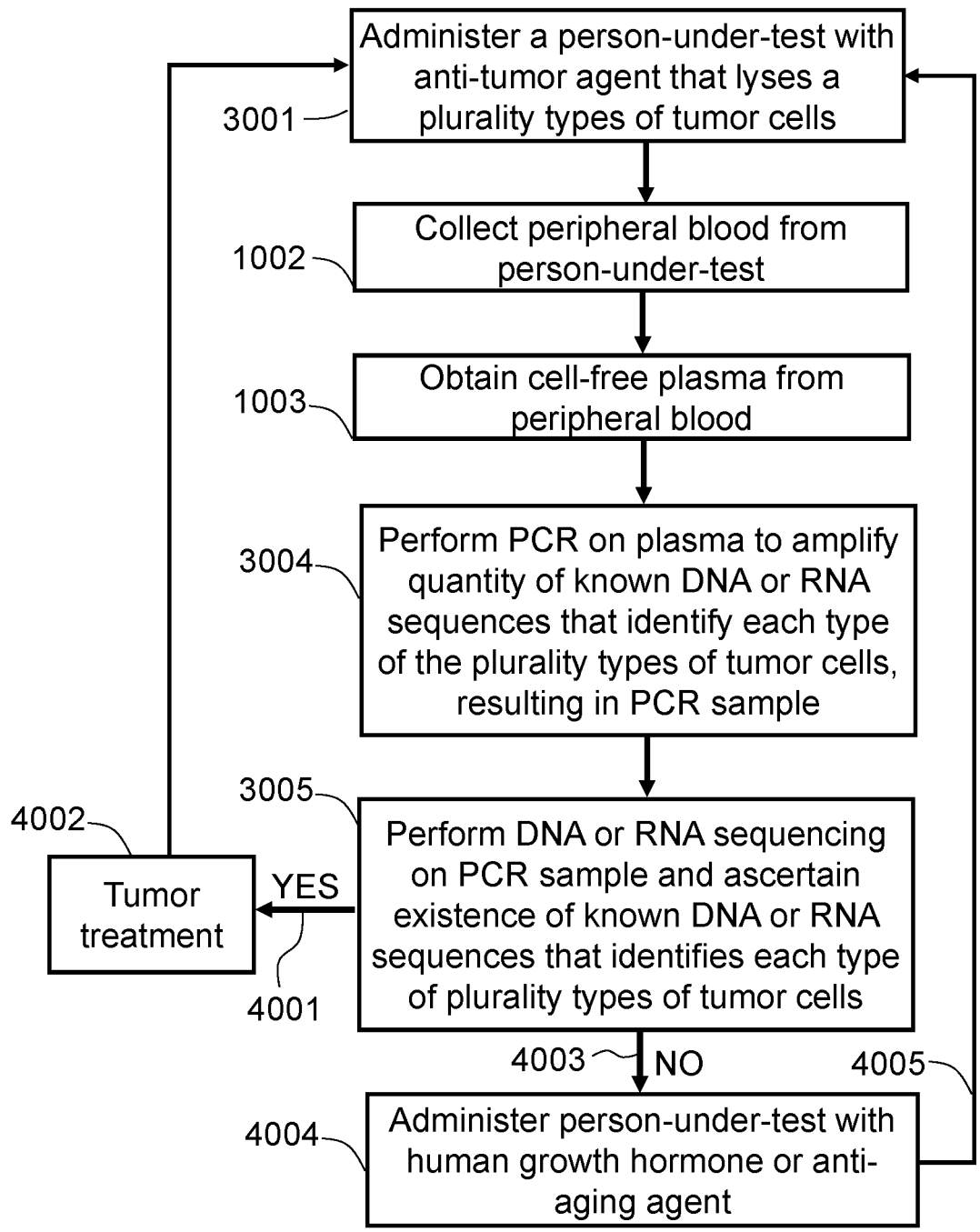

FIG. 86A illustrates first example of cancer treatment.
FIG. 86B illustrates second example of cancer treatment.
FIG. 86C illustrates third example of cancer treatment.
FIG. 87 illustrates first method of tumor detection.
FIG. 88 illustrates second method of tumor detection.
FIG. 89 illustrates third method of tumor detection.
FIG. 90 illustrates embodiment of first process flow to obtain cell-free plasma.
FIG. 91 illustrates embodiment of second process flow to obtain cell-free plasma.
FIG. 92 illustrates embodiment of third process flow to obtain cell-free plasma.
FIG. 93 illustrates method of using tumor detector for anti-aging purpose.

For purposes of clarity and brevity, like elements and components will bear the same designations and numbering throughout the Figures, which are not necessarily drawn to scale.

DETAILED DESCRIPTION OF THE INVENTION

While the current invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

Biological entities refer to hereafter include: cell, bacteria, virus, molecule, particles including RNA and DNA, cell cluster, bacteria cluster, molecule cluster, and particle cluster. Large entities and small entities refer to biological entities within same fluid having relatively larger physical size and smaller physical size. In one embodiment, large entities include any of: cells, bacteria, cell cluster, bacteria cluster, particle cluster, entities bound with magnetic labels, and entities bound with optical label. In another embodiment, small entities include any of: molecules, particles, virus, cellular debris, non-bound free magnetic labels, and non-bound free optical labels. In another embodiment, large entities have a physical size larger than 1 micrometer (um), and small entities have a physical size less than 1 um. In yet another embodiment, large entities have a physical size larger than 2 um, and small entities have a physical size less than 500 nanometer (nm). In yet another embodiment, large entities have a physical size larger than 5 um, and small entities have a physical size less than 2 um. Biological sample include: blood, body fluid, tissue extracted from any part of the body, bone marrow, hair, nail, bone, tooth, liquid and solid from bodily discharge, or surface swab from any part of body. Entity liquid, or fluid sample, or liquid sample, or sample solution, include: biological sample in its original liquid form, biological entities being dissolve or dispersed in a buffer liquid, or biological sample after dissociation from its original biological sample non-liquid form and dispersed in a buffer fluid. Biological entities and biological sample may be obtained from human or animal. Biological entities may also be obtained from plant and environment including air, water and soil. Entity fluid, or fluid sample, or sample may contain various types of magnetic or optical labels, or one or more chemical reagents that may be added during various steps within the embodiments of this invention. Sample flow rate is volume amount of a fluid sample flowing through a cross-section of a channel, or a fluidic part, or a fluidic path, in a unit time, where volume may be in unit of liter (l), milliliter (ml), microliter (ul), nanoliter (nl), and unit time may be in unit of minute (min), second (s), millisecond (ms), microsecond (us), nanosecond (ns). Sample flow speed is the distance of a free molecule or a free entity that travels within a liquid sample in a channel, or a fluidic part, or a fluidic path, in a unit time, where distance may be in unit of meter (m), centimeter (cm), millimeter (mm), micrometer (um). Separation efficiency is percentage of target entities within a liquid sample that are successfully separated from the liquid sample by a method designed to separate the target entities. Buffer fluid is a fluid base where biological entities may be dissolved into, or dispersed into, without introducing additional biological entities.

Figure 1A:
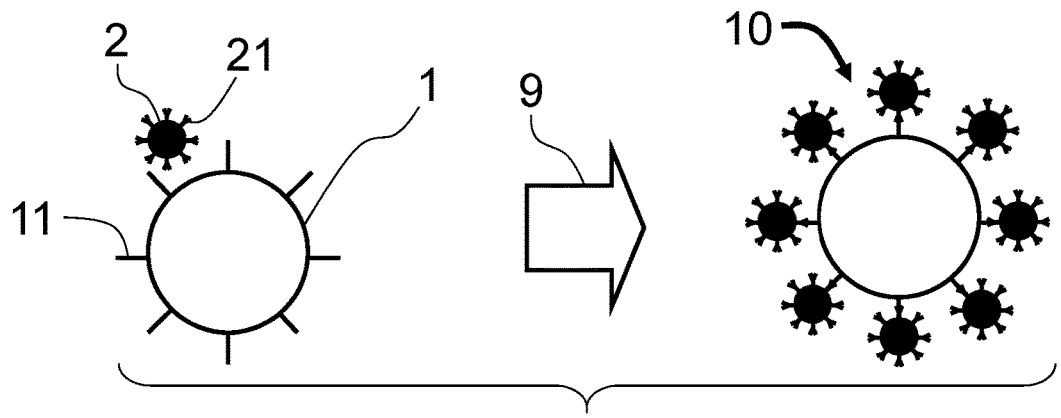
FIG. 1A illustrates superparamagnetic labels (SPL) binding to a cell.
Figure 1B:
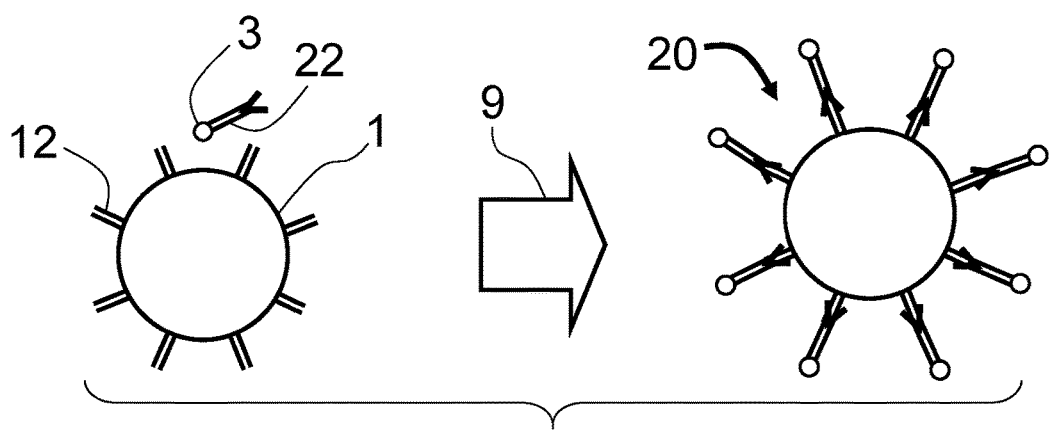
FIG. 1B illustrates optical fluorescent labels (OFL) binding to a cell.
Figure 1C:
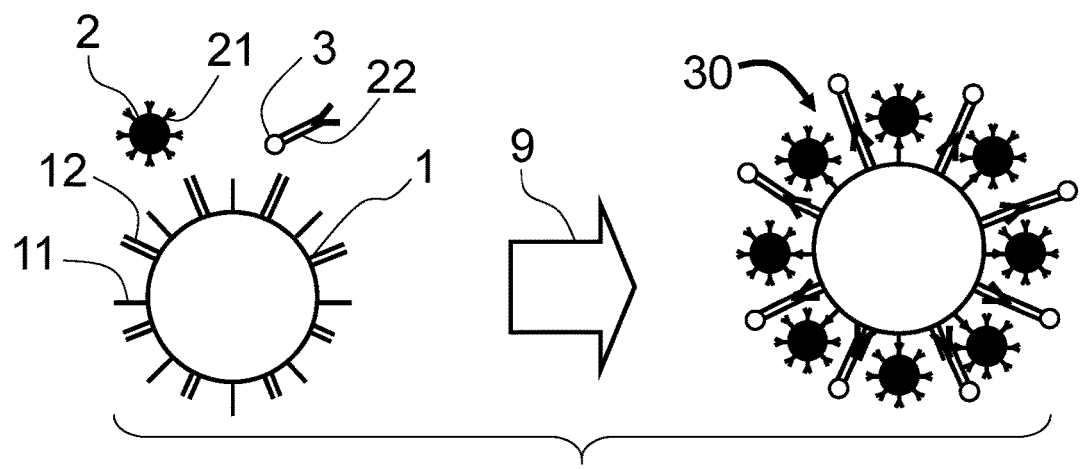
FIG. 1C illustrates SPLs and OFLs binding to a cell.
Figure 2A:
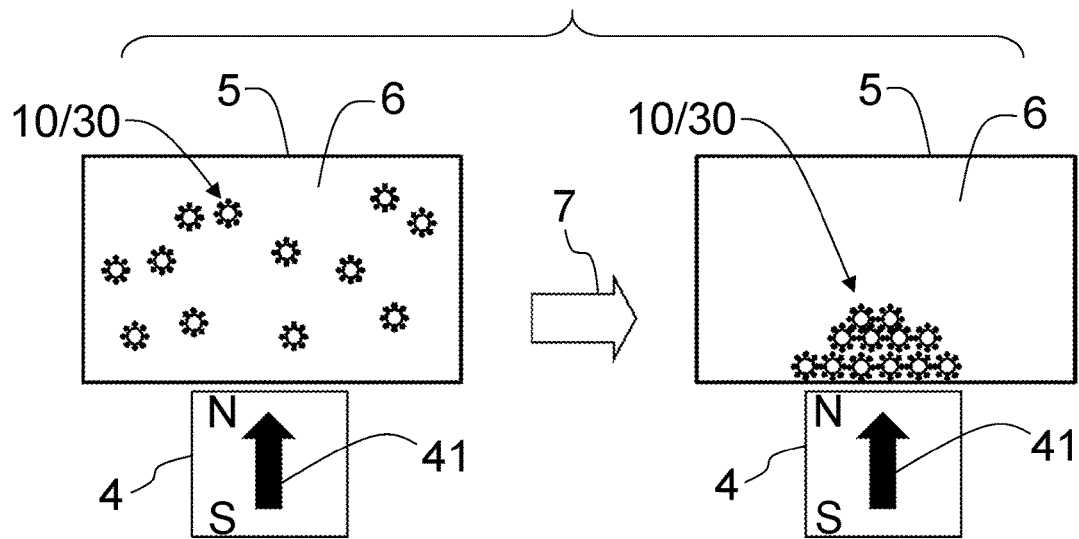
FIG. 2A illustrates cells bound with SPLs being separated by a magnet.
Figure 2B:
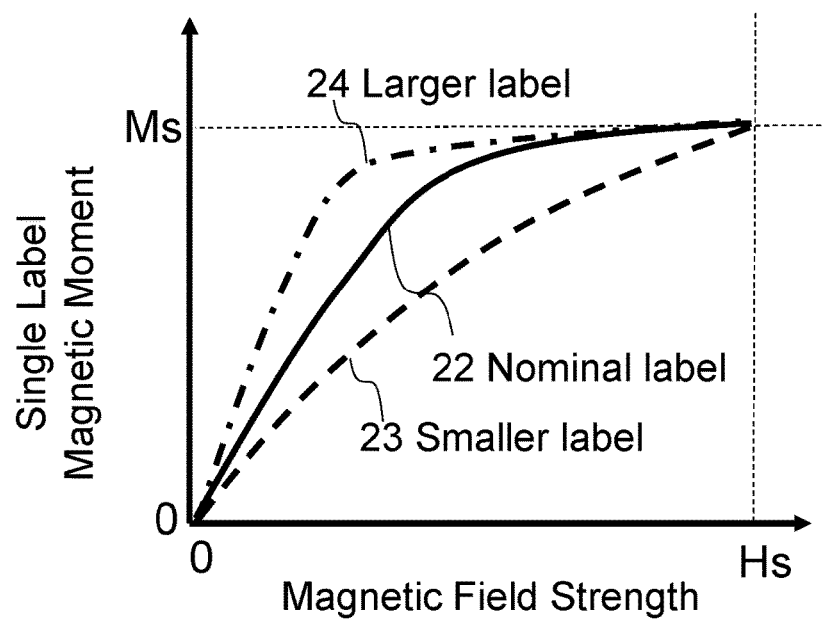
FIG. 2B is a plot of SPL magnetization vs magnetic field strength for different SPL sizes.
Figure 4:
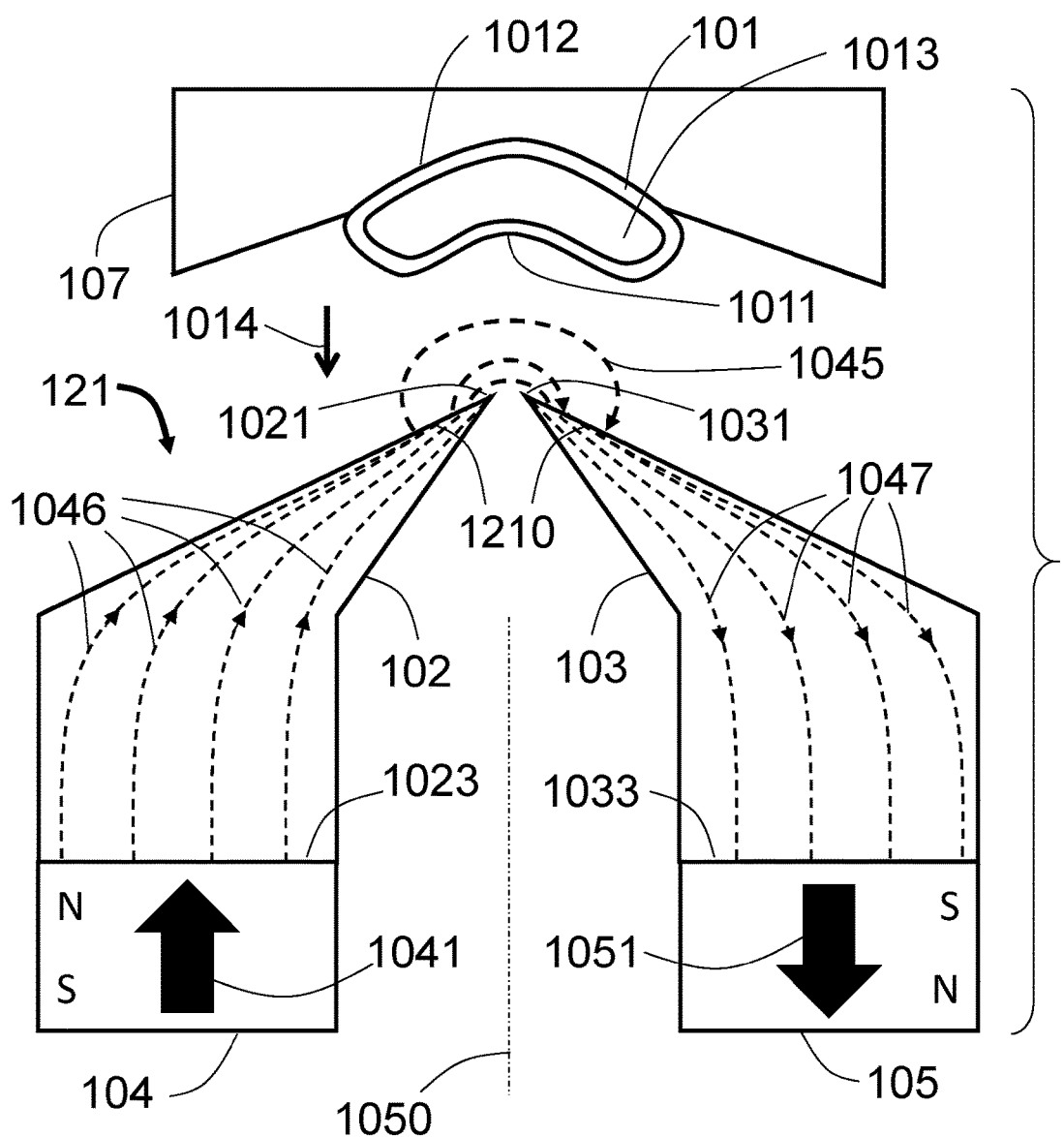
FIG. 4 is a cross-sectional view of the first embodiment of a magnetic separation device ("MAG") with a "C" shape rigid channel.

FIG. 4 shows a cross-sectional view of the first embodiment of a magnetic separation device ("MAG") of the current invention. MAG 121 is composed of two magnetic field producing poles, pole 102 and pole 103. Each of the poles 102 and 103 is composed of soft magnetic material, which may include one or more elements of iron (Fe), cobalt (Co), nickel (Ni), iridium (Ir), manganese (Mn), neodymium (Nd), boron (B), samarium (Sm), aluminum (Al). Pole 102 has a magnetic flux collection end 1023 and a tip end 1021, where shape of the pole 102 is converging from the flux collection end 1023 towards the tip end 1021. In FIG. 4, flux collection end 1023 is a flat surface which is contacting, or in proximity to, the North Pole ("N") surface of a permanent magnet 104. Permanent magnet 104 has a magnetization as shown by arrow 1041 in FIG. 4 which points from the South Pole ("S") surface of to the N surface of the magnet 104. Magnetization 1041 produces magnetic field in free space, which can be described as flux lines 1046 emitting from N surface to returning to S surface of the magnet 104. Pole 102 flux collection end 1023 being in contact with, or in close proximity to, the N surface of magnet 104 as shown in FIG. 4, due to the soft magnetic material of pole 102, magnetic flux 1046 from the N surface of magnet 104 is collected by the pole 102 and enters the body of the pole 102 through flux collection end 1023. Due to the converging shape of the pole 102, the collected magnetic flux is mainly channeled within the soft magnetic body of the pole 102 and emitted from the tip end 1021 of pole 102. Said close proximity between flux collection end 1023 and N surface of magnet 104 may be a gap distance in between surface of 1023 and N surface being less than 1 mm. Tip end 1021 may have a much smaller surface area than flux collection end 1023, which makes flux exiting the tip end 1021 having a higher flux density than when flux 1045 is emitted by N surface of magnet 104, i.e. magnetic flux 1045 is concentrated and thus creating a local high magnetic field and high field gradient around the tip end 1021. It is preferred that tip end 1021 of the pole 102 is as small as possible, for example as a convergence point, to produce largest flux concentration for achieving highest magnetic field. However, in practice, due to manufacturing process, tip end 1021 may have a curved or domed shape, which shall not affect the general concept of flux concentration by the tip end 1021. Pole 103 is similar to pole 102 in that pole 103 has a larger flux collection end 1033 and a smaller tip end 1031, where flux collection end 1033 is in contact with, or in close proximity to, S surface of permanent magnet 105. It is preferred that pole 103 and magnet 105 are identical to pole 102 and magnet 104, but arranged as mirroring to pole 102 and magnet 104 around a center line 1050. Magnet 105 magnetization 1051 is opposite to magnetization 1041 of magnet 104. Magnetic flux 1047 collected by flux collection end 1033 from S surface of pole 103 is opposite to that of pole 102, and flux emitted from tip end 1031 of pole 103 is opposite to that of tip end 1021. Thus, between the gap of tip end 1021 and 1031, emitted flux can form closed loop and further enhance the magnetic field strength and field gradient around the tip ends 1021 and 1031. Dashed lines 1045 are schematic of the flux emitted from tip end 1021 and returns to tip end 1031. Flux lines 1045 closer to tip end 1021 and 1031 being denser indicates stronger magnetic field and larger field gradient closer to the gap area. As shown in FIG. 4, top section of pole 102 is tilted to the right side, while top section of pole 103 is tilted to the left. This tilted shape diverts the magnetic flux within poles 102 and 103 away from bottom section of the poles and helps make the tip end 1021 of pole 102 and tip end 1031 of pole 103 being the closest spaced features of the poles 102 and 103 to achieve high field in gap between tip ends 1021 and 1031 with minimizing flux leakage between lower bodies of pole 102 and 103. In FIG. 4, the tilted top sections of the poles 102 and 103 form a triangle shape, or convex shape, top surface 1210 of the MAG 121, which will be described as "MAG wedge" 1210 of MAG 121 hereafter. Permanent magnets 104 and 105 may be composed of any of, but not limited to, Nd, Fe, B, Co, Sm, Al, Ni, Sr, Ba, O, NdFeB, AlNiCo, SmCo, strontium ferrite (SrFeO), barium ferrite (BaFeO), cobalt ferrite (CoFeO).

FIG. 4 embodiment includes a rigid fixed shape channel 101. Channel 101 has a channel wall enclosing a channel space 1013, where fluid sample may flow through channel 101 in the channel space 1013 along the channel 101 length direction that is perpendicular to the cross-section view of FIG. 4. Channel 101 has a top surface 1012 and a bottom surface 1011. Bottom surface 1011 is formed in a shape conforming to the MAG wedge surface 1210, such that when channel 101 is moved in direction 1014 to be in contact with the MAG 121 poles 102 and 103, bottom surface 1011 of channel 101 is in contact with MAG wedge surface 1210 with no or minimal gap in between bottom surface 1011 and MAG wedge surface 1210. Top surface 1012 of channel 101 is preferred to be conformal to bottom surface 1011 to produce a channel space 1013 with a shape that maximizes exposure of fluid sample flowing through channel 101 to the highest magnetic field region of the MAG wedge gap field 1045.

In FIG. 4 embodiment, poles 102 and 103, magnets 104 and 105, and channel 101 extend in the direction perpendicular to the cross-section view of FIG. 4, which will be referred to as "length direction" hereafter. Fluid sample flows in the channel 101 and is contained in channel space 1013 along the length direction. Channel 101 being a rigid and fixed shape channel, the wall thickness of channel 101 at surface 1011 may be thinner than wall thickness at surface 1012, such that channel 101 mechanical robustness is maintained by the thicker wall at surface 1012, and magnetic field effect on fluid sample is enhanced by thinner wall at surface 1011 allowing fluid sample being closer to the MAG wedge 1210 and tip ends 1021 and 1031. Channel 101 may be attached to a non-magnetic channel holder 107 at the top surface 1012. Channel holder 107 may align channel 101 to MAG wedge 1210, move channel 101 to separation position in contact with MAG 121, or lift channel 101 away from MAG 121 after magnetic separation. Channel holder 107 may be composed of any non-magnetic material including, but not limited to, metal, non-metal element, plastic, polymer, ceramic, rubber, silicon, and glass. In FIG. 4, flux collection ends 1023 and 1033 of the soft magnetic poles 102 and 103 may also be referred to as base ends 1023 and 1033.

Permanent magnets as described in different embodiments of this invention, for example magnets 104 and 105 of FIG. 4, may each have opposite magnetization direction to that is described in the each of the figures and embodiments without affecting the designs, functions and processes of the embodiments.

Figure 5:
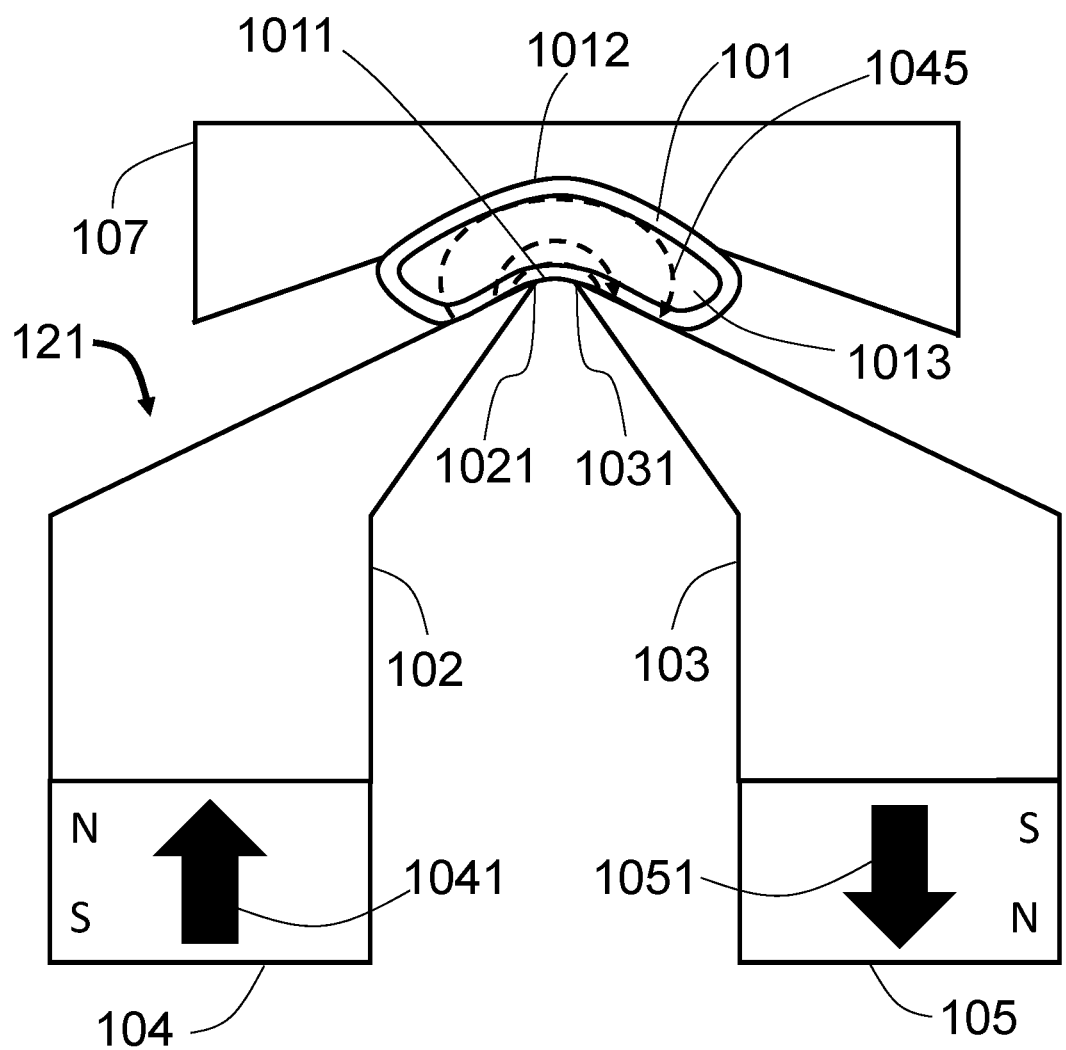
FIG. 5 is a cross-sectional view of the first embodiment of MAG having a "C" shape rigid channel in separation position.

FIG. 5 is the cross-sectional view of FIG. 4 first embodiment of MAG with channel 101 in magnetic separation position. Channel 101 of FIG. 4 moves along direction 1014 and comes into contact with MAG wedge 1210 surface by bottom surface 1011. MAG 121 gap formed by tip ends 1021 and 1031 is brought into contact with, or minimal distance to, wall of channel 101 and the fluid sample flowing in the channel 101. Channel 101 "C" shape matching to the MAG wedge shape helps achieve large cross-sectional area of the channel space 1013 to maintain a high flow rate, and at the same time confines cells 10/30 in the fluid sample flowing in channel 101 to a high field and high gradient region of the MAG 121 gap field as indicated by the field lines 1045. Compared to prior art of FIG. 3A and FIG. 3B, first embodiment MAG 121 does not introduce foreign material in the channel 101 while achieving comparable or higher magnetic field and field gradient on cells 10/30 flowing through the channel 101. Removing of poles 102 and 103 together with magnets 104 and 105 from channel 101 will eliminate field generation source and avoids limitation of prior art domain related cells loss. Compared to prior art of FIG. 3C, MAG wedge of FIG. 5 being in contact with the channel 101 wall brings highest achievable magnetic field and field gradient to the fluid sample in the channel 101 for a more efficient cell 10/30 separation. Channel 101 shape being conformal to MAG wedge shape allows channel 101 to have a large cross-sectional sample flow area, meanwhile avoids the deficiency of prior art that cells 10/30 at top end of a circular channel experiencing much lower magnetic field than at lower end that ultimately limits sample flow rate. Thus, sample flow rate in channel 101 can be higher than prior art while achieving better magnetic separation efficiency.

Figure 6:
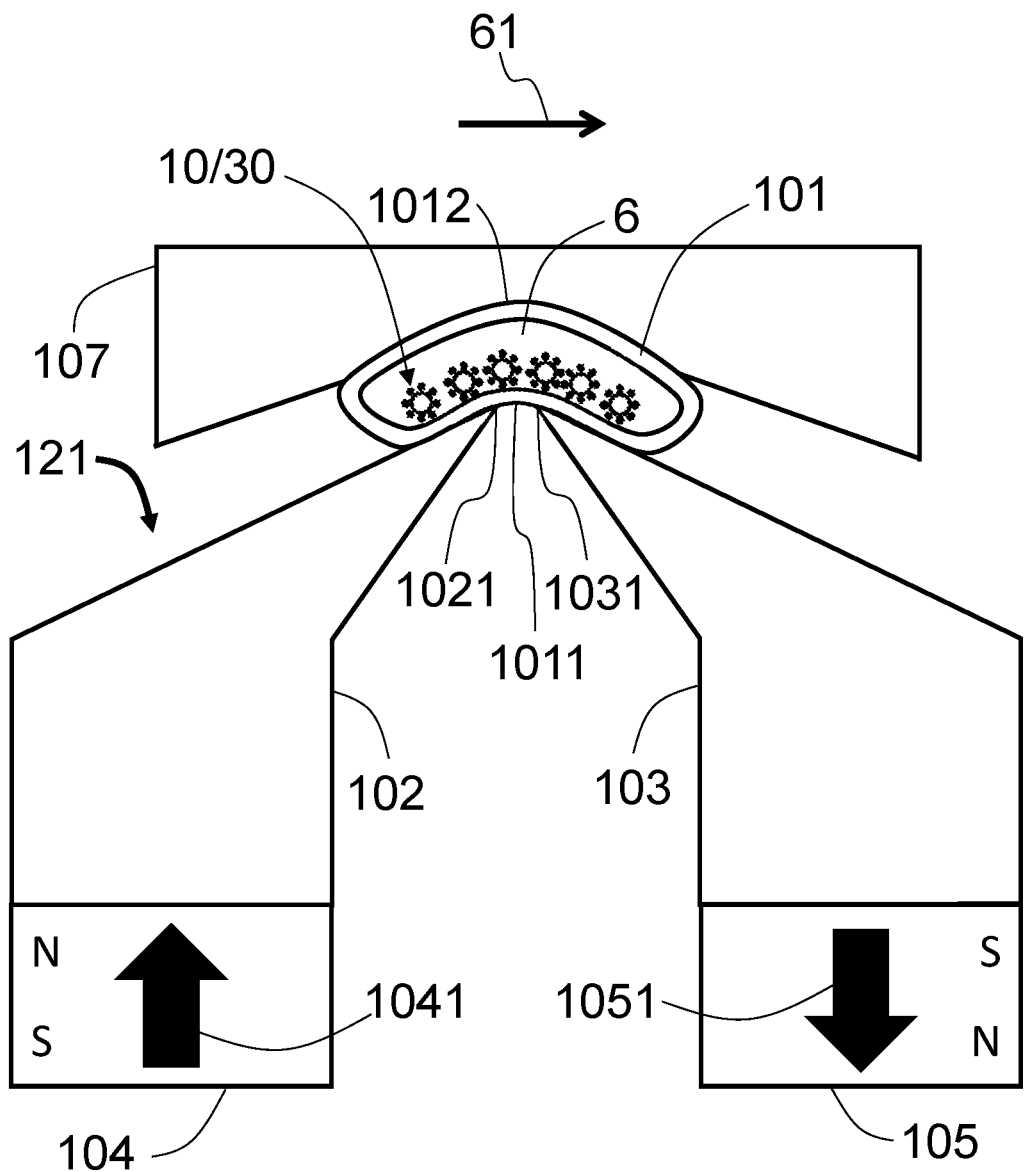
FIG. 6 is a cross-sectional view of the first embodiment of MAG having a "C" shape rigid channel in separation position with cells being separated.

FIG. 6 is same as FIG. 5, except biological entities, or cells 10/30 for simplicity of description, are included to describe magnetic separation by MAG 121 from a fluid sample 6. Fluid sample 6 carrying cells 10/30 is flown through channel 101 along length direction of channel 101 perpendicular to the FIG. 6 cross-sectional view. MAG 121 gap magnetic field magnetizes the SPL 2 attached to cells 10/30 and field gradient pulls cells 10/30 from the fluid 6 towards the MAG wedge to form conglomerate layer against the 1011 bottom surface of channel 101. Due to MAG 121 design and channel 101 shape, cells 10/30 close to top surface 1012 experience magnetic field not significantly lower than close to bottom surface 1011, and distance for cells 10/30 to travel from top surface 1012 to conglomerate on bottom surface 1011 is much shorter than in prior art, these characteristics allow MAG 121 to resolve deficiencies of prior art.

Figure 7:
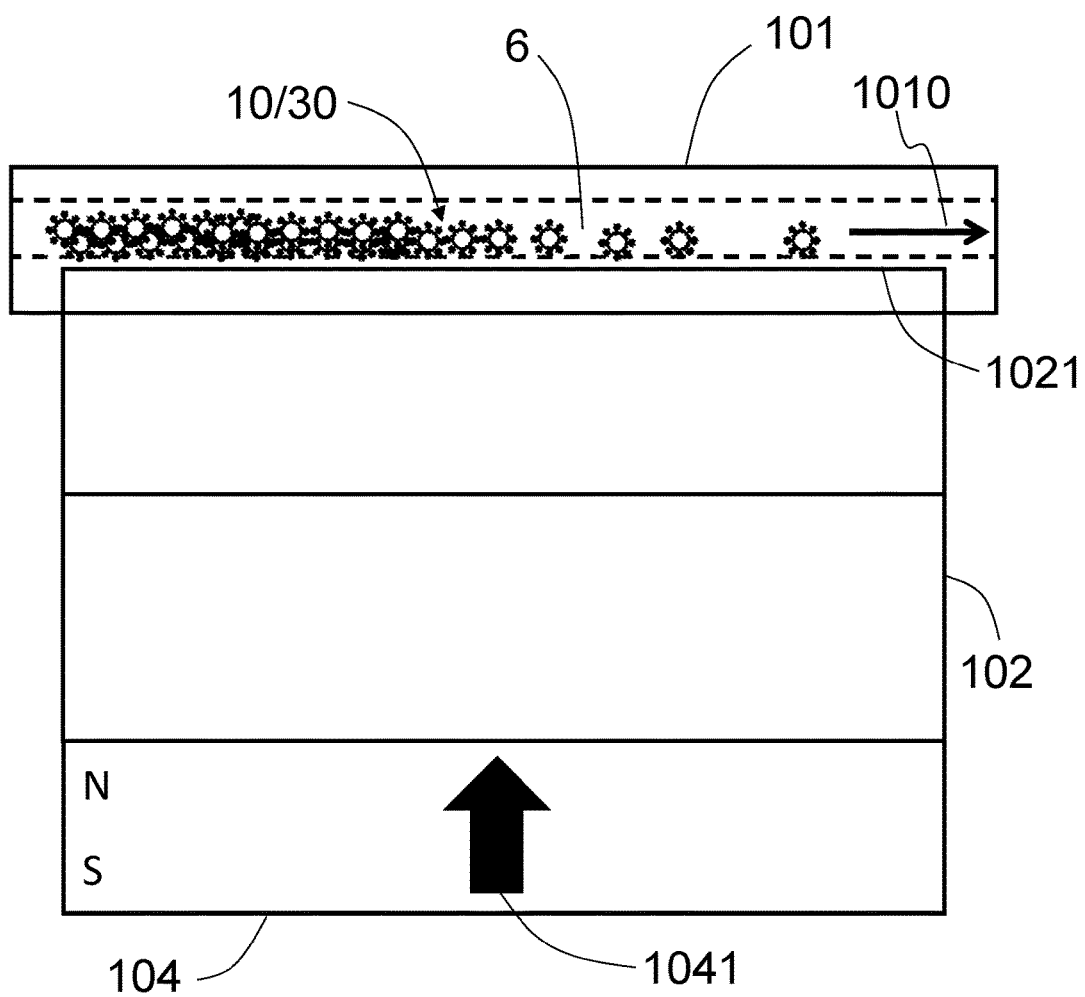
FIG. 7 is a side view of FIG. 6.

FIG. 7 is a side view of FIG. 6 along direction 61 of FIG. 6. Fluid sample 6 carrying cells 10/30 flows from left to right in the channel 101 as indicated by arrow 1010. With the MAG 121 gap field, cells 10/30 are separated from fluid 6 to form conglomerate on the channel wall of bottom surface 1011. FIG. 7 shows that majority of the cells 10/30 are separated from liquid 6 at the earlier section of the channel 101 length, as indicated by the crowded population of cells 10/30. As certain tail population cells 10/30 may have comparatively smaller size SPL 2 or fewer number of SPL 2 bound to it surface, time required for such tail population cells to be pulled to bottom surface 1011 is longer than nominal population during fluid 6 flowing through channel 101. Thus, population of separated cells 10/30 will show density decrease from inlet towards outlet of channel 101.

Figure 8A:
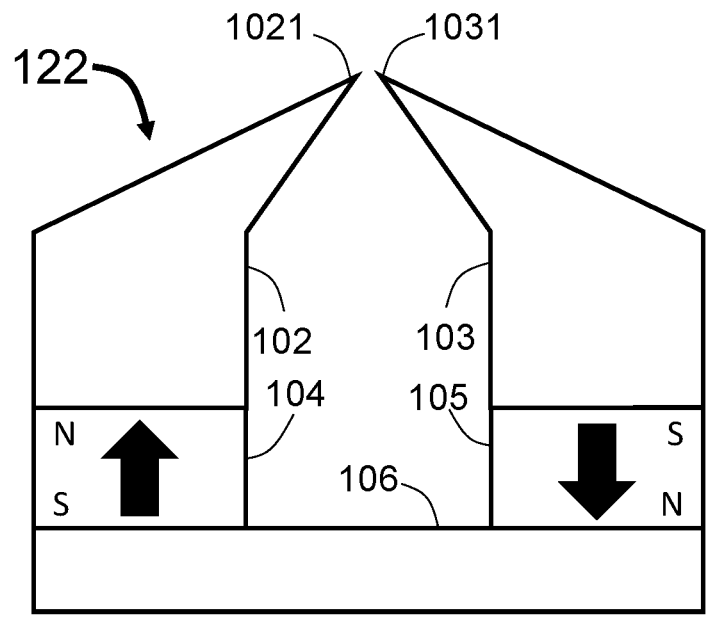
FIG. 8A is a cross-sectional view of the second embodiment of MAG.

FIG. 8A is a cross-sectional view of a second embodiment of MAG of current invention. MAG 122 in FIG. 8A is substantially similar as MAG 121, except a soft magnetic shield 106 is attached to the S surface of magnetic 104 and N surface of magnet 105. Magnetic flux from S surface of magnet 104 and N surface of magnet 105 forms closure path within the soft magnetic shield 106. MAG 122 compared to MAG 121 will have less magnetic flux leakage outside of the MAG 122 structure, where magnetic flux generated by magnets 104 and 105 are mainly confined within the soft magnetic material body of poles 102 and 103, and shield 106. MAG 122 is preferred in applications where magnetic interference from MAG 122 to other surrounding instrument or equipment is desired to be minimized.

Figure 8B:
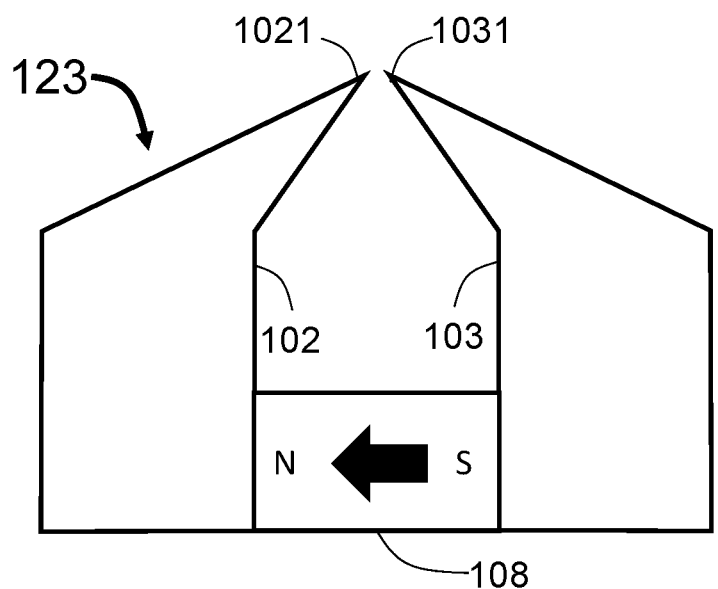
FIG. 8B is a cross-sectional view of the third embodiment of MAG.

FIG. 8B is a cross-sectional view of a third embodiment of MAG of current invention. Compared to MAG 121, MAG 123 of FIG. 8B incorporates only one permanent magnet 108, which is attached to both poles 102 and 103, where flux from N surface of magnet 108 and flux from S surface of magnetic 108 is conducted by poles 102 and 103 to produce MAG 123 gap field by tip ends 1021 and 1031. Compared to MAG 121, magnetic flux generated by magnet 108 is mainly confined within the soft magnetic material body of poles 102 and 103, and MAG 123 is comparatively easier to assemble and produces less magnetic flux leakage.

Figure 9:
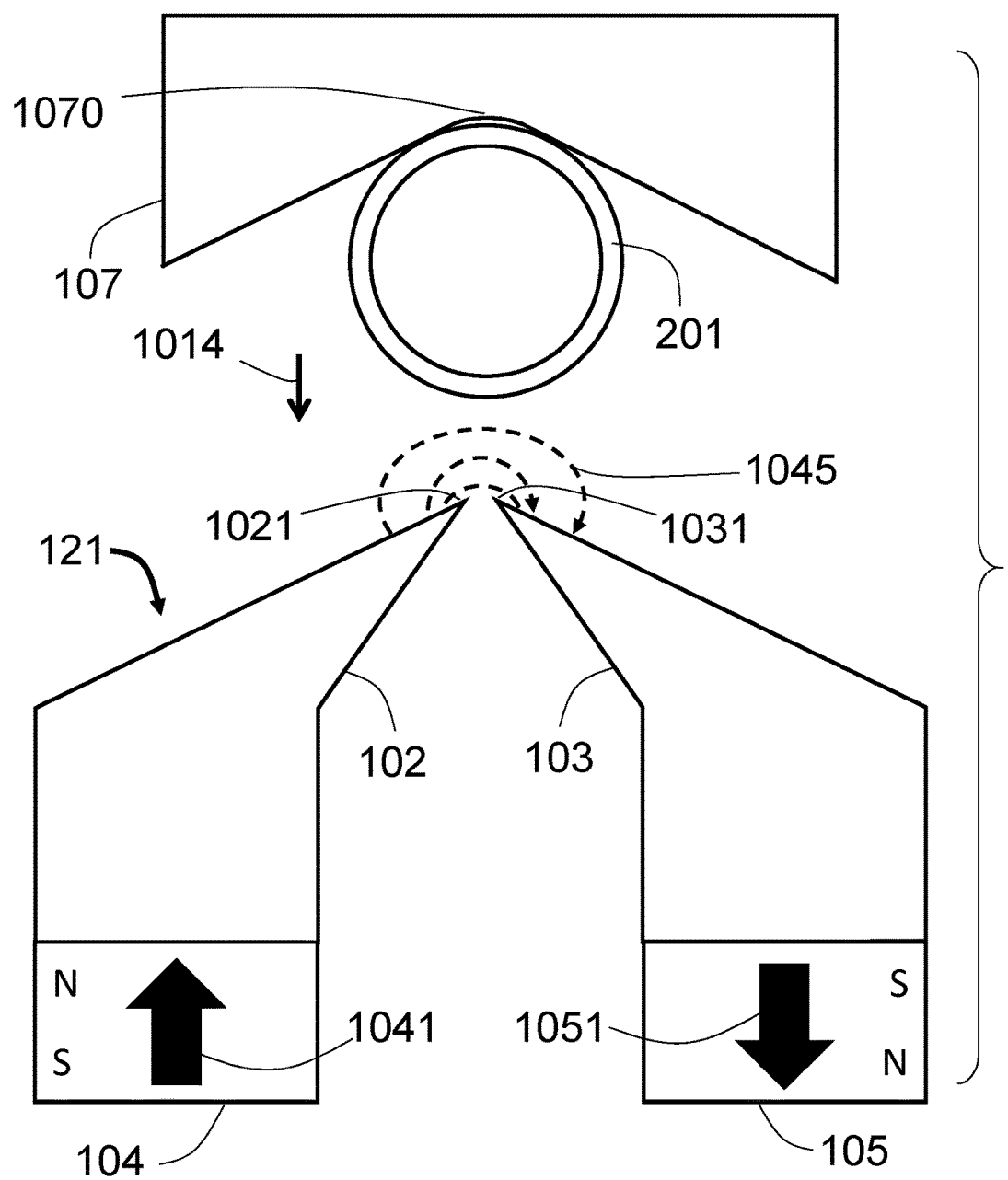
FIG. 9 a cross-sectional view of the first embodiment of MAG with a flexible channel.

FIG. 9 shows a cross-sectional view of the first embodiment MAG 121 being used for magnetic separation in combination with a flexible channel 201. FIG. 9 is similar to FIG. 4, except that the rigid channel 101 is replaced with a flexible channel 201. Flexible channel 201 may assume any shape, including a circular shape tubing form, at its non-deformed state, but can be deformed into other shapes by external force. Wall material of channel 201 is deformable and may be composed of any of, but not limited to, silicone, silicone rubber, rubber, PTFE, FEP, PFA, BPT, Vinyl, Polyimide, ADCF, PVC, HDPE, PEEK, LDPE, Polypropylene, polymer, thin metal or fiber mesh coated with polymer layer, Flexible channel 201 is also shown in FIG. 9 to have a channel holder 107 attached to the back of channel 201. Channel holder 107 may be composed of any non-magnetic material including, but not limited to, metal, non-metal element, plastic, polymer, ceramic, rubber, silicon, and glass. Channel 201 may attach to holder 107 through surface bonding, for example by gluing or injection molding, or via mechanical attachment through components 1074 of FIG. 32. Holder 107 has a bottom surface 1070 in contact with the top surface of channel 201, where surface 1070 being preferred to be substantially conformal to the MAG 121 wedge shape. In FIG. 9, holder 107 aligns attached flexible channel 201 to MAG 121 wedge gap and moves channel 201 towards MAG wedge gap in direction 1014.

Figure 10:
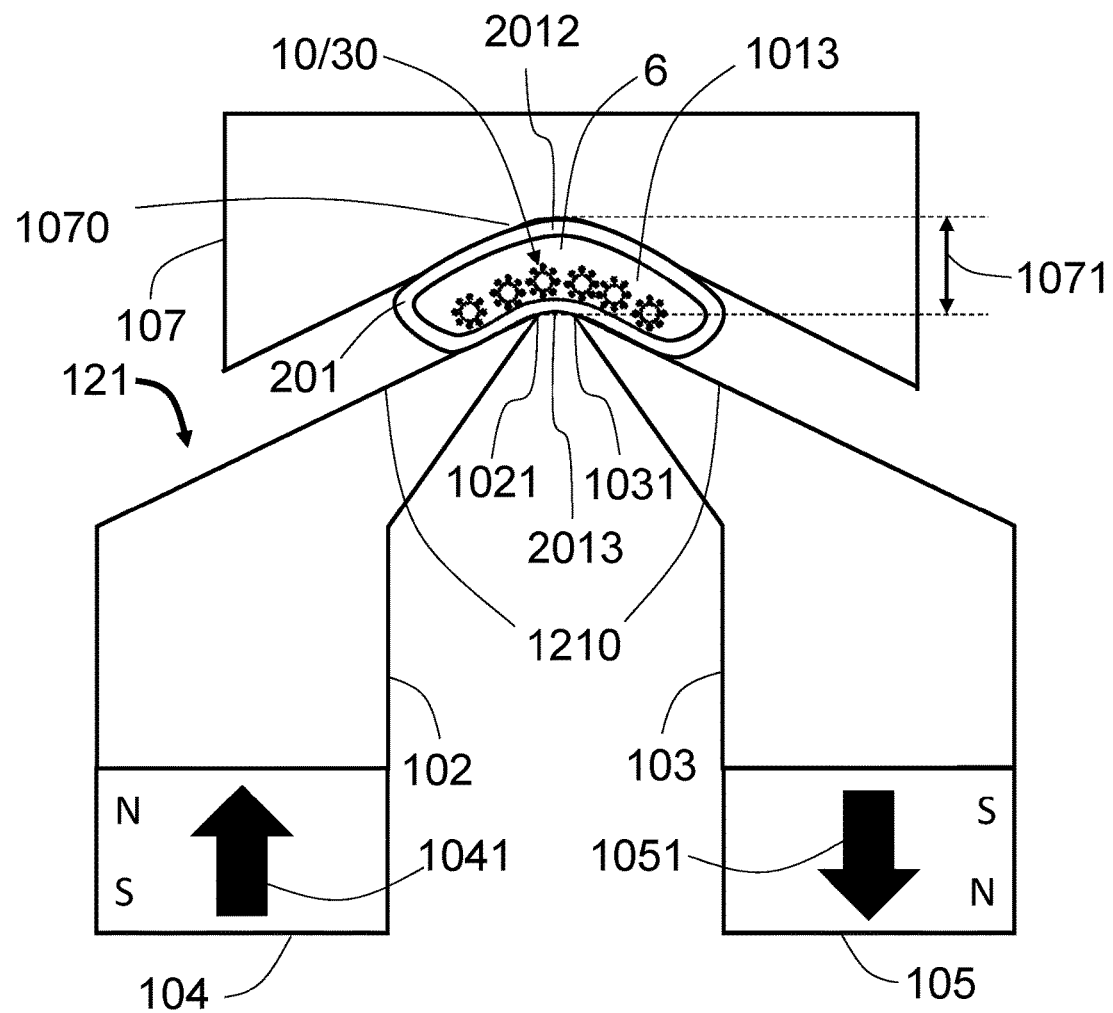
FIG. 10 illustrates the first embodiment of MAG having a flexible channel in separation position with cells being separated.

FIG. 10 illustrates the flexible channel 201 being pushed against the MAG wedge of MAG 121 by the channel holder 107. With pressure exerted by the holder 107 on flexible channel 201 against the MAG wedge of MAG 121, channel 201 is deformed in FIG. 10 with bottom surface 2013 of channel 201 becoming conformal and in surface contact to MAG wedge surface 1210. Meanwhile, as holder 107 bottom surface 1070 may also be conformal to the MAG wedge shape, top surface 2012 of channel may also be forced into a substantially conformal shape to the MAG wedge. FIG. 10 depicts the "separation position" of flexible channel 201 relative to the MAG 121 during magnetic separation of cells 10/30 from sample fluid 6. Shape of flexible channel 201 is substantially similar to channel 101 of FIG. 5 and FIG. 6, except such shape of channel 201 at separation position is result of channel 201 self-aligning and self-conforming to MAG wedge without the need of a manufacturing process to achieve shape of channel 101. Additionally, the flow space within channel 201 at separation position may be adjusted to allow for larger or smaller cross-sectional area of the flow space of channel 201, such that optimization of fluid sample 6 flow rate through channel 201 and cells 10/30 magnetic separation efficiency may be optimized. The flow space adjustment may be achieved by changing the vertical distance 1071 from the holder 107 surface 1070 top point in contact with channel 201 top surface 2012, to tip ends 1021 and 1031 or to an imaginary plane where tip ends 1021 and 1031 reside. With a larger 1071 distance, flexible channel 201 is less deformed and a larger flow space is realized, which allows for a slower flow speed at the same fluid flow rate. While with a smaller 1071 distance, flexible channel 201 has a smaller flow space but top edge 2012 is also closer to the MAG wedge gap and tip ends 1021 and 1031, which allows for higher magnetic field and faster separation of cells 10/30. Thus optimization between flow rate and separation efficiency may be achieved with adjusting the distance 1071 for a given combination of MAG 121 design and flexible channel 201. In one embodiment, distance 1071 is more than 0 mm and less than or equal to 1 mm. In another embodiment, distance 1071 is more than 1 mm and less than or equal to 3 mm. In yet another embodiment, distance 1071 is more than 3 mm and less than or equal to 5 mm. In yet another embodiment, distance 1071 is more than 5 mm and less than or equal to 10 mm. In yet another embodiment, distance 1071 is more than 2 times and less than or equal to 3 times of the wall thickness of flexible channel 201. In yet another embodiment, distance 1071 is more than 3 times and less than or equal to 5 times of the wall thickness of flexible channel 201. In yet another embodiment, distance 1071 is more than 5 times and less than or equal to 10 times of the wall thickness of flexible channel 201. Flexible channel 201 at separation position functions similarly to channel 101 in FIG. 6, where FIG. 10 also shows that during magnetic separation, cells 10/30 form conglomerate along channel 201 wall of lower surface 2013 directly opposing the MAG wedge surface 1210. Thickness of channel 201 wall at bottom surface 2013 may be thinner than channel 201 wall at top surface 2012.

Figure 11:
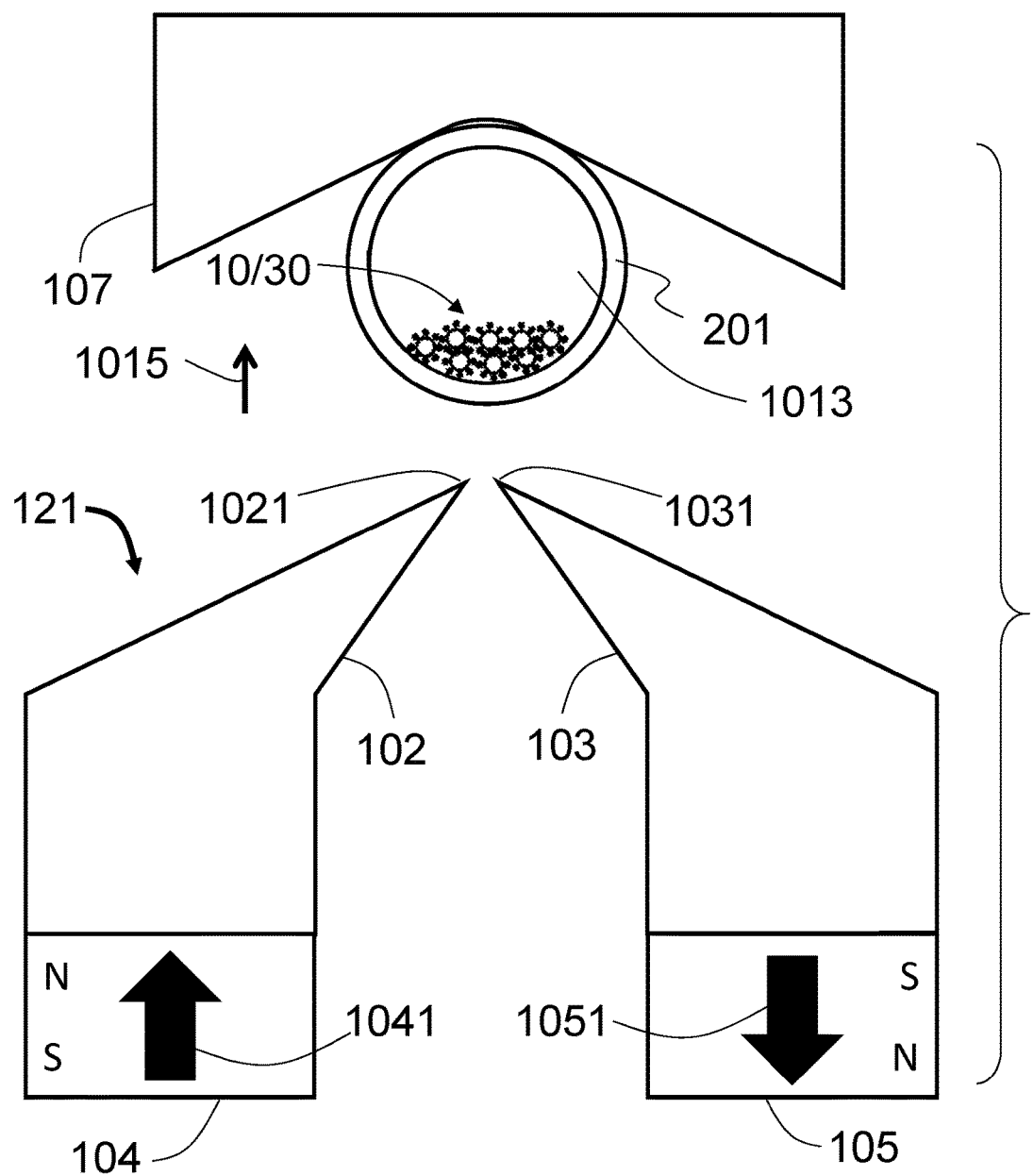
FIG. 11 illustrates the first embodiment of MAG having a flexible channel in lifted position after cell separation.

FIG. 11 illustrates after magnetic separation is completed in FIG. 10, the channel holder 107 moves away from the MAG 121 in direction 1015, causing the flexible channel 201 to separate from MAG wedge of MAG 121 to "lifted position" and flexible channel 201 may also return to its non-deformed shape, for example circular tubing as shown in FIG. 11. Magnetically separated cells 10/30 in FIG. 10 may hold the conglomerate form at the bottom surface of the flexible channel 201 at lifted position. After FIG. 11 lifted position of flexible channels 201 is reached, dissociation procedures on the cells 10/30 within the flexible channel 201 to break up the conglomerate may be performed, as described in FIG. 22A through FIG. 30B. Flexible channel 201 returning to non-deformed shape, for example circular tubing of FIG. 11, provides a larger cross-sectional area of the channel space 1013 as shown in FIG. 11 than at separation position in FIG. 10. Such larger channel space 1013 may be preferred for easier dissociation of cells 10/30 from the conglomerate form. Additional buffer fluid may be injected into the channel space 1013 of channel 201 at lifted position to assist channel 201 return to non-deformed shape.

MAG 121 in FIG. 9 through FIG. 11 may be replaced by MAG 122 or MAG 123 without limitation on described methods and processes.

Figure 12:
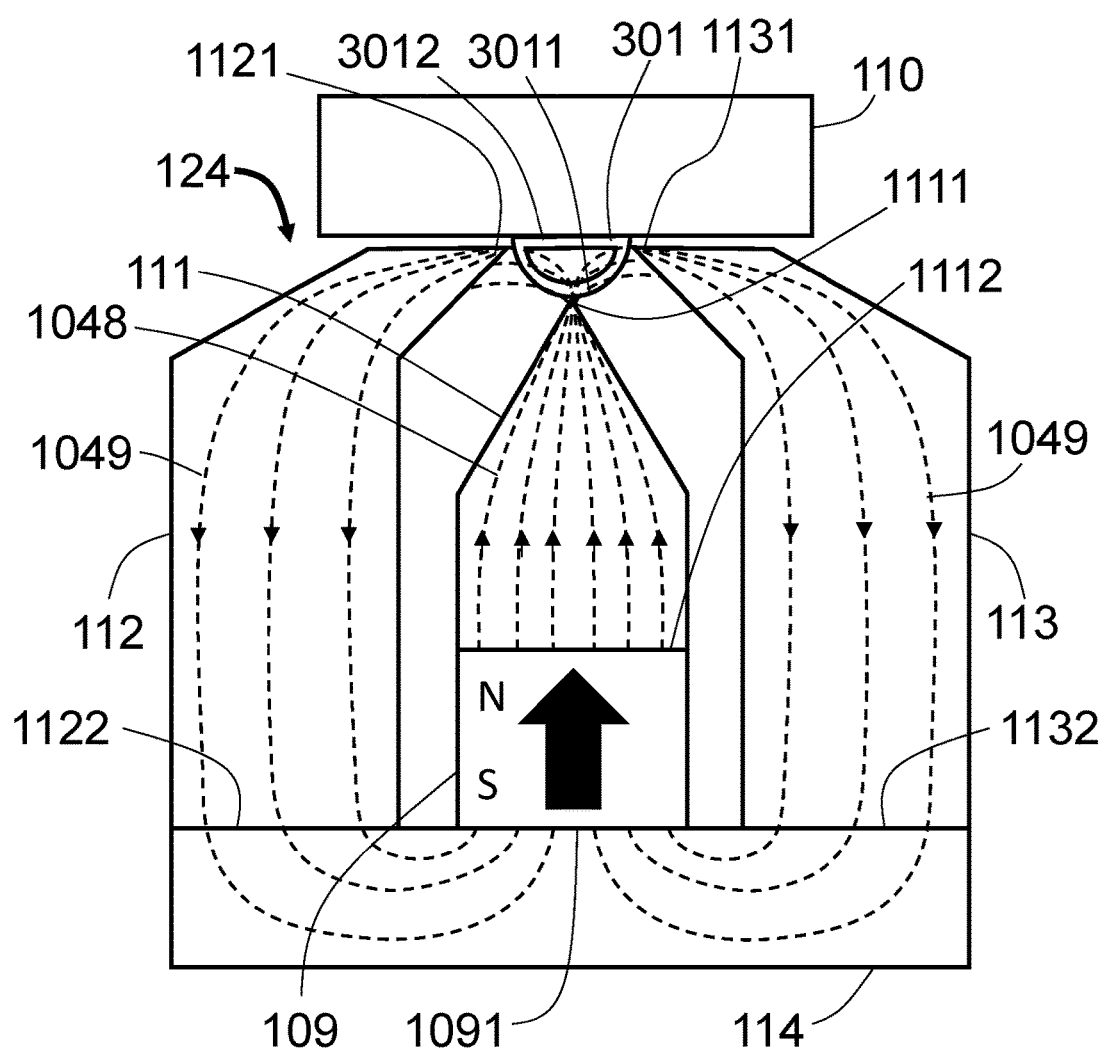
FIG. 12 illustrates cross-sectional view of the fourth embodiment of MAG having a "D" shape rigid channel in separation position.

FIG. 12 illustrates cross-sectional view of the fourth embodiment of MAG 124. MAG 124 has three soft magnetic poles 111, 112 and 113. Center pole 111 is attached to N surface of permanent magnet 109 at a flux collection end 1112, similar to flux collection end 1023 of pole 102 in FIG. 4, and flux 1048 from magnet 109 N surface is conducted by pole 111 soft magnetic body and then emitted from a tip end 1111, which is much smaller in area size than flux collection end 1112, of pole 111, and functions similar to tip end 1021 of FIG. 4 to produce a local high field around tip end 1111 by concentrating the magnetic flux conducted from magnet 109. Side poles 112 and 113 each have a flux collection end 1122 and 1132 respectively, which are attached to same top surface of a soft magnetic bottom shield 114. Bottom shield 114 is then attached to S surface of the permanent magnet 109. Thus the magnetic flux 1049 from the S surface of magnet 109 is conducted in the body of bottom shield 114 and divided between poles 112 and 113 and further conducted to the tip ends 1121 and 1131 of poles 112 and 113 respectively. Tip end 1111 is formed in proximity to tip ends 1121 and 1131. In one embodiment, tip end 1111 may recess from an imaginary plane where tip ends 1121 and 1131 reside towards magnet 109 by an offset distance between 0 mm to 1 mm. In another embodiment, tip end 1111 may recess from an imaginary plane where tip ends 1121 and 1131 reside towards magnet 109 by an offset distance between 1 mm to 5 mm. In yet another embodiment, tip end 1111 may recess from an imaginary plane where tip ends 1121 and 1131 reside towards magnet 109 by an offset distance between 5 mm to 10 mm. Tip end 1111 is preferred to be spaced equally to tip ends 1121 and 1131. Top section of pole 112 is tilted to the right side, while top section of pole 113 is tilted to the left, which is similar to pole 102 and pole 103 of FIG. 4. Such tilting is to increase gap between the main bodies of poles 112 and 113 to main body of pole 111 to reduce flux leakage such that flux concentration around tip ends 1111, 1121 and 1131 is maximized. When flux is emitted from tip ends 1111, 1121 and 1131, since flux 1048 conducted by center pole 111 is opposite to the flux 1049 conducted by side poles 112 and 113, the flux forms closure between tip ends 1111 to 1112, and tip ends 1111 to 1131. Thus, the magnetic flux generated by N and S surface of magnet 109 is conducted within bodies of poles 111,112, 113 and shield 114 with minimal leakage to outside of MAG 124 structure. Flux density is highest around tip end 1111, with tip ends 1121 and 1131 also producing high flux density, which all indicate high magnetic field and field gradient around tip ends 1111, 1121 and 1131. Compared to MAG 121, 122 and 123, MAG 124 has the advantage of more efficient flux closure within the MAG 124 soft magnetic bodies with less leakage and thus higher flux density around tip end 1111 to produce higher magnetic field and field gradient in channel 301.

Channel 301 is a rigid channel similar to channel 101 of FIG. 4, and has a fixed shape similar to a rotated "D". Channel 301 is shown to be in magnetic separation position in FIG. 12, where tip ends 1111, 1121 and 1131 may all be in contact with the curved bottom surface 3011 of the "D" shape of channel 301, which provides highest possible magnetic field and field gradient that MAG 124 can produce in the channel space where fluid sample flows in channel 301. In another embodiment, tip end 1111 may be in contact with the surface 3011 and tip ends 1121 and 1131 are not contacting surface 3011. Top surface 3012 of channel 301, in one embodiment may be on the imaginary plane where tip ends 1121 and 1131 reside, and in another embodiment top surface 3012 may be above the imaginary plane in between 0 mm to 1 mm, and in yet another embodiment top surface 3012 may be above the imaginary plane in between 1 mm to 5 mm. In one embodiment, channel 301 wall thickness at surface 3012 is thicker than wall thickness at surface 3011. Channel 301 may be attached to a non-magnetic channel holder 110 at the top surface 3012. Channel holder 110 may align channel 201 to MAG gap of MAG 124, move channel 301 to separation position in contact with MAG 124 pole 111 tip end 1111, or lift channel 301 away from MAG 124 after magnetic separation.

Figure 13:
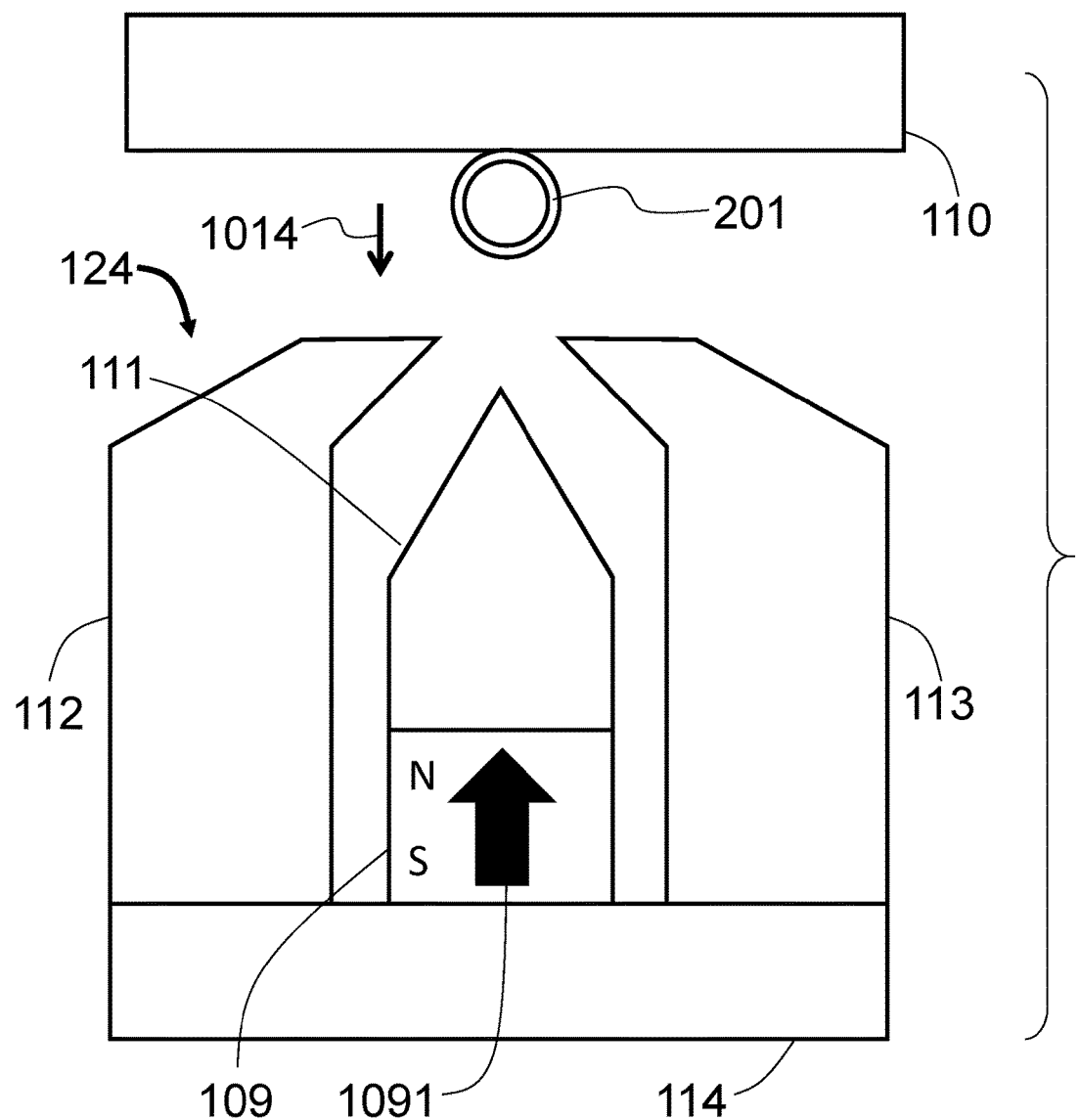
FIG. 13 illustrates cross-sectional view of the fourth embodiment of MAG with a flexible channel.

FIG. 13 shows a cross-sectional view of the fourth embodiment MAG 124 being used for magnetic separation in combination with the flexible channel 201, which is same as in FIG. 9. Channel holder 110 may be different shape than channel holder 107 of FIG. 9. Before magnetic separation, channel holder 110 is attached to channel 201. Channel holder 110 aligns channel 201 to MAG gap of MAG 124 which is composed of tip ends 1111, 1121 and 1131 as in FIG. 12, and moves channel 201 into the MAG gap of MAG 124 in direction 1014.

Figure 14:
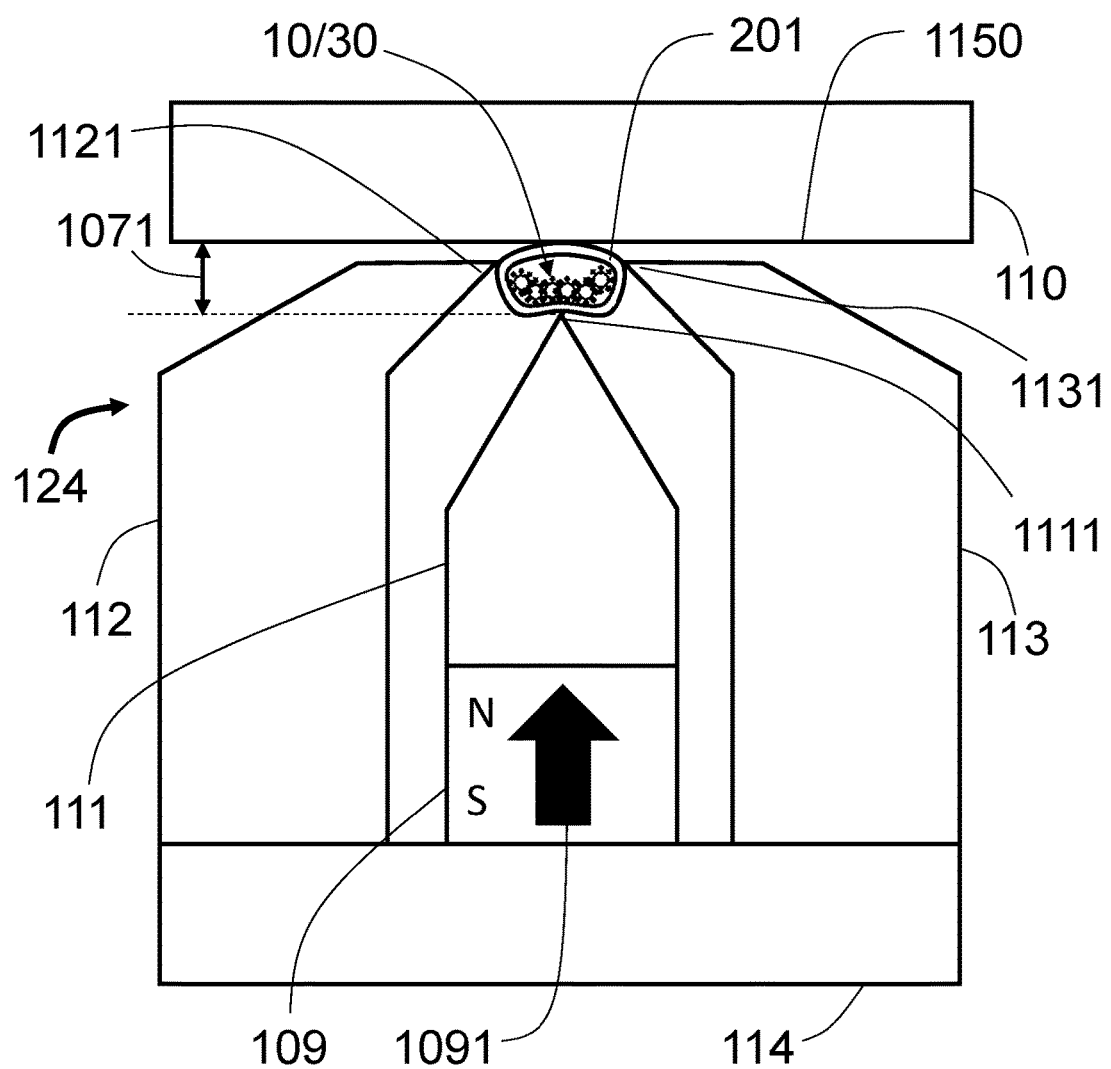
FIG. 14 illustrates cross-sectional view of the fourth embodiment of MAG having a flexible channel in separation position with cells being separated.

FIG. 14 illustrates the flexible channel 201 in separation position in the fourth embodiment MAG 124 with cells 10/30 being separated and form conglomerate around bottom and side walls of the channel 201 close to the tip ends 1111, 1121 and 1131. In FIG. 14, flexible channel 201 is deformed similarly as in FIG. 10 to conform to the MAG gap boundaries, which are mainly the tip ends 1111, 1121 and 1131. Shape of channel 201 may be different than channel 301 at separation position due to flexible channel 201 conforming to the MAG gap boundaries under pressure from holder 110. Shape of channel 201 in FIG. 14 may provide higher liquid sample flow rate with higher separation efficiency than channel 301. Distance 1071 between the lower surface 1150 of holder 110 and tip end 1111 may be adjusted to optimize flow rate in channel 201. Range of distance 1071 is same as 1071 described in FIG. 10.

Figure 15A:
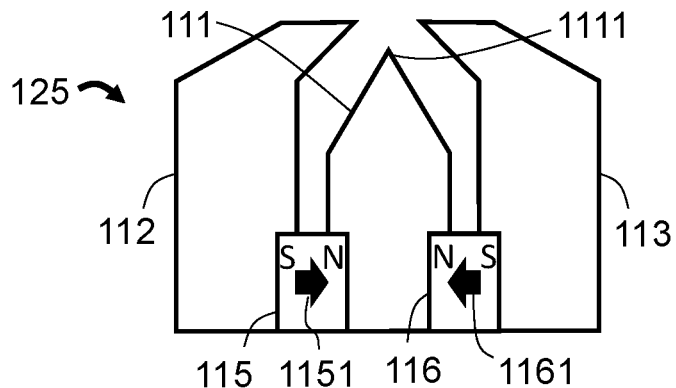
FIG. 15A illustrates cross-sectional view of the fifth embodiment of MAG.

FIG. 15A illustrates cross-sectional view of the fifth embodiment MAG 125. MAG 125 is same as MAG 124, except the magnet 109 and bottom shield 114 of MAG 124 of FIG. 12 are removed in MAG 125. Permanent magnets 115 and 116 with opposing magnetizations 1151 and 1161 are placed in between poles 111 and 112, and between poles 111 and 113, respectively as shown in FIG. 15A. Magnetizations 1151 and 1161 are horizontal in FIG. 15A, which enables center pole 111 conducting N surface flux from both magnets 115 and 116, while side poles 112 and 113 each conducts S surface flux from magnet 115 and 116 respectively. Compared to MAG 124, MAG 125 may produce higher field around tip ends 1111, 1121 and 1131 due to two magnets 115 and 116 are used. MAG 125 may also be easier to assemble than MAG 124.

Figure 15B:
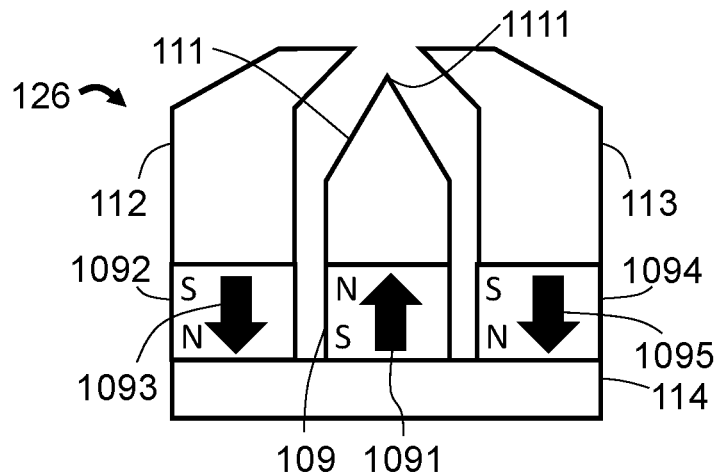
FIG. 15B illustrates cross-sectional view of the sixth embodiment of MAG.

FIG. 15B illustrates cross-sectional view of the sixth embodiment MAG 126. MAG 126 is same as MAG 124, except the side poles 112 and 113 are each attached to S surface of permanent magnets 1092 and 1094 respectively, with magnetizations 1093 and 1095 being opposite to magnetization 1091 of magnet 109. Bottom shield 114 is attached to both N surface of magnet 1092 and 1094, and S surface of magnet 109, and thus forming internal flux closure in shield 114 between magnets 109, 1092 and 1094. Compared to MAG 124, MAG 126 may produce higher field around tip ends 1111, 1121 and 1131 due to three magnets 109, 1092 and 1092 are used in MAG 126.

Figure 15C:
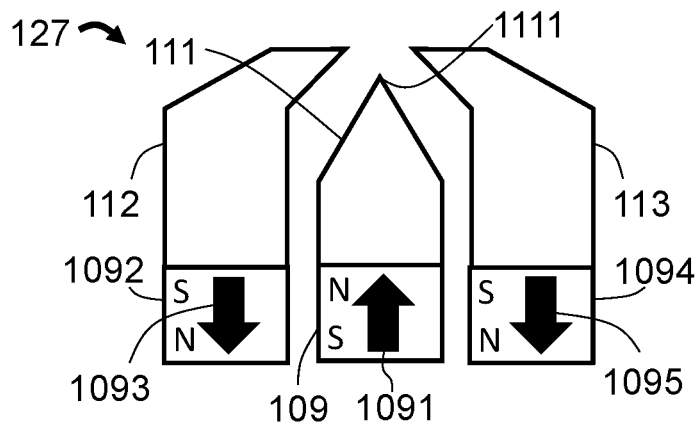
FIG. 15C illustrates cross-sectional view of the seventh embodiment of MAG.

FIG. 15C illustrates cross-sectional view of the seventh embodiment MAG 127. MAG 127 is same as MAG 126 of FIG. 15B, except the bottom shield 114 is removed.

Figure 16:
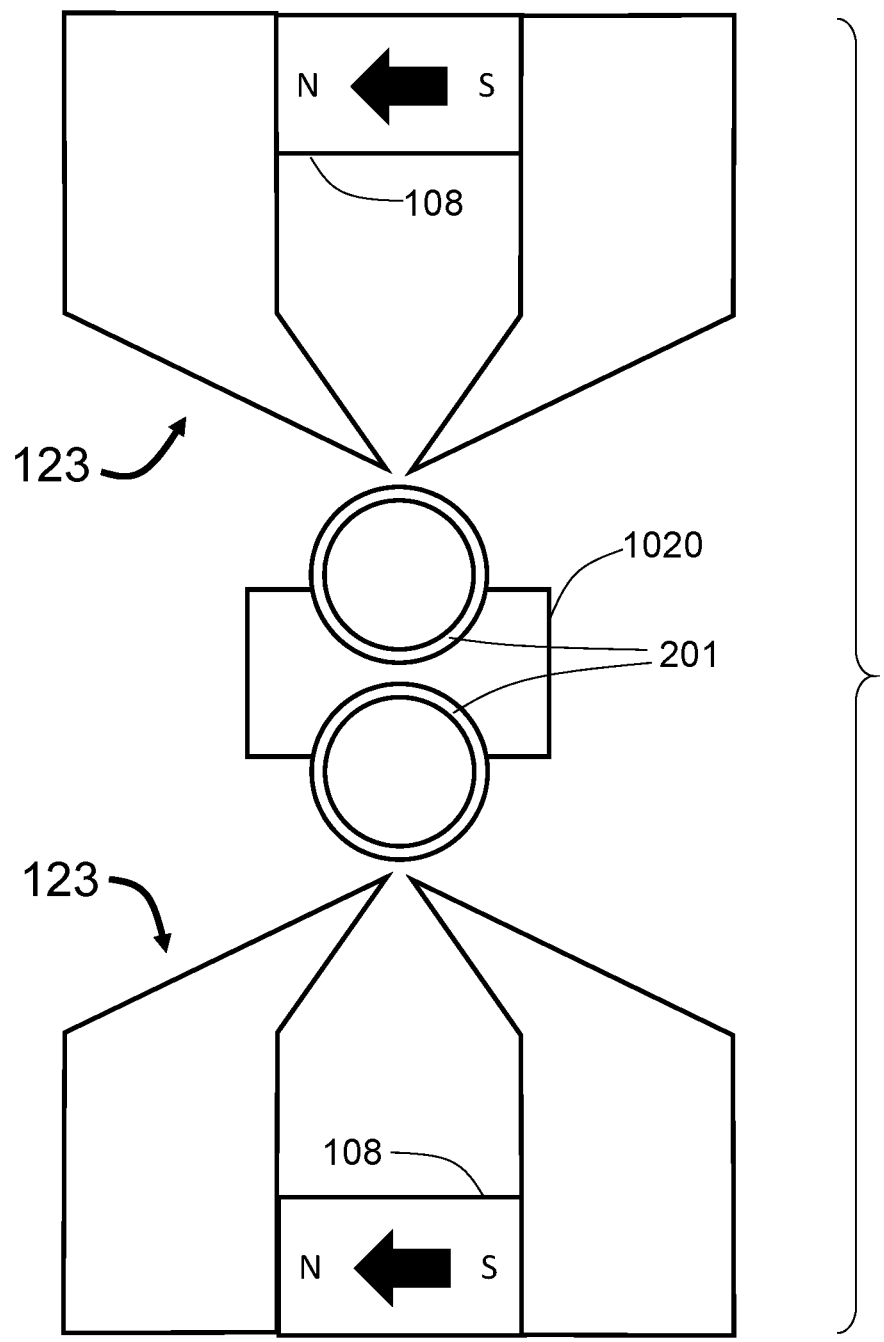
FIG. 16 illustrates cross-sectional view of a pair of third embodiment of MAGs with a pair of flexible channels on a single channel holder.

FIG. 16 illustrates two of the third embodiment MAGs 123 are used for magnetic separation on a pair of flexible channels 201. The pair of flexible channels 201 are fixed on the same channel holder 1020 in FIG. 16. The top MAG 123 and bottom MAG 123 are substantially identical, with top MAG 123 being upside down vertically. MAG wedges of the top and bottom MAGs 123 are substantially aligned with center of top and bottom channels 201. The magnets 108 of both top and bottom MAG 123 may have same magnetization directions, as the arrows within magnets 108 in FIG. 16 indicate, such that the magnetic fields produced in the top and bottom channels 201 by the top MAG 123 and bottom MAG 123 during magnetic separation have same direction horizontal field component, which limits magnetic flux leakage between top MAG 123 soft magnetic poles and bottom MAG 123 soft magnetic poles.

Figure 17:
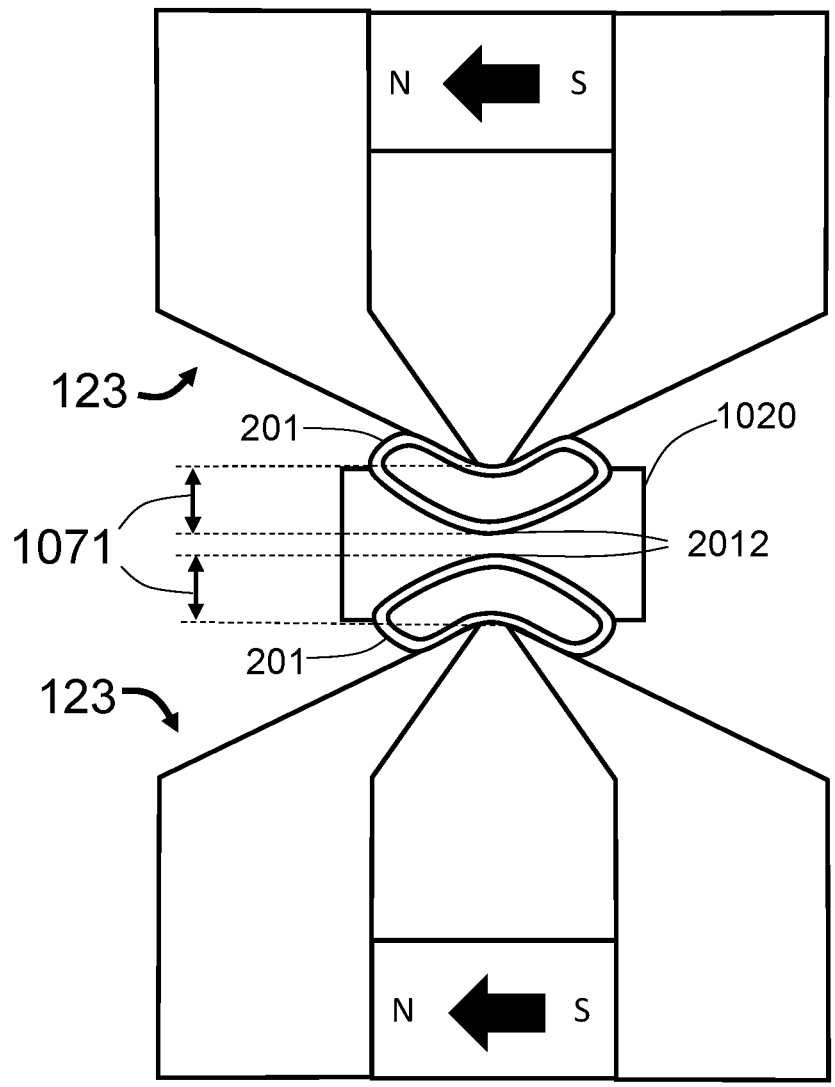
FIG. 17 illustrates cross-sectional view of a pair of third embodiment of MAGs with a pair of flexible channels on a single channel holder in separation position.

FIG. 17 illustrates the two MAG 123 of FIG. 16 are moved into separation position against the two flexible channels 201, which is same process as in FIG. 10. After reaching FIG. 17 separation position, fluid sample carrying cells 10/30 may flow through the channels 201 in length direction perpendicular to the cross-section view to start magnetic separation of cells 10/30 by top and bottom MAG 123. Distance 1071 between the holder 1021 surface contacting the channel 201 outer edge 2012 and MAG 123 tip ends 1021 and 1031, or the imaginary plane where tip ends 1021 and 1031 reside, may be adjusted to optimize flow rate in each of the two channels 201. Range of adjustment of distance 1071 is same as 1071 described in FIG. 10.

MAG 123 in FIG. 16 and FIG. 17 may be replaced by MAG 121 or MAG 122, and channels 201 may also be replaced with channel 101.

Figure 18:
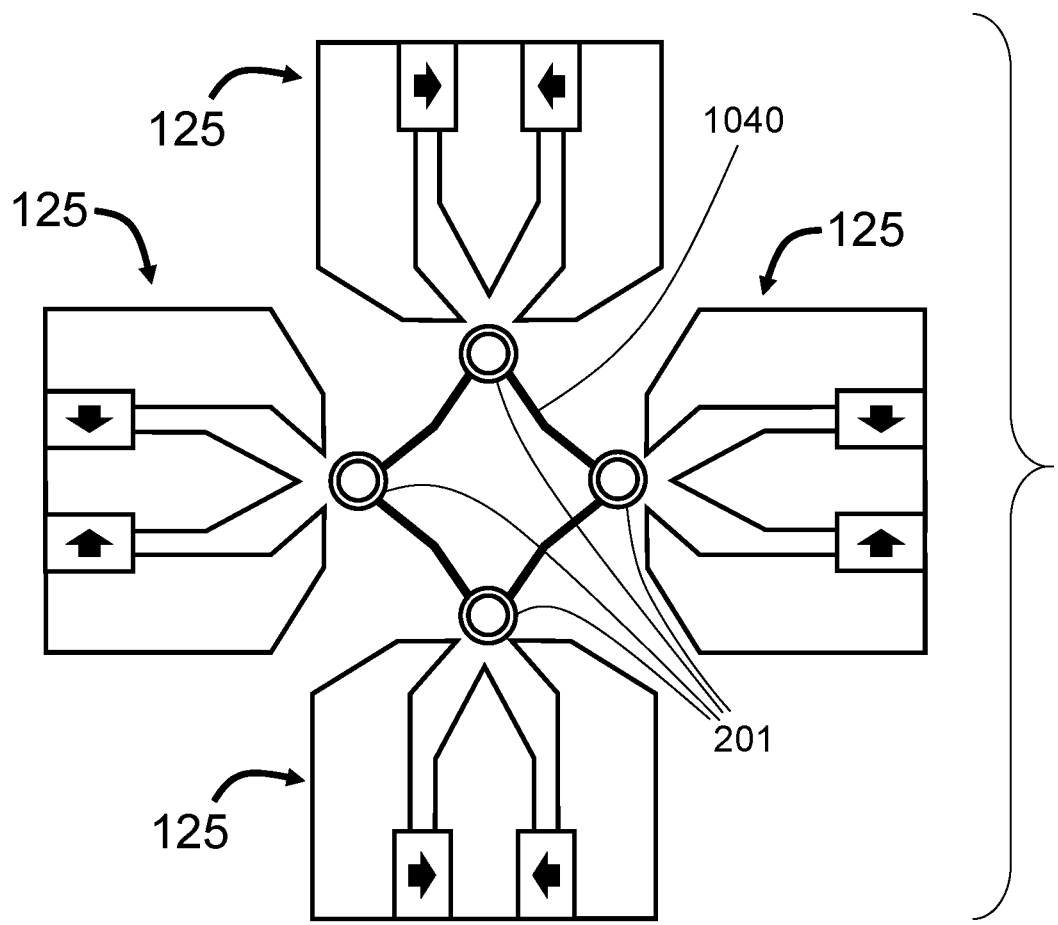
FIG. 18 illustrates cross-sectional view of four of fifth embodiment of MAGs with four flexible channels on a single channel holder.

FIG. 18 illustrates four of the fifth embodiment MAG 125 being used for magnetic separation on four of flexible channels 201. The four flexible channels 201 are fixed on the same channel holder 1040 as in FIG. 18. The four MAG 125 are substantially identical. MAG gaps of the four MAG 125 are substantially aligned with center of each of the corresponding flexible channels 201. The permanent magnets arrangement within each MAG 125 should be identical for example center pole of each of the four MAG 125 is attached to N surfaces of both magnets within each respective MAG 125, and side poles of each of the four MAG 125 are attached to S surfaces of magnets within each MAG 125, as shown in FIG. 18. Thus, neighboring MAG 125 nearest adjacent side poles are of same magnetic polarity, and leakage from side pole to side pole between neighboring MAG 125 may be minimized or avoided. Additionally, four of MAGs used on four of channels 201 in FIG. 18 is only shown in FIG. 18 as an example of multiple channel process capability with a circular channel arrangement, where channels are positioned at center of the MAG 125 circular array. Fewer and more MAG 125 used on corresponding number of channels 201 may be achieved in FIG. 18 type circular arrangement without limitation. FIG. 18 multiple channel circular arrangement with MAG 125 is intrinsically more flexible than MAG 123 as in FIG. 16, as two pole design of FIG. 16 MAG 123 may lead to magnetic flux leakage through the poles of neighboring MAG 123 when number of MAG 123 is more than two.

Figure 19:
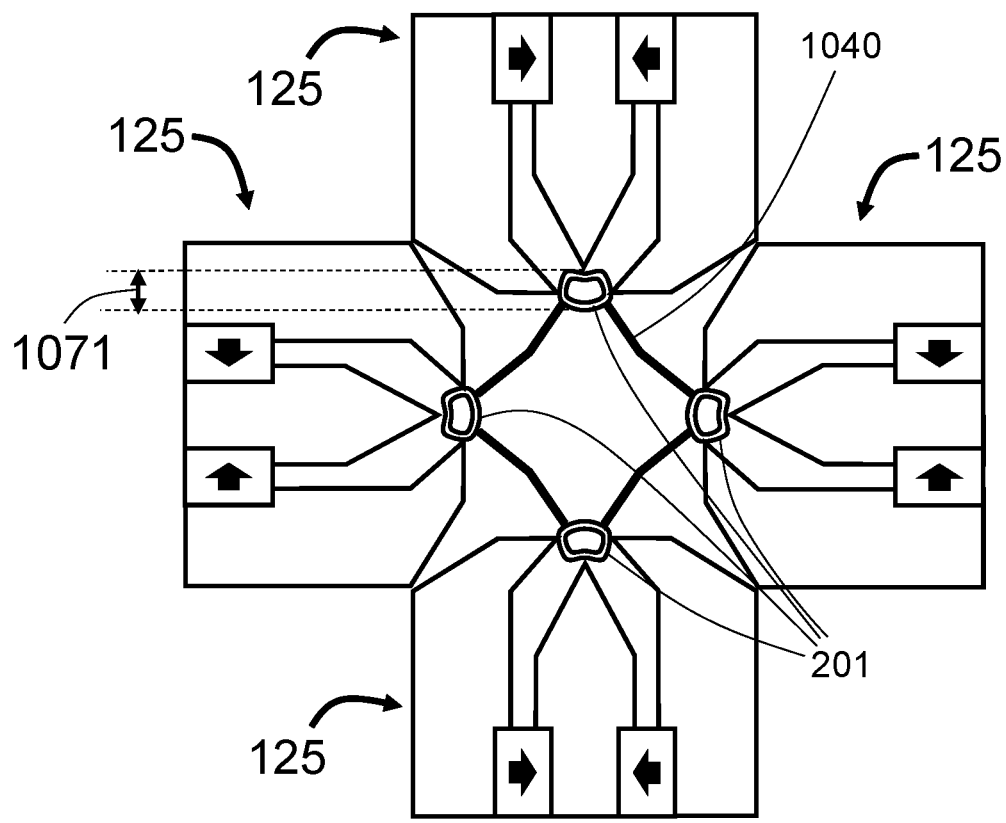
FIG. 19 illustrates cross-sectional view of four of fifth embodiment of MAGs with four flexible channels on a single channel holder in separation position.

FIG. 19 illustrates the four MAG 125 of FIG. 18 are moved into separation position against the four flexible channels 201, which is same process as in FIG. 14. After reaching FIG. 19 separation position, fluid sample carrying cells 10/30 may flow through the channels 201 in length direction perpendicular to the view of FIG. 19 to start magnetic separation of cells 10/30 by the four MAG 125. Similarly as in FIG. 17, distance 1071 between the holder 1040 surface contacting the channel 201 outer edge 2012 and MAG 125 center pole 111 tip end 1111 for each channel 201 and MAG 125 pair may be adjusted to optimize flow rate in each of the four channels 201. Range of adjustment of distance 1071 is same as 1071 described in FIG. 10.

MAG 125 in FIG. 18 and FIG. 19 may be replaced by MAG 124, MAG 126, or MAG 127, and where channels 201 may also be replaced with channel 301.

FIG. 20A illustrates the sixth embodiment of MAG 128 with having a rotated "D" shape rigid channel 320 in separation position. MAG 128 is similar to MAG 123, except that MAG wedge of MAG 123 is modified from a triangle shape to a flat top as in MAG 128. MAG 128 pole 1022 is similar to pole 102 of MAG 123, but with a flat top surface 1042 in pole 1022 instead of a tip end in pole 102. Same flat top 1052 exists on pole 1032 which is similar to pole 103 of MAG 123. Due to the flat top of the MAG wedge in MAG 128, rigid channel 320 may have a flat bottom surface 1062 matching to, and being in contact with, the MAG wedge flat surface in separation position, to gain highest magnetic field and field gradient region from MAG 128. Channel 320 may be attached to a non-magnetic channel holder 1102 at the top surface. Channel holder 1102 may align channel 320 to MAG wedge of MAG 128, move channel 320 to separation position in contact with MAG 128 poles 1022 and 1032 tip ends, or lift channel 320 away from MAG 128 after magnetic separation.

FIG. 20B illustrates the sixth embodiment MAG 128 being used on a flexible channel 201, where channel 201 is attached to channel holder 1102. Channel holder 1102 moves channel 201 towards MAG wedge of MAG 128 along direction 1014.

FIG. 20C illustrates the sixth embodiment MAG 128 having the flexible channel 201 of FIG. 20B moved into separation position with cells 10/30 being separated from a liquid sample to form conglomerate at bottom surface of channel 201 against the top flat surface of the MAG wedge of MAG 128. Channel 201 is forced to form into a rotated "D" shape channel by holder 1102 pushing channel 201 against the flat top of MAG wedge of MAG 128, where channel 201 shape at separation position shows similarity to channel 320 of FIG. 20A. Distance 1071 between the holder 1102 bottom surface 1062 contacting the channel 201 top edge 2012 and MAG 128 pole surfaces 1042 and 1052 may be adjusted to optimize flow rate in channel 201. Range of adjustment of distance 1071 is same as 1071 described in FIG. 10.

Magnet 108 of MAG 128 may be replaced by placement of magnets 104 and 105 as in MAG 121, and by placement of magnets 104 and 105 and bottom shield 106 as in MAG 122.

FIG. 21A illustrates the seventh embodiment MAG 129 with having a "V" shape rigid channel 330 in separation position. MAG 129 is different from MAG 123 in pole shape, where pole 1024 and pole 1034 of MAG 129 have flux concentration tip ends 3301 and 3302 that forms a "V" shaped concave, instead of the triangle wedge shape of the MAG 123. With the V shape MAG concave of MAG 129, rigid channel 330 is also made into a V shape, with the lower edges 3303 and 3304 making direct contact with the surface of the tip ends 3301 and 3302. Additionally, channel 330 may also preferably have a V shape notch into the channel at the top edge 3305 following the V shape of the 3303 and 3304 edges, which helps confine fluid sample in the V shaped channel space 3306 to flow closer to the pole surfaces 3303 and 3004 that provide higher field and field gradient. Channel 330 may be attached to a non-magnetic channel holder 1103 at the top surface 3305. Channel holder 1103 may align channel 330 to MAG concave of MAG 129, move channel 323 to separation position in contact with poles 1024 and 1034 tip ends surface, or lift channel 330 away from MAG 129 after magnetic separation.

FIG. 21B illustrates the seventh embodiment MAG 129 being used with a flexible channel 201, where channel 201 is attached to channel holder 1103 at the top edge of channel 201. Channel holder 1103 moves channel 201 towards MAG 129 concave along direction 1014. Channel holder 1103 has a triangle shape, where a convergence point of the triangle touches the channel 201 top edge.

FIG. 21C illustrates the seventh embodiment MAG 129 having the flexible channel 201 of FIG. 21B moved into separation position with cells 10/30 being separated from a liquid sample to form conglomerate at bottom surface of channel 201 against the top surfaces of the MAG concave of tip ends 3301 and 3302 of MAG 129. Channel 201 is forced to form into a "V" shape channel by holder 1103. In FIG. 21C, holder 1103 forces channel 201 against the MAG concave of MAG 129 with the lower convergence point and deforms the top wall of the channel 201 downwards to move closer to the tip ends 3301 and 3302, while the same force also causes lower wall of channel 201 to conform to the MAG concave of MAG 129 to make contact with the tip ends 3301 and 3302 top surfaces 3303 and 3304. Thus, channel 201 shape in FIG. 21C at separation position shows V shape similar to channel 330 of FIG. 21A, which brings cells 10/30 in channel space 3306 closer to high field and high gradient tip ends 3301 and 3302 and tip surfaces 3303 and 3304. Vertical distance 1071 between the holder 1103 bottom convergence point contacting the channel 201 top edge 2012, and MAG 129 tip ends 3301 and 3302 or an imaginary plane where tip ends 3301 and 3302 reside, may be adjusted to optimize flow rate in channel 201. Range of adjustment of distance 1071 is same as 1071 described in FIG. 10.

Magnet 108 of MAG 129 may be replaced by placement of magnets 104 and 105 as in MAG 121, and by placement of magnets 104 and 105 and bottom shield 106 as in MAG 122.

Figure 22A:
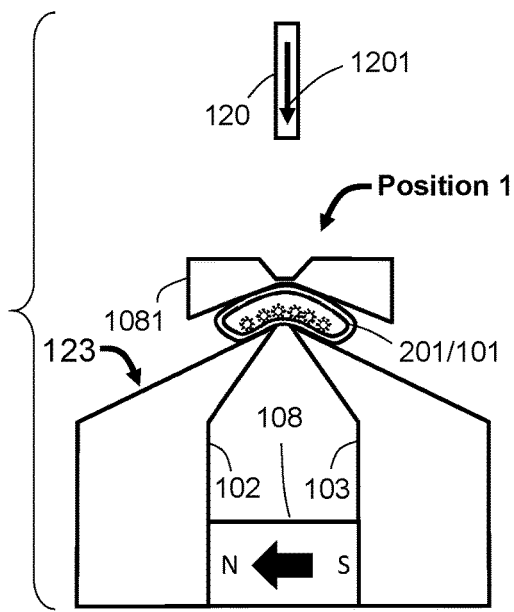
FIG. 22A illustrates the third embodiment of MAG having a flexible channel in separation position with cells being separated, and a demagnetization ("DMAG") magnet positioned over and away from MAG.

From FIG. 22A through FIG. 27D, various methods to demagnetize or dissociate magnetically separated cells 10/30 from conglomerate in MAG channel will be described. For simplicity of description, flexible channel 201 is used. However, channels in FIG. 22A through FIG. 27D may be labeled as "201/101", indicating flexible channel 201 as used for description may be replaced with rigid channel 101 without affecting the function and results of the described method. Also for the simplicity of description, MAG 123 is used in FIG. 22A through FIG. 27D, while any other MAG embodiment together with corresponding channel as described in prior figures may be used under same concepts without limitation FIG. 22A is substantially similar to FIG. 10, where channel 201 is at separation position and cells 10/30 have been separated by magnetic field from MAG. In FIG. 22A, MAG 123 is used instead of MAG 121 of FIG. 10. Channel holder 1081 may be different from channel holder 107 of FIG. 10 by having a top surface notch that allows the cells 10/30 demagnetization or dissociation magnetic structure ("DMAG"), which is permanent magnet 120 in FIG. 22A, to be able to reach closer to the channel 201/101 to provide sufficient field to demagnetize or dissociate cells 10/30 from the conglomerate in channel 201/101. Such notch is preferred, but may not be required. DMAG magnet 120 is positioned away from MAG 123 of FIG. 22A without affecting magnetic separation of cells 10/30 by MAG 123. DMAG magnet 120 magnetization is labeled as in vertical direction 1201, but may also be in horizontal direction without causing functional difference. Channel 201/101 position relative to the MAG 123 and DMAG 120 in FIG. 22A is "Position 1".

Figure 22B:
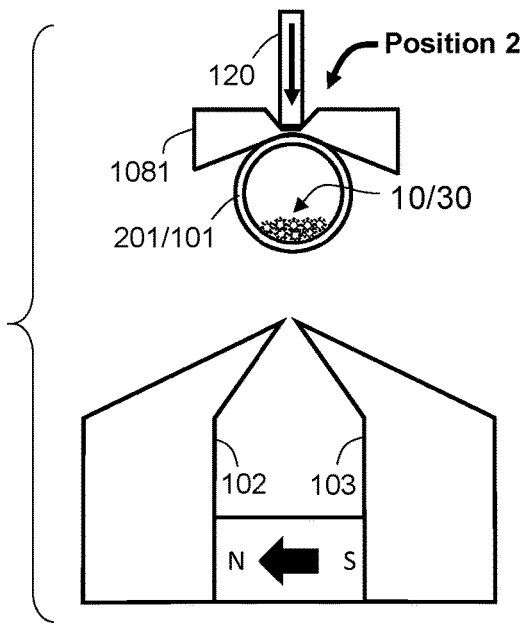
FIG. 22B illustrates the flexible channel of FIG. 22A departing MAG and moving into position where flexible channel holder is in close proximity to, or contacts, the DMAG magnet.

FIG. 22B is similar to FIG. 11, where channel holder 1081 moves channel 201/101 away from MAG 123 and come into contact with, or is in close proximity to, DMAG magnet 120 at the top surface of holder 1081, where the magnet 120 may fit into the notch of holder 1081 to provide highest magnetic field on cells 10/20 conglomerate in channel 201/101. Cells 10/30 form conglomerate after magnetic separation by MAG and do not break free from the conglomerate automatically due to SPL 2 on cells 10/30 not self-demagnetize when they are part of a conglomerate. By removing cells 10/30 gradually with magnetic field gradient from magnet 120, for example cells 10/30 with higher magnetic moment SPL 2 that respond to weaker magnetic field from DMAG 120 faster, conglomerate may reach to a critical volume that remaining cells 10/30 in the conglomerate do not see enough magneto-static field from other cells 10/30 and will self-demagnetize into individual cells 10/20 due to the regained superparamagnetic nature of SPL 2. Therefore, to dissociate cells 10/30 from conglomerate, removing certain amount of cells 10/30, or breaking up the conglomerate from a continuous large piece into multiple smaller pieces will help cells 10/30 to achieve self-demagnetization. Channel 201/101 position relative to the MAG 123 and DMAG 120 in FIG. 22B is "Position 2". Channel 201 compared to channel 101 may have an advantage during cells 10/30 dissociation by DMAG magnet 120, as channel 201 provides a larger channel space that allows farther separation between free cells 10/30 and from conglomerate, or between broken-up conglomerate pieces, which helps reduce magneto-static coupling and enhances self-demagnetization speed of SPL 2 on cells 10/30. For flexible channel 201, before Position 2 or at Position 2, it is preferred to fill the channel 201 with additional buffer fluid to return the channel 201 to circular shape for larger channel space.

Figure 22C:
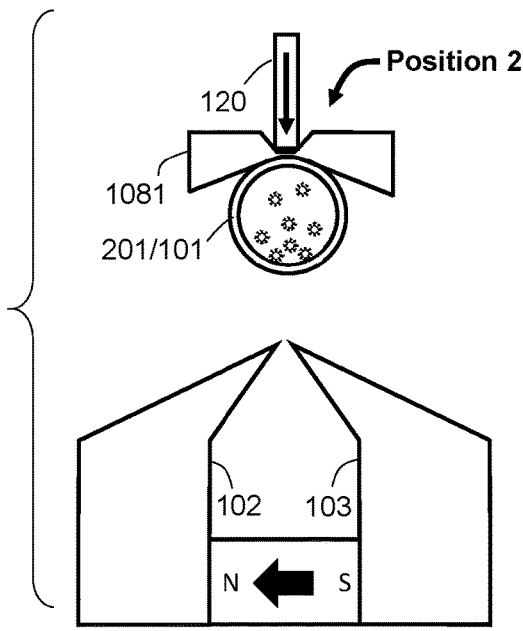
FIG. 22C illustrates the cells in the flexible channel of FIG. 22B being dissociated from conglomerate by the DMAG magnet.

FIG. 22C illustrates the cells 10/30 in the channel 201/101 of FIG. 22B being dissociated from conglomerate by the DMAG magnet 120 at Position 2.

Figure 22D:
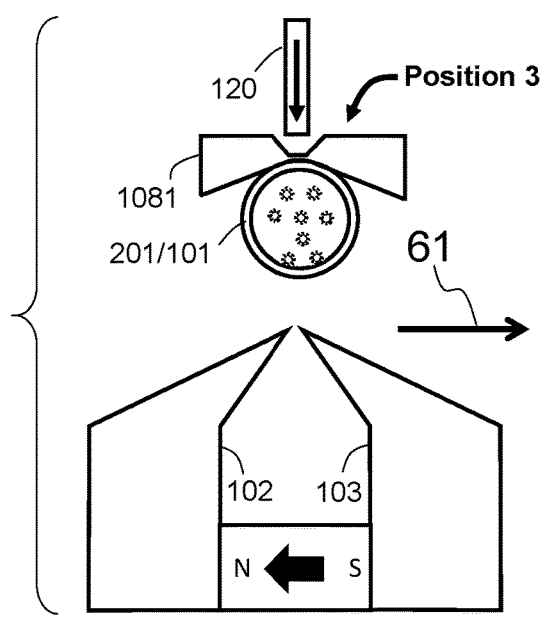
FIG. 22D illustrates the flexible channel of FIG. 22C moving into a low magnetic field position between MAG and DMAG magnet.

FIG. 22D illustrates the channel holder 1081 moves channel 201/101 from FIG. 22C DMAG Position 2 to a position, "Position 3", between MAG 123 and DMAG magnet 120. At Position 3, combined field on the cells 10/30 within channel 201/101 may be the smallest, which may help SPL 2 to self-demagnetize. Channel 201/101 may be kept at Position 3 for extensive time to allow SPL 2 and cells 10/30 to fully self-demagnetize and conglomerate to dissociate.

For an effective break up of conglomerate, mechanical agitations may be added to the conglomerate by the magnetic force exerted by MAG and DMAG magnets. For example, channel holder 1081 may alternate channel 201/101 between Positions 1 and 2, or Positions 2 and 3, or Positions 1, 2 and 3, such that alternating magnetic force by MAG and DMAG may move whole or part of the conglomerate in the channel space, thus helping break up the conglomerate into smaller pieces or cause enough cells 10/30 to break free from the conglomerate and conglomerate may self-dissociate. After conglomerate is sufficiently dissociated, free cells 10/30 may be flushed out of channel 201/101 at Position 3 or Position 2.

Figure 23A:
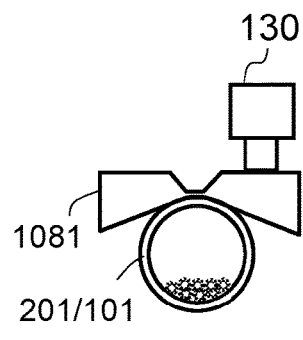
FIG. 23A illustrates mechanical vibration is applied to a flexible channel holder by a motor after cells are magnetically separated inside the flexible channel.

FIG. 23A illustrates mechanical vibration may be applied to the channel holder 1081 by a motor 130 when channel 201/101 is at Position 2 or Position 3 of FIG. 22B and FIG. 22C. Such vibration may be transferred from holder 1081 through wall of channel 201/101 and into the fluid within the channel 201/101 to cause localized turbulence flow at various locations within the channel 201/101, which may help mechanically break up the conglomerate into small pieces to assist conglomerate dissociation.

Figure 23B:
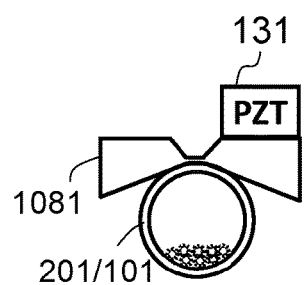
FIG. 23B illustrates ultrasound vibration is applied to a flexible channel holder by a piezoelectric transducer ("PZT") after cells are magnetically separated inside the flexible channel.

FIG. 23B illustrates ultrasound vibration by a piezoelectric transducer ("PZT") 131 may be applied to the channel holder 1081. Similar to FIG. 23A, ultrasound vibration may be transferred into the fluid within the channel 201/101 to cause localized high frequency turbulence within the channel 201/101, which may help mechanically break up the conglomerate into small pieces to assist conglomerate dissociation.

Figure 23C:
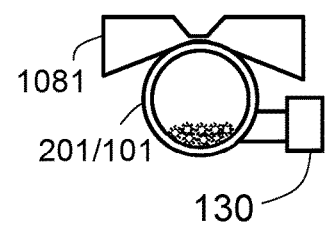
FIG. 23C illustrates mechanical vibration is applied to a flexible channel by a motor after cells are magnetically separated inside the flexible channel.

FIG. 23C illustrates mechanical vibration of FIG. 23A may be applied to the channel 201/101 wall directly by motor 130.

Figure 23D:
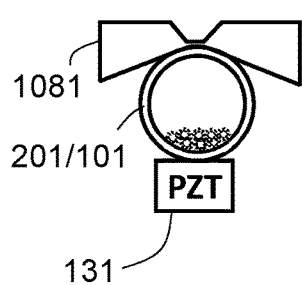
FIG. 23D illustrates ultrasound vibration is applied to a flexible channel by a PZT after cells are magnetically separated inside the flexible channel.

FIG. 23D illustrates ultrasound vibration of FIG. 23B may be applied to the channel 201/101 wall directly by PZT 131.

Figure 23E:
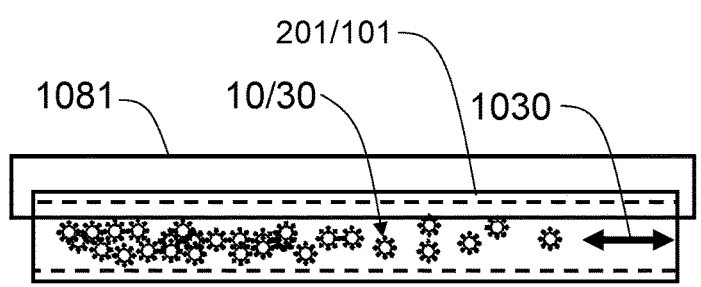
FIG. 23E is a side view of the flexible channel of FIG. 22D.

FIG. 23E is a side view of the channel 201/101 along the direction 61 as in FIG. 22D. Arrow 1030 represents alternating direction pulsed fluid flow may be applied to the channel liquid sample to produce a flow jittering in the liquid within the channel 201/101, which may also produce local turbulence flow with fluid in channel 201/101 to help mechanically break up the conglomerate into small pieces to assist conglomerate self-dissociation. FIG. 23E alternating pulsed flow may be combined with FIG. 23A through FIG. 23D vibration methods to apply to channel 201/101 at Position 2 or Position 3 of FIG. 22B through FIG. 22D.

When conglomerate in channel 201/101 is of large size, multiple rounds of cells 10/30 dissociation with FIG. 22B to FIG. 23E methods, and flushing of cells 10/30 out of channel 201/101, may be used. During each flush, a certain part of cells 10/30 may be washed out of channel, making dissociation of remaining cells 10/30 still in the conglomerate in channel 201/101 easier in next round.

Figure 24A:
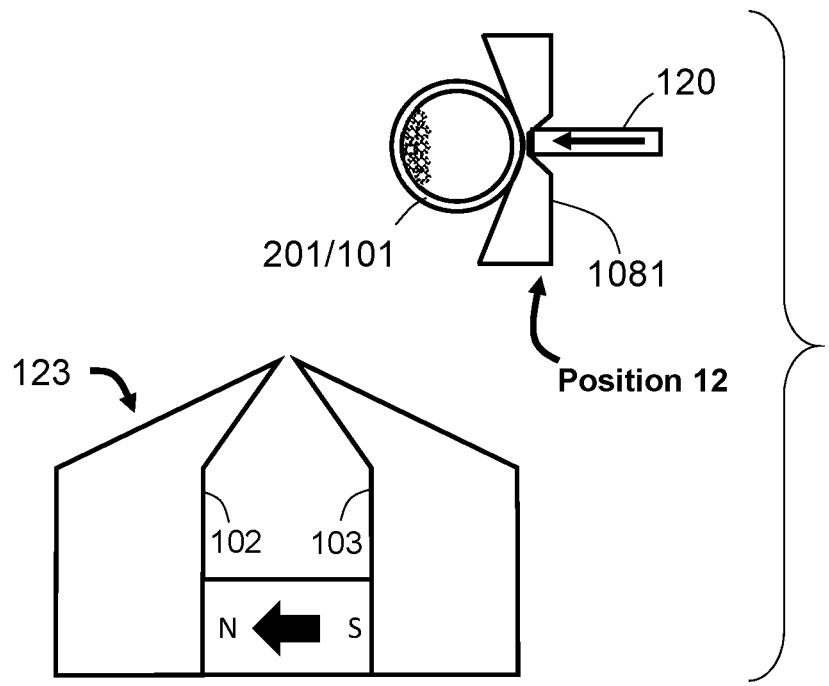
FIG. 24A illustrates the third embodiment of MAG having a flexible channel holder in close proximity to, or in contact with, a DMAG magnet after cells are magnetically separated by MAG, where DMAG magnet is positioned on the side and away from MAG.

FIG. 24A is similar to FIG. 22B, where channel holder 1081 is in contact, or in close proximity to, DMAG magnet 120 after cells 10/30 are magnetically separated by MAG 123. Different than in FIG. 22B, DMAG magnet 120 of FIG. 24A is positioned on the side of and away from MAG 123, and holder 1081 is also rotated compared to FIG. 22B to fit its top surface notch to the magnet 120. Placement of magnet 120 in FIG. 24 may reduce magnetic field interference between MAG 123 and DMAG magnet 120. Channel 201/101 position relative to the MAG 123 and DMAG 120 in FIG. 24A is "Position 12".

Figure 24B:
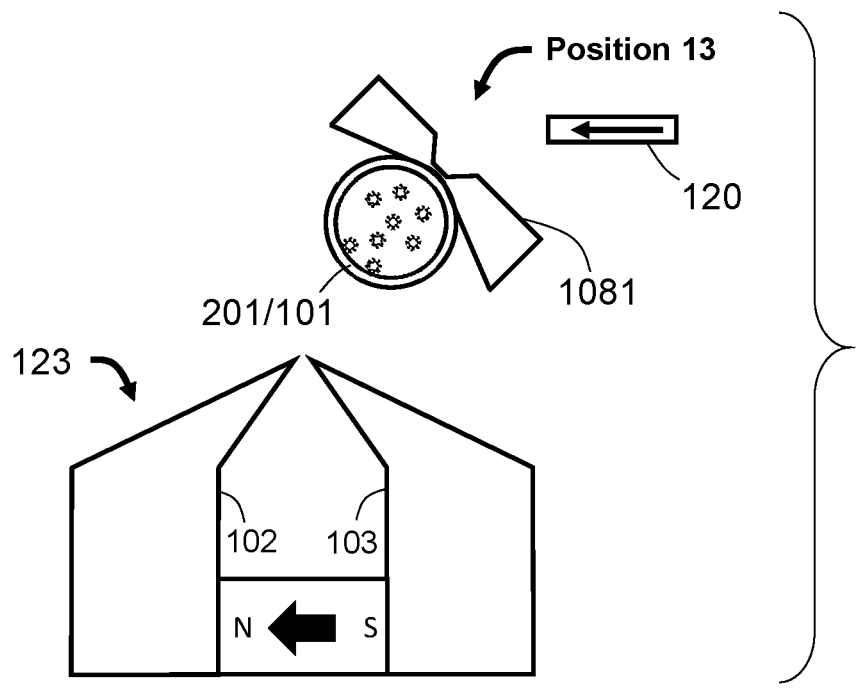
FIG. 24B illustrates the flexible channel of FIG. 24A rotating into a low magnetic field position between MAG and DMAG magnet.

FIG. 24B illustrates that after cells 10/30 are dissociated at Position 12 of FIG. 24A, the channel 201/101 together with channel holder 1081 of FIG. 24A are rotated away from magnet 120 of FIG. 24A into a position between MAG 123 and DMAG magnet 120, where combined magnetic field from MAG 123 and DMAG magnet 120 on channel 201/101 and cells 10/30 therein is lowest, which is similar to Position 3 of FIG. 22D. Channel 201/101 position relative to the MAG 123 and DMAG 120 in FIG. 24B is "Position 13".

FIG. 25A illustrates DMAG structure that is same as in FIG. 22B, where DMAG structure includes only permanent magnet 120 with magnetization 1201.

FIG. 25B illustrates DMAG structure that includes permanent magnet 120 and a soft magnetic pole 1202 with convergence shape towards channel 201/101. Soft magnetic pole 1202 convergence shape helps concentrate magnetic flux from magnet 120 to produce higher field and high field gradient on cells 10/30 in channel 201/101 at Position 2 to more effectively demagnetize and dissociate the conglomerate of cells 10/30.

FIG. 25C illustrates DMAG structure that includes permanent magnet 120 and a pair of soft magnetic poles 1203 and 1204. Magnetization 1201 of magnet 120 is in horizontal direction, and each of poles 1203 and 1204 has an convergence shape pointing towards channel 201/101, where the convergence ends of poles 1203 and 1204 form a DMAG gap sitting in, or in close proximity to, the channel holder 1081 top surface notch, where flux from magnet 120 is conducted by the poles 1203 and 1204 and concentrated in the DMAG gap to produce high field and high field gradient on cells 10/30 in channel 201/101 at Position 2 to more effectively demagnetize and dissociate the conglomerate of cells 10/30.

FIG. 25D illustrates DMAG structure that includes an electromagnet including a soft magnetic core 1205 and coils 1206, where electric current following in the coils 1206 may produce magnetization in core 1205 in directions of 1207, and core 1205 functions like magnet 120 to product magnetic field on cells 10/30 in channel 201/101 at Position 2 to demagnetize or dissociate the conglomerate of cells 10/30. By changing the electric current amplitude and direction in coils 1206, magnetic field from core 1205 on cells 10/30 may change strength and direction. In one embodiment, DC current is applied to coils 1206. In another embodiment, AC current with alternating polarities is applied to coils 1206. In yet another embodiment, current applied to coils 1206 is programmed to vary in amplitude, or in direction, or in frequency, or in amplitude ramp up or ramp down rates, to more effectively demagnetize and dissociate the conglomerate of cells 10/30.

FIG. 25E illustrates that motor 130 as shown in FIG. 23A may produce mechanical vibrations on DMAG structure of FIG. 25C, such vibrations may transfer from DMAG structure to holder 1081 through DMAG structure to holder 1081 contact, and finally transferred to fluid in channel 201/101, where DMAG structure can be changed to any of DMAG structures described in FIG. 25A through FIG. 25D.

FIG. 25F illustrates that PAT 131 as shown in FIG. 23B may produce ultrasound vibrations on DMAG structure of FIG. 25C, such vibrations may transfer from DMAG structure to holder 1081 through DMAG structure to holder 1081 contact, and finally transferred to fluid in channel 201/101, where DMAG structure can be changed to any of DMAG structures described in FIG. 25A through FIG. 25D.

To achieve demagnetization and dissociation of cells 10/30 from conglomerate in channel 201/101, an alternative method as described in FIG. 26A through FIG. 26D may be used without using a DMAG structure, where function of DMAG structure is achieved with same MAG.

FIG. 26A is same as FIG. 22A, where channel 201/101 is at separation position and cells 10/30 are separated by magnetic field of MAG 123 in channel 201/101, except channel holder 1082 may not have the top surface notch as holder 1081. Channel 201/101 position relative to the MAG 123 in FIG. 26A is "Position 21".

FIG. 26B illustrates channel 201/101 of FIG. 26A is lifted from MAG 123 to a lower field position, "Position 22". At Position 22 channel 201/101 may rotate around its center as indicated by arrow 210, preferable by 180 degrees. Such rotation may require channel 201/101 not being permanently fixed to holder 1082

FIG. 26C illustrates channel 201/101 of FIG. 26B after rotation of 180 degrees at Position 22, the cells 10/30 conglomerate formed on inner wall of channel 201/101 rotates together with channel wall to be at the top end of the channel 201/101 relative to MAG 123.

FIG. 26D illustrates that channel 201/101 is moved from Position 22 closer to MAG 123 to a Position 23 in between Position 21 and Position 22, where magnetic field from MAG 123 on cells 12/30 is stronger than Position 22 but weaker than Position 21. Cells 10/30 in conglomerate at top end of channel 201/101 may then be pulled away by MAG 123 field from conglomerate and demagnetization and dissociation of conglomerate may start. The process of FIG. 26B through FIG. 26D may repeat multiple times, where channel 201/101 may return to Position 22 from Position 23 to perform another rotation and then move back to Position 23, until cells 10/30 are sufficiently dissociated in channel 201/101. At end of demagnetization, cells 10/30 may be flushed out of channel 201/101 preferably at Position 22. Mechanical vibrations and flow jittering as described in FIG. 23C through FIG. 23E may be applied to channel 201/101 at Position 22 and Position 23.

Figure 27A:
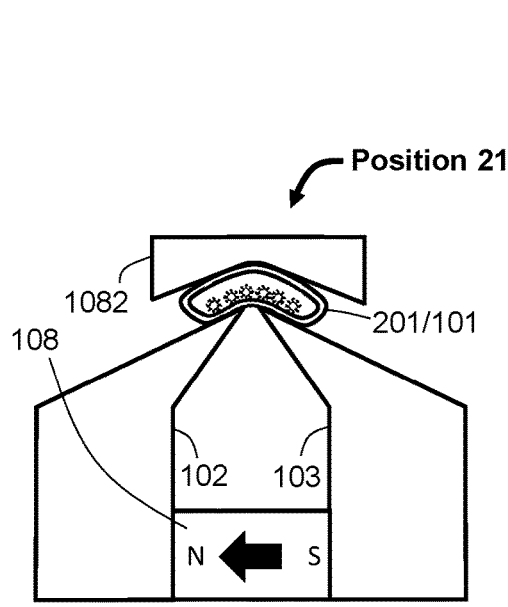
FIG. 27A illustrates the third embodiment of MAG having a flexible channel in separation position with cells being separated.

FIG. 27A is same as FIG. 26A, where channel 201/101 is at separation position and cells 10/30 are separated by magnetic field of MAG 123. Channel 201/101 position relative to the MAG 123 is "Position 21". Channel 201/101 is attached to holder 1082 in FIG. 27A.

Figure 27B:
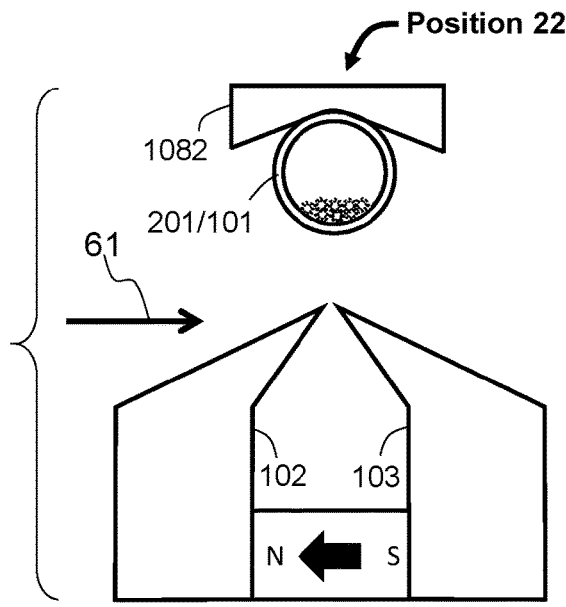
FIG. 27B illustrates the flexible channel and its holder of FIG. 27A depart from MAG.

FIG. 27B illustrates channel 201/101 of FIG. 27A is lifted from MAG 123 to lower field Position 22 by holder 1082.

Figure 27C:
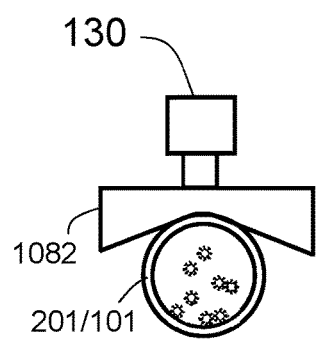
FIG. 27C illustrates mechanical vibration is applied to the channel holder by a motor.

FIG. 27C illustrates that at Position 22, dissociation of cells 10/30 in channel 201/101 may be achieved only through mechanical vibration exerted by motor 130. FIG. 27C shows that motor 130 applies mechanical vibration to holder 1082, where such vibration may be transferred from holder 1082 through wall of channel 201/101 and into the fluid within the channel 201/101 to cause localized turbulence flow at various locations within the channel 201/101, which may help mechanically break up the conglomerate into small pieces to assist self-dissociation of cells 10/30 conglomerate. Motor 130 may also exert vibration directly on channel 201/101 as shown in FIG. 23C instead of through holder 1082. Alternating direction pulsed fluid flow as described in FIG. 23E may be applied to the channel liquid sample to produce a flow jittering in the liquid within the channel 201/101 at the same time of motor 130 vibration application.

Figure 27D:
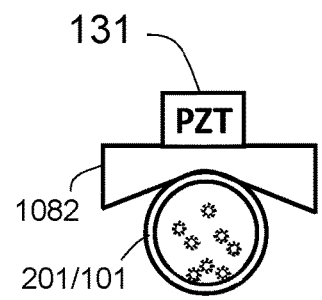
FIG. 27D illustrates ultrasound vibration is applied to the channel holder by a PZT.

FIG. 27D illustrates that at Position 22, dissociation of cells 10/30 in channel 201/101 may be achieved primarily through ultrasound vibration exerted by PZT 131. FIG. 27D shows that PZT 131 applies ultrasound vibration to holder 1082, where the ultrasound vibration may be transferred into the fluid within the channel 201/101 to cause localized high frequency turbulence within the channel 201/101, which may help mechanically break up the conglomerate into small pieces to assist self-dissociation of cells 10/30 conglomerate. PZT 131 may also exert ultrasound vibration directly on channel 201/101 as shown in FIG. 23D. Alternating direction pulsed fluid flow as described in FIG. 23E may be applied to the channel liquid sample to produce a flow jittering in the liquid within the channel 201/101 at the same time of PZT 131 ultrasound vibration application.

FIG. 28A through FIG. 30B describe embodiments of methods to assist cells 10/30 conglomerate dissociation by mechanical agitations, which may be applied to channel 201/101 as in FIG. 27B at Position 22 and applied to channel 201/101 as in FIG. 22B through FIG. 22D, FIG. 23A through FIG. 23D, FIG. 24A through FIG. 25F, FIG. 26B through FIG. 26D, FIG. 27B through FIG. 27D.

Figure 28A:
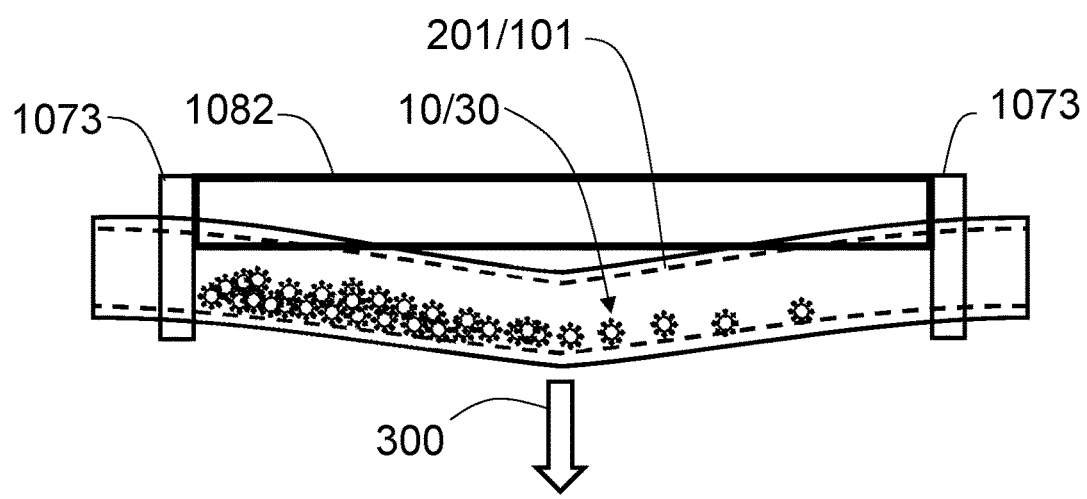
FIG. 28A illustrates a side view of a flexible channel where there flexible channel is mechanically stretched.

FIG. 28A shows a side view of channel 201/101 and holder 1082 along direction 61 of FIG. 27B, where cells 10/30 are magnetically separated by MAG field and form conglomerate on lower side of the channel 201/101 wall. Channel mounts 1073 may be used to attach channel 201/101 to channel holder 1082. Channel mounts 1073 may fix channel 201/101 at sections attached to mounts 1073 as anchors against channel 201/101 deformation, compression or elongation during mechanical agitation process. Channel mounts 1073 may also perform a valve function that closes fluid flow into or out of flexible channel 201 section between two channel mounts 1073 before mechanical agitation process of FIG. 28A, such that fluid enclosed in channel 201 may more efficiently produce localized turbulence within the channel 201. FIG. 28A illustrates that an externally applied force 300 may stretch or deform the channel 201/101 in a direction away from the holder 1082, for example perpendicular to the channel 201/101 length direction. Such deformation or stretch of channel 201/101 builds up elastic energy in the channel 201/101 wall material.

Figure 28B:
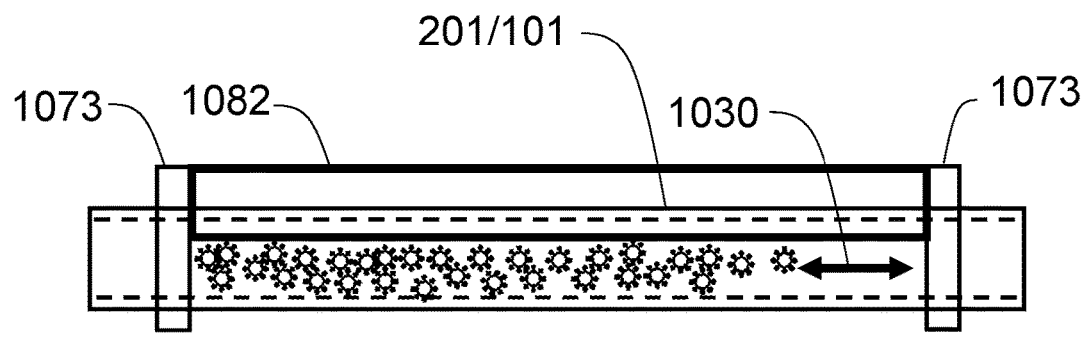
FIG. 28B illustrates cells being dissociated from conglomerate after removal of the external force of FIG. 28A.

FIG. 28B illustrates that force 300 of FIG. 28A is released, and elastic energy built up in channel 201/101 wall acts to spring back channel 201/101 towards its original non-deform and non-stretch position. Depending on channel 201/101 wall material property, such spring back may provide a transient turbulence flow at various locations within the channel 201/101, which may help mechanically break up the cells 10/30 conglomerate into smaller pieces to assist self-dissociation of cells 10/30 conglomerate. After release of force 300 and channel 201/101 spring back, alternating flow 1030 may be applied similarly as in FIG. 23E to assist dissociation process of conglomerate of cells 10/30, where valve function of 1073 may turn off to allow fluid flow within channel 201/101.

The FIG. 28A and FIG. 28B channel 201/101 deform/stretch and release process may be repeated as many times as needed until conglomerate of cells 10/30 are sufficiently dissociated, which may then be flushed out of channel 201/101by buffer fluid.

Figure 29A:
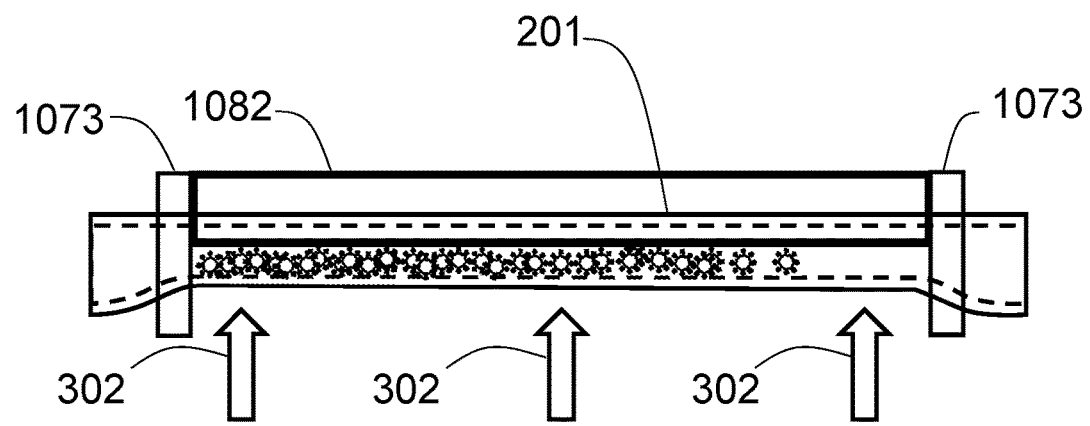
FIG. 29A illustrates a side view of a flexible channel where the flexible channel is mechanically compressed.

FIG. 29A illustrates an alternative method of mechanical agitation from FIG. 28A. Every aspect is same as in FIG. 28A, except that a compressive force 302 may be applied to compress channel 201 in direction perpendicular to the channel 201 length direction, for example compressing channel 201 against channel holder 1082 as shown in FIG. 29A. As liquid within channel 201 has limited compressibility, force 302 may cause channel 201/101 wall to expand in direction perpendicular to the view of FIG. 29A, i.e. in direction perpendicular to both channel length direction and force 302 direction. Such expansion of channel 201/101 wall will again build up elastic energy in the channel 201 wall material.

Figure 29B:
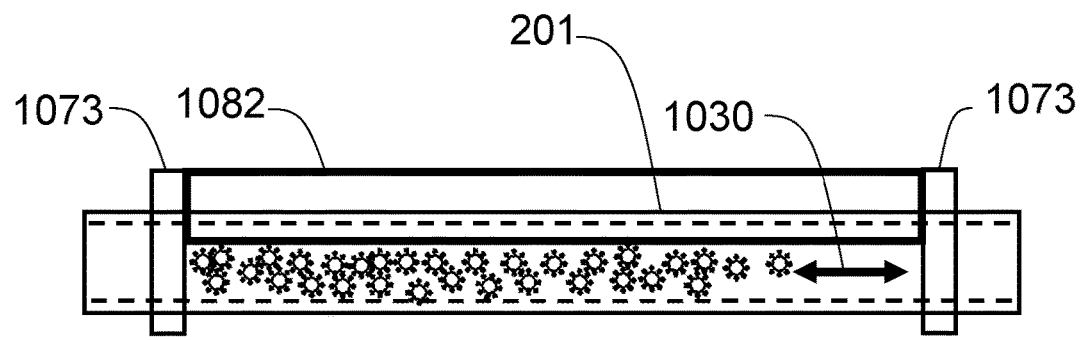
FIG. 29B illustrates cells being dissociated from conglomerate after removal of the external force of FIG. 29A.

FIG. 29B is same as FIG. 28B in every aspect, except that FIG. 29B is after compressive force 302 of FIG. 29A is released, and elastic energy built up in channel 201 wall acts to spring back channel 201 to its original non-compressed shape. Such spring back may provide a strong transient turbulence flow at various locations within the channel 201, which may help mechanically break up the cells 10/30 conglomerate into smaller pieces to assist self-dissociation of cells 10/30 conglomerate. After release of force 302 and channel 201 shape spring back, alternating flow 1030 may be applied similarly as in FIG. 23E to assist dissociation process of conglomerate of cells 10/30, where valve function of 1073 may turn off.

The FIG. 29A and FIG. 29B channel 201 compression and release process may be repeated as many times as needed until conglomerate of cells 10/30 are sufficiently dissociated, which may then be flushed out of channel 201.

Figure 30A:
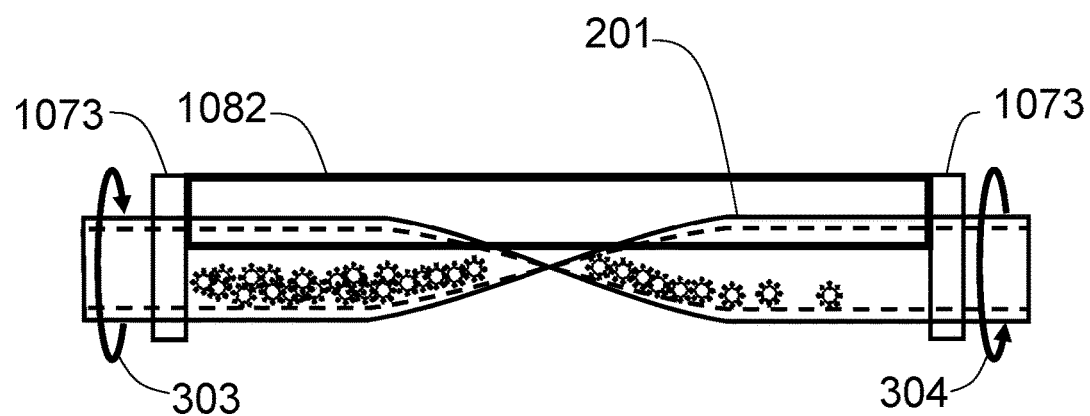
FIG. 30A illustrates a side view of a flexible channel where the flexible channel is mechanically twisted.

FIG. 30A illustrates another alternative method of mechanical agitation. Every aspect is same as in FIG. 28A, except that rotational twisting force 303 or 304 may be applied to channel 201 to twist channel 201 along channel length direction, as shown in FIG. 30A. In one embodiment, only one of rotational force 303 or 304 is applied to one end of channel 201. In another embodiment, both rotational force 303 and force 304 are applied to difference ends of the channel 201 in opposite rotational directions to cause the channel 201 to twist along channel length direction. Such twist deformation of channel 201 will again build up elastic energy in the channel 201 wall material.

Figure 30B:
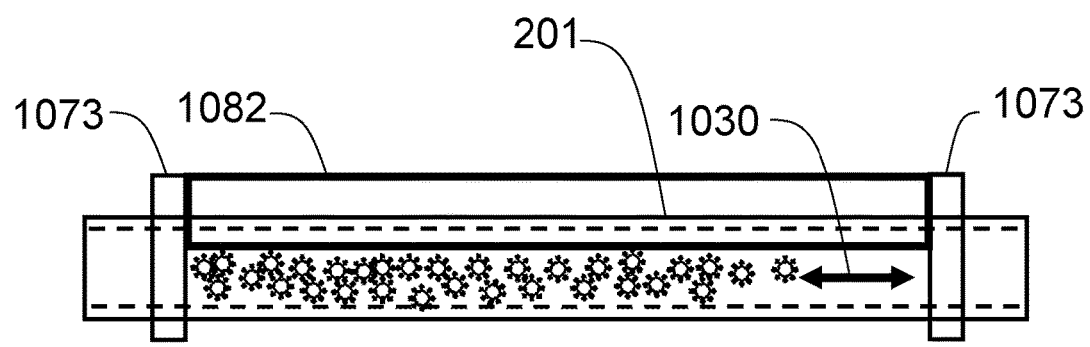
FIG. 30B illustrates cells being dissociated from conglomerate after removal of the external force of FIG. 30A.

FIG. 30B is same as FIG. 28B in every aspect, except that FIG. 30B is after rotational force 303 and force 304 of FIG. 30A are released, and elastic energy built up in channel 201 wall acts to spring back channel 201 towards its original non-twisted shape. Such spring back may provide a strong transient turbulence flow at various locations within the channel 201, which may help mechanically break up the cells 10/30 conglomerate into smaller pieces to assist self-dissociation of cells 10/30 conglomerate. After release of forces 303 and 304, and channel 201 shape spring back, alternating flow 1030 may be applied similarly as in FIG. 23E to assist dissociation process of conglomerate of cells 10/30, where valve function of 1073 may turn off.

The FIG. 30A and FIG. 30B channel 201 twist and release process may be repeated as many times as needed until conglomerate of cells 10/30 are sufficiently dissociated, which may then be flushed out of channel 201 by buffer fluid.

Mechanical forces 300, 302, 303 and 304 may be applied by mechanical structures that are motorized and able to apply such forces repeatedly to channel 201, examples may include a flap for providing force 300, a compressor for provide force 302, and twisters for providing forces 303 and 304.

Figure 31:
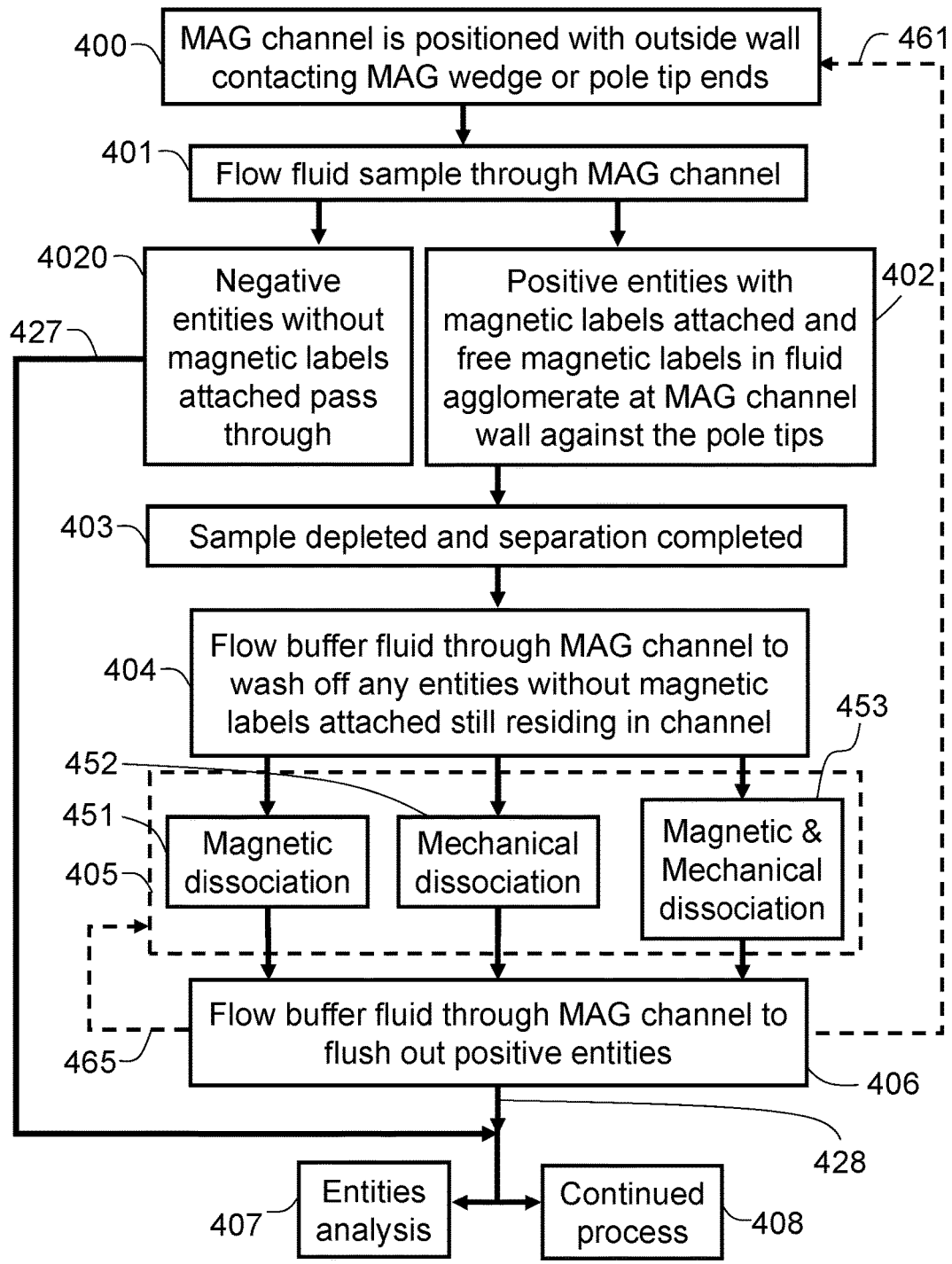
FIG. 31 is a schematic diagram illustrating methods to use MAG to magnetically separate biological entities from fluid solution.

FIG. 31 is a schematic diagram illustrating a method to use MAG to separate biological entities conjugated with magnetic labels, for example cells 10/30, from a fluid solution. MAG channel of FIG. 31 may be any of channels 101, 201, 301, 320, or 330 described in any of the figures of this specification, and MAG of FIG. 31 may be any of the MAG 121, 122, 123, 124, 125, 126, 127, 128, or 129 described with the corresponding channel in any of the said figures. Method of FIG. 31 may include the following steps in sequence. In step 400, MAG channel is positioned with its outside wall contacting MAG wedge surface or pole tip ends, i.e. separation position of Position 1 or Position 21 as in FIG. 5, FIG. 10, FIG. 12, FIG. 14, FIG. 17, FIG. 19, FIG. 20A, FIG. 20C, FIG. 21A, FIG. 21C, FIG. 22A, FIG. 26A, FIG. 27A. In step 401, fluid sample is flown through the MAG channel in separation position. Then in step 402, positive entities with magnetic labels SPL 2 attached, for example cells 10/30, and free magnetic labels SPL 2 within the fluid sample are attracted by the magnetic field of MAG and agglomerate at the MAG channel wall against the MAG wedge or MAG pole tip ends. Meanwhile, in step 4020, negative entities without magnetic labels SPL 2 attached pass through the MAG channel without being attracted. The negative entities may then be processed directly in subsequent procedures as shown by path 427, where subsequent procedures may include entities analysis 407, for example processes as included in FIG. 79 through FIG. 81, or negative entities may be passed for continued process 408, for example through a UFL device as shown in FIG. 46A through FIG. 46C, FIG. 50 through FIG. 52, or through repeated MAG process as in FIG. 54A and FIG. 54B. After step 402, in step 403, sample may be depleted at input of the MAG channel and magnetic separation of positive entities may be completed. In step 404, which is an optional step, buffer fluid may be flown through MAG channel with MAG channel still at separation position to wash off any negative entities without magnetic labels SPL 2 but may have resided with the conglomerate of positive entities due to non-specific bindings. Then in step 405, MAG channel may be moved away from MAG to dissociation position including Position 2 and Position 22 at in FIG. 11, FIG. 22B, FIG. 22D, FIG. 24B, FIG. 26B, FIG. 26D, FIG. 27B, and magnetic dissociation 451, as shown in FIG. 22A through FIG. 26D, or mechanical dissociation 452 as shown in FIG. 27C through FIG. 30B, or magnetic together with mechanical dissociate 453 may be applied to the positive entities in MAG channel. In step 406, buffer fluid may be flown through MAG channel to flush out dissociated positive entities. If positive entities are not completely dissociated, 465 shows that repeated dissociation process 405 may be applied to remaining positive entities in MAG channel after prior flush out step, until positive entities are sufficiently dissociated and flushed out of the MAG channel. In the case that fluid sample is in large volume, fluid sample may be separated into multiple sub-volumes, where after process of a sub-volume from step 400 to step 406, a next sub-volume may be input into the MAG channel starting from step 400 for continued process as shown by 461 until completion of the fluid sample of the large volume. After positive entities are collected after step 406, they may be processed in subsequent procedures as shown by path 428, where subsequent procedures may include entities analysis 407 or continued process 408.

Figure 32:
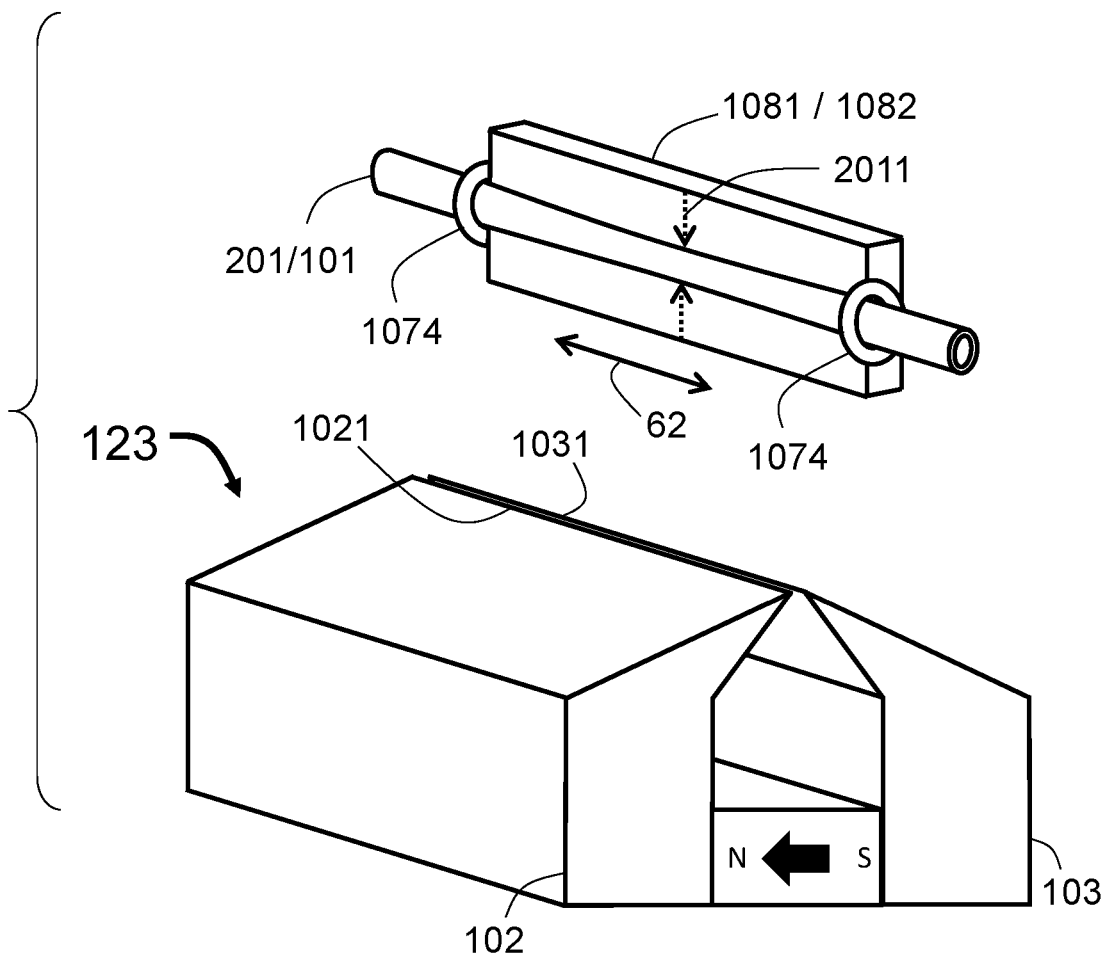
FIG. 32 illustrates a method to align a flexible channel MAG wedge of a MAG device.

FIG. 32 illustrates a method to align channel 201/101 to MAG gap of MAG 123 device. Precise alignment of channel 201/101 to MAG wedge or MAG pole tip ends is of importance as descried in embodiments of this invention. In FIG. 32, side fixtures 1074 may be used to align and position channel 201/101 to designated locations on channel holder 1081 or 1082, where the fixtures 1074 may be fit into a pre-defined slot, notch, clip or other physical features on the sides of the channel holder 1081/1082. In one embodiment, channel 201/101 may be slightly stretched in channel length direction, thus channel 201/101 may have a reduced width 2011 in between the fixtures 1074, where such stretch helps guarantee a straight channel which may be then aligned with a straight MAG wedge of MAG 123. After channel 201/101 is attached to holder 1081/1082 by fixtures 1074, holder 1081/1082 may then move channel 201/101 to separation position, where holder 1081/1082 may have pre-determined physical orientation to MAG 123, for example a hinge, which aligns channel 201/101 to MAG wedge or MAG pole tip ends of MAG 123 precisely. Fixtures 1074 may be the same as 1073 as in FIG. 28A through FIG. 30B.

FIG. 33A through FIG. 37 illustrate method to utilize peristaltic pumps in embodiments of this invention.

Figure 33A:
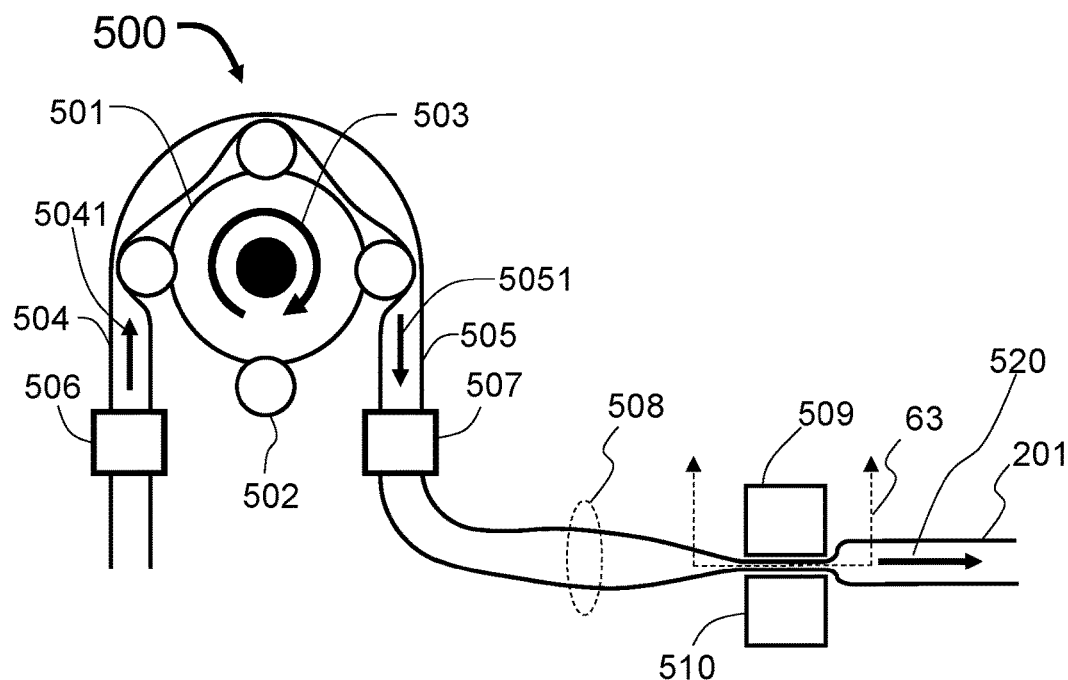
FIG. 33A illustrates a flexible channel attached to the output port of a peristaltic pump, where a flow limiter is attached to the flexible channel to reduce the flow rate pulsation.

FIG. 33A illustrates a typical peristaltic pump 500, which includes a rotor 501, drivers 502 attached to the rotor 501, and pump tubing 504/505, where tubing 504 is fluid incoming section and tubing 505 is fluid outgoing section of the same pump tubing. When rotor 501 rotates in direction 503, drivers 502 will squeeze pump tubing and force fluid to move from incoming section 504 to outgoing section 505 in directions 5041 and 5051 respectively. In the case when rotor rotates reversely to direction 503, fluid moves from outgoing section 505 to incoming section 504 of the pump tubing. Connectors 506 and 507 may be optional connections to incoming fluid line and outgoing fluid line 508 respectively. Advantage for peristaltic pump is the tubing 504/505 may be included as a continuous part of an enclosed fluid line as shown in FIG. 55A through FIG. 60B, which may be made disposable and single use, as well as sterile for clinical purpose. However, due to the spaced drivers 502 along the circumference of the rotor 501, flow rate of fluid output from section 505 has pulsation behavior, where flow rate increases and decreases with moving of each of the driver 502. Such pulsation is not desired for MAG and UFL fluid driving. FIG. 33A shows output section 505 outputs fluid through connector to channel 508. Channel 508 is preferred to be flexible tubing. Channel 508 may also be a section of channel 201. Flow limiter parts 509 and 510 function together to effectively clamp onto the channel 508 to reduce the fluid flow rate passing through the limiter. With reduced flow rate through the limiter, continued fluid output from pump 500 section 505 into the channel 508 will build up fluid pressure within channel 508. Due to the flexible nature of channel 508, channel 508 may enlarge its width perpendicular to the channel length direction, and forms fluid reservoir within channel 508 with elastic stress built up in channel wall. During pulsation of output flow from pump 500, when 5051 flow rate increases, channel 508 width will increase to build up stress in 508 channel wall and pressure within channel 508 and increase volume of channel 508 absorbs most of the instantaneous incoming flow, while flow rate 520 through limiter 509/510 into channel 501 shows smaller increase. When 5051 flow rate decreases, built-in elastic stress in channel 508 wall and fluid pressure in channel 508 continues to push fluid through the limiter 509/510, and flow rate 520 shows smaller flow rate decrease.

Figure 33B:
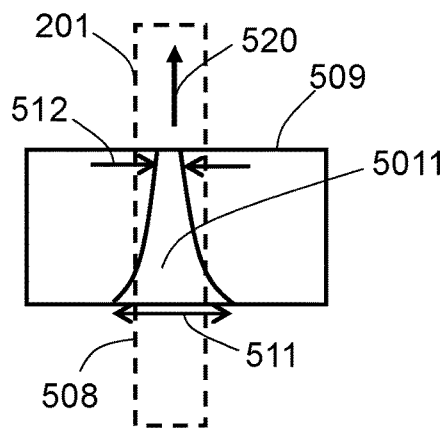
FIG. 33B illustrates a top-down view of the inner structure of a first type flow limiter.

FIG. 33B illustrates top-down view of the inner structure of first type flow limiter 509 along the direction 63. FIG. 33B shows that flow limiter 509 has a shaped trench 5011, which allows fluid to flow through channel 508 when limiters 509 and 510 clamp onto channel 508 as in FIG. 33A. Trench 5011 has entrance width 511 to incoming fluid and exit width 512 to channel 201, where width 511 may be larger than width 512. Decreased trench 5011 width from 511 to 512 reduces the flow rate through the limiter 509/510. Flow limiter 510 may have same top down view and structure as limiter 509 when view in direction opposite to 63.

Figure 33C:
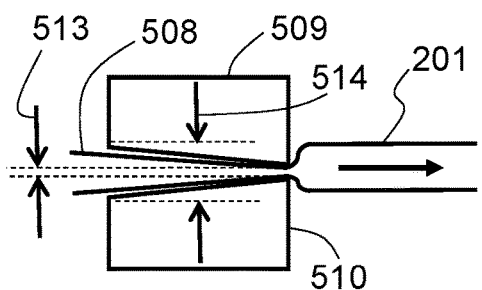
FIG. 33C illustrates a side view of a second type flow limiter.

FIG. 33C illustrates a second type flow limiter in same view as FIG. 33A, where after flow limiters 509 and 510 clamp onto channel 508, flow limiters 509/510 form an effective opening of 514 towards channel 508, and opening of 513 towards channel 201. Opening 513 may be smaller than opening 514, which reduces flow rate through the limiter 509/510.

Figure 34A:
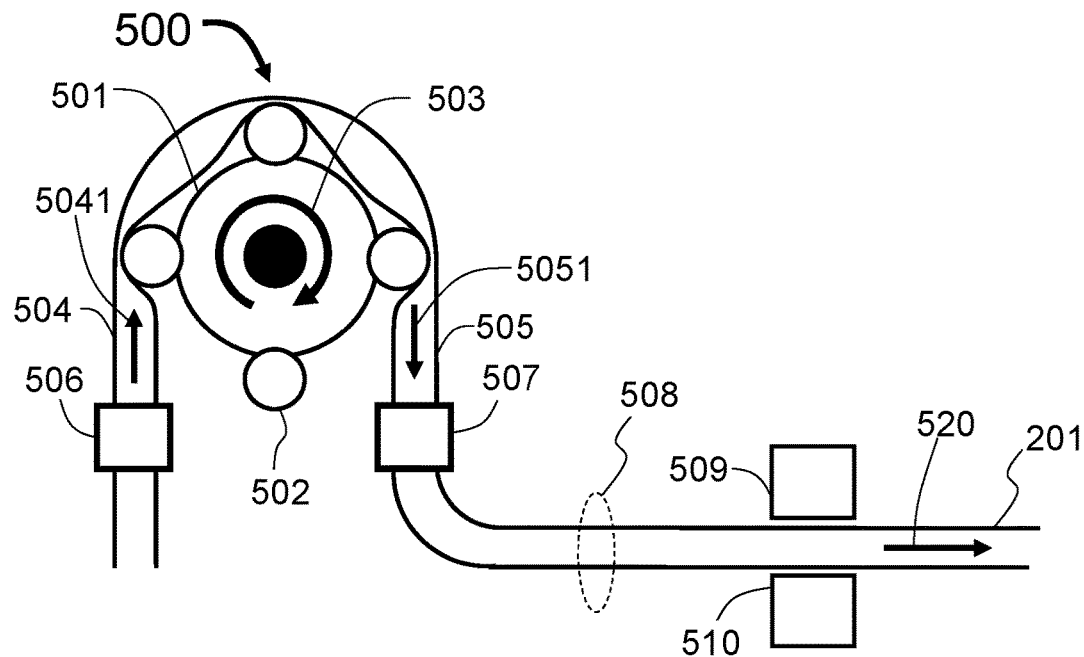
FIG. 34A illustrates FIG. 33A flow limiter being disengaged from the flexible channel.

FIG. 34A is same as FIG. 33A except flow limiters 509/510 are disengaged from the flexible channel 508, where flow from pump 500 through channel 508 and channel 201 is continuous without limiter 509/510 and there is no elastic stress built up in channel 508 wall.

Figure 34B:
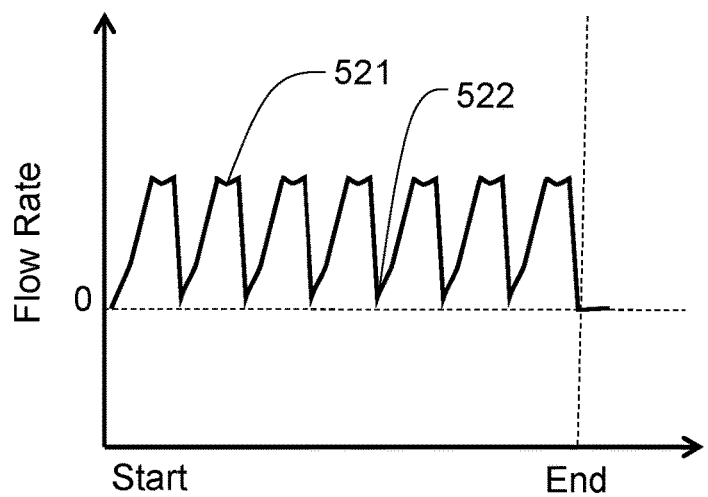
FIG. 34B is a schematic illustration of fluid flow rate with large pulsation.

FIG. 34B is a schematic illustration of fluid flow rate 520 as in FIG. 34A situation, which shows large pulsation in flow rate 520. FIG. 34B shows the example 520 flow rate value vs pump 500 operation time from pumping start to pumping end. Value 521 illustrates the high flow rate and value 522 illustrates low flow rate of the pulsation behavior.

Figure 35A:
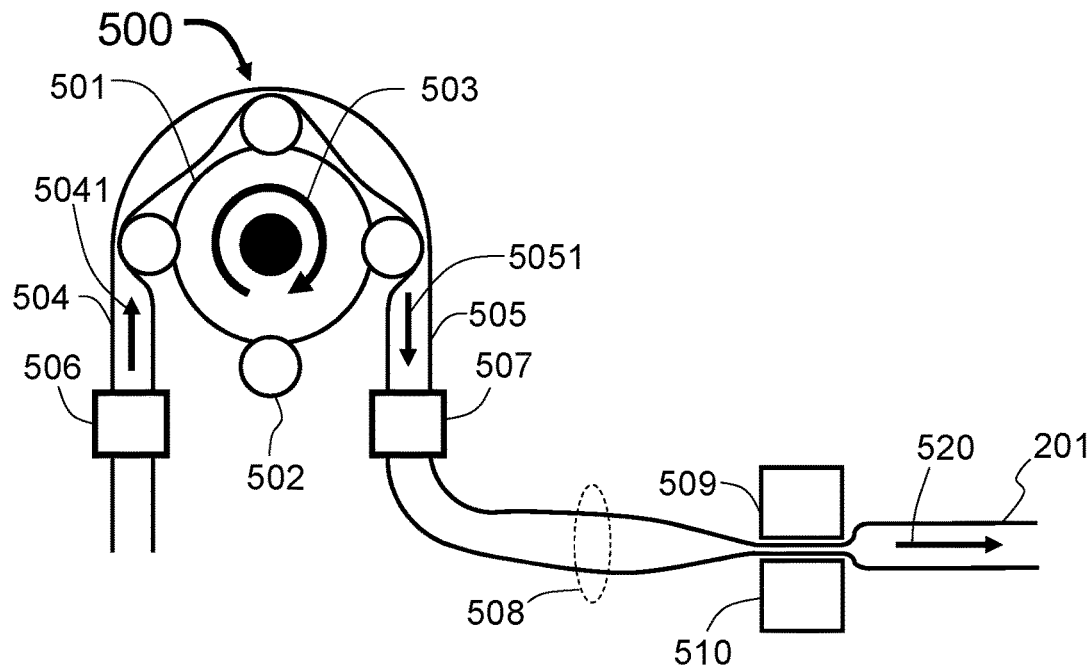
FIG. 35A illustrates FIG. 33A flow limiter being engaged upon the flexible channel.

FIG. 35A is same as FIG. 33A, where flow limiters 509/510 are clamped upon flow channel 508, flow rate through the flow limiters 509/510 is reduced, and channel 508 has enlarged channel width with elastic stress built up in channel 508 wall.

Figure 35B:
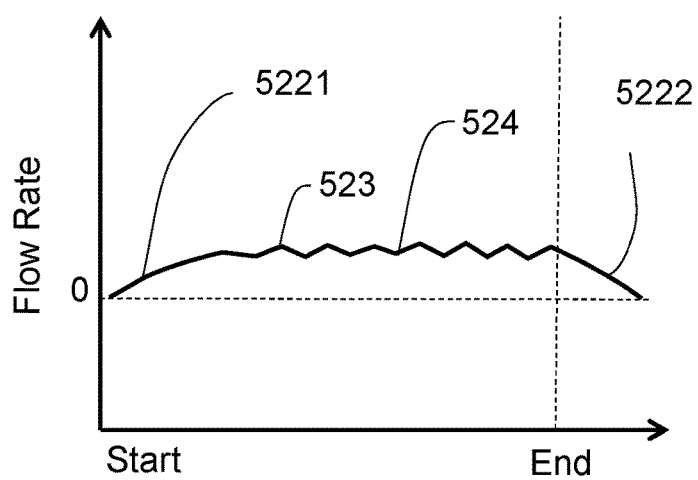
FIG. 35B is a schematic illustration of fluid flow rate with reduced pulsation.

FIG. 35B is a schematic illustration of fluid flow rate 520 as in FIG. 35A situation, which shows pulsation reduction in flow rate 520 compared to FIG. 34B. Value 523 corresponds to value 521 of FIG. 34B, and value 524 corresponds to value 522 of FIG. 34B. FIG. 35B illustrates that limiters 509/510 effectively reduce 520 flow rate pulsation. Due to the channel 508 liquid pressure build up at the start of pumping, and channel 508 liquid pressure dissipation at end of pumping, while limiters 509 and 510 are engaged, a flow rate ramp up slope 5221 after pump start and flow rate ramp down slope 5222 after pump end may exist in FIG. 35B.

Figure 36A:
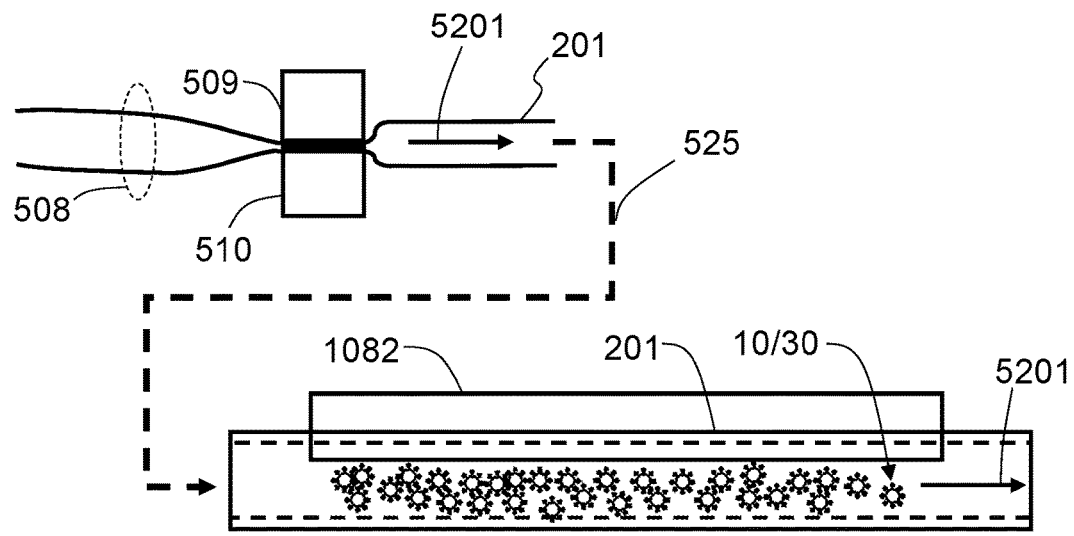
FIG. 36A illustrates FIG. 33A flow limiter causing pressure built up at the fluid incoming end of the flow limiter.
Figure 36B:
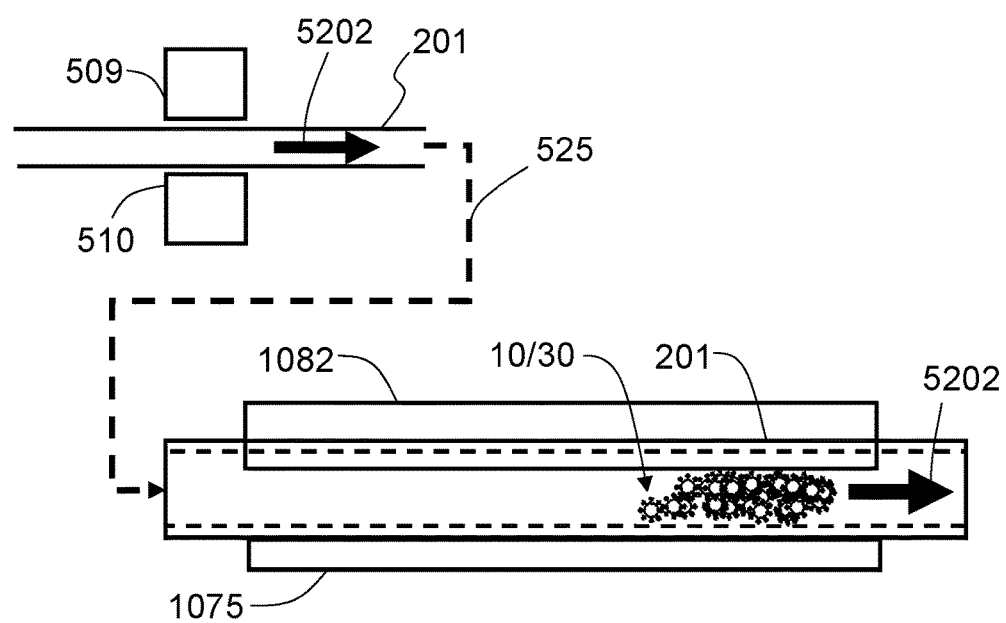
FIG. 36B illustrates FIG. 36A flow limiter being disengaged and causing high speed fluid pulse that pushes the dissociated cells of FIG. 36A out of the channel.

FIG. 36A and FIG. 36B illustrate method to use flow limiter 509/510 to generate instantaneous high flow rate short pulse through channel 201 for flushing out magnetically separated entities, for example dissociated cells 10/30.

FIG. 36A illustrates FIG. 33A and FIG. 35A situation, where flow limiters 509 and 510 are clamped onto the flexible channel 508 while pump 500 pumps fluid into channel 508, where pressure is built up within the flexible channel 508, and elastic stress is built up in wall of channel 508. Line 525 represents a continuous channel 201 from after the limiters 509/510 to channel 201 over MAG structure. Flow rate 5201 represents averaged flow rate of flow rates 523 and 524 of FIG. 35B when flow limiters 509 and 510 are engaged.

FIG. 36B illustrates that flow limiters 509 and 510 are disengaged from the flexible channel 508, similar to FIG. 34A situation, while pump 500 still pumps fluid into channel 508, or immediately after pump 500 stops pumping and before pressure within channel 508 dissipates. At disengagement of limiters 509 and 510, liquid pressure in channel 508 and elastic stress in wall of channel 508 produces an instant high speed fluid pulse flow 5202 into channel 201 which may flush the magnetically separated entities out of the channel 201. Such high speed short pulse flow 5202 may help achieve complete flush out of cells 10/30 with small volume of fluid that is originally contained in channel 508 of FIG. 36A. FIG. 36B also shows that a rigid cladding structure 1075 may be put into contact with channel 201 to help reduce deformation of flexible channel 201 during the cells 10/30 flush out to maintain the flow speed in channel 201.

Figure 37:
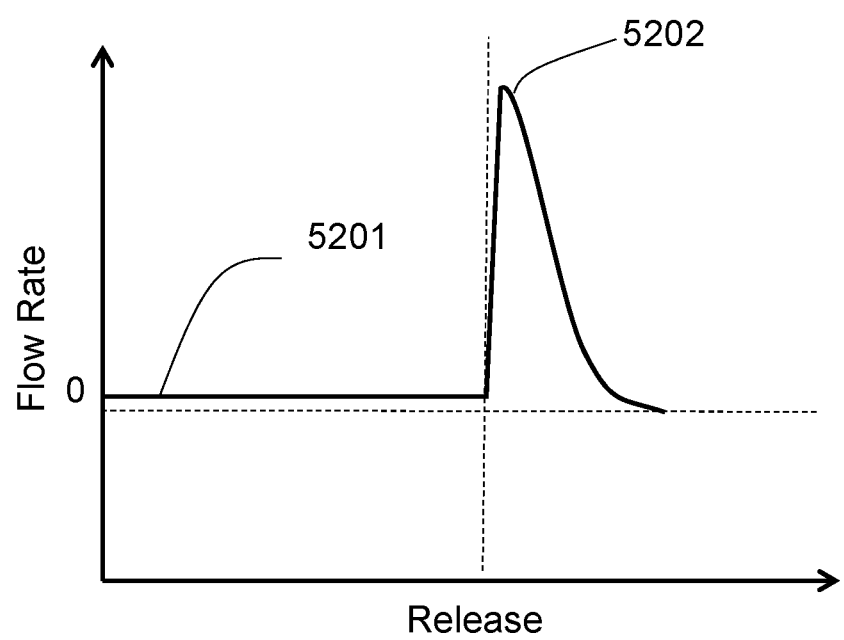
FIG. 37 is a schematic illustration of fluid flow rate pulse created by the process of FIG. 36A to FIG. 36B transition where flow limiter is disengaged.

FIG. 37 is a schematic illustration of fluid flow rate pulse created by the flow limiter operation of FIG. 36A to FIG. 36B, where 5201 is the fluid flow rate in channel 201 before limiters 509 and 510 release, and 5202 is flow rate peak value after limiters 509 and 510 release.

From FIG. 33A through FIG. 36B, channel 508 is a flexible channel, while channel 201 may be replaced by a rigid channel 101, 301, 320, or 330.

FIG. 38A through FIG. 43 describe various embodiments of micro-fluidic chip ("UFL") and method of use.

Figure 38A:
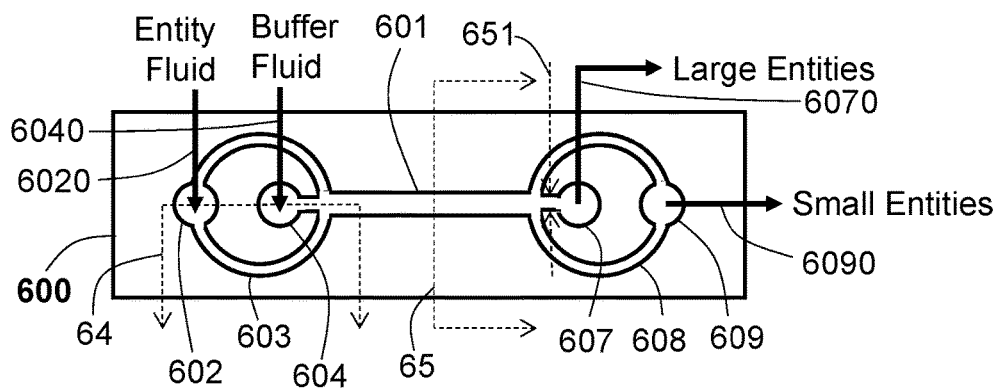
FIG. 38A is a top-down view of a micro-fluidic chip ("UFL").

FIG. 38A is a top-down view of a first UFL embodiment UFL 600, where micro-fluidic channels are formed as trenches into a substrate material 611. UFL contains an entity fluid 6020 inlet 602, a buffer fluid 6040 inlet 604, a main channel 601, a large entities 6070 outlet 607, and a small entities 6090 outlet 609. Two side channels 603 connect inlet 602 to main channel 601 from the two sides of the main channel 601. Inlet 604 is directly connected to the main channel 601 at the center of the main channel 601. Main channel 601 connects to outlet 607 at the center of the main channel 601, and connects to outlet 609 from two sides of main channel 601 through two side channels 608. Entities fluid 6020 contains both large entities 6070 and small entities 6090. Buffer fluid 6040 is fluid for providing UFL function but without biological entities. Large entities 6070 fluid from outlet 607 contains mainly large entities 6070 and buffer fluid 6040. Small entities 6090 fluid from out 609 contains mainly small entities 6090 and fluid of entities fluid 6020 and may contain certain amount of buffer fluid 6040. During operation of UFL 600, buffer fluid 6040 and entity fluid 6020 are simultaneously pumped into outlets 604 and 602 respectively, where buffer fluid 6040 flows along center line of the main channel 601 and entity fluid flows close to the two side of the main channel as laminar flow. Buffer fluid 6040 carries large entities 6070 to exit outlet 607 and entity fluid carries remaining small entities 6090 to exit outlet 609. Channel 601 is substantially straight and linear along channel length direction from inlet 604 to outlet 607.

Figure 38B:
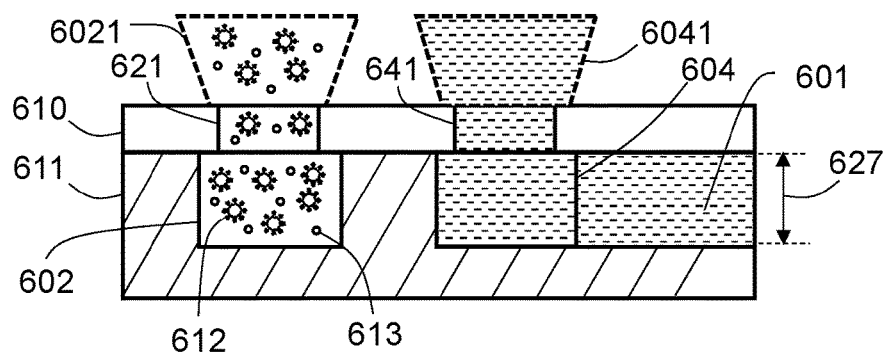
FIG. 38B is a cross-sectional view of a portion of the FIG. 38A UFL including entity fluid inlet, buffer fluid inlet, and part of the UFL.

FIG. 38B is a cross-sectional view of a portion of the FIG. 38A UFL 600 along direction 64, which includes entity fluid inlet 602, buffer fluid inlet 604, and part of the UFL main channel 601. FIG. 38B illustrates UFL 600 is compose of two components, substrate 611 and cover 610. Inlets 602 and 604, outlets 607 and 609, channels 601, 603 and 608 are formed in substrate 611 as trenches of same depth 627 and preferably formed in a single step. In one embodiment, depth 627 is between 100 nm to 500 nm. In another embodiment, depth 627 is between 500 nm to 1 um. In yet another embodiment, depth 627 is between 1 um to 10 um. In yet another embodiment, depth 627 is between 10 um to 100 um. In yet another embodiment, depth 627 is between 100 um to 1 mm. Cover 610 contains external access ports to inlets and outlets of UFL 600 to allow entities fluid 6020 and buffer fluid 6040 to enter inlets 602 and 604, and to allow large entities 6070 fluid and small entities 6090 fluid to exit outlets 607 and 609. Inlets 602 and 604, outlets 607 and 609 are shown to be circular shape in FIG. 38A, but may be any other shape, including ellipse, square, rectangle, triangle, polygon, as suitable for application. Access ports of cover 610 are clearances, i.e. holes, through cover 610 directly over the inlets and outlets 602, 604, 607 and 609. FIG. 38B shows example of access ports 621 and 641 clearances matching to inlets 602 and 604 positions. After manufacture of the UFL 600 substrate 611 with the trenches of inlets, outlets and channels, and cover 610 with the access ports, cover 610 is positioned over the substrate 611 to form enclosed channels 601, 603 and 608, where cover 610 may bond to substrate 611 through any of: (1) surface to surface Van der Waals force; (2) gluing; (3) ultrasound thermal melting when one or both of substrate 611 and cover 610 being made of plastic or polymer material. Access ports clearances of cover 610, for example 621 and 641 to inlets and outlets 602, 604, 607 and 609 are preferred to be smaller in size than the corresponding inlets and outlets, which allows for positioning error during cover 610 to substrate 611 alignments without causing function loss of UFL due to misalignment. Injectors 6021 and 6041 then show example of possible external fluid injection to inlets of UFL 611 through cover 610 access ports clearance, where the injectors 6021 and 6041 may have a larger nozzles size than the matching access ports 621 and 641 for managing positioning errors between injectors and access ports. FIG. 38B shows that entities fluid 6020 containing large entities 612 and small entities 613, which may be injected by injector 6021, passing through assess port 621 and into inlet 602 and passing into main channel 601 as side laminar flows, while buffer fluid 6040 may be injected by injector 6041, passing through assess port 641 and into inlet 604 and passing into main channel 601 as center laminar flow.

Substrate 601 may be composed of any of: glass, silicone, aluminum-titanium-carbon (AlTiC), plastic, polymer, ceramic, or metal, where metal may be composed any one or any alloy of iron, nickel, chromium, platinum, tungsten, rhenium. In one embodiment, forming of inlets, outlets and channels in substrate 611 includes the steps of: (1) providing a substrate 611 having one substantially flat surface; (2) forming etching mask on top of said flat surface; (3) etch of substrate with a first etching method including: wet etch with fluid chemical, dry etch with chemical gas, plasma enhanced dry etch, sputter etch with ion plasma, and ion beam etch (IBE). In forming of etch mask of step (2), etch mask may be composed of photo resist (PR), which may include deposition or spin coating of PR on said flat surface; exposure by optical or ion/electron radiation with patterns of inlets, outlets and channels; development of PR after said exposure, where remaining PR with said patterns serves as etch mask. Etch mask may also be made of a hard mask material that has lower etch rate than the substrate material under the first etching method, and step (2) may include: deposition of a hard mask layer on said flat surface; deposition or spin coating PR layer on hard mask layer; exposure of said PR by optical or ion/electron radiation with patterns of inlets, outlets and channels, development of PR after said optical exposure, where remaining PR with said pattern serves as etching mask of said hard mask; hard mask is etched through with a second etch method including any of: wet etch with fluid chemical, dry etch with chemical gas, plasma enhanced dry etch, sputter etch with ion beam; removal of remaining PR layer. Second etch method and first etch method may be different in type, or different in chemistry.

In another embodiment, inlets, outlets and channels in substrate 611 may be formed by thermal press involving using a heated stencil with physical pattern of the inlets, outlets and channels to melt and deform part of substrate 611 to construct the inlets, outlets and channels, then cooling down substrate 611 and remove the stencil. In thermal press, substrate material is preferred to be plastic or polymer. In yet another embodiment, inlets, outlets and channels in substrate 611 may be formed by imprint, which involves using a stencil with physical pattern of the inlets, outlets and channels to imprint into a partially or completely melt substrate 611, and then cooling the substrate 611 and finally removing stencil, where cooled substrate retains the pattern transferred from stencil of the inlets, outlets and channels. In imprint, substrate material is preferred to be plastic or polymer. In another embodiment, inlets, outlets and channels are formed in substrate 611 by injection molding, where melted substrate 611 materials are injected into a mold cavity where substrate 611 body with engraved inlets, outlet and channels are defined by the mold cavity. Cover 610 may compose similar to substrate 611 materials, and assess ports of cover 610 may be formed in cover 610 similarly as the inlets, outlet and channels formed in substrate 611 as described above.

Figures 38C, 38D:
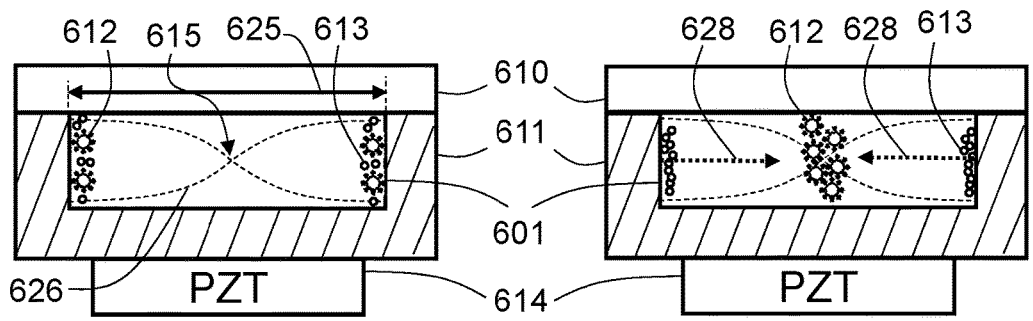
FIG. 38C is a schematic diagram illustrating a single fluidic pressure node created between two side walls of the UFL of FIG. 38A by ultrasound vibration generated by a PZT.
FIG. 38D is a schematic diagram illustrating the fluid acoustic wave of FIG. 38C causing larger size entities to move around center of the UFL.

FIG. 38C is a schematic diagram illustrating a single fluidic pressure node 615 created between two side walls of the UFL 600 channel 601 of FIG. 38A by ultrasound vibration generated by a PZT 614. FIG. 38C is a cross-section view along direction 65 of FIG. 38A for part of the UFL 600 including main channel 601, substrate 611, cover 610 and PZT transducer 614 attached to the bottom of substrate 611. FIG. 38C shows that after injection of entities fluid 6020 and buffer fluid 6040, entities fluid 6020 containing large entities 612 and small entities 613 mainly flow along the edges of the channel 601 as laminar flow. AC voltage is applied to PZT 614, where frequency (Fp) of AC voltage is preferred to be at a frequency matching to the PZT resonance frequency (Fr). PZT 614 produces ultrasound vibrations to the substrate 611 at frequency Fp. Said ultrasound vibrations transfer to the fluid contained in channel 601. Channel 601 has channel width 625 defined as the normal distance between the two side walls of channel 601. In one embodiment, width 625 is between 100 nm to 1 um. In another embodiment, width 625 is between 1 um to 10 um. In yet another embodiment, width 625 is between 10 um to 100 um. In yet another embodiment, width 625 is between 100 um to 500 um. In yet another embodiment, width 625 is between 500 um to 5 mm. When channel width 625 is half wavelength, or an integer multiple of half wavelength, of the ultrasound mode in the fluid within channel 601 at frequency Fp, standing wave may be present in between the two side walls of channel 601 as indicated by the dashed lines 626. FIG. 38C shows when channel width 625 is half wavelength of fluid ultrasound mode at frequency Fp, where a single fluidic pressure node 615 is formed along the center line of channel 601 in the direction of channel length, which is perpendicular to the view of FIG. 38C. In another embodiment, channel width 625 is an integer times of half wavelength of fluid ultrasound mode at frequency Fp, where integer is larger than 1, and said integer number of fluidic pressure nodes may then be formed across the width 635 with each node being a line along the direction of channel length. Presence of standing wave 626 and pressure node 615 exert acoustic force, which is shown in FIG. 38D as arrows 628, on entities in the entities fluid laminar flow along the side walls of channel 601 and cause large size entities 6070 to move close to center node 615 during flowing through the channel 601. Said acoustic force 628 has the characteristics of: (1) largest amplitude close to channel 601 side walls with force direction pointing from the side walls towards the node 615; (2) smallest force, or close to zero force, around node 615; (3) being linearly proportional to size of the entities; (4) is a function of the density and compressibility of both the buffer fluid 6040 and the entities. Due to these characteristics, with proper optimization of buffer fluid composition, buffer fluid 6040 laminar flow speed, and entities fluid 6020 laminar flow speed, large entities 612 may be optimized to preferably break the laminar flow barrier to enter the buffer laminar flow due to a larger acoustic force acting on large entities 612, and be concentrated around the center node 615.

FIG. 38D is a schematic diagram illustrating the fluid acoustic wave of FIG. 38C causing larger size entities 612 to move into buffer fluid laminar flow around center of the channel 601. When fluid within the channel 601 exits the channel to outlets 607 and 609, channel 601 center sub-channel width 651 of FIG. 38A to outlet 607 may be much smaller than the width 625 of the channel 601, thus only allow large entities 612 at center flow within channel 601 to exit outlet 607 as large entities 6070 fluid. While smaller entities 613 mainly in the close to side wall laminar flow exit channel 601 through side channels 308 to exit from outlet 609 as small entities 6090 fluid.

Frequency Fp of PZT 614 vibration in one embodiment is between 100 kHz to 500 Hz, between 500 kHz to 1 MHz in another embodiment, between 1 MHz to 3 MHz in yet another embodiment, between 3 MHz to 10 MHz in yet another embodiment, and between 10 MHz to 100 MHz in yet another embodiment. In FIG. 38C and FIG. 38D, PZT 614 may also be attached to top of cover 610 in FIG. 38C and FIG. 38D, and ultrasound vibrations from PZT 614 is transferred from PZT 614 through cover 610 to fluid within channel 601, or through cover 601 to substrate 611 and then to the fluid within channel 601.

Figure 39:
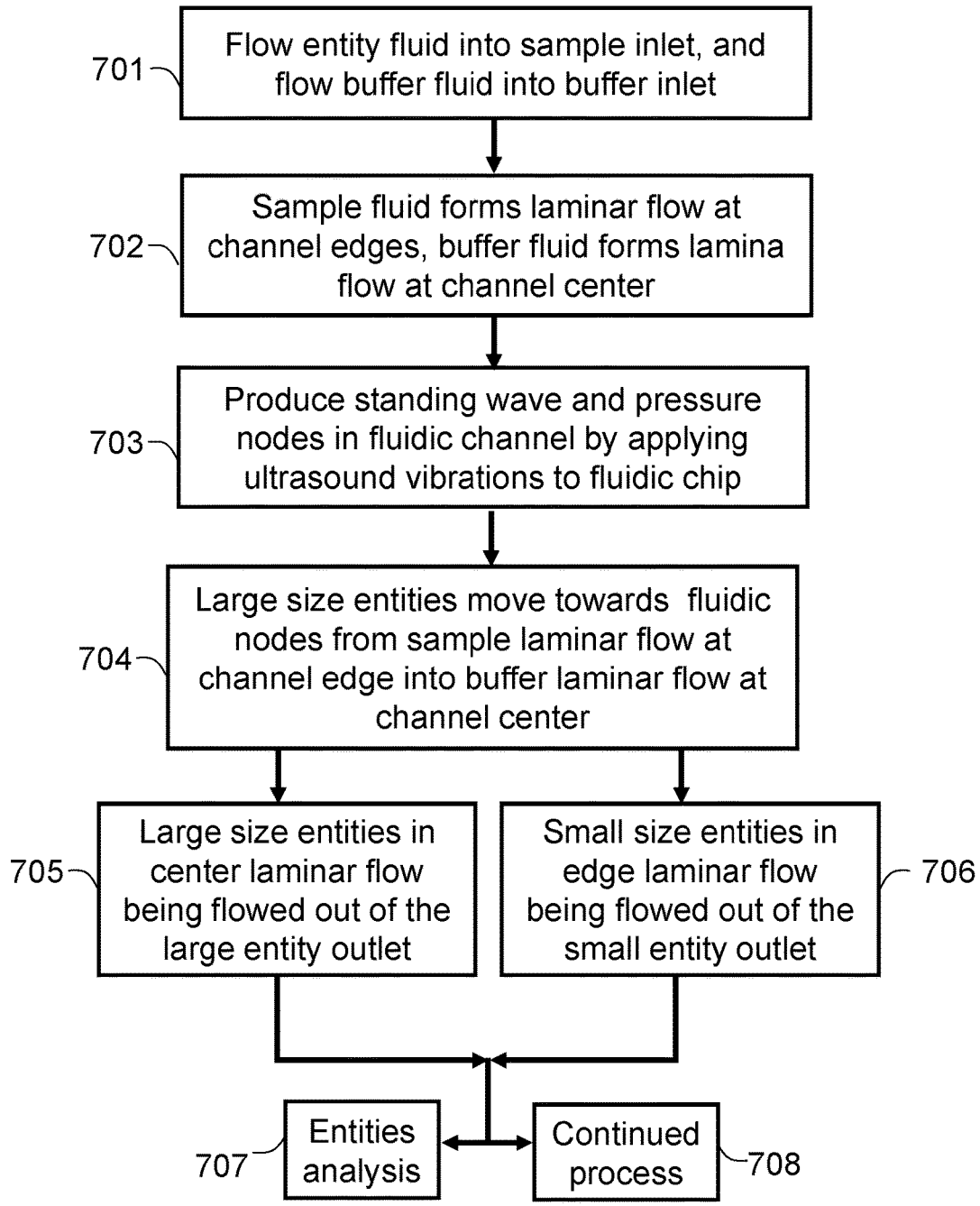
FIG. 39 is a schematic diagram illustrating methods to use UFL to separate biological entities of different sizes.
Figure 40A:
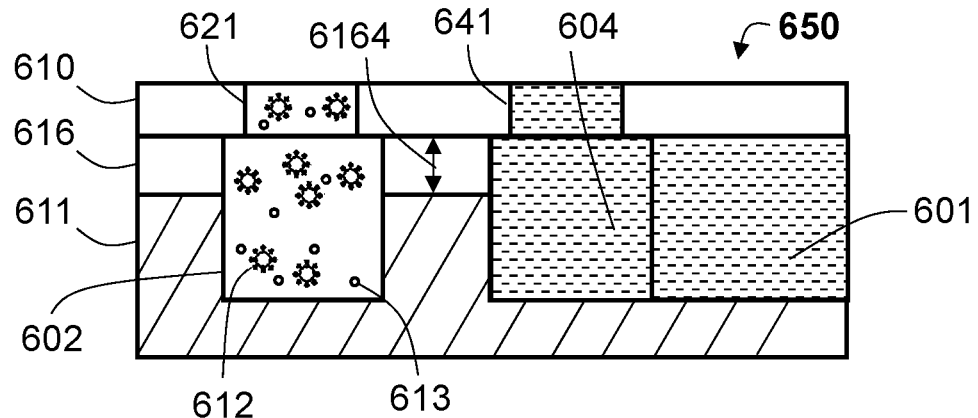
FIG. 40A is a cross-sectional view of a portion of first embodiment UFL which includes a uniformly formed soft magnetic layer.

FIG. 39 is a schematic diagram illustrating methods to use a UFL to separate biological entities of different sizes, where UFL may be UFL 600 from FIG. 38A or FIG. 40A, UFL 620, 630 and 640 from FIG. 41A through FIG. 43. Sequential steps of 701 to 705 and 706 are substantially similar as described in FIG. 38A, FIG. 38B, FIG. 38C, and FIG. 38D, except steps 703 and 704 refer to possibility of multiple pressure nodes, as shown in FIG. 41B and FIG. 42B. Step 707 entities analysis can be performed on both the large entities 6070 and small entities 6090, and may include processes 903, 904, 905, 906, 5824, 5825, 5826 as described in FIG. 53, FIG. 79, FIG. 80, FIG. 82 and FIG. 83 on corresponding UFL output samples. Continued process 708, for example through a MAG device as shown in FIG. 44A through FIG. 45C, FIG. 47 through FIG. 49, or through cascaded UFL process as in FIG. 54C.

FIG. 40A is a cross-sectional view of a portion of a UFL 650 similar to FIG. 38B. UFL 650 is identical to UFL 600 from a top-down view as in FIG. 38A, except that a uniform soft magnetic layer ("SML") 616 is deposited on top the substrate 611 of UFL 650, and patterned together with the substrate 611 to form inlets 602 and 604, outlets 607 and 609, and channel 601, 603 and 608. SML 616 may be composed of at least one element from iron (Fe), cobalt (Co), and nickel (Ni). SML 616 thickness 6164 is between 10 nm to 100 nm in one embodiment, between 100 nm to 1 um in another embodiment, between 1 um to 10 um in yet another embodiment, between 10 um to 100 um in yet another embodiment, between 100 um to 1 mm in yet another embodiment, and between 1 mm to 3 mm in yet another embodiment. Deposition of SML layer 616 on substrate 611 may be by any of: electro-plating, vacuum plating, plasma-vapor-deposition (PVD), atomic layer deposition (ALD), chemical vapor deposition (CVD). Etching of layer 616 together with substrate 611 to form inlets 602 and 604, outlets 607 and 609, and channel 601, 603 and 608 may be by any of: dry etch, plasma enhanced dry etch, ion plasma etch, and IBE. Layer 616 may be a continuous layer along the channel 601 length direction and forms as part of the side walls of the channel 601.

Figure 40B:
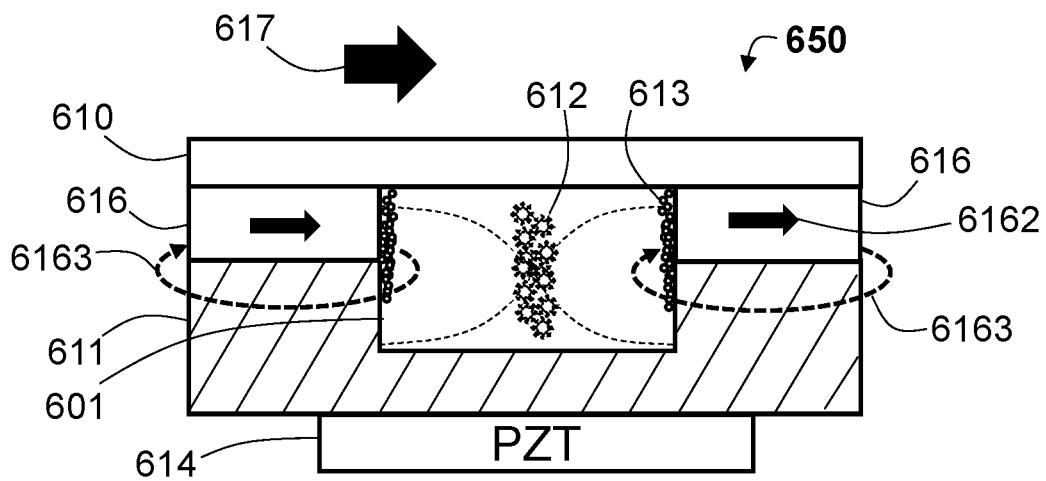
FIG. 40B is a schematic diagram illustrating the fluid acoustic wave and entities separation in UFL of FIG. 40A in presence of a magnetic field.

FIG. 40B is similar as FIG. 38D and shows a schematic diagram illustrating the large entities 612 if concentrated by acoustic force 628 to the channel 601 center around the pressure node 615 and small entities 613 mainly remain around the channel 601 side wall. Additionally, a magnetic field 617 is applied in plane and induces magnetization 6162 in the SML layer 616. For the SML layer 616 located as part of the side walls of the channel 601, magnetization 6162 produces local magnetic field 6163, which has strongest magnetic field strength and field gradient close to the channel 601 side walls. Field 6163 may help maintain magnetic small entities, for example free magnetic labels SPL 2 that is part of the entities fluid 6020 in positive sample after MAG separation as shown in FIG. 82 and FIG. 83, to stay within the laminar flow close of channel 601 side walls and output from outlet 609 of FIG. 38A.

Figure 40C:
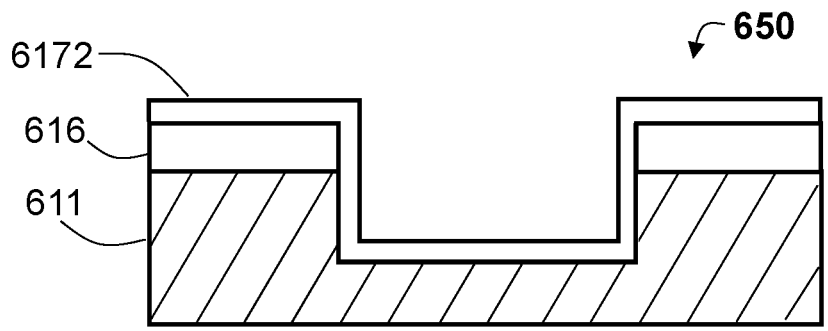
FIG. 40C is a schematic diagram illustrating a protection layer conformably deposited around the UFL surface before attached cap.

FIG. 40C shows that after etching of SML layer 616 together with substrate 611, and before cover 610 is attached to substrate 611, a passivation layer 6172 may be deposited covering exposed surfaces of SML layer 616 and substrate 611, Layer 6172 may help isolate fluid reaction with material of SML layer 616. Layer 6172 may be deposited over the etched surfaces of SML 616 and substrate 61, preferably conformably, by vacuum plating, electro-plating, PVD, ALD, CVD, molecular beam deposition (MBE), and diamond like carbon (DLC) deposition. Layer 6172 may be an oxide, or a nitride, or a carbide, of any one or more of elements of: Si, Ti, Ta, Fe, Al, W, Zr, Hf, V, Cu, Cr, Zn, Mg, Nb, Mo, Ni, Co, Fe, Ir, Mn, Ru, Pd, and C. Layer 6273 may compose at least one of: Si, Ti, Ta, Fe, Al, W, Zr, Hf, V, Cu, Cr, Zn, Mg, Nb, Mo, Ni, Co, Fe, Ir, Mn, Ru, Pd, and C. Layer 6273 may be a DLC layer. Thickness of layer 6273 may be between 1 nm to 10 nm in one embodiment, between 10 nm to 100 nm in another embodiment, between 100 nm to 10 um in another embodiment, and between 10 um to 100 um in another embodiment.

Figure 41A:
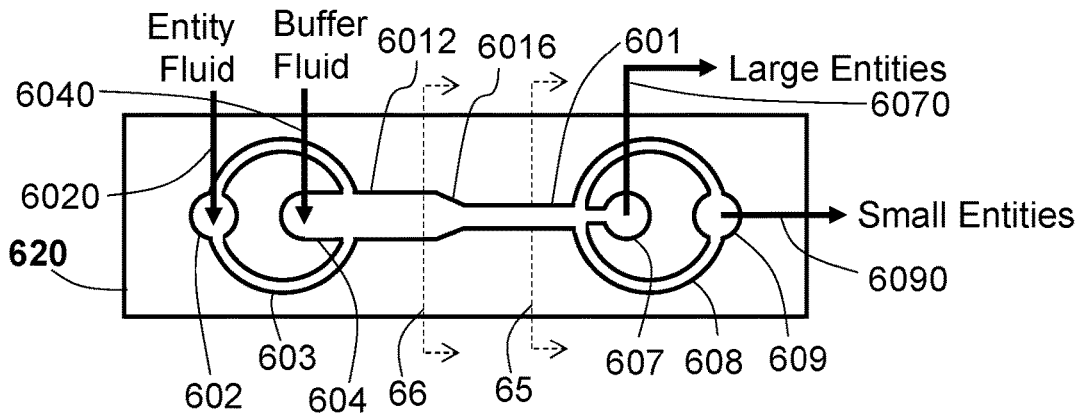
FIG. 41A is a top-down view of a second embodiment UFL including a wide channel and a narrow channel in sequential arrangement.

FIG. 41A is a top-down view of a second UFL embodiment UFL 620, which is same as FIG. 38A, except including a wider section 6012 of the main channel connecting between the inlet 604, and the narrower channel section 601 of FIG. 38A. Slope 6016 represents a transition section 6016 from wider section 6012 to narrow section 601. Channel sections 6012 and 601 are substantially straight and linear along channel length direction. Transition section 6016 may be a section of the main channel, where the main channel includes channel section 6012 connecting through the transition section 6016 to channel section 601. Transition section 6016 functions to funnel fluid flow from wider section 6012 into the narrower section 601. Channel wall of transition section 6016 may intersect with straight wall of wider section 6012 at a transition start point. Channel wall of transition section 6016 may intersect with straight wall of narrower section 601 at a transition stop point. In one embodiment, the channel shape of the transition section 6016 between transition start point and transition stop point may be a straight slope as shown in FIG. 41A. In another embodiment, the channel shape of the transition section 6016 between transition start point and transition stop point may be a curvature, whereas the curvature may be tangential to one of, or both of, channel wall of wider section 6012, and channel wall of narrower section 601.

Figure 41B:
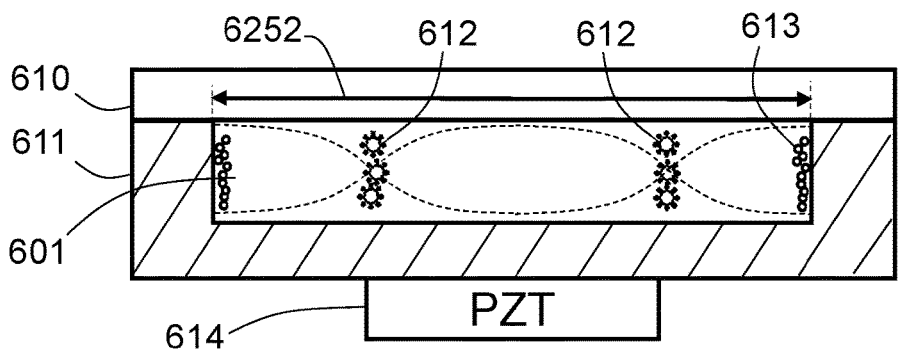
FIG. 41B is a cross-sectional view of second embodiment UFL across wide channel.

FIG. 41B is a cross-sectional view of UFL 620 along direction 66 in FIG. 41A, which is across the wider section 6012. Wider section 6012 has a channel width 6252, which is the full wavelength of the ultrasound mode in the liquid within channel section 6012 at PZT 614 operating frequency Fp as described in FIG. 38C, and effectively twice the channel width 625 of channel 601 as in FIG. 38C and FIG. 41C. Due channel width 6252 being equal to the full wavelength of ultrasound mode at Fp, two pressure nodes may exist in channel section 6012, where acoustic force from the ultrasound mode may move and concentrate large entities 612 at each of the two nodes from the channel wall entity laminar flow.

Figure 41C:
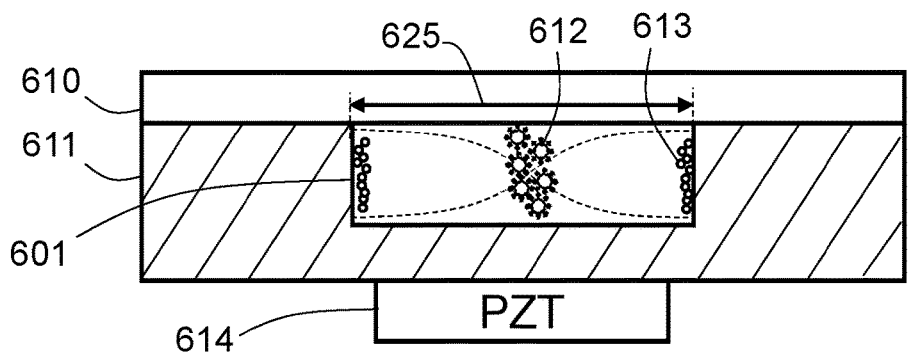
FIG. 41C is a cross-sectional view of second embodiment UFL across narrow channel.

FIG. 41C is a cross-sectional view of UFL 620 along direction 65 in FIG. 41A, which is across the narrower section 601, which is identical to FIG. 38D. After fluid within channel section 6012 flows through the transition 6016 to channel section 601, single pressure node of channel section 601 forces the large entities 612 to concentrate at channel section 601 center same as in FIG. 41C. Wider section 6012 provides a first stage large entities 612 separation from small entities 613. After transition section 6016, flow rates of center buffer laminar flow and channel side wall entities laminar flow increase to about twice the speed of same flow in section 6012 due to the channel width reduction from 6252 to 625. Channel section 601 provides a second stage large entities separation from small entities, together with the increase flow rate in channel section 601, purity of large entities 612 in 6070 fluid output from outlet 607, as well as purity of small entities 613 in 6090 fluid output from outlet 609, may be enhanced compared to UFL 600 of FIG. 38A.

Figure 42A:
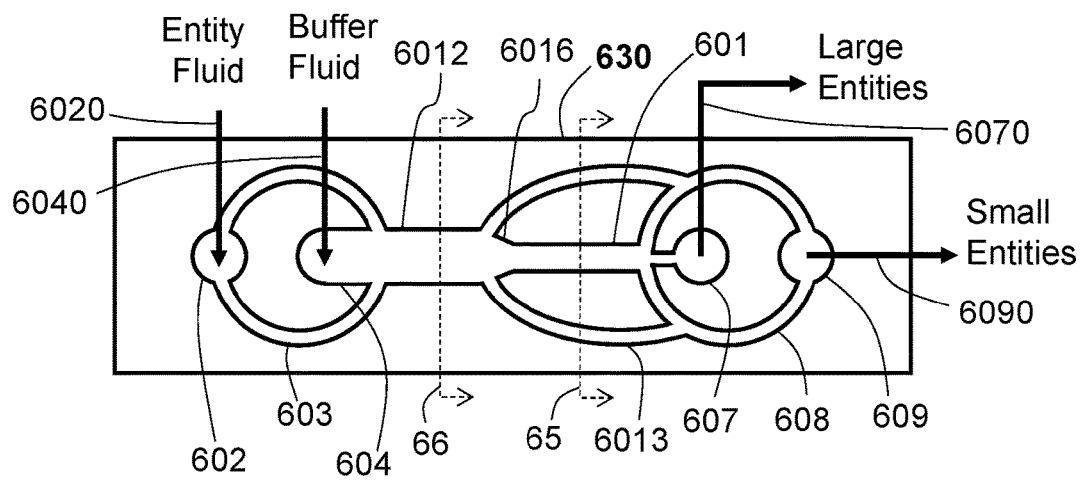
FIG. 42A is a top-down view of a third embodiment UFL including a wide channel and a narrow channel, and side channels from wide channel to narrow channel transition section.
Figure 42B:
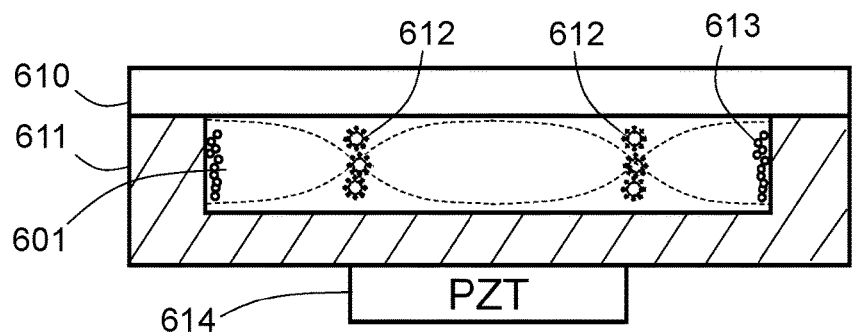
FIG. 42B is a cross-sectional view of third embodiment UFL across wide channel.

FIG. 42A is a top-down view of a third UFL embodiment UFL 630, which is a further enhancement from the UFL 620 of FIG. 41A. Every aspect of FIG. 42A is same as FIG. 41A, except that when compared to UFL 620 of FIG. 41A, UFL 630 of FIG. 43A includes additional side channels 6013 that connect from around the transition section 6016 to side channels 608, or in another embodiment directly to the outlet 609, to divert side wall laminar flow of small entities 613 from wider section, or referred to as first stage section, 6012, as shown in FIG. 42B, directly to output 6090 without entering narrower section, or referred to as second stage section, 601. Channel sections 6012 and 601 are substantially straight and linear along channel length direction. In one embodiment, side channels 6013 connect from first stage section 6012 before the transition start point of section 6012 intersecting section 6016. In another embodiment, side channels 6013 connect from the transition start point of section 6012 intersecting section 6016. In yet another embodiment, side channels 6013 connect from the within the transition section 6016 between the transition start point of section 6012 intersecting section 6016 and the transition stop point of section 6012 intersection section 601. In yet another embodiment, side channels 6013 connect from the transition stop point of section 6012 intersecting section 601. In yet another embodiment, side channels 6013 connect from the second stage section 601 after the transition stop point of section 6012 intersecting section 601.

FIG. 42B is a cross-sectional view of UFL 630 along direction 66 in FIG. 42A, which is across the wider section 6012. FIG. 42B is identical to FIG. 41B.

Figure 42C:
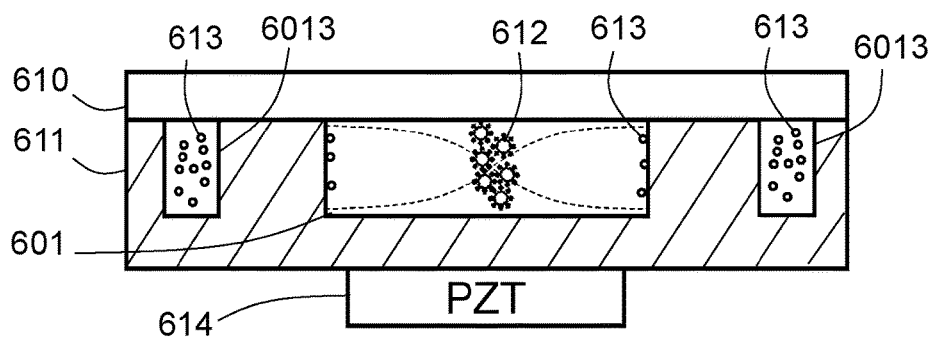
FIG. 42C is a cross-sectional view of third embodiment UFL across narrow channel and side channels.

FIG. 42C is cross-sectional view of UFL 630 along direction 65 in FIG. 42A, which is across the narrower section 601 and side channels 6013. Compared to FIG. 41C, side channels 6013 connecting from around the transition section 6016 of FIG. 42A contains mainly, or purely, small entities 613. While the channel 601 of FIG. 42C shows large entities 612 separation and concentration to channel 601 center pressure node similar as in FIG. 41C, but small entities 613 around section 601 channel walls is reduced in density when compared to FIG. 41C. Due to the pre-channel section 601 small entities diversion by side channel 6013, UFL 630 may have an even higher purity of large entities 612 in 6070 fluid output from outlet 607, as well as higher purity of small entities 613 in 6090 fluid output from outlet 609.

Figure 43:
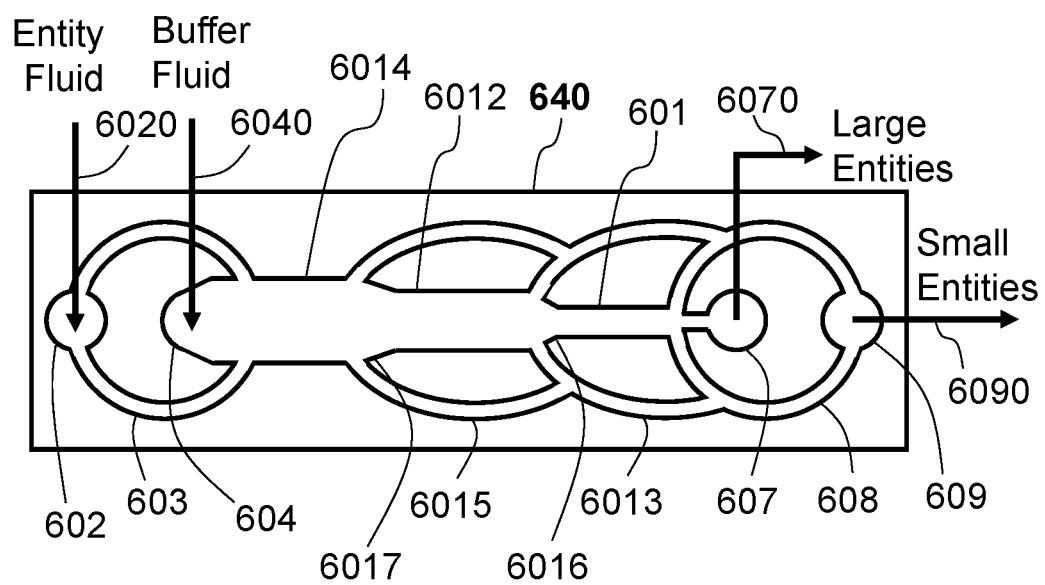
FIG. 43 is a top-down view of a fourth embodiment UFL having three-stage channel width reduction along channel flow direction, and side channels from transition sections.

FIG. 43 is a top-down view of a fourth UFL embodiment UFL 640 having a multiple-stage UFL channel with sequential channel width reduction along the channel flow path. FIG. 43 shows a further enhancement in increasing large entities purity in 6070 and small entities purity in 6090. FIG. 43 shows an additional wider width section 6014 is added between inlet 604 and channel section 6012. Channel width of 6014 may be three times of the half wavelength of ultrasound mode of the liquid flowing through the UFL 640 channel at PZT frequency Fp, which is one half wavelength wider than channel width 6252 of section 6012. Channel width of 6014 may also be wider than the channel width 6252 of next stage channel section 6012 by an integer times of the half wavelength, where said integer is larger than one. Channel section 6014 changes to reduced channel width section 6012 through a transition section 6017. Side channels 6015 connect from around the transition section 6017 to side channels 6013, or 608, or directly to outlet 609 to divert small entities 613 from channel side wall laminar flow of section 6014 from entering section 6012, thereby increasing purity of large entities concentration in section 6012. Channel sections 6014, 6012 and 601 are substantially straight and linear along channel length direction.

As a further extension from FIG. 43, a multiple-stage UFL 640 may have multiple channel sections along the UFL 640 channel flow path, where each earlier section of the UFL channel along the channel flow path may have a channel width that is wider than the immediate next section channel width by an integer number of a half wavelength of ultrasound mode in the fluid flow at the PZT frequency Fp, where said integer is equal to or larger than 1. Final channel section before flow exiting the outlets of the UFL 640 is preferred to have a channel width equal to said half wavelength in one embodiment, but may also have a channel width that equals to an integer number of said half wavelength in another embodiment where integer is larger than one. Side channels connecting to each of the transition area between adjacent channel sections divert small entities from the earlier channel in the entities laminar flow close to the earlier channel walls towards the outlet 609 to reduce number of small entities entry into immediate next stage channel section.

FIG. 44A through FIG. 65B illustrate various embodiments of method to utilize MAG and UFL device to separate biological entities from an entity fluid. For simplicity of description UFL 600 of FIG. 38A and MAG 123 with channel 201 are used in the figures for explanation. However, UFL 600 may be replaced with UFL 650, 630, 640 of FIG. 40A, FIG. 41A, FIG. 42A, FIG. 43, while MAG 123 may be replaced with MAG 121, 122, 124, 124,125, 126, 127, 128, 129 and corresponding channel types as described in prior figures without limitation and without sacrifice of performance.

Figure 44A:
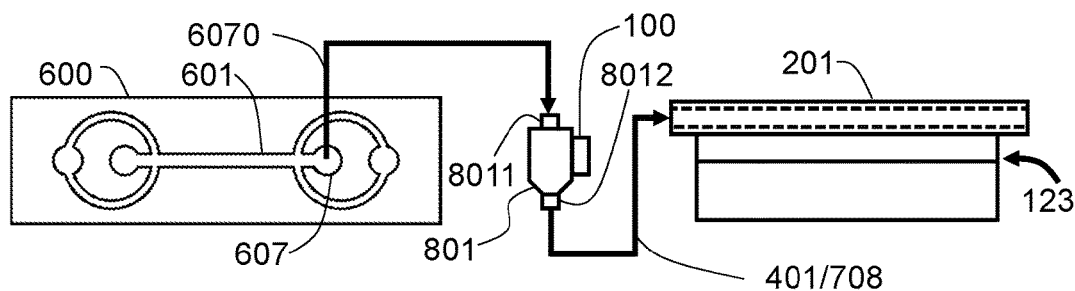
FIG. 44A illustrates first type sample processing method including UFL and MAG, with a first type flow connector connecting the UFL large entity outlet and MAG inlet.

FIG. 44A illustrates first type sample processing method where biological sample is first passed through UFL 600 and the large entity output 6070 of UFL 600 is then passed through channel 201 adapted to MAG 123, with a first type flow connector 801 connecting the UFL 600 large entity outlet 607 and MAG inlet flow as in step 401 of FIG. 31 or step 708 of FIG. 39. For the in series operation of UFL 600 and MAG 123 devices, optimal flow rate for UFL channel 601 and optimal flow rate for MAG channel 201 may be different. Optimal flow rate for UFL channel 601 acoustic force separation of large and small entities are determined by laminar flow condition, and separation efficiency between large and small entities. Optimal flow rate for MAG 123 separation is determined by the length of channel 201 and magnetic field force on magnetic labels attached to the entities. Direct fluidically coupled flow from UFL 600 outlet 607 to MAG channel 201 inlet will force the flow rate being the same through UFL 600 channel and MAG channel 201, which may incur negative impact on separation efficiency for either one or both of UFL 600 and MAG 123. It is necessary to decouple the fluid flows through UFL 600 and MAG 123 channel 201. Flow connector 801 serves to decouple flow rates of the UFL 600 and MAG 123. Output fluid 6070 is first injected into connector 801 through inlet 8011, and fluid in connector 801 is output through outlet 8012 as flow as in steps 401/708 into inlet of channel 201 of MAG 123. Both UFL 600 and MAG 123 channel 201 may operate at their respective optimal flow rate. In one embodiment where MAG 123 channel 201 optimal flow rate is larger than UFL 600 optimal flow rate, MAG 123 extracts fluid 401/708 from connector 801 faster than UFL 600 injects fluid 6070 into the connector 801. A fluid level sensor 100 may be attached to connector 801 to sense fluid level remaining in connector 801. If fluid level drops below a low threshold, sensor 100 may signal MAG 123 to pause flow as in steps 401/708 intake to wait for connector 801 internal liquid level to increase to another higher level before MAG 123 may restart extracting fluid as in steps 401/708 from connector 801. In another embodiment where MAG 123 channel 201 optimal flow rate is smaller than UFL 600 optimal flow rate, MAG 123 extracts fluid as in steps 401/708 from connector 801 slower than UFL 600 injects fluid 6070 into the connector 801. If fluid level increases above a low threshold, sensor 100 may signal UFL 600 to pause flow 6070 output to wait for connector 801 internal liquid level to drop to another lower level before UFL 600 may restart outputting fluid 6070 into connector 801. Flow connector 801 may be in the design as shown in FIG. 44A, where inlet 8011 is at a higher vertical location than outlet 8012, where flow 6070 enters connector 801 and accumulates at outlet 8012 at inside of 801 due to gravity. Alternatively, liquid sample may be completely processed through UFL 600 first and stored in connector 801. MAG 123 then extracts fluid from connector 801 as input into the MAG 123 channel 201 and completes processing of all liquid sample from connector 801. Connector 801 may be made as part of an enclosed fluidic line, where during the path of flow 6070 from UFL 600 outlet 607 to inlet 8011 of connector 801, to outlet 8012, to flow as in steps 401/708 into inlet of channel 201, fluid sample is not exposed to air, and being sterile.

Figure 44B:
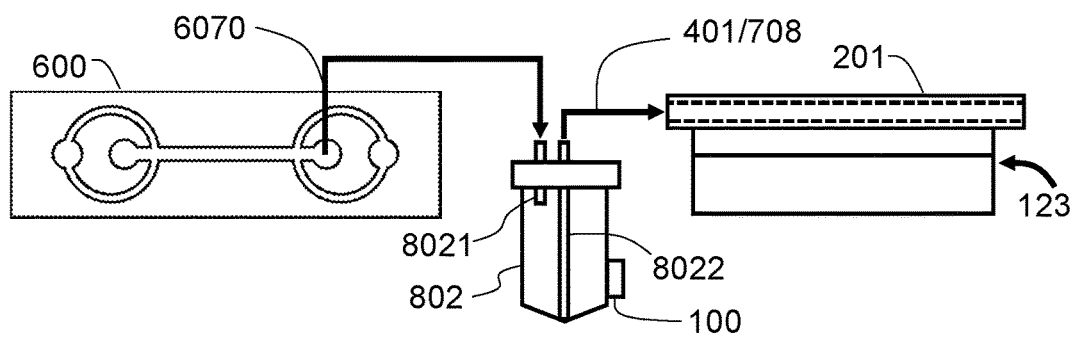
FIG. 44B illustrates first type sample processing method with a second type flow connector connecting the UFL large entity outlet and MAG inlet.

FIG. 44B illustrates first type sample processing method of FIG. 44A with using a second type flow connector 802 connecting the UFL 600 large entity outlet 607 and MAG 123 channel 201 inlet. Connector 802 as shown in FIG. 44B takes the form similar to a vial. Flow 6070 enters connector 802 through a short length inlet tube 8021 of connector 802 and drips to bottom of the connector 802 due to gravity. Flow as in steps 401/708 is extracted from the fluid at the bottom of the connector 802 by a long length outlet tube 8022 to input of channel 201. Fluid level sensor 100 may be attached to connector 802 to sense fluid level within connector 802. UFL 600 and MAG 123 may both operate at their respective optimal flow rate, and fluid level sensor 100 may function to pause UFL 600 operation or MAG 123 operation with the same method as described in FIG. 44A. Alternatively, liquid sample may be completely processed through UFL 600 and stored in connector 802. MAG 123 then extracts fluid from connector 801 as input into the MAG 123 channel 201 and completes processing of all liquid sample from connector 802. Connector 802 may be made as part of an enclosed fluidic line similar as connector 801.

Figure 44C:
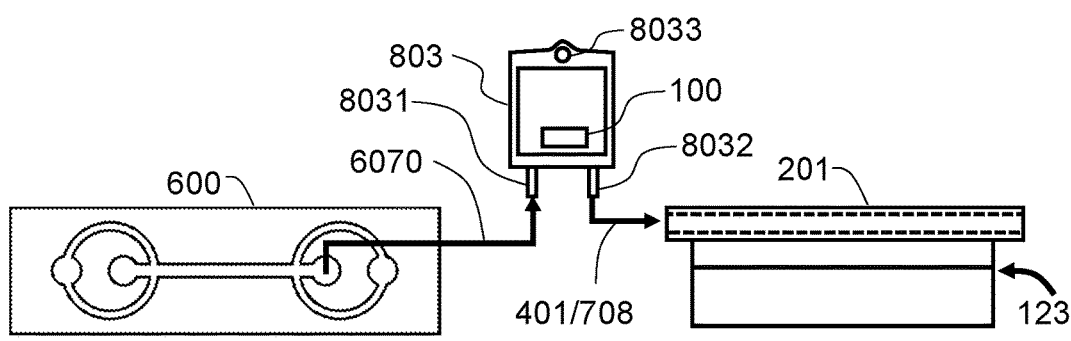
FIG. 44C illustrates first type sample processing method with a third type flow connector connecting the UFL large entity outlet and MAG inlet.

FIG. 44C illustrates first type sample processing method of FIG. 44A with using a third type flow connector 803 connecting the UFL 600 large entity outlet 607 and MAG 123 channel 201 inlet. Connector 803 as shown in FIG. 44C takes the form similar to a fluid bag or blood bag. Flow 6070 enters connector 803 through a bottom inlet 8031 fills connector 803 from bottom of the connector 803 due to gravity. Flow as in steps 401/708 is extracted from the fluid at the bottom of the connector 803 through outlet 8032 to input of channel 201. Fluid level sensor 100 may be attached to connector 803 to sense fluid level within connector 803. UFL 600 and MAG 123 may both operate at their respective optimal flow rate, and fluid level sensor 100 may function to pause UFL 600 operation or MAG 123 operation with the same method as described in FIG. 44A. Alternatively, liquid sample may be completely processed through UFL 600 and stored in connector 803. MAG 123 then extracts fluid from connector 801 as input into the MAG 123 channel 201 and completes processing of all liquid sample from connector 803. Connector 803 may be made as part of an enclosed fluidic line similar as connector 801.

Figure 45A:
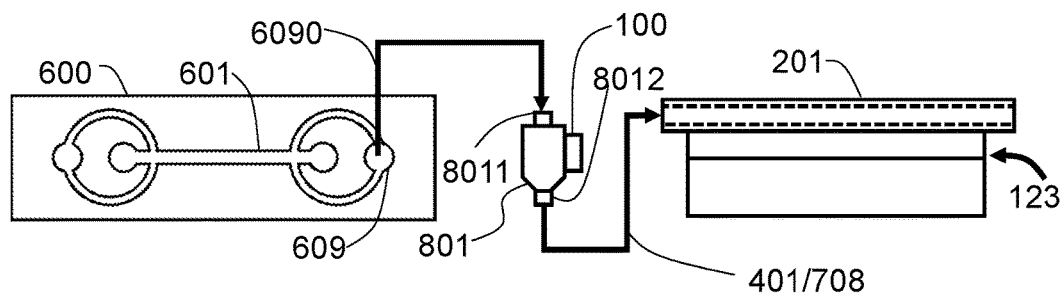
FIG. 45A illustrates second type sample processing method including UFL and MAG, with a first type flow connector connecting the UFL small entity outlet and MAG inlet.

FIG. 45A illustrates second type sample processing method where biological sample is first passed through UFL 600 and the small entity output 6090 of UFL 600 is then passed through MAG 123, with first type flow connector 801 connecting the UFL small entity 6090 outlet 609 and MAG 123 channel 201 inlet. FIG. 45A is identical to FIG. 44A in every aspect except small entities flow 6090 from outlet 609 is injected into the inlet 8011 of connector 801.

Figure 45B:
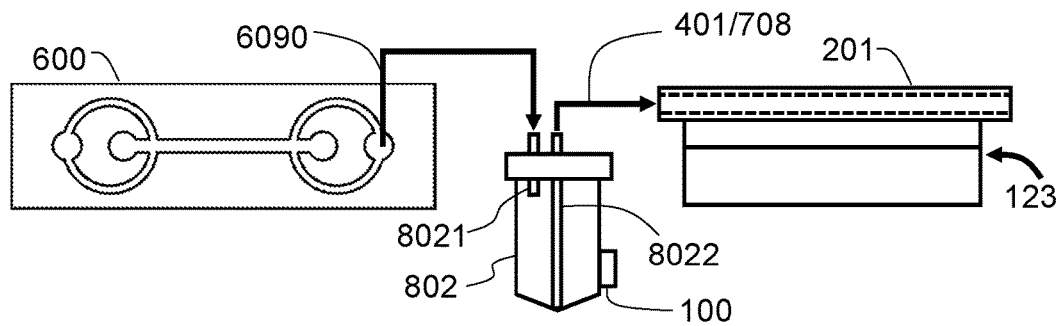
FIG. 45B illustrates second type sample processing method with a second type flow connector connecting the UFL small entity outlet and MAG inlet.

FIG. 45B illustrates second type sample processing method where biological sample is first passed through UFL 600 and the small entity output 6090 of UFL 600 is then passed through MAG 123, with second type flow connector 802 connecting the UFL small entity 6090 outlet 609 and MAG 123 channel 201 inlet. FIG. 45B is identical to FIG. 44B in every aspect except small entities flow 6090 from outlet 609 is injected into the inlet 8021 of connector 802.

Figure 45C:
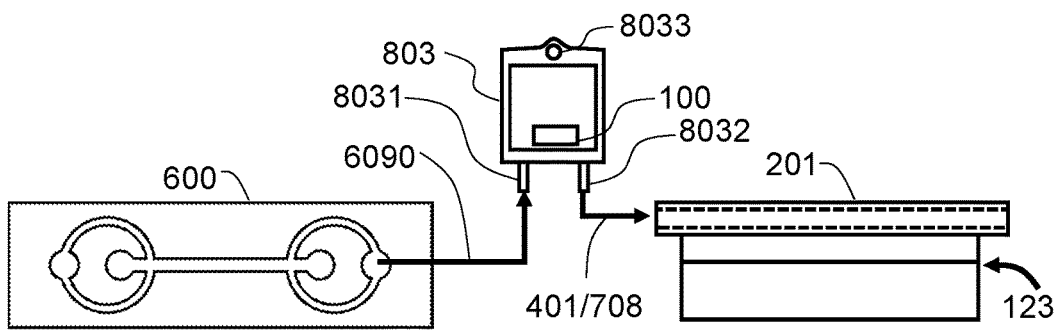
FIG. 45C illustrates second type sample processing method with a third type flow connector connecting the UFL small entity outlet and MAG inlet.

FIG. 45C illustrates second type sample processing method where biological sample is first passed through UFL 600 and the small entity output 6090 of UFL 600 is then passed through MAG 123, with third type flow connector 803 connecting the UFL small entity 6090 outlet 609 and MAG 123 channel 201 inlet. FIG. 45C is identical to FIG. 44C in every aspect except small entities flow 6090 from outlet 609 is injected into the inlet 8031 of connector 803.

Figure 46A:
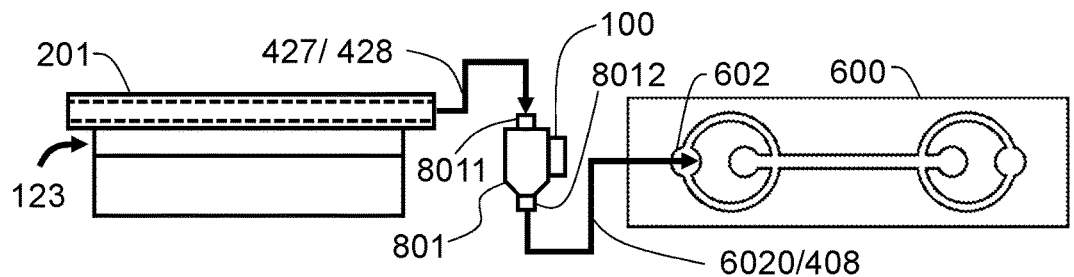
FIG. 46A illustrates third type sample processing method including MAG an dUFL, with a first type flow connector connecting the MAG outlet and UFL entity fluid inlet.

FIG. 46A illustrates third type sample processing method where biological sample is first passed through MAG 123 channel 201, and following procedure 427 or 428 of FIG. 31, the output of MAG 123 channel 201 is then passed through UFL 600 as entity fluid 6020 into inlet 602 as in step 408 of FIG. 31, with first type flow connector 801 connecting the MAG 123 channel 201 outlet and UFL 600 entity fluid 6020 inlet 602. In FIG. 46A, output from MAG 123 can be either negative entities that do not have attached SPL 2, or positive entities separated by MAG 123 magnetic field and subsequently dissociated and flushed out of channel 201 as described in FIG. 31. Similar as in FIG. 44A, MAG 123 and UFL 600 may each operate with their respective optimal flow rate. Fluid level sensor 100 may be attached to connector 801 to sense fluid level remaining in connector 801. Fluid level sensor 100 operates similarly as in FIG. 44A to sense fluid in connector 801, and depending on the flow rate difference between MAG 123 and UFL 600, may pause MAG 123 or UFL 600 flow to maintain fluid level in connector 801 above a low level or below a high level. Alternatively, liquid sample may be completely processed through MAG 123 first and stored in connector 801. UFL 600 then extracts fluid from connector 801 as input into the inlet 602 and completes processing of all liquid sample from connector 801. Connector 801 may be made as part of an enclosed fluidic line similarly as in FIG. 44A.

Figure 46B:
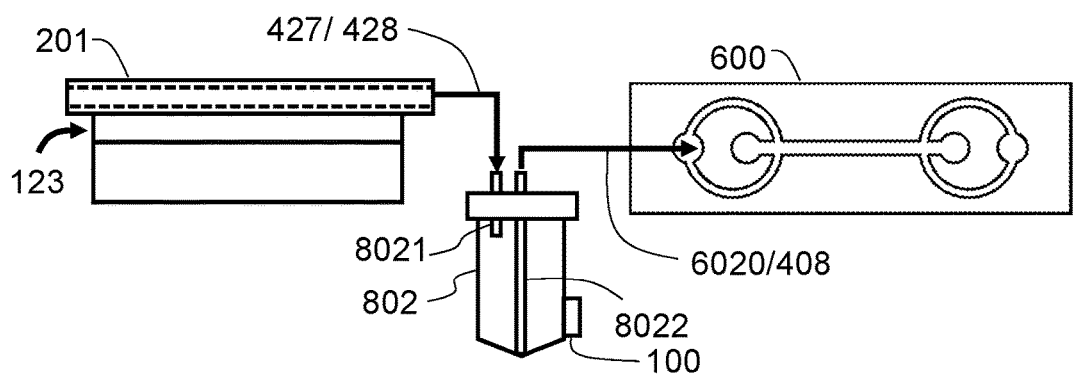
FIG. 46B illustrates third type sample processing method with a second type flow connector connecting the MAG outlet and UFL entity fluid inlet.

FIG. 46B is same as FIG. 46A in every aspect, except replacing connector 801 with connector 802, where operation of connector 802 and attached sensor 100 is same as described FIG. 44B.

Figure 46C:
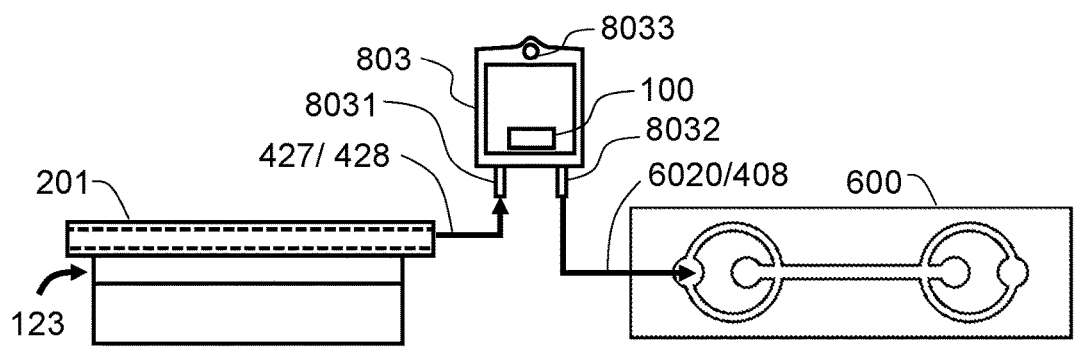
FIG. 46C illustrates third type sample processing method with a third type flow connector connecting the MAG outlet and UFL entity fluid inlet.

FIG. 46C is same as FIG. 46A in every aspect, except replacing connector 801 with connector 803, where operation of connector 803 and attached sensor 100 is same as described FIG. 44C.

Figure 47:
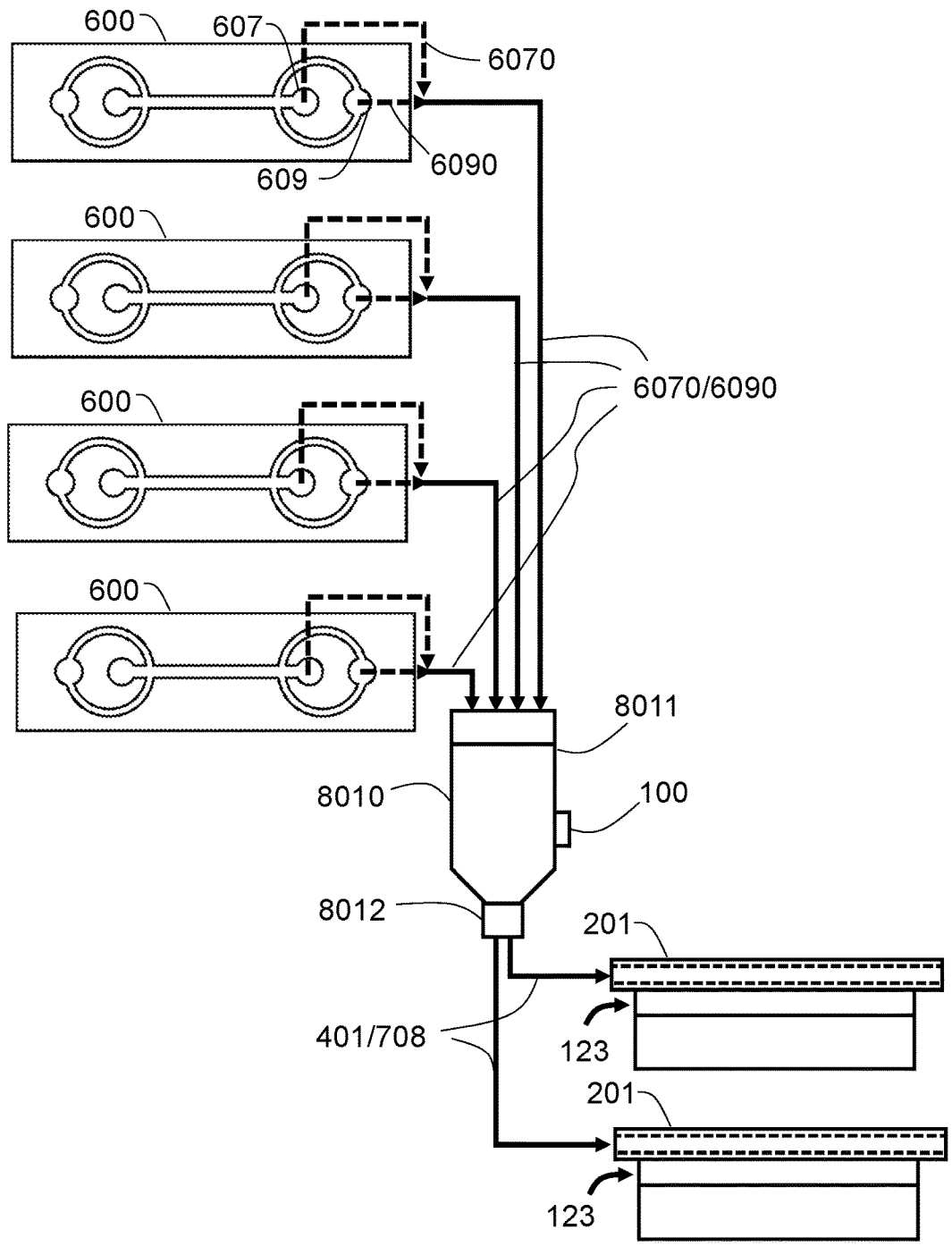
FIG. 47 illustrates fourth type sample processing method including multiple UFLs, a fourth type flow connector, and multiple MAGs.

FIG. 47 illustrates fourth type sample processing method where biological sample is first passed through multiple UFLs 600, output fluids from the UFLs 600, which can be either large entities 6070 or small entities 6090, are then fed into inlets 8011 of a fourth type flow connector 8010, and from connector 8010 outlets 8012 into the inlets of channels 201 of multiple MAGs 123. FIG. 47 is functionally similar to FIG. 44A and FIG. 45A. Connector 8010 is also functionally same as connector 801, except inlet 8011 of connector 8010 accept multiple fluid output from multiple UFLs 600, and outlet 8012 of connector 8010 outputs to input of multiple channels 201 of multiple MAGs 123.

Figure 48:
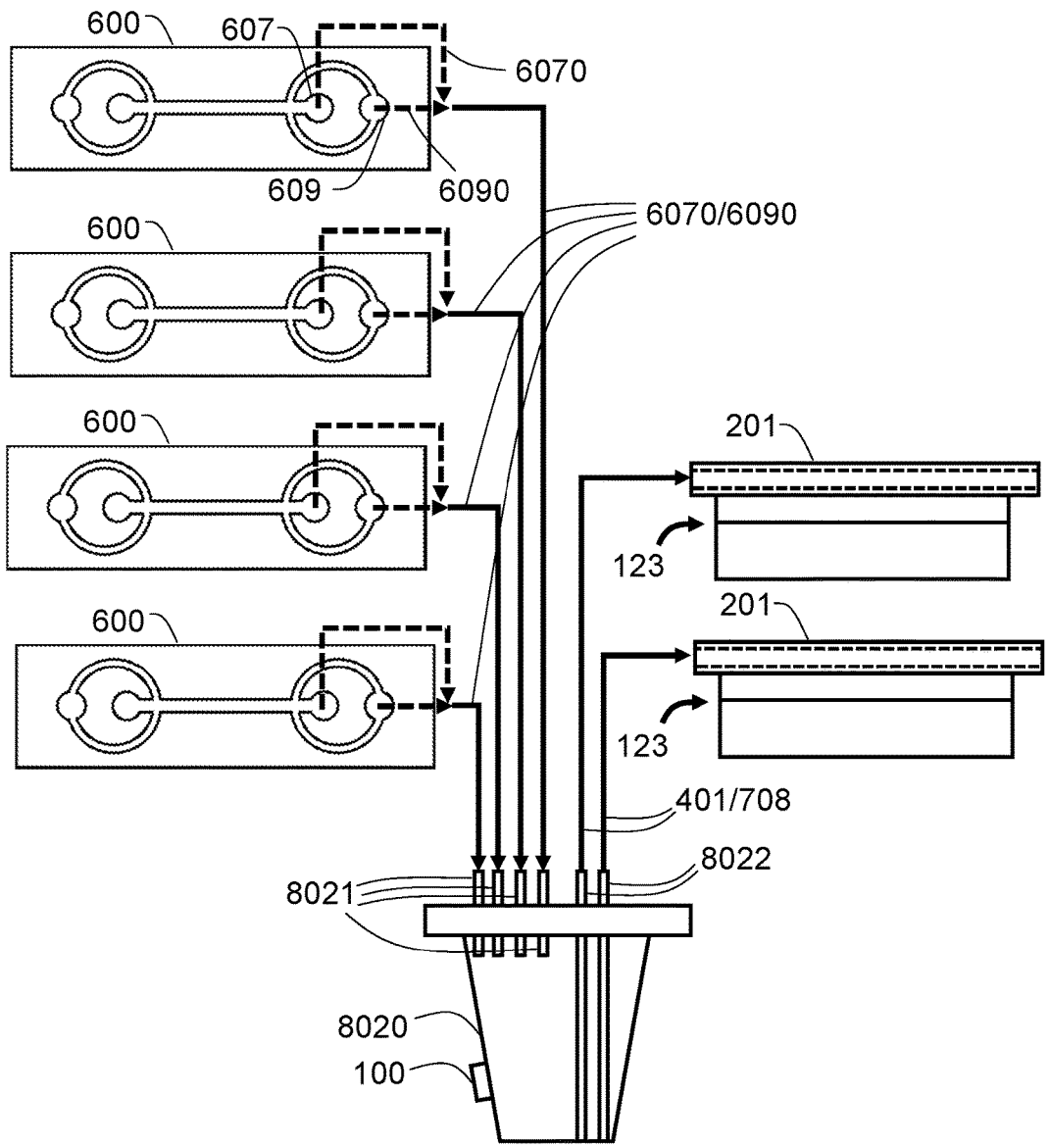
FIG. 48 illustrates fifth type sample processing method including multiple UFLs, a fifth type flow connector, and multiple MAGs.

FIG. 48 illustrates fifth type sample processing method where biological sample is first passed through multiple UFLs 600, output fluids from the UFLs 600, which can be either large entities 6070 or small entities 6090, are then fed into inlets 8021 of a fifth type flow connector 8020, and from connector 8020 outlets 8022 into the inlets of channels 201 of multiple MAGs 123. FIG. 48 is functionally similar to FIG. 44B and FIG. 45B. Connector 8020 is also functionally same as connector 802, except inlet 8021 of connector 8020 accept multiple fluid output from multiple UFLs 600, and outlet 8022 of connector 8020 outputs to input of multiple channels 201 of multiple MAGs 123.

Figure 49:
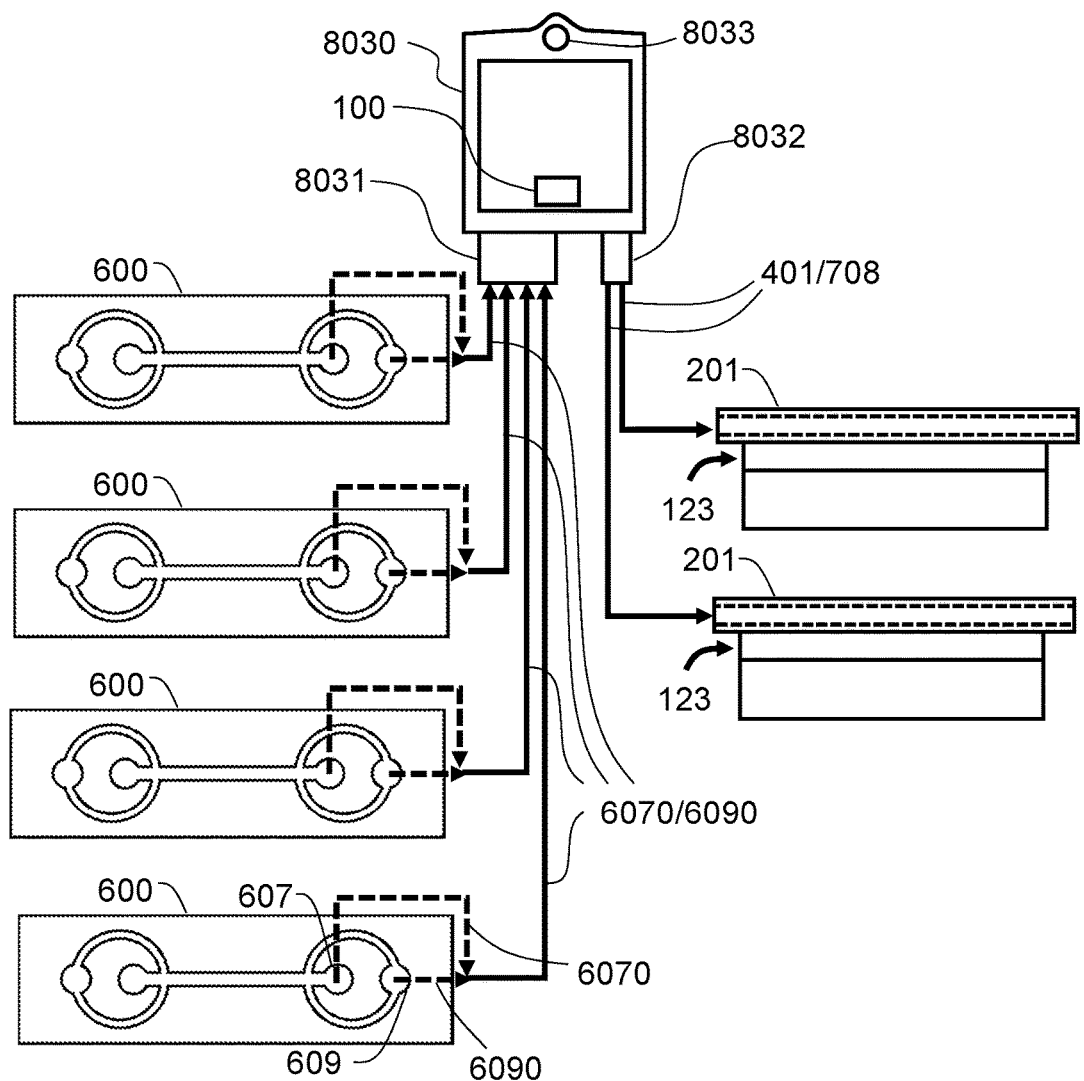
FIG. 49 illustrates fifth type sample processing method including multiple UFLs, a sixth type flow connector, and multiple MAGs.

FIG. 49 illustrates sixth type sample processing method where biological sample is first passed through multiple UFLs 600, output fluids from the UFLs 600, which can be either large entities 6070 or small entities 6090, are then fed into inlets 8031 of a sixth type flow connector 8030, and from connector 8030 outlets 8032 into the inlets of channels 201 of multiple MAGs 123. FIG. 49 is functionally similar to FIG. 44C and FIG. 45C. Connector 8030 is also functionally same as connector 803, except inlet 8031 of connector 8030 accept multiple fluid output from multiple UFLs 600, and outlet 8032 of connector 8030 outputs to input of multiple channels 201 of multiple MAGs 123.

In each of FIG. 47, FIG. 48, and FIG. 49, in one embodiment, same biological sample is divided and processed simultaneously through multiple UFLs 600. In another embodiment, each of the UFLs 600 processes a different biological sample. Output from each UFL 600, either large entities 6070 fluid from outlet 607 or small entities fluid from outlet 609, shown as dashed lines in FIG.

47, FIG. 48 and FIG. 49, may be individually input into the inlet 8011 of connector 8010 of FIG. 47, or into inlet 8021 of connector 8020 of FIG. 48, or into inlet 8031 of connector 8030 of FIG. 49, as shown by solid lines 6070/6090 in each of FIG. 47, FIG. 48 and FIG. 49. From outlet 8012, 8022, 8032 of FIG. 47, FIG. 48 and FIG. 49 respectively, following steps of 401 or 708, each of the MAGs 123 of FIG. 47, FIG. 48, or FIG. 49 may extract fluid sample from corresponding connector 8010, 8020, and 8030 into its corresponding channel 201. Each of the UFL 600 and each of the MAG 123 of FIG. 47, FIG. 48, or FIG. 49 may operate at its own respective optimal sample flow rate, which may be different between different UFLs 600 and different between different MAGs 123 within same figure. Due to the existence of the connector 8010, 8020, and 8030, flow rate interference between the different UFLs 600 and MAGs 123 within each of FIG. 47, FIG. 48 and FIG. 49 are minimized or eliminated. Fluid level sensor 100 may be attached to buffers 8010, 8020, and 8030 to sense fluid level remaining in each of the flow connectors 8010, 8020, and 8030. Fluid level sensor 100 operates similarly as in FIG. 44A through FIG. 44C in sensing fluid in flow connectors 8010, 8020, and 8030, and depending on the flow rate difference between MAGs 123 and UFLs 600 of each figure, may pause operation of one or more MAGs 123, or may pause operation of one or more UFLs 600 of each figure to maintain fluid level in corresponding connector 8010, 8020, or 8030 to be above a low level threshold or below a high level threshold. Alternatively, liquid sample may be completely processed through all UFLs 600 first and stored in corresponding connector 8010, 8020, or 8030 of each FIG. 47, FIG. 48 and FIG. 49. MAGs 123 then extract fluid from corresponding connector 8010, 8020, or 8030 of each figure and complete processing of all liquid sample from each corresponding connector 8010, 8020, or 8030. Connectors 8010, 8020, and 8030 may each be made as part of a set of enclosed fluidic lines, which may include UFLs 600, channels 201 and connections from UFLs 600 to each connector 8010, 8020, 8030 and from each connector 8010, 8020, and 8030 to channels 201, similar as described in FIG. 44A through FIG. 44C.

Figure 50:
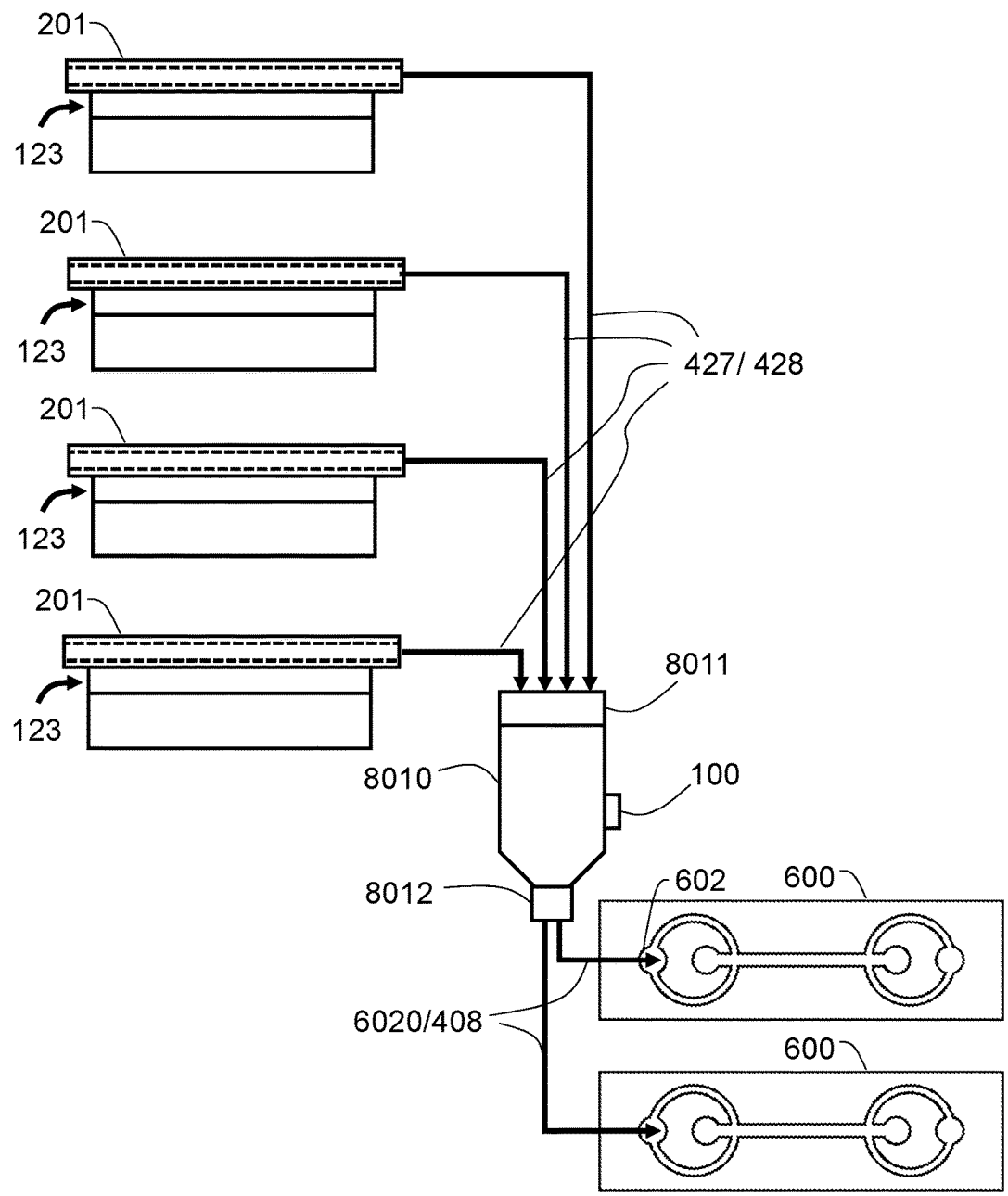
FIG. 50 illustrates seventh type sample processing method including multiple MAGs, a fourth type flow connector, and multiple UFLs.

FIG. 50 illustrates seventh type sample processing method where biological sample is first passed through multiple MAGs 123, output fluids from the MAGs 123 channels 201 are then fed into inlets 8011 of flow connector 8010 of FIG. 47, and from flow connector 8010 outlets 8012 into the entity fluid inlets 602 of multiple UFLs 600.

Figure 51:
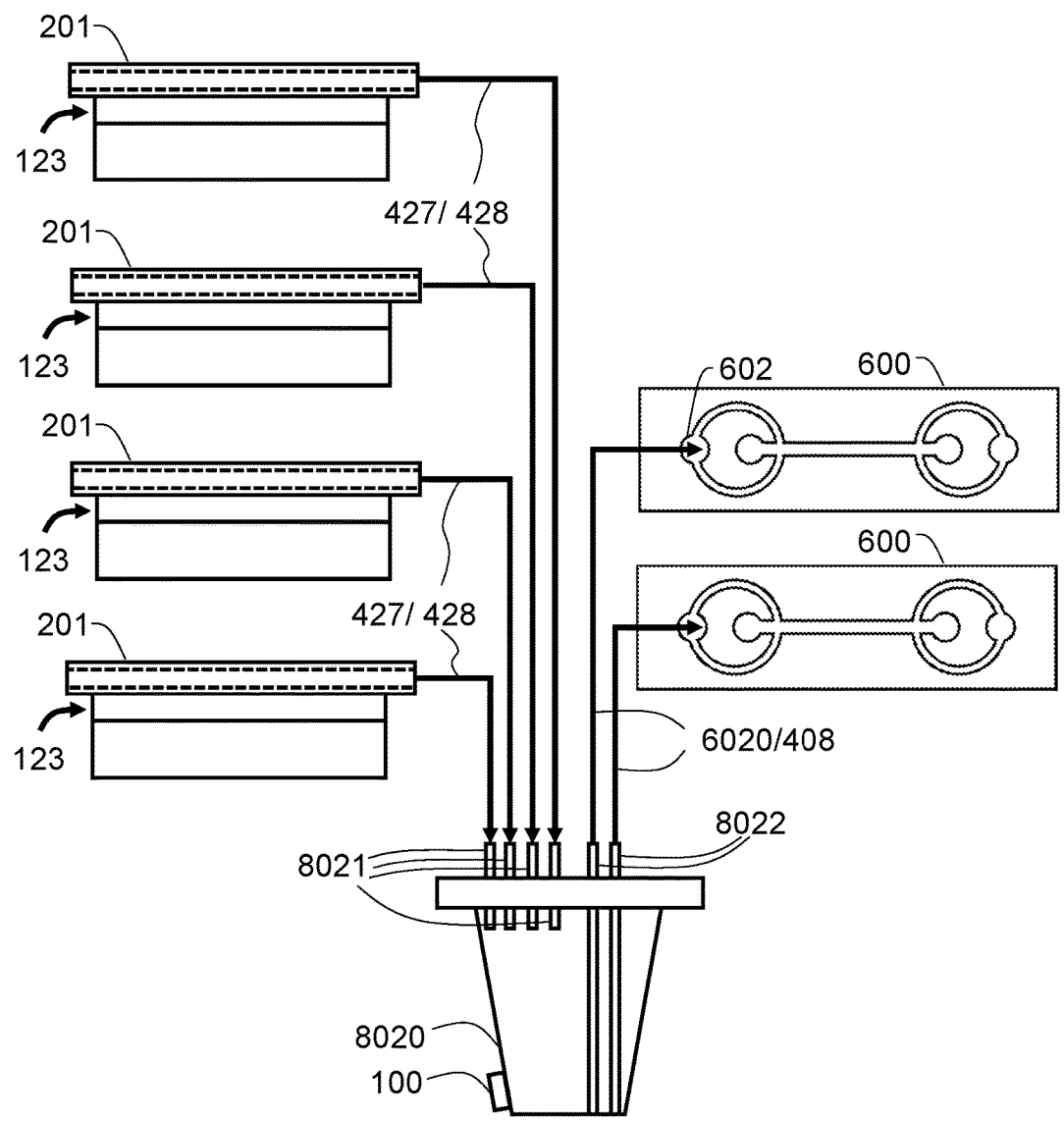
FIG. 51 illustrates eighth type sample processing method including multiple MAGs, a fifth type flow connector, and multiple UFLs.

FIG. 51 illustrates eighth type sample processing method where biological sample is first passed through multiple MAGs 123, output fluids from the MAGs 123 channels 201 are then fed into inlets 8021 of flow connector 8020 of FIG. 48, and from flow connector 8020 outlets 8022 into the entity fluid inlets 602 of multiple UFLs 600.

Figure 52:
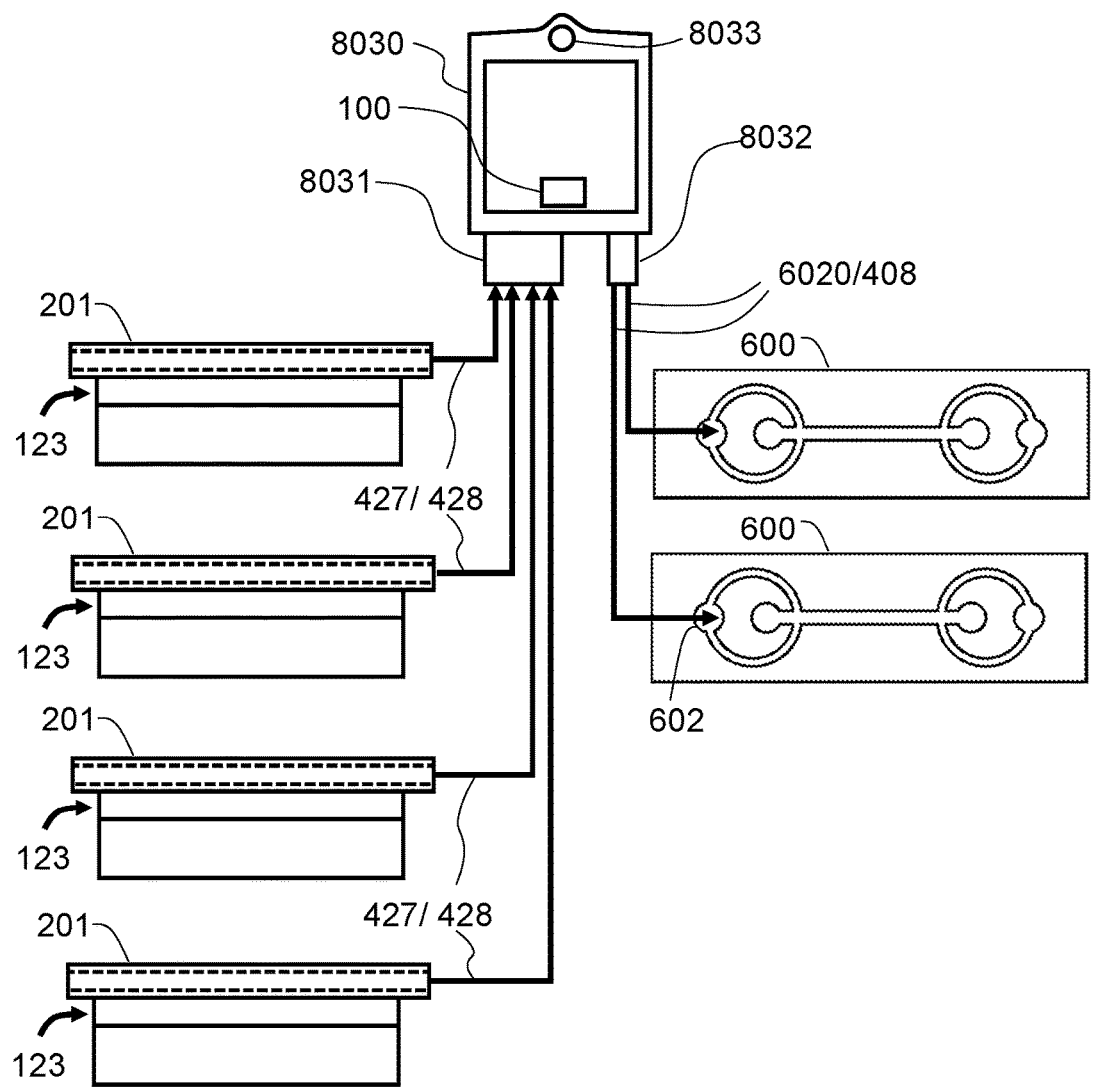
FIG. 52 illustrates ninth type sample processing method including multiple MAGs, a sixth type flow connector, and multiple UFLs.

FIG. 52 illustrates ninth type sample processing method where biological sample is first passed through multiple MAGs 123, output fluids from the MAGs 123 channels 201 are then fed into inlets 8031 of flow connector 8030 of FIG. 49, and from flow connector 8030 outlets 8032 into the entity fluid inlets 602 of multiple UFLs 600.

In each of FIG. 50, FIG. 51, and FIG. 52, in one embodiment, same biological sample is divided and processed simultaneously through multiple MAGs 123. In another embodiment, each of the MAGs 123 processes a different biological sample. Output from each MAG 123, either negative entities following procedure 427, or positive entities following procedure 428, may be individually input into the inlet 8011 of connector 8010 of FIG. 50, or into inlet 8021 of connector 8020 of FIG. 51, or into inlet 8031 of connector 8030 of FIG. 52, as shown by solid lines 427/428 in each of FIG. 50, FIG. 51 and FIG. 52. From outlet 8012, 8022, 8032 of FIG. 50, FIG. 51 and FIG. 52 respectively, following step of 408, each of the UFLs 600 of FIG. 50, FIG. 51, or FIG. 52 may extract fluid sample as entity fluid 6020 from corresponding connector 8010, 8020, and 8030 into its corresponding entities inlet 602, Each of the UFL 600 and each of the MAG 123 of FIG. 50, FIG. 51, or FIG. 52 may operate at its own respective optimal sample flow rate, which may be different between different UFLs 600 and different between different MAGs 123 within same figure. Due to the existence of the connector 8010, 8020, and 8030, flow rate interference between the different UFLs 600 and MAGs 123 within each of FIG. 50, FIG. 51 and FIG. 52 are minimized or eliminated. Fluid level sensor 100 may be attached to flow connectors 8010, 8020, and 8030 to sense fluid level remaining in each of the flow connectors. Fluid level sensor 100 operates similarly as in FIG. 46A through FIG. 47C in sensing fluid in flow connectors 8010, 8020, and 8030, and depending on the flow rate difference between MAGs 123 and UFLs 600 of each figure, may pause operation of one or more MAGs 123, or may pause operation of one or more UFLs 600 of each figure to maintain fluid level in corresponding connector 8010, 8020, or 8030 to be above a low level threshold or below a high level threshold. Alternatively, liquid sample may be completely processed through all MAGs 123 first and stored in corresponding connector 8010, 8020, or 8030 of each FIG. 50, FIG. 51 and FIG. 52. UFLs 600 then extract fluid from corresponding connector 8010, 8020, or 8030 of each figure and complete processing of all liquid sample from each corresponding connector 8010, 8020, or 8030. Flow connectors 8010, 8020, and 8030 may each be made as part of a set of enclosed fluidic lines, which may include UFLs 600, channels 201 and connections from channels 201 to each connector 8010, 8020, 8030 and from each connector 8010, 8020, and 8030 to UFLs 600, similar as described in FIG. 46A through FIG. 46C.

Figure 53:
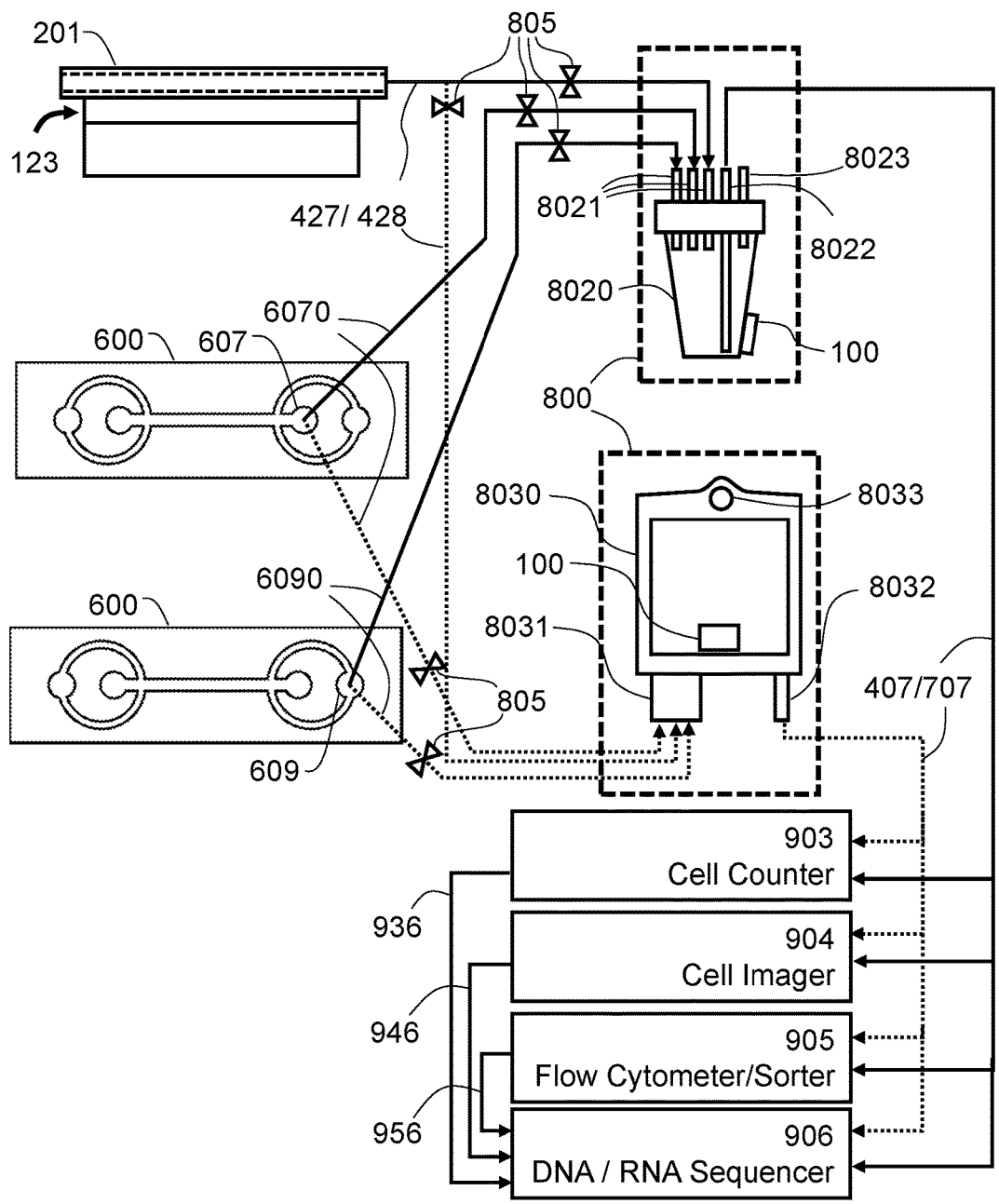
FIG. 53 illustrates tenth type sample processing method including one or more of UFLs and MAGs, a fifth or a sixth type flow connector, and different type of cell processing devices.

FIG. 53 illustrates tenth type sample processing method where biological sample after being passed through one or more of UFLs 600 or MAGs 123, output fluids from the UFLs 600 and MAGs 123 are fed into inlets of a flower connector 8020 or a flow connector 8030, and from the flow connectors 8020 and 8030 outlets into different type of cell processing devices. FIG. 53 shows example of liquid sample output from MAG 123 channel 201, including negative entities following procedure 427 and positive entities following procedure 428, may be injected to inlet 8021 of connector 8020 or inlet 8031 of connector 8030 similar as in FIG. 51 and FIG. 52. Alternatively, UFL 600 large entities output 6070 from outlet 607 or small entities output 6090 from outlet 609 may be also injected into to inlet 8021 of connector 8020 or inlet 8031 of connector 8030 similar as in FIG. 48 and FIG. 49. After sample fluid is completely processed through UFL 600 or MAG 123, and injected into, and stored within, connector 8020 or connector 8030, entities analysis as in step 407 of FIG. 31 and step 707 of FIG. 39 may be performed by sending sample fluid containing entities from connector 8020 or connector 8030 to any of: cell counter 903, cell imager 904, flow cytometer or sorter 905, and DNA or RNA sequencer 906. Entities may be further sent to DNA or RNA sequencer 906 after cell counter 903 as in 936, or after cell imager 904 as in 946, or after flow cytometer or sorter 905 as in 956. For sending the sample fluid from outlet 8022 of connector 8020, or from outlet 8032 of connector 8030, pressurized chamber 800 may be used to contain the connector 8020 or connector 8030 inside, and force sample fluid out of connector 8020 or connector 8030 in a steady and continuous flow stream. Chamber 800 may be a chamber filled with pressurized air inside. Connector 8020 in vial type may have an additional air port 8023 open to chamber 800 internal pressurized air to help push sample fluid out of connector 8020. While connector 8030 may be in a flexible blood bag form, which when under pressured air of chamber 800, will automatically deflate and force sample liquid out through outlet 8032. To avoid back flow into UFL 600 or MAG 123 channel 201, shut off valves 805 may be implemented on output lines from MAG 123 channel 201 and UFL 600 to connector 8020 or connector 8030.

Figure 54A:
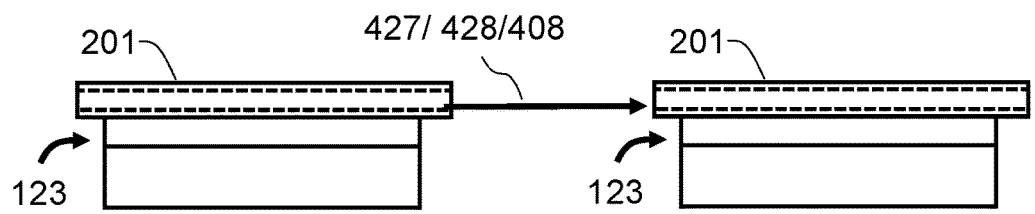
FIG. 54A illustrates eleventh type sample processing method including a multi-stage MAG process.

FIG. 54A illustrates eleventh type sample processing method where biological sample after being passed through a first MAG 123 channel 201 during a magnetic separation may output negative entities fluid following procedure 427, or positive entities fluid following procedure 428, into inlet of a second MAG 123 channel 201 input as in step 408 of a continued process. FIG. 54A illustrates a multi-stage MAG process.

Figure 54B:
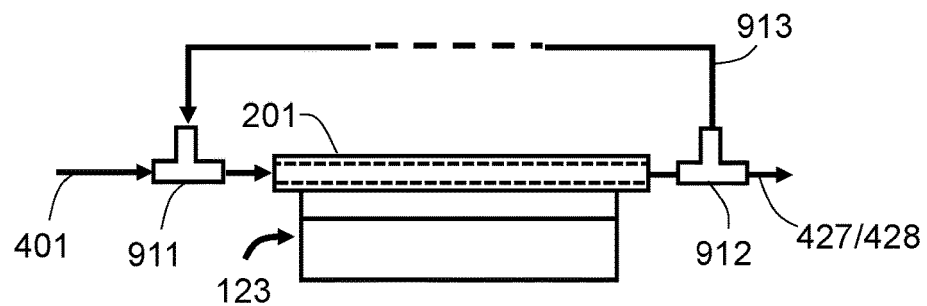
FIG. 54B illustrates twelfth type sample processing method including a multi-cycle MAG process.

FIG. 54B illustrates twelfth type sample processing method where after biological sample passed through MAG 123 for magnetic separation, output fluid from MAG 123 channel 201, containing either negative entities or position entities, may be diverted through a T-connector 912 into flow 913. Flow 913 may then be re-input back into the input of the channel 201 of MAG 123 for another round of magnetic separation through T-connector 911. T-connector 911 allows initial fluid sample input as in step 401 and recycled flow 913 input to channel 201. T-connector 912 allows output from channel 201 into recycled flow 913 or output from MAG 123 as in procedures 427 and 428. In one embodiment, recycled flow 913 contains negative entities, repeated magnetic separation in FIG. 54B helps achieve complete depletion of all magnetic entities in the negative entities flow before output into 427/428 procedure. In another embodiment, recycled flow 913 contains positive entities after dissociation, repeated process as in FIG. 54B helps increase purity in positive magnetic entities to allow wash off of non-magnetic entities that may be in the conglomerate by non-specific bindings. FIG. 54B illustrates using same MAG 123 as a multi-cycle MAG process.

Figure 54C:
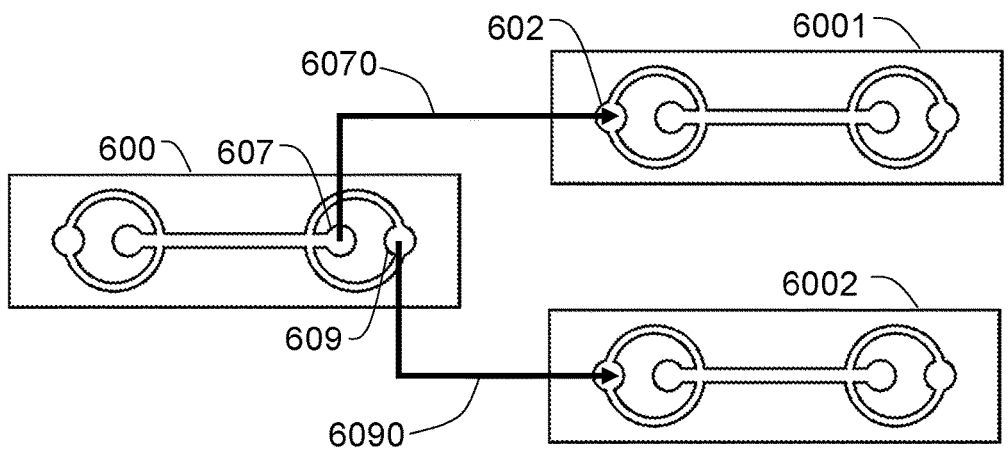
FIG. 54C illustrates thirteenth type sample processing method including a multi-stage UFL process.

FIG. 54C illustrates thirteenth type sample processing method where biological sample after being passed through a first UFL 600, output fluids from first UFL 600, for example large entities 6070 fluid from outlet 607 or small entities 6090 fluid from outlet 609, may be passed into entity fluid inlets 602 of one or more subsequent UFLs 600 as a multi-stage UFL process.

Figure 55A:
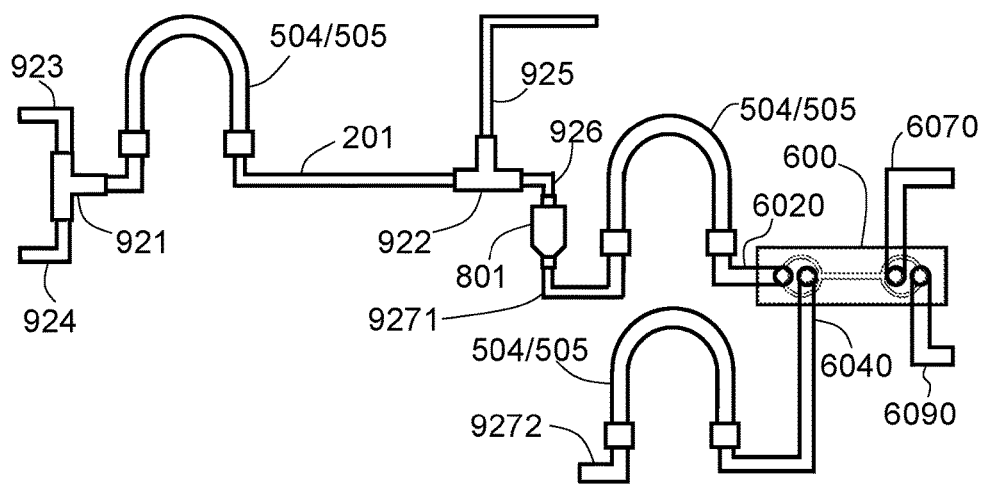
FIG. 55A illustrates first example of closed and disposable fluidic lines for third type sample processing method.

FIG. 55A illustrates first embodiment of closed and disposable fluidic lines for third type sample processing method as shown in FIG. 46A, where connector 801 may be replaced with connector 802 or connector 803 without limitation. Input line 923 may connect to a sample liquid container. Input line 924 may connect to a MAG buffer container. Input line 923 and input line 924 are connected through a T-connector 921 to the inlet of the first pump tubing 504/505 that may be mounted into a peristaltic pump. First pump tubing 504/505 outlet connects to channel 201 which may be used as part of MAG 123. Output of channel 201 connects to T-connector 922, which connects to output line 925 and output line 926. Output line 925 may connect to an MAG out sample container and output line 926 connects to inlet of connector 801. In one embodiment, output line 925 may output negative entities to said MAG out sample container, and output line 926 may output positive entities to connector 801. In another embodiment, output line 925 may output positive entities to said MAG out sample container, and output line 926 may output negative entities to connector 801. Connector 801 outlet connects to input line 9271 of a second pump tubing 504/505. Said second pump tubing 504/505 outlet then connects to UFL 600 sample input line 6020. Input line 9272 may connect to UFL buffer container and connects to inlet of a third pump tubing 504/505. Said third pump tubing 504/505 outlet then connects to UFL 600 buffer input line 6040. UFL 600 large entities 6070 output line may connect to a large entities sample container. UFL 600 small entities 6090 output line may connect to a small entities sample container. FIG. 55A illustrates that besides the input and output lines 923, 924, 925, 9272, 6070, and 6090 that connect to external containers, entire fluid path from sample liquid input to line 923, to sample output to lines 925, 6070, 6090, all pumps, MAG 123 and other fluidic line components will be externally attached to the lines of FIG. 55A. Thus, lines of FIG. 55A are internally enclosed, suitable for single use disposable purpose and sterile applications.

Figure 55B:
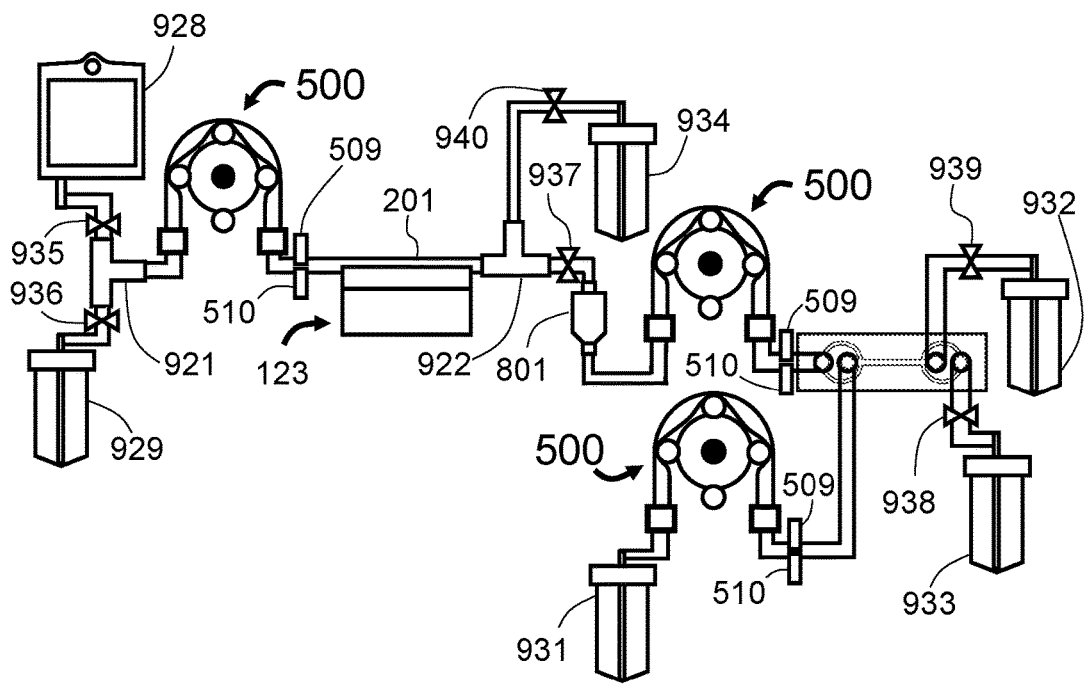
FIG. 55B illustrates fluidic lines of FIG. 55A being connected to, or attached with, various fluidic devices to realize third type sample processing method.

FIG. 55B illustrates fluidic lines of FIG. 55A being connected to, or attached with, various fluidic components. Input line 923 connects to a liquid sample container 928 in blood bag form. Input line 924 connects to buffer container 929. Valves 935 and 936 are attached to lines 923 and 924 to control either sample liquid from bag 928 or buffer from container 929 is flown through T-connector 921 into first pump tubing 504/505. First, second and third pump tubing 504/505 is each installed into a peristaltic pump 500. Three pumps 500 operate to pump either sample fluid or buffer fluid into MAG 123 and UFL 600. A flow limiter 509/510 may be attached to the output line from each pump 500, including lines 201, 6020, 6040 to reduce flow rate pulsation from the pumps 500. Channel line 201 is mounted into MAG 123. Output line 925 connects to MAG out sample container 934. Valve 940 is attached to line 925 and valve 937 is attached to line 926, which control negative entities or positive entities from MAG 123 going into either container 934 or the connector 801 through the T-connector 922. Valves 940 and 937 may both shut down the flow in lines 925 and 926 during demagnetization/dissociation process of MAG 123. Input line 9272 may connect to UFL buffer container 931. UFL output line 6070 connects to large entities container 932 and output line 6090 connects to small entities 933. Adjustable valves 939 and 938 may be attached to the lines 6070 and 6090 to adjust the flow rate within each line of 6070 and 6090, which in turn controls the laminar flow speed in UFL channel for channel center buffer flow and channel edge entities sample flow.

Figure 56A:
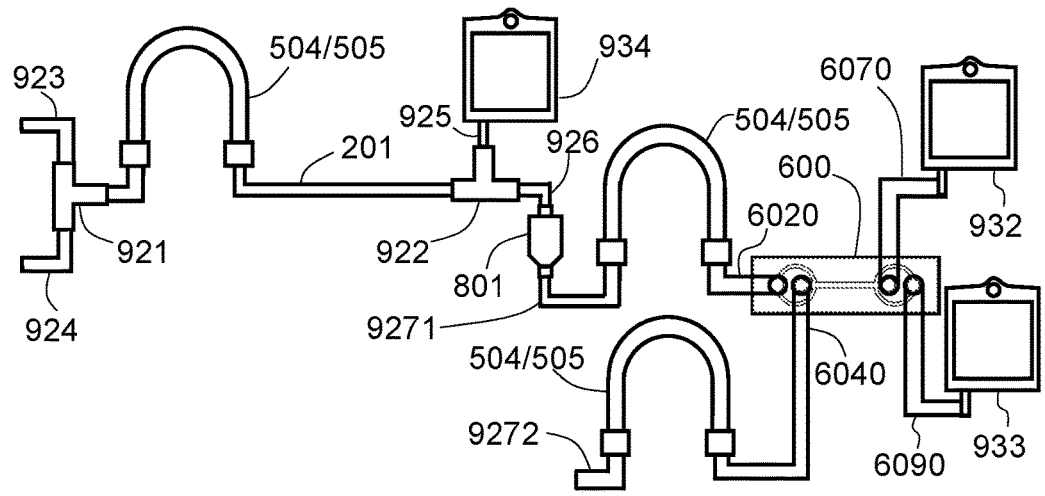
FIG. 56A illustrates second example of closed and disposable fluidic lines for third type sample processing method.

FIG. 56A illustrates second embodiment of closed and disposable fluidic lines for third type sample processing method as shown in FIG. 46A. FIG. 56A is identical to FIG. 55A, except the output line 925 is connected to a MAG sample container 934, UFL output line 6070 is connected to a large entities container 932, and UFL output line 6090 is attached to a small entities container 933. FIG. 56A illustrates containers 934, 932, 933 are in the form of blood bags. Bags 932, 933, 934 as part of the enclose lines of FIG. 56A may be disposable and made sterile, and may also be separated from the lines after separation process for steps 407 and 408 of FIG. 31, or steps 707 and 708 of FIG. 39.

Figure 56B:
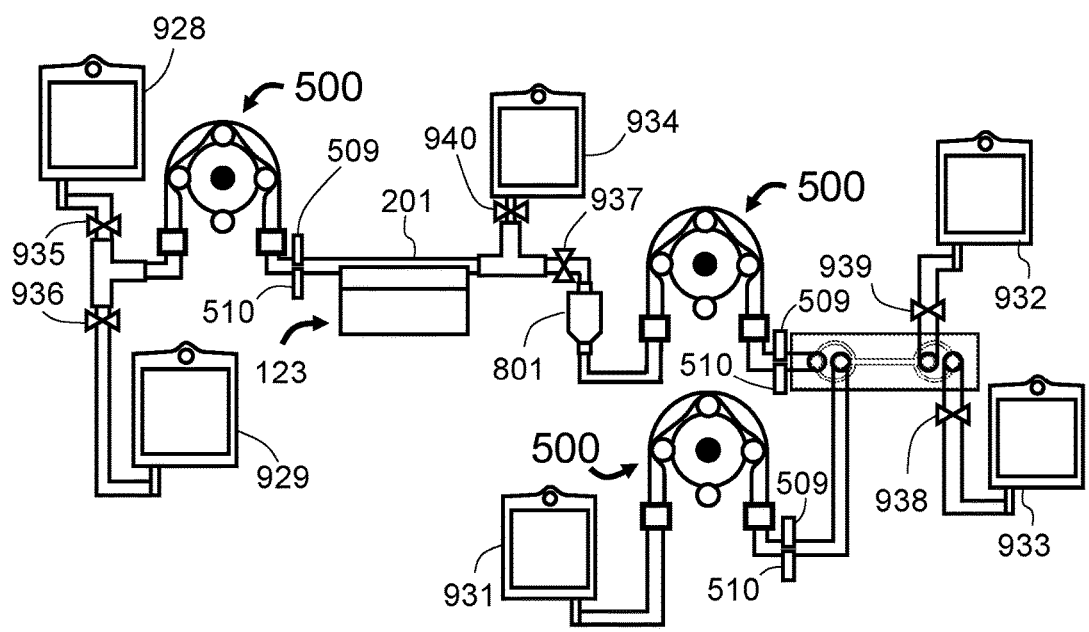
FIG. 56B illustrates fluidic lines of FIG. 56A being connected to, or attached with, various fluidic devices to realize third type sample processing method.

FIG. 56B describes the identical process of: connecting sample container 928, buffer container 929, buffer container 931 to the lines 923, 924 and 9272 respectively, same as in FIG. 55B. Containers 928, 929, 931 are in blood bag form.

Also same as described in FIG. 55B, three pump tubing 504/505 are installed in the three peristaltic pumps 500, valves 935, 936, 940, 937, 939, 938, are each attached to the corresponding lines, and flow limiters 509/510 may be attached at output line of each pump 500 same as in FIG. 55B.

Figure 57A:
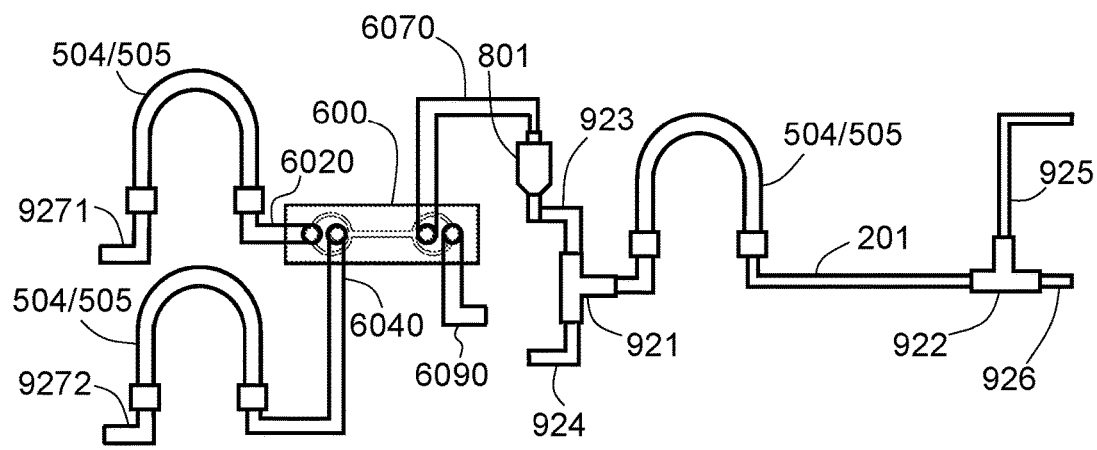
FIG. 57A illustrates example of closed and disposable fluidic lines for first type sample processing method.

FIG. 57A illustrates embodiment of closed and disposable fluidic lines for first type sample processing method as shown in FIG. 44A, where connector 801 may be replaced with connector 802 or connector 803 without limitation. Input line 9271 may connect to a UFL sample liquid container, and also connects to inlet of a first pump tubing 504/505, which further connect to entities input line 6020 of UFL 600. Input line 9272 may connect to a UFL buffer container, and also connects to inlet of a second pump tubing 504/505, which further connect to buffer input line 6040 of UFL 600. UFL 600 large entities output line 6070 connects to inlet of connector 801. UFL 600 small entities output line 6090 may connect to a small entities container. Outlet of connector 801 connects to MAG sample input line 923. MAG buffer input line 924 may connect to a MAG buffer container. Input lines 923 and 924 are connected through a T-connector 921 to the inlet of the third pump tubing 504/505. Third pump tubing 504/505 outlet connects to channel 201 which may be used as part of MAG 123. Output of channel 201 connects to T-connector 922, which connects to output line 925 and output line 926. Output lines 925 and 926 may each connect to an MAG out sample container. In one embodiment, output line 925 may output negative entities to a first MAG out sample container, and output line 926 may output positive entities to a second MAG out sample container. FIG. 57A illustrates that besides the input and output lines 9271, 9272, 924, 6090, 925, and 926 that connect to external containers, entire fluid path from UFL sample and UFL buffer input lines 9271 and 9272, to sample output lines 6090, 925 and 926, all pumps, MAG 123 and other fluidic line components will be externally attached to the lines of FIG. 57A. Thus, lines of FIG. 57A are internally enclosed, suitable for single use disposable purpose and sterile applications.

Figure 57B:
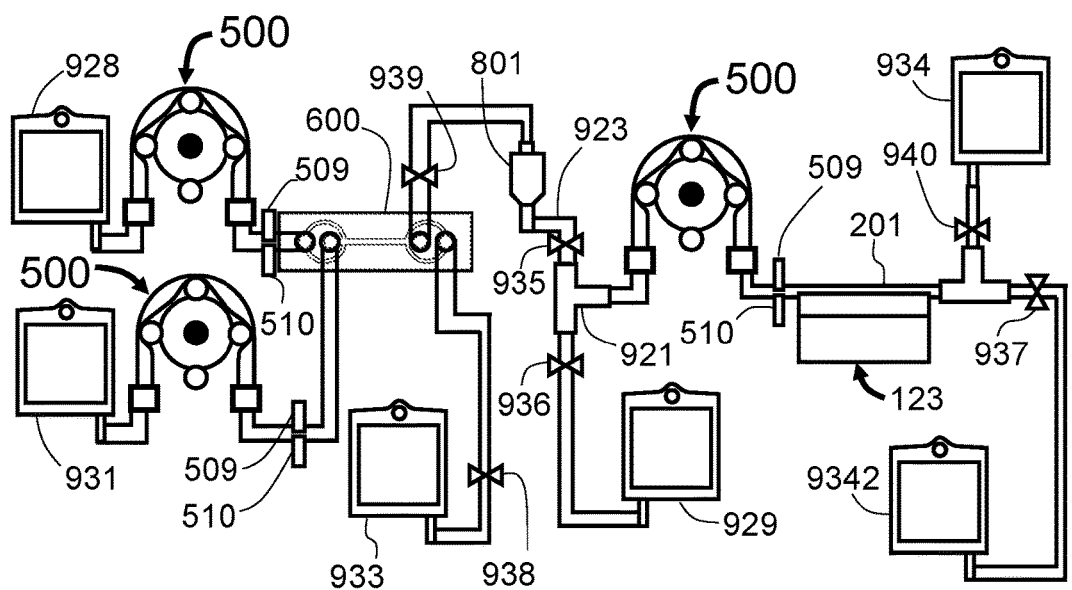
FIG. 57B illustrates fluidic lines of FIG. 57A being connected to, or attached with, various fluidic devices to realize first type sample processing method.

FIG. 57B illustrates fluidic lines of FIG. 57A being connected to, or attached with, various fluidic components. First, second and third pump tubing 504/505 is each installed into a peristaltic pump 500. Three pumps 500 operate to pump either sample fluid or buffer fluid into MAG 123 and UFL 600. A flow limiter 509/510 may be attached to the output line from each pump 500, including lines 201, 6020, 6040 to reduce flow rate pulsation from the pumps 500. Input line 9271 connects to a liquid sample container 928 in blood bag form. Input line 9272 connects to UFL buffer container 931 also in blood bag form. UFL output line 6090 connects to small entities container 933 in blood bag form. Adjustable valves 939 and 938 may be attached to the lines 6070 and 6090 to adjust the flow rate within each line of 6070 and 6090, which in turn controls the laminar flow speed in UFL 600 channel for channel center buffer flow and channel edge entities sample flow. Input line 924 connects to MAG buffer container 929. Valves 935 and 936 are attached to lines 923 and 924 to control either sample liquid from connector 801 or buffer fluid from container 929 is flown through T-connector 921 into third pump tubing 504/505. Channel line 201 is mounted into MAG 123. Output line 925 connects to first MAG out sample container 934. Output line 926 connects to second MAG out sample container 9342. Valve 940 is attached to line 925 and valve 937 is attached to line 926, which control negative entities and positive entities from MAG 123 going into either container 934 or container 9342 through the T-connector 922. Valves 940 and 937 may both shut down the flow in lines 925 and 926 during demagnetization/dissociation process of MAG 123.

Figure 58A:
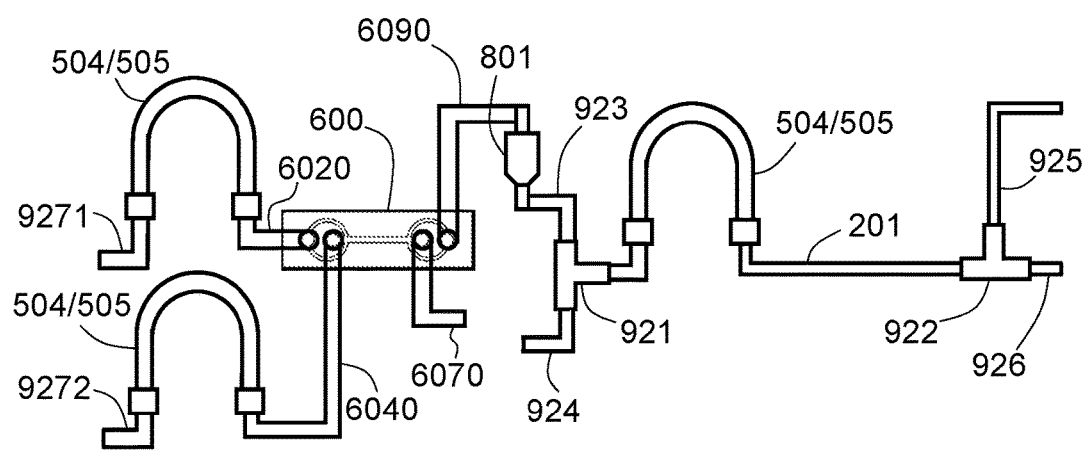
FIG. 58A illustrates example of closed and disposable fluidic lines for second type sample processing method.

FIG. 58A illustrates embodiment of closed and disposable fluidic lines for second type sample processing method as shown in FIG. 45A. FIG. 58A is identical to FIG. 57A in every aspect, except the UFL 600 small entities output line 6090 connects to the inlet of the connector 801 instead of the output line 6070 as in FIG. 57A. Large entities output line 6070 of FIG. 58A may connect to a large entities container.

Figure 58B:
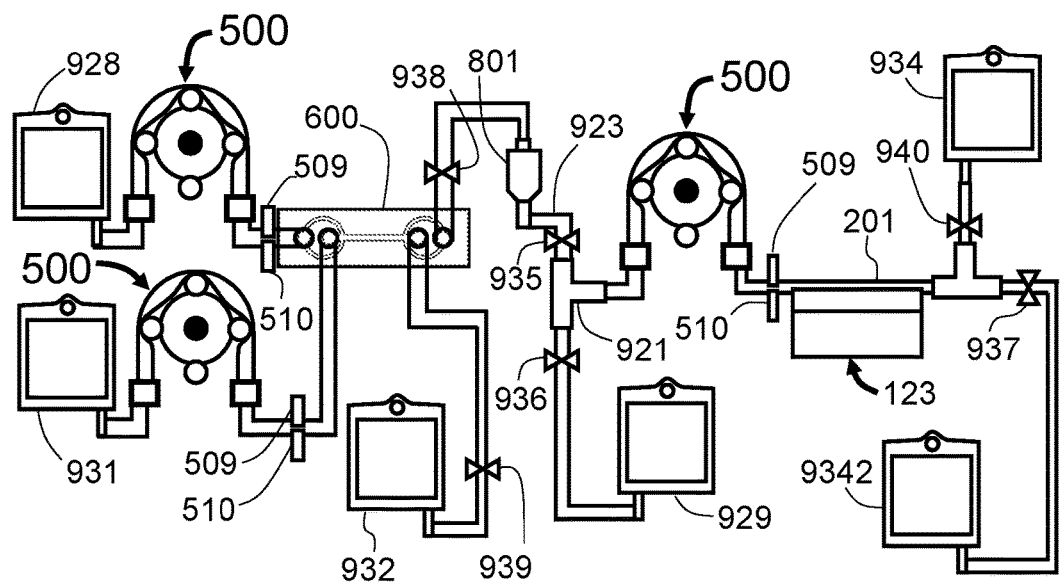
FIG. 58B illustrates fluidic lines of FIG. 58A being connected to, or attached with, various fluidic devices to realize second type sample processing method.

FIG. 58B illustrates fluidic lines of FIG. 58A being connected to, or attached with, various fluidic components. FIG. 58B is identical to FIG. 57B in every aspect, except the UFL 600 small entities output line 6090 connects to the inlet of the connector 801 instead of the output line 6070 as in FIG. 57B. Large entities output line 6070 of FIG. 58B connects to a large entities container 932 in blood bag form.

Figure 59A:
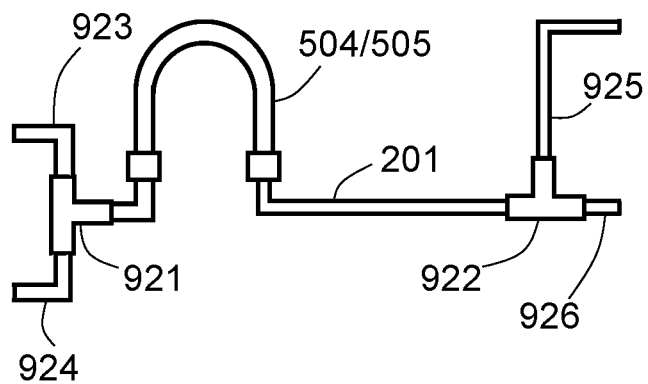
FIG. 59A illustrates example of closed and disposable fluidic lines for sample processing through a single MAG.

FIG. 59A illustrates embodiment of closed and disposable fluidic lines for sample processing through a single MAG. Input line 923 may connect to a sample liquid container. Input line 924 may connect to a MAG buffer container. Input line 923 and input line 924 are connected through a T-connector 921 to the inlet of the pump tubing 504/505 that may be mounted into a peristaltic pump. Pump tubing 504/505 outlet connects to channel 201 which may be used as part of MAG 123. Output of channel 201 connects to T-connector 922, which connects to output line 925 and output line 926. Output lines 925 and 926 may each connect to an MAG out sample container.

Figure 59B:
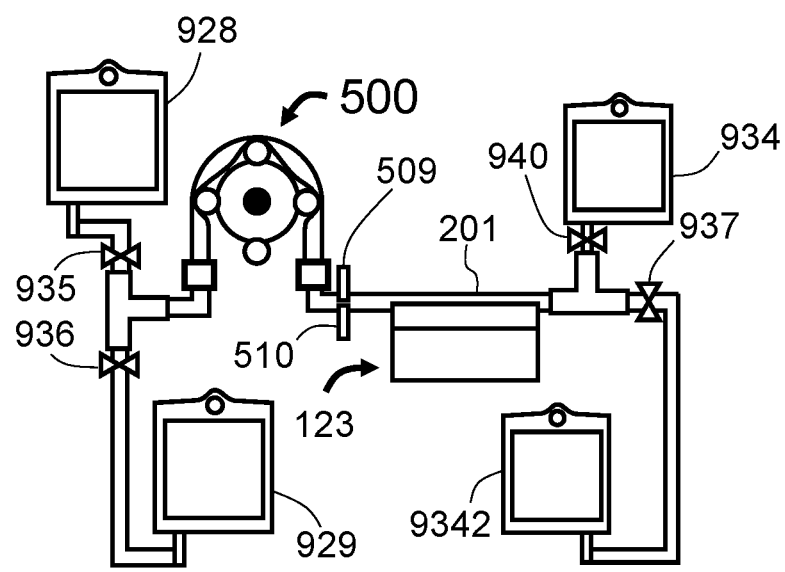

FIG. 59B illustrates fluidic lines of FIG. 59A being connected to, or attached with, various fluidic components. Input line 923 connects to a liquid sample container 928. Input line 924 connects to buffer container 929. Valves 935 and 936 are attached to lines 923 and 924 to control either sample liquid from bag 928 or buffer from container 929 is flown through T-connector 921 into first tubing 504/505. Pump tubing 504/505 is installed into a peristaltic pump 500. Pump 500 operates to pump either sample fluid or buffer fluid into MAG 123. A flow limiter 509/510 may be attached to the output line 201 from pump 500 to reduce flow rate pulsation from the pumps 500. Channel line 201 is mounted into MAG 123. Output line 925 connects to MAG out sample container 934. Output line 926 connects to MAG out sample container 9342. Valve 940 is attached to line 925 and valve 937 is attached to line 926, which control negative entities and positive entities from MAG 123 going into either container 934 or container 9342. Valves 940 and 937 may both shut down the flow in lines 925 and 926 during demagnetization/dissociation process of MAG 123. FIG. 59B shows containers 928, 929, 934 and 9342 may be in the form of blood bags, but may also be in other physical forms of vial or bottles.

FIG. 60A illustrates embodiment of closed and disposable fluidic lines for sample processing through a single UFL 600. Input line 9271 may connect to a UFL sample liquid container, and also connects to inlet of a first pump tubing 504/505, which further connects to entities input line 6020 of UFL 600. Input line 9272 may connect to a UFL buffer container, and also connects to inlet of a second pump tubing 504/505, which further connects to buffer input line 6040 of UFL 600. UFL 600 large entities output line 6070 may connect to a large entities container. UFL 600 small entities output line 6090 may connect to a small entities container.

FIG. 60B illustrates fluidic lines of FIG. 60A being connected to, or attached with, various fluidic components. First and second pump tubing 504/505 is each installed into a peristaltic pump 500. The two pumps 500 operate to pump sample fluid and buffer fluid into UFL 600. A flow limiter 509/510 may be attached to the output line from each pump 500, including lines 6020 and 6040 to reduce flow rate pulsation from the pumps 500. Input line 9271 connects to a liquid sample container 928. Input line 9272 connects to UFL buffer container 931. UFL output line 6070 connects to large entities container 932. UFL output line 6090 connects to small entities container 933. Adjustable valves 939 and 938 may be attached to the lines 6070 and 6090 to adjust the flow rate within each line of 6070 and 6090, which in turn controls the laminar flow speed in UFL 600 channel for channel center buffer flow and channel edge entities sample flow. FIG. 60B shows containers 928, 931, 932 and 933 may be in the form of blood bags, but may also be in other physical forms of vial or bottles without limitation.

Figure 61A:
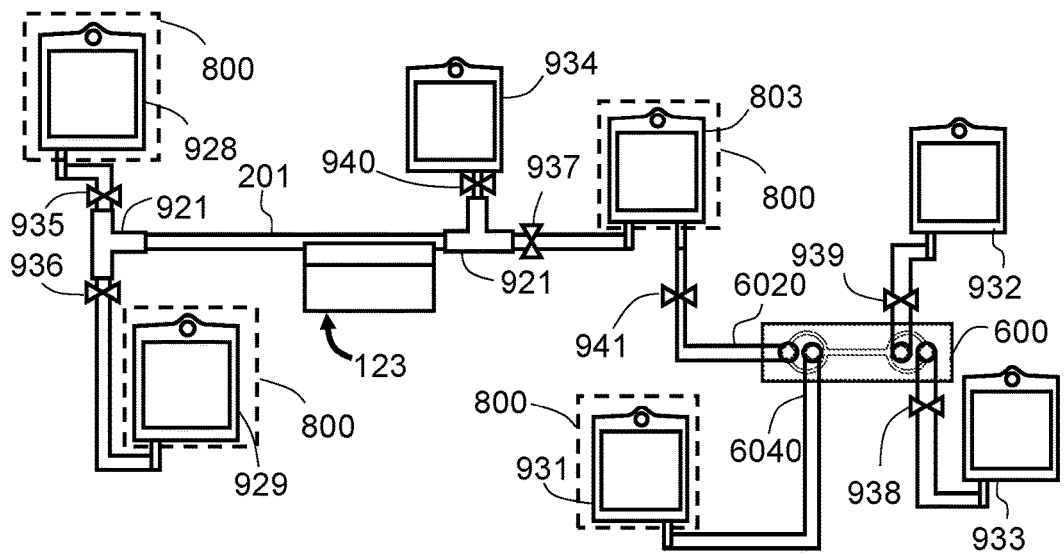

FIG. 61A illustrates replacing peristaltic pumps of FIG. 56B with using pressurized chambers 800 on input sample bags to drive fluid through fluidic lines. In FIG. 61A, pumps 500, pump tubing 504/505, and flow limiters 509/510 of FIG. 56B are removed. Channel 201 is connected directly to T-connector 921. Connector 801 is replaced with connector 803 bag. UFL entity liquid line 6020 is connected to connector 803. Sample liquid bag 928, MAG buffer bag 929, connector 803 bag and UFL buffer bag 931 are each enclosed in a pressure chamber 800. Pressure chamber 800 may operate by increasing pressure of chamber medium, for example air or other fluid, where the bags enclosed in chambers are submerged in the chamber medium. With increase of chamber medium pressure, liquid contained in the bags may be forced out of the bags and into the fluid lines. FIG. 61A operation may need separate MAG 123 and UFL 600 operations. At first stage, valve 941 attached to line 6020 closes. Pressure in chambers 800 enclosing bags 803 and 931 is released. Pressure in chambers 800 enclosing bags 928 and 929 are increased to force sample fluid or buffer fluid into channel 201 to start MAG 123 separation. After MAG 123 separation and sample fluid in bag 928 is depleted, bag 934 and connector 803 are each filled with output samples from MAG 123 after MAG separation. Then, at second stage, valve 937 is closed and valve 941 is open. Chambers 800 around connector 803 and bag 931 increase in pressure to force connector 803 sample and buffer fluid in 931 to flow into the UFL 600 to start UFL separation. After sample in connector 803 is depleted, and UFL 600 separation finish, bags 932 and 933 contain large and small entities from UFL output. Connector 803 maybe replaced by connector 8020 of FIG. 52 which has an air port 8023.

Figure 61B:
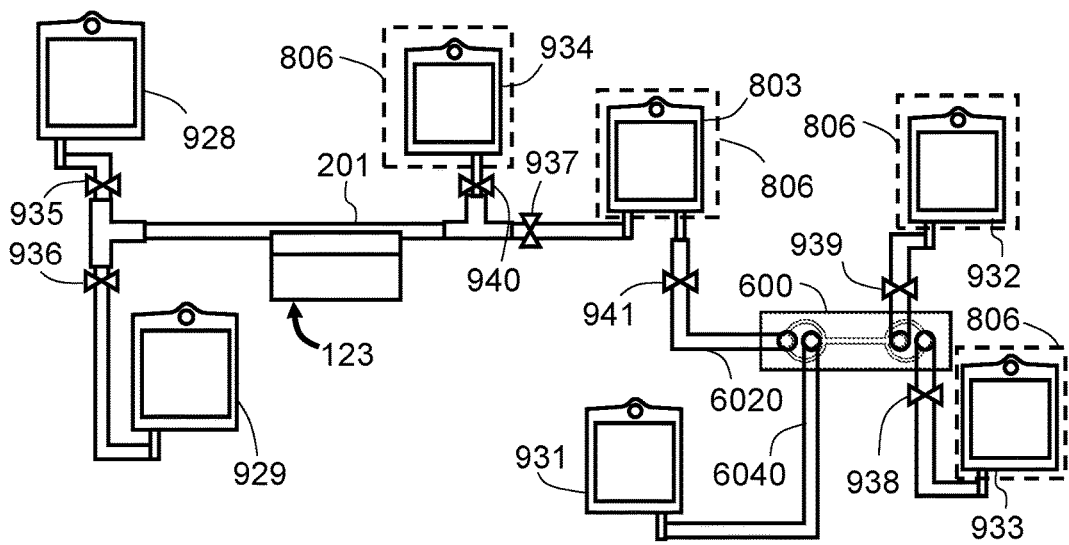

FIG. 61B illustrates replacing peristaltic pumps of FIG. 56B with using vacuum chambers 806 on output sample bags to drive fluid through fluidic lines. FIG. 61B is same as FIG. 61A, except pressure chambers 800 are removed. Bag 934, 932, 933, and connector 803 are each enclosed in a vacuum chamber 806. Vacuum chamber 806 may operate by increasing vacuum level within each chamber 806, where fluid from the fluid lines connected to the bags is forced into the bags enclosed in chambers due to fluid line pressure being larger than the vacuum pressure. FIG. 61B operation may also need separate MAG 123 and UFL 600 operations. At first stage, valve 941 attached to line 6020 closes. Vacuum in chambers 806 enclosing bags 932 and 933 is released. Vacuum in chambers 806 enclosing bags 934 and 803 are increased to force sample fluid or buffer fluid into channel 201 to start MAG 123 separation. After MAG 123 separation and sample fluid in bag 928 is depleted, bag 934 and connector 803 are each filled with output samples from MAG 123 after MAG separation. Then, at second stage, valve 937 is closed and valve 941 is open. Vacuum in chamber 806 around connector 803 is released. Vacuum in chambers 806 enclosing bags 932 and 933 are increased to force connector 803 sample and buffer fluid in 931 to flow into the UFL 600 to start UFL separation. After sample in connector 803 is depleted, and UFL 600 separation finish, bags 932 and 933 contain large and small entities from UFL output. Connector 803 maybe replaced by connector 8020 of FIG. 52 which has an air port 8023.

Figure 62A:
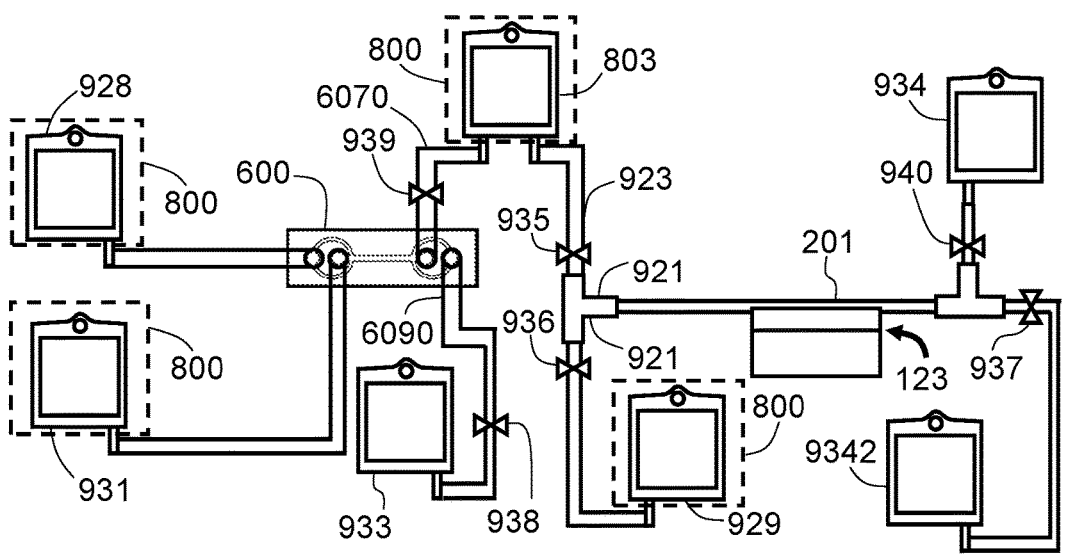

FIG. 62A illustrates replacing peristaltic pumps of FIG. 57B with using pressurized chambers 800 on input sample bags to drive fluid through fluidic lines. In FIG. 62A, pumps 500, pump tubing 504/505, and flow limiters 509/510 of FIG. 57B are removed. Channel 201 is connected directly to T-connector 921. Connector 801 is replaced with connector 803 bag. MAG sample line 923 is connected to connector 803. Sample liquid bag 928, MAG buffer bag 929, connector 803 bag and UFL buffer bag 931 are each enclosed in a pressure chamber 800. FIG. 62A may separate UFL 600 and MAG 123 operations. At first stage, valve 935 attached to line 923 closes. Pressure in chambers 800 enclosing bags 803 is released. Pressure in chambers 800 enclosing bags 928 and 931 are increased to force sample fluid and UFL buffer fluid into UFL 600 inlets to start UFL 600 separation. After UFL 600 separation and sample fluid in bag 928 is depleted, bag 933 contains small entities fluid and connector 803 contains large entities fluid from UFL 600 separation. Then, at second stage, valve 939 is closed and valve 935 is open. Chambers 800 around connector 803 and bag 929 increase in pressure to force connector 803 large entities fluid sample or MAG buffer fluid in 929 to flow into channel 201 of MAG 123 to start MAG 123 separation. After sample in connector 803 is depleted, and MAG 123 separation finish, bags 934 and 9342 contain positive sample and negative sample from MAG 123 channel 201 output. Connector 803 maybe replaced by connector 8020 of FIG. 52.

Figure 62B:
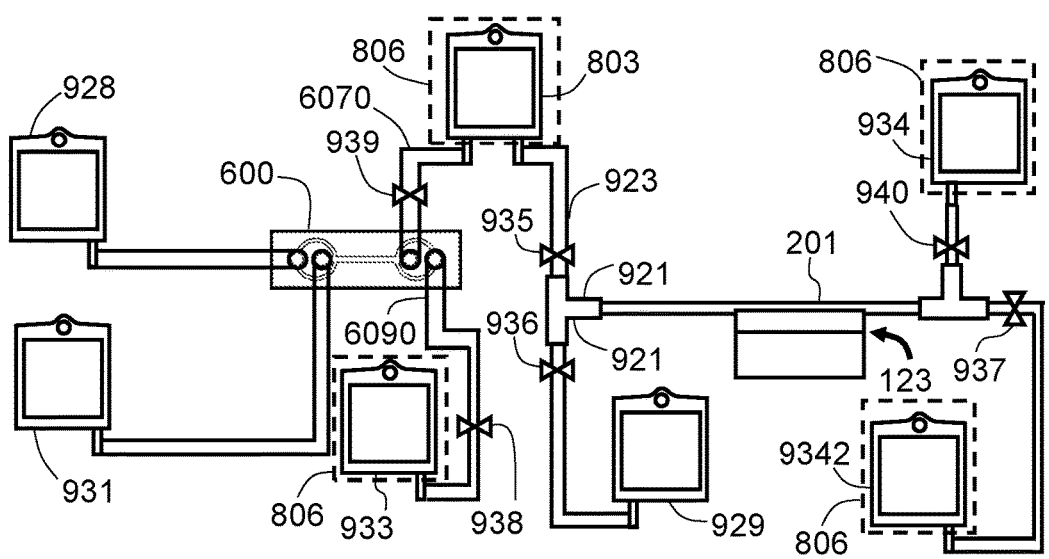

FIG. 62B illustrates replacing peristaltic pumps of FIG. 57B with using vacuum chambers 806 on output sample bags to drive fluid through fluidic lines. FIG. 62B is same as FIG. 62A, except pressure chambers 800 are removed. Bag 934, 9342, 933, and connector 803 are each enclosed in a vacuum chamber 806. FIG. 62B operation may separate MAG 123 and UFL 600 operations. At first stage, valve 935 attached to line 923 closes. Vacuum in chambers 806 enclosing bags 933 and 803 are increased to force sample fluid and UFL buffer fluid into inlets of UFL 600 to start UFL 600 separation. After UFL 600 separation and sample fluid in bag 928 is depleted, bag 933 contains small entities fluid and connector 803 contains large entities fluid from UFL 600 separation. Then, at second stage, valves 938 and 939 are closed and valve 923 is open. Vacuum in chamber 806 around connector 803 is released. Vacuum in chambers 806 enclosing bags 934 and 9342 are increased to force connector 803 large entities sample or MAG buffer fluid in 929 to flow into channel 201 of MAG 123 to start MAG 123 separation. After sample in connector 803 is depleted, and MAG 123 separation finish, bags 934 and 9342 contain positive sample and negative sample from MAG 123 channel 201 output. Connector 803 maybe replaced by connector 8020 of FIG. 52.

Figure 63A:
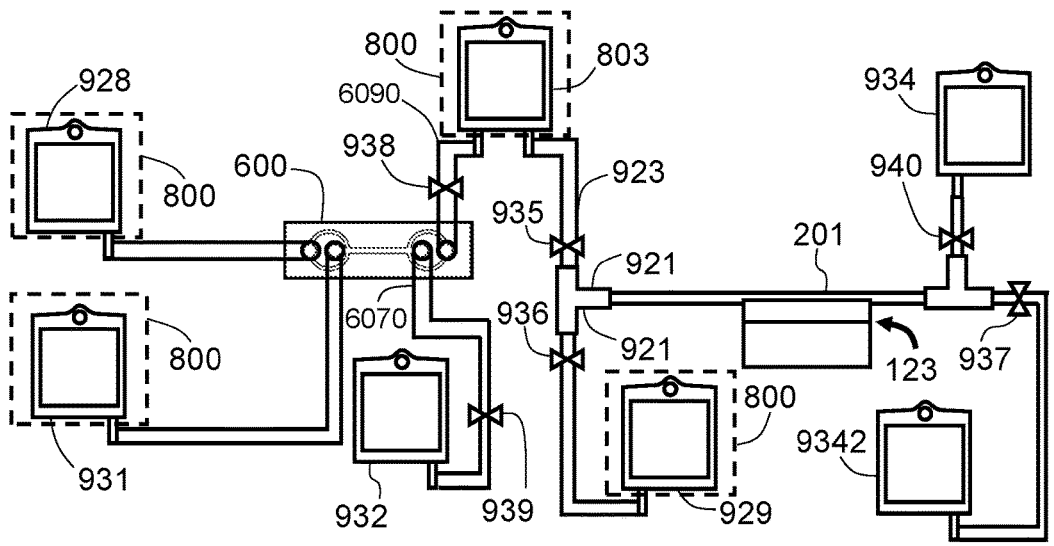

FIG. 63A illustrates replacing peristaltic pumps of FIG. 58B with using pressurized chambers 800 on input sample bags to drive fluid through fluidic lines. FIG. 63A is identical to FIG. 62A in fluid line layout and in operation of UFL 600 and MAG 123 with chambers 800, except that the UFL large entities output 6070 connects to large entities container 932 in blood bag form, and small entities output 6090 connects to connector 803.

Figure 63B:
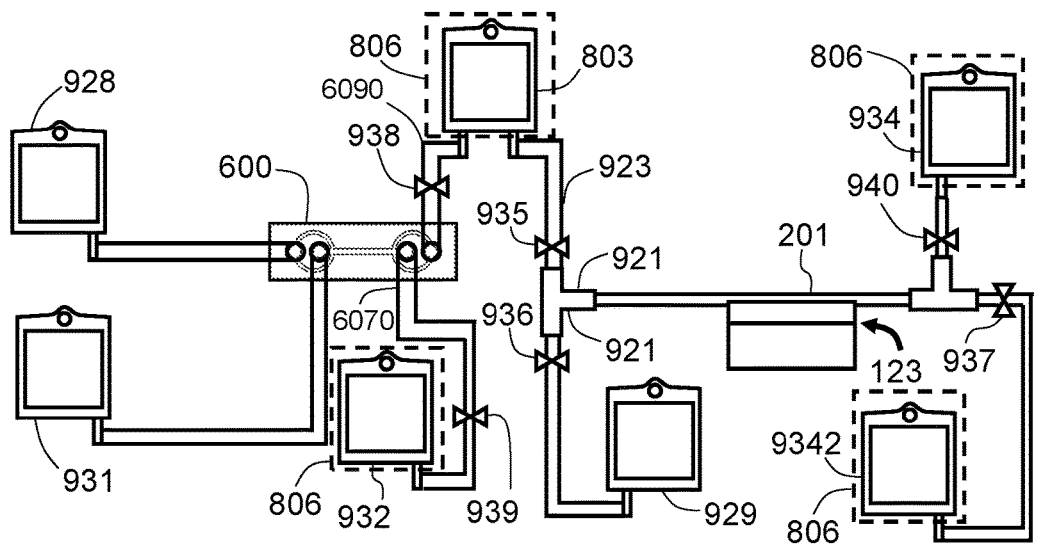

FIG. 63B illustrates replacing peristaltic pumps of FIG. 58B with using vacuum chambers 806 on output sample bags to drive fluid through fluidic lines. FIG. 63A is identical to FIG. 62B in fluid line layout and in operation of UFL 600 and MAG 123 with chambers 806, except that the UFL large entities output 6070 connects to large entities container 932 in blood bag form with small entities container 932 enclosed in vacuum chamber 806 replacing container 933 of FIG. 62B, and small entities output 6090 connects to connector 803.

Figure 64A:
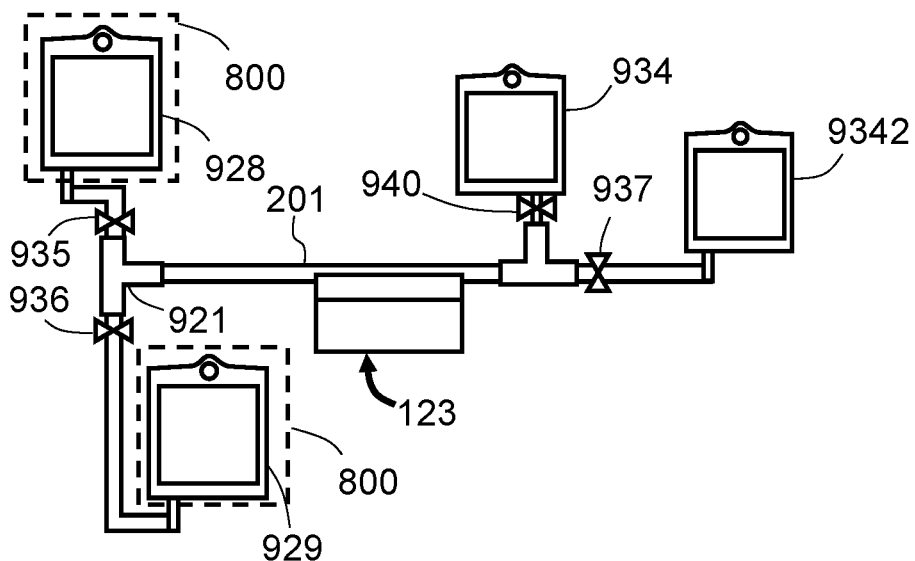

FIG. 64A illustrates replacing peristaltic pumps of FIG. 59B with using pressurized chambers 800 on input sample bags 928 and 929 to drive fluid through channel 201 of MAG 123. In FIG. 64A, pump 500, pump tubing 504/505, and flow limiter 509/510 of FIG. 59B are removed. Channel 201 is connected directly to T-connector 921. Sample liquid bag 928 and MAG buffer bag 929 are each enclosed in a pressure chamber 800. Pressure in chambers 800 enclosing bags 928 and 929 are increased to force sample fluid or buffer fluid into channel 201 to start MAG 123 separation. After MAG 123 separation and sample fluid in bag 928 is depleted, bag 934 and bag 9342 are each filled with either negative entities or positive entities from MAG 123 after MAG separation.

Figure 64B:
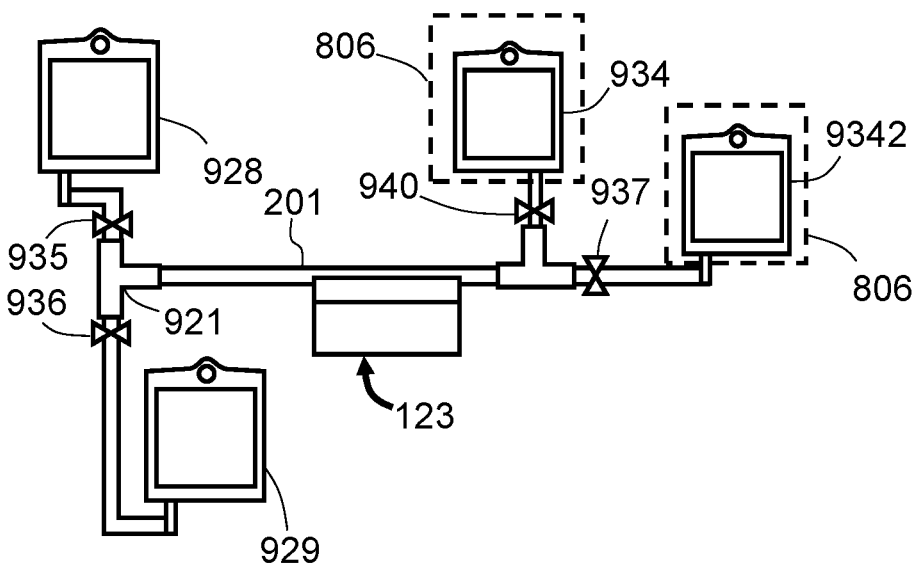

FIG. 64B illustrates replacing peristaltic pumps of FIG. 59B with using vacuum chambers 806 on output sample bags 934 and 9342 to drive fluid through channel 201 of MAG 123. FIG. 64B is same as FIG. 64A, except pressure chambers 800 are removed. Output sample bags 934 and 9342 are each enclosed in a vacuum chamber 806. Vacuum in chambers 806 enclosing bags 934 and 9342 are increased to force entities sample from bag 928 or MAG buffer fluid from bag 929 to flow into channel 201 of MAG 123 to start MAG 123 separation. After sample in bag 928 is depleted, and MAG 123 separation finish, bags 934 and 9342 contain positive sample and negative sample from MAG 123 channel 201 output.

FIG. 65A illustrates replacing peristaltic pumps of FIG. 60B with using pressurized chambers 800 on sample liquid bag 928 and UFL buffer bag 931 to drive fluid through UFL 600. In FIG. 65A, pump 500, pump tubing 504/505, and flow limiter 509/510 of FIG. 60B are removed. Sample liquid bag 928 and UFL buffer bag 931 are each enclosed in a pressure chamber 800. Pressure in chambers 800 enclosing bags 928 and 931 are increased to force sample fluid and UFL buffer fluid into UFL 600 inlets to start UFL 600 separation. After UFL 600 separation, sample fluid in bag 928 is depleted, bag 932 contains large entities fluid and bag 933 contains small entities fluid.

FIG. 65B illustrates replacing peristaltic pumps of FIG. 60B with using vacuum chambers 906 on output sample bags 932 and 933 to drive fluid through UFL 600. FIG. 65B is same as FIG. 65A, except pressure chambers 800 are removed. Output sample bags 932 and 933 are each enclosed in a vacuum chamber 806. Vacuum in chambers 806 enclosing bags 932 and 933 are increased to force sample liquid from bag 928 and UFL buffer fluid from bag 931 to flow through UFL 600 to start UFL separation. After sample in bag 928 is depleted, and UFL 600 separation finish, bag 932 contains large entities fluid and bag 933 contains small entities fluid.

Structures, components, and methods as described from FIG. 55A through FIG. 65B on enclosed fluidic lines including one UFL 600 and one MAG 123, may be applied to FIG. 47 through FIG. 52 without limitation, where enclosed fluidic lines including multiple MAGs 123 and multiple UFLs 600 may be achieved with replicating the components on single UFL 600 and single MAG 123 from FIG. 55A through FIG. 65B on each of the UFLs 600 and MAGs 123 of FIG. 47 through FIG. 52.

FIG. 66 through FIG. 88 illustrate embodiments of process flows to utilize MAG and UFL devices to separate biological entities from various biological samples. For simplicity of description, terms UFL and MAG are used in these figures for explanation. However, UFL may be any of UFL 600, 650, 620, 630, 640 of FIG. 40A, FIG. 41A, FIG. 42A, FIG. 43, while MAG may be any of MAG 121, 122, 123, 124, 124,125, 126, 127, 128, 129 with corresponding channel types as described in prior figures without limitation and without sacrifice of performance. If a component, or a structure, in FIG. 66 through FIG. 88 shares same name as in prior figures, it then means the same component, or same structure as in prior figures.

FIG. 66 illustrates embodiment of a first process flow to separate biological entities from peripheral blood using UFL and MAG. In step 5801, peripheral blood sample is collected from a patient or person under test; in step 5802, red blood cell lysing may be performed on said peripheral blood sample, where step 5802 in another embodiment may be skipped; in step 5803, said blood sample from step 5802, or directly from step 5801, is injected in UFL entity fluid inlet 602, while UFL buffer fluid is injected in outlet 604; in step 504, set frequency and vibration strength of PZT attached to UFL to produce standing wave and pressure nodes in UFL fluid; in step 5805, UFL outlet 607 outputs target sample that contains large size entities or cells; in step 5806, add into target sample from step 5805 magnetic labels hybridized with antibodies or ligands, which specifically bind to surface antigens or receptors on target cells or entities; in step 5807, target sample from step 5806 is incubated to form magnetic labels binding to target cells or entities; in step 5808, flow target sample from step 5807 through MAG channel at magnetic separation positon, where during step 5808, negative MAG sample may be forwarded as in 5815 to be collected in step 5813; in step 5809, target cells or entities bound with magnetic label are separated by MAG within the MAG channel; in step 5810, after step 5809, buffer fluid may be flown through MAG channel to wash out residue non-target entities without magnetic label, the washed out fluid may be forwarded as in 5816 to be collected as negative MAG sample in step 5813, where step 5810 may be skipped in another embodiment; in step 5811, after step 5810 or directly after step 5809, separated entities conglomerate in MAG channel may be dissociated into isolated cells or entities; in step 5812, buffer fluid is flown through MAG channel to washed out dissociated cells and entities in MAG channel, which, as shown by 5817, may be collected as positive MAG sample in step 5814.

Peripheral blood sample of FIG. 66 may also be other body fluids, including but not limited to: saliva, tear, mucus, urine, secretion from various organs of body.

FIG. 67 illustrates an embodiment of second process flow to separate biological entities from peripheral blood using MAG. Every other aspect of FIG. 67 is same as FIG. 66, except step 5803, step 5804, and step 5805 of FIG. 66 are removed between step 5802 and step 5806 in FIG. 67. While in FIG. 67, blood sample from step 5802, or blood sample directly from step 5801, is centrifuged in step 6201 to extract target sample containing white blood cells. Target sample form step 6201 is then sent to step 5806, from step 5806 FIG. 67 flow is same as in FIG. 66.

FIG. 68 illustrates an embodiment of third process flow to separate biological entities from peripheral blood using MAG. Every other aspect of FIG. 68 is same as FIG. 66, except step 5803, step 5804, and step 5805 of FIG. 66 are removed between step 5802 and step 5806 in FIG. 68. While in FIG. 68, peripheral blood sample collected from patient or person under test as in step 6301, which is same as step 5801 of FIG. 66, is regarded target sample. Target sample form step 5802 after red blood cell lysing after step 6301, or directly from step 6301, is then sent to step 5806. From step 5806, FIG. 68 flow is same as in FIG. 66.

FIG. 69 illustrates an embodiment of fourth process flow to separate biological entities from peripheral blood using MAG. Every other aspect of FIG. 69 is same as FIG. 66, except step 5801, step 5802, step 5803, step 5804, and step 5805 of FIG. 66 are removed before step 5806 in FIG. 69. While in FIG. 69, target sample is collected after apheresis of peripheral blood sample collected from patient or person under test. Target sample form step 6401 is then sent to step 5806. From step 5806, FIG. 69 flow is same as in FIG. 66.

FIG. 70 illustrates an embodiment of fifth process flow to separate biological entities from tissue sample using UFL and MAG. Every other aspect of FIG. 70 is same as FIG. 66, except step 5801, step 5802, and step 5803 are removed before step 5804 in FIG. 70. In FIG. 70, tissue sample is collected in step 6501. In step 6502, tissue sample from step 6501 is dissociated in a fluid base. In step 6503, dissociated tissue fluid of step 6502 is injected into UFL channel through inlet 602 and UFL buffer fluid is injected through inlet 604. From step 5804, FIG. 70 flow is same as in FIG. 66. Tissue sample of FIG. 70 may include any of: human body tissue aspirate, human organ tissue aspirate, bone marrow, animal body or organ tissue aspirate. Target cells or entities of FIG. 70 may be rare disease cells, for example cancer cells, or micro-organisms, for example bacteria.

FIG. 71 illustrates an embodiment of sixth process flow to separate biological entities from tissue sample using MAG. Every other aspect of FIG. 71 is same as FIG. 70, except step 6503, step 5804, and step 5805 are removed before step 5806 in FIG. 71. In FIG. 71, tissue sample from step 6501 is dissociated in a fluid base in step 6502 to form target sample, and continues process in step 5806. From step 5806, FIG. 71 flow is same as in FIG. 70.

FIG. 72 illustrates an embodiment of seventh process flow to separate biological entities from surface swab sample using UFL and MAG. Every other aspect of FIG. 72 is same as FIG. 66, except step 5801, step 5802, and step 5803 are removed before step 5804 in FIG. 72. In FIG. 72, surface entities are collected in step 6701 by swab. In step 6702, surface entities collected on swab are dissolved in a fluid base. In step 6703, fluid base with dissolved surface entities from step 6702 is injected into UFL channel through inlet 602 and UFL buffer fluid is injected through inlet 604. From step 5804, FIG. 72 flow is same as in FIG. 66. Surface entities of FIG. 72 may be collected by swab from subjects including any of: human body, saliva, body fluid, human body discharge, animal, plant, soil, air, water, and merchandise. Target cells or entities of FIG. 72 may include cells from human body, or animal body, or plant, or include micro-organisms, for example bacteria, mold, or spores.

FIG. 73 illustrates an embodiment of eighth process flow to separate biological entities from surface swab sample using MAG. Every other aspect of FIG. 73 is same as FIG. 72, except step 6703, step 5804, and step 5805 are removed before step 5806 in FIG. 73. In FIG. 73, surface entities collected on swab in step 6701 are dissolved in a fluid base in step 6702 to form target sample, and continues process in step 5806. From step 5806, FIG. 73 flow is same as in FIG. 72.

FIG. 74 illustrates an embodiment of ninth process flow to separate biological entities from solid sample using UFL and MAG. Every other aspect of FIG. 74 is same as FIG. 66, except step 5801, step 5802, and step 5803 are removed before step 5804 in FIG. 74. In FIG. 74, solid sample is collected in step 6901. In step 6902, solid sample from step 6901 is dissociated in a fluid base. In step 6903, dissociated solid sample fluid of step 6902 is injected into UFL channel through inlet 602 and UFL buffer fluid is injected through inlet 604. From step 5804, FIG. 74 flow is same as in FIG. 66. Tissue sample of FIG. 70 may include any of: solid biological products or waste generated by human, animal, or plant, powder, and soil. Target cells or entities of FIG. 74 may include cells from human body, or animal body, or plant, or include micro-organisms, for example bacteria, mold, or spores.

FIG. 75 illustrates an embodiment of tenth process flow to separate biological entities from solid sample using MAG. Every other aspect of FIG. 75 is same as FIG. 74, except step 6903, step 5804, and step 5805 are removed before step 5806 in FIG. 75. In FIG. 75, solid sample from step 6901 is dissociated in a fluid base in step 6902 to form target sample, and target sample is continuously processed in step 5806. From step 5806, FIG. 75 flow is same as in FIG. 74.

FIG. 76A illustrates addition of both magnetic and fluorescent labels into fluid samples for specific binding to target cells or entities. FIG. 76A shows that step 5806 of FIG. 66 through FIG. 75 may be modified to step 58061, where in addition to magnetic labels, fluorescent labels hybridized with antibodies or ligands, which specifically bind to surface antigens or receptors on target cells or entities, may also be added in target sample from step 5805.

FIG. 76B then illustrates that incubation step 5807 of FIG. 66 through FIG. 75 may also be modified to step 58071, which includes incubation of both magnetic and fluorescent labels at the same time to form specific binding to target cells or entities. Binding sites of magnetic labels and fluorescent labels on same target cells or entities may be different.

Steps S806 and step 58061 may be realized in a flow connector including any one of 801, 802, 803, 8010, 8020, 8030 of prior figures, where flow connector may contain pre-filled hybridized magnetic labels and fluorescent labels in liquid solution, or in dry powder form. Step 5807 and step 58071 may also occur in said flow connector, where said flow connector may also be located in a temperature control chamber to control incubation speed and quality. In another embodiment, said flow connector may have attached or embedded temperature control circuit to control incubation in flow connector.

FIG. 77A illustrates process of removing non-bound free magnetic labels from sample fluid by UFL before magnetic separation by MAG. FIG. 77A shows that for each of FIG. 66 through FIG. 75, step 5818 and step 5819 may be added between step 5807 and step 5808. After target sample is incubated in step 5807, in step 5818, target sample may be injected into second UFL through inlet 602, and buffer fluid may be injected into second UFL through inlet 604. In step 5819, second UFL outputs target sample containing large entities from outlet 607, and non-bound free magnetic labels are output from second UFL outlet 609. Then in step 5808, target sample containing large entities from second UFL outlet 607 is passed through MAG channel for magnetic separation. Target sample in step 5819 may contain cells 10/30 or entities bound with magnetic labels. Second UFL having an attached PZT that operates with a specified ultrasound vibration amplitude and frequency to create standing wave in second UFL channel fluid is assumed in step 5819.

FIG. 77B illustrates process of removing non-bound free magnetic labels from sample fluid by UFL after magnetic separation by MAG. FIG. 77B shows that for each of FIG. 66 through FIG. 75, step 5820 and step 5821 may be added between step 5812 and step 5814, replacing path 5817. After magnetic conglomerate within MAG channel is dissociated and the positive MAG sample entities from MAG channel are flushed out as in step 5812, flushed out positive MAG sample may be injected into third UFL through inlet 602, and buffer fluid may be injected into third UFL through inlet 604. In step 5821, third UFL outputs positive MAG sample containing large entities from outlet 607, and non-bound free magnetic labels are output from third UFL outlet 609. Then in step 5814, positive MAG sample with reduced or depleted free magnetic labels may be collected. Third UFL having an attached PZT that operates with a specified ultrasound vibration amplitude and frequency to create standing wave in third UFL channel fluid is assumed in step 5821.

FIG. 78A illustrates process of removing non-bound free magnetic labels and free fluorescent labels from sample fluid by UFL before magnetic separation by MAG. FIG. 78A is similar as FIG. 77A, with replacing step 5807 of FIG. 77A with step 58071 of FIG. 76B, and replacing step 5819 with step 58191. After adding magnetic labels and fluorescent labels into target sample as in step 58061 of FIG. 76A, target sample is incubated in step 58071 same as in FIG. 76B to form magnetic label and fluorescent label binding to target cells or entities. In step 5818, target sample may be injected into second UFL through inlet 602, and buffer fluid may be injected into second UFL through inlet 604. In step 58191, second UFL outputs target sample containing large entities from outlet 607, and non-bound free magnetic labels and free fluorescent labels are output from second UFL outlet 609. Then in step 5808, target sample containing large entities from second UFL outlet 607 is flown through MAG channel for magnetic separation. Target sample in step 58191 may contain cells 30 or entities bound with magnetic and fluorescent labels. Second UFL having an attached PZT that operates with a specified ultrasound vibration amplitude and frequency to create standing wave in second UFL channel fluid is assumed in step 58191.

FIG. 78B illustrates process of removing non-bound free magnetic labels and free fluorescent labels from sample fluid by UFL after magnetic separation by MAG. FIG. 78B is similar as FIG. 77B, with replacing step 5821 of FIG. 77A with step 58211. Separated entities in step 5812 and step 5820 of FIG. 78B may contain: cells 30 or entities bound with magnetic and fluorescent labels, non-bound free magnetic labels, and small amount of non-bound free fluorescent labels due to non-specific binding to conglomerate in MAG channel during magnetic separation. In step 58212, third UFL outputs positive MAG sample containing large entities from outlet 607, and non-bound free magnetic and free optical labels are output from third UFL outlet 609. Then in step 5814, positive MAG sample with reduced or depleted free magnetic labels and free fluorescent labels may be collected. Third UFL having an attached PZT that operates with a specified ultrasound vibration amplitude and frequency to create standing wave in third UFL channel fluid is assumed in step 58212.

FIG. 79 illustrates continued process of negative MAG sample after MAG separation, as in step 408 of FIG. 31, through UFL to remove small entities and passing of large entities into various cell processing devices and procedures. Step 5813 is same as in FIG. 66 through FIG. 75, where negative MAG sample is collected during MAG separation of a target sample. In step 5822, negative MAG sample of step 5813 is injected into fourth UFL inlet 602, and UFL buffer is injected into inlet 604 of fourth UFL. In step 5823, fourth UFL outputs negative MAG sample containing large entities from outlet 607, and small size entities are removed from large entities and output from fourth UFL outlet 609, a PZT that attaches to fourth UFL and operates with a specified ultrasound vibration amplitude and frequency to create standing wave in fourth UFL is assumed. Finally, negative MAG sample containing large entities from outlet 607 of fourth UFL may be sent to be analyzed by any of: cell counter 903, cell imager 904, flow cytometer or sorter 905, DNA/RNA sequencer 906. Alternatively, output from cell counter 903, or output from cell imager 904, or output from flow cytometer or sorter 905, may be further sent to be processed by DNA/RNA sequencer 906 as indicated respectively by path 936, 946, and 956. Negative MAG sample containing large entities from outlet 607 of fourth UFL in step 5823 may also be sent into the process of cell genetic modification and cell expansion 5824. Prior to DNA/RNA sequencing in DNA/RNA sequencer 906, a polymerase chain reaction (PCR) procedure on DNA/RNA sample obtained from cell lysing of large size entities from outlet 607 of fourth UFL from step 5823 may be performed, where PCR may be targeting one or more target DNA/RNA sequences and amplifies the number of target DNA/RNA sequences in the DNA/RNA sample.

FIG. 80 illustrates continued process of negative MAG sample after MAG separation, as in step 408 of FIG. 31, through UFL to retrieve small entities and passing of small entities into various molecule or small entity processing devices. After step 5813 of FIG. 66 through FIG. 75, where negative MAG sample is collected during MAG separation of a target sample, in step 5822, negative MAG sample of step 5813 is injected into fourth UFL inlet 602, and UFL buffer is injected into inlet 604 of fourth UFL. In step 5825, fourth UFL outputs negative MAG sample containing large entities from outlet 607, and small size entities including DNA, RNA, molecules, and other small particles are output from fourth UFL outlet 609, a PZT that attaches to fourth UFL and operates with a specified ultrasound vibration amplitude and frequency to create standing wave in fourth UFL is assumed. Finally, small size entities from outlet 609 of fourth UFL may be sent to be analyzed by any of: particle counter 5835, particle imager 5836, flow cytometer or sorter 905, DNA/RNA sequencer 906. Alternatively, output from particle counter 5835, or output from particle imager 5836, or output from flow cytometer or sorter 905, may be further sent to be processed by DNA/RNA sequencer 906 as indicated respectively by path 5827, 5828, and 956. DNA/RNA sequencer 906 may contain a PCR step on small size entities from outlet 609 of fourth UFL from step 5825 prior to DNA/RNA sequencing, where PCR may target one or more particular DNA/RNA sequences to amplify in quantity.

FIG. 81 illustrates entities analysis of negative MAG sample after MAG separation, as in step 407 of FIG. 31, into various analyzing devices. After step 5813 of FIG. 66 through FIG. 75, where negative MAG sample is collected during MAG separation of a target sample, collected negative MAG sample may be sent to be analyzed by any of: cell counter 903, cell imager 904, flow cytometer or sorter 905, particle counter 5835, particle imager 5836, DNA/RNA sequencer 906. Alternatively, output from cell counter 903, or output from cell imager 904, or output from flow cytometer or sorter 905, or output from particle counter 5835, or output from particle imager 5836, may be further sent to be processed by DNA/RNA sequencer 906 as indicated respectively by path 936, 946, 956, 5827, and 5828. Negative MAG sample may also be sent into the process of cell genetic modification and cell expansion 5824. DNA/RNA sequencer 906 may contain a PCR step on: (1) DNA/RNA obtained after cell lysing of cells contained within negative MAG sample; and (2) DNA/RNA/molecules contained within negative MAG sample. Prior to DNA/RNA sequencing, PCR may target one or more particular DNA/RNA sequences to amplify in quantity.

FIG. 82 illustrates continued process of positive MAG sample after MAG separation, as in step 408 of FIG. 31, through UFL to remove small entities and passing of large entities into various cell processing devices and procedures. Step 5814 is same as in FIG. 66 through FIG. 75, where positive MAG sample is collected after MAG separation of a target sample. In step 5829, positive MAG sample of step 5814 is injected into fifth UFL inlet 602, and UFL buffer is injected into inlet 604 of fifth UFL. In step 5830, fifth UFL outputs positive MAG sample containing large entities from outlet 607, and small size entities are removed from large entities and output from fifth UFL outlet 609, a PZT that attaches to fourth UFL and operates with a specified ultrasound vibration amplitude and frequency to create standing wave in fifth UFL is assumed. Finally, positive MAG sample containing large entities from outlet 607 of fifth UFL may be sent to be analyzed by any of: cell counter 903, cell imager 904, flow cytometer or sorter 905, DNA/RNA sequencer 906. Alternatively, output from cell counter 903, or output from cell imager 904, or output from flow cytometer or sorter 905, may be further sent to be processed by DNA/RNA sequencer 906 as indicated respectively by path 936, 946, and 956. Positive MAG sample containing large entities from outlet 607 of fifth UFL in step 5830 may also be sent into the process of cell genetic modification and cell expansion 5824. DNA/RNA sequencer 906 may contain a PCR step on DNA/RNA obtained after cell lysing of large size entities from outlet 607 of fifth UFL from step 5830 prior to DNA/RNA sequencing, where PCR may target one or more particular DNA/RNA sequences to amplify in quantity.

FIG. 83 illustrates continued process of positive MAG sample after MAG separation, as in step 408 of FIG. 31, through UFL to retrieve small entities and passing of small entities into various molecule or small entity processing devices. After step 5814 of FIG. 66 through FIG. 75, where positive MAG sample is collected after MAG separation of a target sample, in step 5829, positive MAG sample of step 5814 is injected into fifth UFL inlet 602, and UFL buffer is injected into inlet 604 of fifth UFL. In step 5831, fifth UFL outputs positive MAG sample containing large entities from outlet 607, and small size entities including DNA, RNA, molecules, and other small particles bound by magnetic labels are output from fifth UFL outlet 609, a PZT that attaches to fifth UFL and operates with a specified ultrasound vibration amplitude and frequency to create standing wave in fifth UFL is assumed. Finally, small size entities from outlet 609 of fifth UFL may be sent to any of: particle counter 5835, particle imager 5836, flow cytometer or sorter 905, DNA/RNA sequencer 906. Alternatively, output from particle counter 5835, or output from particle imager 5836, or output from flow cytometer or sorter 905, may be further sent to be processed by DNA/RNA sequencer 906 as indicated respectively by path 5827, 5828, and 956. DNA/RNA sequencer 906 may contain a PCR step on small size entities from outlet 609 of fifth UFL from step 5831 prior to DNA/RNA sequencing, where PCR may target one or more particular DNA/RNA sequences to amplify in quantity.

FIG. 84 illustrates entities analysis of positive MAG sample after MAG separation, as in step 407 of FIG. 31, into various analyzing devices. After step 5814 of FIG. 66 through FIG. 75, where positive MAG sample is collected after MAG separation of a target sample, collected positive MAG sample may be sent to be analyzed by any of: cell counter 903, cell imager 904, flow cytometer or sorter 905, particle counter 5835, particle imager 5836, DNA/RNA sequencer 906. Alternatively, output from cell counter 903, or output from cell imager 904, or output from flow cytometer or sorter 905, or output from particle counter 5835, or output from particle imager 5836, may be further sent to be processed by DNA/RNA sequencer 906 as indicated respectively by path 936, 946, 956, 5827, and 5828. Positive MAG sample may also be sent into the process of cell genetic modification and cell expansion 5824. DNA/RNA sequencer 906 may contain a PCR step on: (1) DNA/RNA obtained after cell lysing of cells contained within positive MAG sample; and (2) DNA/RNA/molecules contained within positive MAG sample, prior to DNA/RNA sequencing, where PCR may target one or more particular DNA/RNA sequences to amplify in quantity.

FIG. 85A illustrates adding fluorescent labels to specifically bind to target entities within negative MAG sample immediately after negative MAG sample collection. FIG. 85A shows that in step 58131, immediately after step 5813, where negative MAG sample is collected during MAG separation, fluorescent labels which are hybridized with antibodies or ligands, and specifically bind to surface antigens or receptors on target cells or entities are added into the negative MAG sample, and then negative MAG sample is incubated to form fluorescent labels binding to target cells or entities. Step 58131 may be inserted in FIG. 79 and FIG. 80 between step 5813 and step 5822, or inserted in FIG. 81 immediately after step 5813 and before devices or processes 903, 904, 905, 906, 5824, 5825, and 5826.

FIG. 85B illustrates adding fluorescent labels to specifically bind to target entities within positive MAG sample immediately after positive MAG sample collection. FIG. 85B shows that in step 58141, immediately after step 5814, where positive MAG sample is collected after MAG separation, fluorescent labels which are hybridized with antibodies or ligands, and specifically bind to surface antigens or receptors on target cells or entities are added into the positive MAG sample, and then positive MAG sample is incubated to form fluorescent labels binding to target cells or entities. Step 58141 may be inserted in FIG. 82 and FIG. 82 between step 5814 and step 5829, or inserted in FIG. 84 immediately after step 5814 and before devices or processes 903, 904, 905, 906, 5824, 5825, and 5826.

FIG. 86A through FIG. 93 describe methods to achieve pre-symptom early stage tumor detection, especially in asymptomatic tumor patients who are in very early stage, or have not been diagnosed with tumor, or showing no symptom, or tumor is in such infancy or early stage that may not be detected or located by conventional methods, including imaging or blood test. In the description, terms of "cancer" and "tumor" may be used interchangeably for same meaning.

Malignant tumor, or cancer, is a disease that results from genetic mutation of normal body cells, which become astray from original cell functions, multiplying fast, and evading normal cell life cycle of programmed cell death by human immune system. To increase the survival chance of a patient carrying cancer, it is imperative to identify and locate the cancer at as earliest stage as possible. In state-of-art medicine practiced today, tumors are still found or identified either after physical identification by imaging methods including ultrasound, X-ray, computerized tomography (CT), magnetic resonance imaging (MM), and in most cases after patient showing symptoms due to cancer growth. For cancer to be identified by imaging methods or by patient showing symptoms, cancer growth is typically already underway, and in most cases well developed with cancer cells in the body already growing in significant numbers. For certain cancers, for example pancreatic cancer which is typically asymptomatic even in late stages, detection by conventional method would usually be too late to provide meaningful medical intervention. It is desirable, and imperative, to have a cancer detection method that is able to detect occurrence of a cancer, with location of origination, at its infancy stage, where such detection is preferred to before cancer's significant growth, and before any statistical possibility of cancer's spreading from a local growth to other parts of body. This detection method is desirable to be administered to a person-under-test through conventional clinical means, for example typical peripheral blood collection and blood test. By achieving pre-symptom early stage cancer detection and knowing with confidence of cancer type and location, medical intervention may provide most effectiveness in removal of cancer cells, significantly increase survival rate, and eventually cure of cancer, and at the same time significantly reducing financial and social burden of cancer treatment.

FIG. 86A illustrates first example of cancer treatment. Cancer cell 2002 exhibits surface antigen, ligand or surface marker 2004, which can be used to identity and kill cancer cell 2002 in human body by an immune cell 2001 with a surface anti-body, or receptor 2003 that specifically binds to surface marker 2004, as shown by 2034. Immune cell 2001 may be extracted from the person-under-test (PUT), or from a donor person. Immune cell 2001 may be genetically modified after being collected from the PUT or donor to express surface receptor 2003. Immune cell 2001 with antibody 2003 may be expanded or cultivated in ex vivo environment. Immune cell 2001 may be engineered to suppress, or evade, immune system response of the PUT if immune cell is collected from donor. In practice, immune cells 2001 with antibody 2003 may be administered to PUT with blood infusion, where immune cells 2001 will then find and bind to cancer cells 2002 in vivo through antibody-antigen bond 2034 between antibody 2003 and marker 004 and kill the cancer cell 2002. For example, cell 2001 may be a type of ex vivo engineered chimeric antigen receptor T cell (CAR-T) with 2003 being chimeric antigen receptor (CAR) that targets cancer cell 2001 which has a surface marker 2004. Receptor 2003 may be any of, but not limited to, CD19, CD20, CD22, CD30, ROR1, κ light chain, CD123, CD33, CD133, CD138, and B-cell maturation antigen.

FIG. 86B illustrates second example of cancer treatment. In PUT, the person's internal immune cell 2007, for example a T cell, functions to identify cells which need to be terminated as a normal cell life cycle. For a normal cell, immune cell 2007 forms receptor 2051 to antigen 2052 bond, which enables immune cell 2007 to terminate a normal cell at end of life cycle of the normal cell. Receptor 2501 may include T-cell receptor (TCR), CD 28. However, cancer cell 2002 evades such programmed death from immune cell 2007 by forming another ligand 2054 and receptor 2053 bond with immune cell 2007, which effectively disables the receptor 2051 to antigen 2052 bond that functions to terminate the cancer cell 2002, for example ligand 2054 and receptor may be PD-L1 and PD-1 respectively. In FIG. 86B method, antibody 2056 or antigen 2055 may be administered to PUT, such that antibody 2056 may bind to ligand 2054 and antigen 2055 may bind to receptor 2053 in vivo of PUT body, causing effective disconnection of 2053 to 2054 bond, and making termination of the cancer cell 2002 by the immune cell 2007 through 2051-2052 bond being possible.

FIG. 86C illustrates third example of cancer treatment. In FIG. 86C method, part of immune system cells, for example dendritic cell 2008, may be inserted with cancer cell 2002 RNA or antigen ex vivo, so that cell 2008 may express cancer 2008 surface antigen 2004. When dendritic cell 2008 with surface antigen 2004 is injected into PUT as in 2009, immune cell 2007 of PUT, for example T cell, may be trained or directed as in 2010 by the dendritic cell 2008 to recognize the expressed cancer antigen 2004 with expressing corresponding receptor 2003 on immune cell 2007. Immune cell 2007 then is able to recognize cancer cell 2002 in PUT with receptor 2003 to antigen 2004 binding 2034, and subsequently terminate cancer cell 2002.

During termination of cancer cell 2002 in FIG. 86A, FIG. 86B and FIG. 86C, lysis of cancer cell 2002 occurs and genetic material, including tumor DNA and RNA, within cancer cell 2002 is released and will finally enter blood stream of PUT. In this invention, cell 2001 with receptor 2003 of FIG. 86A, antibody 2056 and antigen 2055 of FIG. 86B, cell 2008 with antigen 2004 of FIG. 86C, will be categorially referred to as "anti-tumor agent", which may be administer externally to a PUT and causing a target type of cancer cell 2002, if existing in PUT, to terminate and release genetic material into blood stream of PUT.

FIG. 87 illustrates first method of this invention to achieve pre-symptom early stage tumor detection, which includes the sequential steps of: (step 1001) administer anti-tumor agent to a person-under-test (PUT) to cause termination and lysis of target tumor cells, if existing in PUT, and release genetic material into blood stream of PUT; (step 1002) collect peripheral blood from PUT; (step 1003) obtain cell-free plasma from the collected peripheral blood; (step 1004) perform PCR on the cell-free plasma to amplify quantity of known DNA or RNA sequences that identify target tumor cells, resulting in PCR sample; (step 1005) perform DNA or RNA sequencing on PCR sample and ascertain existence of known DNA or RNA sequence that identifies target tumor cells.

Step 1001 anti-tumor agent may be one of, or a combination of, anti-tumor agents as described in FIG. 86A, FIG. 86B and FIG. 86C. Anti-tumor agent may be in sufficiently small amount that does not eliminate target tumor cells in PUT, but will cause lysis of a plurality of target tumor cells to release genetic material to be collected in step 1003, amplified in step 1004 and detected in step 1005. With anti-tumor agent being in sufficiently small amount, adverse effects of FIG. 86A, FIG. 86B and FIG. 86C process, including cytokine release syndrome, neurotoxicity, or off-tumor aplasia, may be limited to not cause clinical conditions of PUT requiring medical attention. FIG. 87 method implies that the DNA or RNA sequence of step 1004 and step 1005 is generic to the type of target tumor cells and is independent of PUT.

PUT of FIG. 87 may be a person without prior history of tumor, or without showing symptom of tumor, or without showing any physical sign or results of tumor through conventional medical examination methods. PUT may be a person at risk of target tumor, for example due to genetic mutation, family history, age, environment, or occupation.

PUT may be a person who has been treated for target tumor, but needing monitor of recurrence of target tumor. PUT may or may not carry target tumor cells. In the case that step 1005 confirms existence of known DNA or RNA sequence that identifies target tumor cells, it may be concluded that PUT carries target tumor, where the amount of DNA or RNA detected in step 1005 may be used to project stage and severity of tumor in PUT. Due to the specificity of known DNA or RNA sequence that identifies target tumor, existence of such DNA or RNA may also confirm simultaneously most probable location of occurrence of such tumor when PUT is a pre-symptom and very early stage patient. In the case that step 1005 does not detect known DNA or RNA sequence that identifies target tumor cells, or does not detect such DNA or RNA sequence at an amount that is above a confidence threshold value, it may be concluded that PUT does not carry target tumor.

In practice, a time lapse may be needed after administering anti-tumor agent in step 1001, and before tumor genetic material may be released into blood stream of PUT after tumor cell lysis for collection in step 1002. Therefore, a scheduled waiting period, or a peripheral blood collection time window, may be implemented between step 1001 and step 1002. Said scheduled waiting period may be between 15 minutes to 30 minutes in one embodiment, between 30 minutes to 1 hour in another embodiment, between 30 minutes to 1 hour in yet another embodiment, between 1 hour to 2 hours in yet another embodiment, between 2 hours to 6 hours in yet another embodiment, between 6 hours to 12 hours in yet another embodiment, between 12 hours to 24 hours in yet another embodiment, between 1 day to 2 days in yet another embodiment, between 2 days to 4 days in yet another embodiment, between 4 days to 10 days in yet another embodiment, between 10 days to 15 days in yet another embodiment, and between 15 days to 30 days in yet another embodiment. Said collection time window has a start time and an end time after the time of said administering of said anti-tumor agent, where the start time and end time may be between 15 minutes to 30 minutes in one embodiment, between 30 minutes to 1 hour in another embodiment, between 30 minutes to 1 hour in yet another embodiment, between 1 hour to 2 hours in yet another embodiment, between 2 hours to 6 hours in yet another embodiment, between 6 hours to 12 hours in yet another embodiment, between 12 hours to 24 hours in yet another embodiment, between 1 day to 2 days in yet another embodiment, between 2 days to 4 days in yet another embodiment, between 4 days to 10 days in yet another embodiment, between 10 days to 15 days in yet another embodiment, and between 15 days to 30 days in yet another embodiment. Additionally, a multiple-cycled repeated step 1002 to step 1005 process may be performed as shown by procedure 1009, where procedure 1009 may include a scheduled waiting period, such that existence of target tumor cells in PUT may be monitored and ascertained during an extended amount of time for a more complete anti-tumor agent action on target tumor cells. Said scheduled waiting period in procedure may be between 6 hours to 12 hours in one embodiment, between 12 hours to 24 hours in another embodiment, between 1 day to 2 days in yet another embodiment, between 2 days to 4 days in yet another embodiment, between 4 days to 10 days in yet another embodiment, between 10 days to 15 days in yet another embodiment, and between 15 days to 30 days in yet another embodiment.

Advantages of FIG. 87 method are: (1) PUT may be a person carrying tumor at early stage but without tumor indication in conventional tests, thus enabling pre-symptom early stage cancer intervention; (2) by administering anti-tumor agent targeting a specific tumor, for example breast cancer, pancreatic cancer, lung cancer, detection of corresponding tumor DNA or RNA signal also confirms type and origin of such cancer enabling fast and targeted treatment; (3) by administering anti-tumor agent targeting a specific tumor, released DNA or RNA in blood stream may spike in a well-defined time window afterwards, which provides an enhanced signal-to-noise ratio (SNR) of tumor DNA or RNA detection and may enable high sensitivity and high accuracy detection even when the actual amount of tumor cells in PUT is still at much fewer than being detectable by conventional tests; (4) this method may allow a panel of multiple anti-tumor agents targeting multiple types of tumors being applied simultaneously to PUT to detect existence of multiple types of target tumors at the same time, as described in FIG. 89. Although FIG. 87 method targets pre-symptom early stage tumor, it is possible to implement same method against dormant tumor, which may not show fast growth, but has genetic mutation that has high risk of malignancy.

FIG. 88 illustrates a second method of tumor detection. FIG. 88 process is same as FIG. 87 in every other aspects, except that: after step 1001, instead of collecting peripheral blood as in step 1002 of FIG. 87, step 1006 of FIG. 88 collects body fluid from around organ of PUT where target tumor may occur, such body fluid would be where released DNA or RNA by lysed target tumor cells may be found, for example urine for bladder cancer, or prostate secretion for prostate cancer; then in step 1007 replacing step 1003 of FIG. 87, obtain cell-free fluid from the collected body fluid of step 1006; and then in step 108 replacing step 1004 of FIG. 87, perform PCR on cell-free fluid to amplify quantity of known DNA or RNA sequences that identify target tumor cells, resulting in PCR sample. PCR sample of step 1008 then undergoes same step 1005 as in FIG. 87.

FIG. 89 illustrates a third method of tumor detection. FIG. 89 process is same as FIG. 87, but expanding tumor detection from one target tumor to multiple types of tumor. FIG. 89 process includes the sequential steps of: (step 3001) administer anti-tumor agents to PUT to cause lysis of a plurality types of target tumor cells to release genetic material into blood stream of PUT; (step 1002) collect peripheral blood from PUT; (step 1003) obtain cell-free plasma from the collected peripheral blood; (step 3004) perform PCR on the cell-free plasma to amplify quantity of known DNA or RNA sequences that identify each type of the plurality types of target tumor cells, resulting in PCR sample; (step 3005) perform DNA or RNA sequencing on PCR sample and ascertain existence of known DNA or RNA sequence that identifies each type of the plurality types of target tumor cells. In FIG. 89, ascertaining of existence of any of the multiple types of tumors may be performed at same time in PUT. Anti-tumor agents in step 3001 may be one of anti-tumor agents as described in FIG. 86A, FIG. 86B and FIG. 86C, which lyses multiple types of tumors simultaneously. Anti-tumor agents in step 3001 may be a combination of more than one anti-tumor agents as described in FIG. 86A, FIG. 86B and FIG. 86C, where different anti-tumor agent lyses one type, or a sub-set of types, of the plurality types of tumors. Steps 1002 and 1003 of FIG. 89 may be replaced by steps 1006 and 1007 of FIG. 88 to collect body fluids, where step 3004 may correspondingly be updated with performing PCR on cell-free fluid from step 1007.

FIG. 90, FIG. 91, and FIG. 92 illustrate embodiments of process flows to utilize MAG and UFL devices to obtain cell-free plasma from peripheral blood. For simplicity of description, terms UFL and MAG are used in these figures for explanation. However, UFL may be any of UFL 600, 620, 630, 640 of FIG. 40A, FIG. 41A, FIG. 42A, FIG. 43, while MAG may be any of MAG 121, 122, 123, 124, 124,125, 126, 127, 128, 129 with corresponding channel types as described in prior figures without limitation and without sacrifice of performance.

FIG. 90 illustrates embodiment of first process flow to obtain cell-free plasma of step 1003 from collected peripheral blood as in step 1002. After collection of peripheral blood in step 1002, peripheral blood may be centrifuged as in step 5001, and result of centrifuge may contain cell-free plasma that may directly achieve step 1003 as indicated by path 5005. Alternatively, after centrifuge step 5001, blood plasma may be depleted of certain blood cells, for example red blood cells, but may not have enough purity for later stage PCR process. Plasma from step 5001 may then be sent as in 5008 to undergo a UFL separation in step 5002, where UFL large entities output contains any remaining cells in plasma, while UFL small entities output contains DNA or RNA and may be more concentrated than plasma from step 5001. In yet another alternative path, peripheral blood from step 1002 may skip step 5001 but directly input into UFL separation step 5002 as shown by path 5007, where the UFL separates cells through large entities output while maintaining DNA and RNA in small entities output. Small entities output from UFL separation of step 5002 may then be used towards step 1003 as cell-free plasma as in path 5009. Further alternatively, magnetic labels hybridized with antibodies or ligands may be added to the plasma from UFL small entities output of step 5002 to bind to DNA or RNA within the plasma as in step 5003. MAG device may be used to separate the DNA and RNA bound with the magnetic labels in step 5004, and the resulting positive MAG sample containing DNA and RNA then may be regarded the cell-free plasma of step 1003.

FIG. 91 illustrates embodiment of second process flow to obtain cell-free plasma of step 1003 from collected peripheral blood as in step 1002. After collection of peripheral blood in step 1002, peripheral blood may be centrifuged as in step 5001, and resulting blood plasma may be depleted of certain blood cells, for example red blood cells. Then in step 5003, magnetic labels hybridized with antibodies or ligands may be added to the plasma from step 5001 to bind to DNA or RNA within the plasma. Alternatively, peripheral blood from step 1002 may be used directly in step 5003 without step 5001 centrifuge as shown by path 5015, and magnetic labels bind to the DNA or RNA in peripheral blood in step 5003. After step 5003, MAG device may be used to separate the DNA and RNA bound with the magnetic labels in step 5004, and the resulting positive MAG sample containing DNA and RNA may be regarded the cell-free plasma of step 1003 as indicated by path 5013. Further alternatively, positive MAG sample of step 5004 may undergo a UFL separation as in step 5002, where UFL large entities output contains any remaining cells in plasma, while UFL small entities output contains DNA or RNA that are bound with magnetic labels. Small entities output from UFL separation of step 5002 may then be used towards step 1003 as cell-free plasma as in path 5017.

FIG. 92 illustrates embodiment of third process flow to obtain cell-free plasma of step 1003 from collected peripheral blood as in step 1002. After collection of peripheral blood in step 1002, peripheral blood may be centrifuged as in step 5001, and resulting blood plasma may be depleted of certain blood cells, for example red blood cells. Then in step 5023, magnetic labels hybridized with antibodies or ligands may be added to the plasma from step 5001 to bind to cells within the plasma. Alternatively, peripheral blood from step 1002 may be used directly in step 5003 without step 5001 centrifuge as shown by path 5015, and magnetic labels bind to the cells in peripheral blood in step 5023. After step 5023, MAG device may be used to separate the cells bound with the magnetic labels in step 5024 from the plasma that contains DNA or RNA, and the resulting negative MAG sample containing DNA and RNA may be regarded the cell-free plasma of step 1003 as indicated by path 5013. Alternatively, negative MAG sample of step 5024 may undergo a UFL separation as in step 5002, where UFL large entities output contains any remaining cells in plasma from step 5012, while UFL small entities output contains DNA or RNA. Small entities output from UFL separation of step 5002 may then be used towards step 1003 as cell-free plasma as in path 5017.

FIG. 93 illustrates a method to extend method of FIG. 89 for anti-aging purpose. For conditions relating to aging, for example Alzheimer's Disease, dementia, osteoporosis, and arthritis, human growth hormone or other anti-aging agent may be used to help cell growth to delay or alleviate symptoms occurrence of the conditions. For aging in general, human growth hormone or other anti-aging agents may help improve overall body conditions due to tissue or cell replenishment. However, in use of such anti-aging agent, a possible limitation is increased risk of tumor occurrence. Due to the nature of tumor cells being fast growth and evading cell death by immune system, administering human growth hormone or anti-aging agent in presence of any tumor, especially pre-symptom tumor or dormant tumor, such hormone or agent may incur growth of these tumor cells. Thus, for low risk implementation of human growth hormone or anti-aging agent, a tumor free condition of PUT is desired. FIG. 93 initial flow steps of 3001, 1002, 1003, 3004 and 3005 are identical to FIG. 89, where existence of any of the multiple types of target tumors in PUT may be ascertained in step 3005. In FIG. 93, after step 3005, in the case that at least one type of tumor is confirmed to exist in PUT as in judgement 4001, corresponding tumor treatment may be performed in step 4002. After step 4002, another cycle of process from step 3001 to step 3005 may be performed to ascertain tumor absence after treatment of step 4002. In the case that step 3005 finds no tumor existence as in judgement 4003, growth hormone or anti-aging agent may be administered to the PUT as in step 4004. After step 4004, another cycle of step 3001 through step 3005 may be performed to ascertain no tumor was promoted by the step 4004. Flow from step 3001 to step 4004 may be repeated as many cycles as needed to achieve aging related conditions treatment goal.

While the current invention has been shown and described with reference to certain embodiments, it is to be understood that those skilled in the art will no doubt devise certain alterations and modifications thereto which nevertheless include the true spirit and scope of the current invention. Thus the scope of the invention should be determined by the appended claims and their legal equivalents, rather than by examples given.

What is claimed is:

1. A method to separate biological entities with magnetic labels from a fluid sample comprising steps of:

passing said fluid sample through a channel positioned in contact with a separation magnet by a first surface of said channel wherein said channel is attached to a channel holder;

said separation magnet separating said biological entities with magnetic labels from said fluid sample to form a magnetic conglomerate on internal surface of said channel opposing said first surface;

detaching said channel from said separation magnet and positioning said holder in contact with a mechanical excitation means; and causing dissociation of said magnetic conglomerate using said mechanical excitation means.

2. The method according to claim 1, wherein said mechanical excitation means includes one of:

a motor producing vibration;

a piezoelectric element producing ultrasound vibration; and a mechanical structure producing stretch, compression or twisting of said channel.

* * * * *